US012643949B2

(12) United States Patent
Rondon et al.

(10) Patent No.: US 12,643,949 B2
(45) Date of Patent: Jun. 2, 2026

(54) MULTI-SPECIFIC ANTIBODIES AND METHODS OF USE

(71) Applicant: Gritstone bio, Inc., Emeryville, CA (US)

(72) Inventors: Isaac J. Rondon, Emeryville, CA (US); Christine Janson, Emeryville, CA (US); Manankumar Anilkumar Shah, Emeryville, CA (US); Karin Jooss, San Diego, CA (US)

(73) Assignee: Gritstone bio, Inc., Emeryville, CA (US)

( * ) Notice: Subject to any disclaimer, the term of this patent is extended or adjusted under 35 U.S.C. 154(b) by 335 days.

(21) Appl. No.: 18/351,184

(22) Filed: Jul. 12, 2023

(65) Prior Publication Data

US 2024/0279343 A1      Aug. 22, 2024

Related U.S. Application Data

(63) Continuation of application No. PCT/US2022/012573, filed on Jan. 14, 2022.

(60) Provisional application No. 63/137,702, filed on Jan. 14, 2021.

(51) Int. Cl.
| | |
|---|---|
| *C07K 16/28* | (2006.01) |
| *A61K 39/00* | (2006.01) |
| *A61P 35/00* | (2006.01) |
| *C07K 16/46* | (2006.01) |

(52) U.S. Cl.
CPC .......... *C07K 16/2833* (2013.01); *A61P 35/00* (2018.01); *C07K 16/2809* (2013.01); *C07K 16/468* (2013.01); *A61K 2039/505* (2013.01); *C07K 2317/31* (2013.01); *C07K 2317/622* (2013.01); *C07K 2317/626* (2013.01); *C07K 2317/732* (2013.01); *C07K 2317/92* (2013.01); *C07K 2317/94* (2013.01)

(58) Field of Classification Search
CPC ................................................ C07K 16/2833
See application file for complete search history.

(56) References Cited

U.S. PATENT DOCUMENTS

| | | |
|---|---|---|
| 3,843,638 A | 10/1974 | Nicki et al. |
| 4,452,773 A | 6/1984 | Molday |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,795,698 A | 1/1989 | Owen et al. |
| 4,816,567 A | 3/1989 | Cabilly et al. |
| 4,927,762 A | 5/1990 | Darfler |
| 4,946,778 A | 8/1990 | Ladner et al. |
| 5,122,469 A | 6/1992 | Mather et al. |
| 5,132,405 A | 7/1992 | Huston et al. |

| | | |
|---|---|---|
| 5,200,084 A | 4/1993 | Liberti et al. |
| 5,204,244 A | 4/1993 | Fell et al. |
| 5,219,740 A | 6/1993 | Miller et al. |
| 5,229,275 A | 7/1993 | Goroff |
| 5,500,362 A | 3/1996 | Robinson et al. |
| 5,514,578 A | 5/1996 | Hogness et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,589,369 A | 12/1996 | Seidman et al. |
| 5,591,669 A | 1/1997 | Krimpenfort et al. |
| 5,624,821 A | 4/1997 | Winter et al. |
| 5,648,260 A | 7/1997 | Winter et al. |
| 5,662,907 A | 9/1997 | Kubo et al. |
| 5,693,761 A | 12/1997 | Queen et al. |
| 5,693,762 A | 12/1997 | Queen et al. |
| 5,731,168 A | 3/1998 | Carter et al. |
| 5,821,337 A | 10/1998 | Carter et al. |
| 5,849,589 A | 12/1998 | Tedder et al. |
| 6,040,177 A | 3/2000 | Riddell et al. |
| 6,171,586 B1 | 1/2001 | Lam et al. |
| 6,180,370 B1 | 1/2001 | Queen et al. |
| 6,194,551 B1 | 2/2001 | Idusogie et al. |
| 6,207,453 B1 | 3/2001 | Maass et al. |
| 6,245,531 B1 | 6/2001 | Hogness et al. |
| 6,267,958 B1 | 7/2001 | Andya et al. |
| 6,410,319 B1 | 6/2002 | Raubitschek et al. |
| 6,451,995 B1 | 9/2002 | Cheung et al. |
| 6,737,056 B1 | 5/2004 | Presta |

(Continued)

FOREIGN PATENT DOCUMENTS

| | | | |
|---|---|---|---|
| EP | 0452342 A1 | 10/1991 |
| EP | 0453082 A1 | 10/1991 |

(Continued)

OTHER PUBLICATIONS

International Search Report and Written Opinion in PCT/US2019/046967, mailed Jan. 21, 2020, 13 pages.
International Search Report and Written Opinion in PCT/US2020/015736, mailed Jul. 1, 2020, 18 pages.
International Search Report and Written Opinion in PCT/US2020/058982, mailed Jun. 3, 2021, 15 pages.
International Search Report and Written Opinion in PCT/US2021/018912, mailed May 21, 2021, 9 pages.
International Search Report and Written Opinion in PCT/US2021/043796, mailed Dec. 29, 2021, 14 pages.
International Search Report and Written Opinion in PCT/US2021/055261, mailed Apr. 5, 2022, 18 pages.

(Continued)

*Primary Examiner* — Prema M Mertz
(74) *Attorney, Agent, or Firm* — The Marbury Law Group, PLLC

(57) ABSTRACT

Provided herein are multispecific antigen binding proteins that selectively bind a particular KKLC-1 (CT-83) shared antigen and CD3, as well as related methods, kits, and compositions. Included herein are multispecific antigen binding proteins with a circularized conformation.

18 Claims, 72 Drawing Sheets

Specification includes a Sequence Listing.

(56) References Cited

U.S. PATENT DOCUMENTS

| | | |
|---|---|---|
| 7,070,995 B2 | 7/2006 | Jensen |
| 7,091,038 B2 | 8/2006 | Palli et al. |
| 7,129,330 B1 | 10/2006 | Little et al. |
| 7,250,297 B1 | 7/2007 | Beste et al. |
| 7,265,209 B2 | 9/2007 | Jensen |
| 7,332,581 B2 | 2/2008 | Presta |
| 7,354,762 B2 | 4/2008 | Jensen |
| 7,371,826 B2 | 5/2008 | Presta |
| 7,446,179 B2 | 11/2008 | Jensen et al. |
| 7,446,190 B2 | 11/2008 | Sadelain et al. |
| 7,446,191 B2 | 11/2008 | Jensen |
| 7,521,056 B2 | 4/2009 | Chang et al. |
| 7,527,787 B2 | 5/2009 | Chang et al. |
| 7,534,866 B2 | 5/2009 | Chang et al. |
| 7,550,143 B2 | 6/2009 | Chang et al. |
| 7,569,664 B2 | 8/2009 | Jakobsen et al. |
| 7,585,940 B2 | 9/2009 | Skerra et al. |
| 7,612,181 B2 | 11/2009 | Wu et al. |
| 7,695,936 B2 | 4/2010 | Carter et al. |
| 8,258,082 B2 | 9/2012 | Ladner |
| 8,324,353 B2 | 12/2012 | Jensen |
| 8,339,645 B2 | 12/2012 | Nakawaki |
| 8,389,282 B2 | 3/2013 | Sadelain et al. |
| 8,398,282 B2 | 3/2013 | Kuhlman et al. |
| 8,479,118 B2 | 7/2013 | Lyndersay et al. |
| 8,586,713 B2 | 11/2013 | Davis et al. |
| 8,592,562 B2 | 11/2013 | Kannan et al. |
| 8,592,563 B2 | 11/2013 | Bates et al. |
| 8,691,730 B2 | 4/2014 | Vasquez et al. |
| 8,858,931 B2 | 10/2014 | Langlade-Demoyen et al. |
| 8,911,993 B2 | 12/2014 | June et al. |
| 8,969,526 B2 | 3/2015 | Baehner et al. |
| 9,150,641 B2 | 10/2015 | Kettenberger et al. |
| 9,309,326 B2 | 4/2016 | Davis et al. |
| 9,587,020 B2 | 3/2017 | Wu et al. |
| 9,644,025 B2 | 5/2017 | Black et al. |
| 9,683,052 B2 | 6/2017 | Blein et al. |
| 9,809,958 B2 | 11/2017 | Shang et al. |
| 9,822,186 B2 | 11/2017 | Bernett et al. |
| 9,982,013 B2 | 5/2018 | Davis et al. |
| 10,055,540 B2 | 8/2018 | Yelensky et al. |
| 10,611,842 B2 | 4/2020 | Liu et al. |
| 11,792,145 B2 | 10/2023 | Lapic et al. |
| 2002/0131960 A1 | 9/2002 | Sadelain et al. |
| 2003/0215914 A1 | 11/2003 | Houtzager et al. |
| 2005/0014934 A1 | 1/2005 | Hinton et al. |
| 2006/0122119 A1 | 6/2006 | Linard et al. |
| 2007/0123479 A1 | 5/2007 | Kufer et al. |
| 2007/0196369 A1 | 8/2007 | Hoogenboom et al. |
| 2008/0069820 A1 | 3/2008 | Fuh et al. |
| 2008/0206312 A1 | 8/2008 | Robertson et al. |
| 2009/0215991 A1 | 8/2009 | Lazar et al. |
| 2009/0253694 A1 | 10/2009 | Ono et al. |
| 2010/0228007 A1 | 9/2010 | Hoogenboom et al. |
| 2010/0316653 A1 | 12/2010 | Slifka et al. |
| 2011/0003380 A1 | 1/2011 | Miltenyi et al. |
| 2011/0014213 A1 | 1/2011 | Torikai et al. |
| 2011/0091489 A1 | 4/2011 | Andersen |
| 2011/0245209 A1 | 10/2011 | Xiao et al. |
| 2012/0058906 A1 | 3/2012 | Smider et al. |
| 2013/0149337 A1 | 6/2013 | Cooper et al. |
| 2013/0287748 A1 | 10/2013 | June et al. |
| 2013/0315935 A1 | 11/2013 | Schwabe |
| 2015/0018530 A1 | 1/2015 | Miao et al. |
| 2016/0024147 A1 | 1/2016 | Tustian et al. |
| 2016/0152725 A1 | 6/2016 | Cheung et al. |
| 2016/0176953 A1 | 6/2016 | Purcell et al. |
| 2017/0166877 A1 | 6/2017 | Bayle et al. |
| 2017/0199961 A1 | 7/2017 | Yelensky et al. |
| 2017/0218078 A1 | 8/2017 | Raum et al. |
| 2017/0292952 A1 | 10/2017 | Hantash |
| 2018/0118827 A1 | 5/2018 | Moore et al. |
| 2018/0142040 A1 | 5/2018 | Moore et al. |
| 2018/0153975 A1 | 6/2018 | Fritsch et al. |
| 2018/0179283 A1 | 6/2018 | Peled Kamar et al. |
| 2018/0326002 A1 | 11/2018 | Powlesland et al. |
| 2018/0330055 A1 | 11/2018 | Yelensky et al. |
| 2019/0031713 A1 | 1/2019 | Davis et al. |
| 2019/0034585 A1 | 1/2019 | Yelensky et al. |
| 2019/0065675 A1 | 2/2019 | Yelensky et al. |
| 2019/0135891 A1 | 5/2019 | Stevanovic et al. |
| 2019/0279742 A1 | 9/2019 | Bulik-Sullivan et al. |
| 2020/0390899 A1 | 12/2020 | Ackerman et al. |
| 2021/0061914 A1 | 3/2021 | Jooss et al. |
| 2021/0147550 A1 | 5/2021 | Jooss et al. |
| 2021/0196806 A1 | 7/2021 | Yelensky et al. |
| 2021/0213122 A1 | 7/2021 | Blair et al. |
| 2022/0162320 A1 | 5/2022 | Jooss et al. |
| 2022/0213196 A1 | 7/2022 | Jooss et al. |
| 2023/0041030 A1 | 2/2023 | Jooss et al. |
| 2023/0287128 A1 | 9/2023 | Rainey et al. |
| 2023/0295305 A1 | 9/2023 | Rainey et al. |
| 2023/0382997 A1 | 11/2023 | Jooss et al. |
| 2024/0059797 A1 | 2/2024 | Rainey et al. |
| 2025/0353914 A1 | 11/2025 | Rainey et al. |

FOREIGN PATENT DOCUMENTS

| | | |
|---|---|---|
| EP | 0517805 B1 | 7/2002 |
| EP | 2537416 A1 | 12/2012 |
| EP | 1746107 B1 | 12/2014 |
| EP | 2975051 A1 | 1/2016 |
| WO | 8700185 A1 | 1/1987 |
| WO | 8700195 A1 | 1/1987 |
| WO | 9003430 A1 | 4/1990 |
| WO | 9308829 A1 | 5/1993 |
| WO | 9316185 A2 | 8/1993 |
| WO | 9429351 A2 | 12/1994 |
| WO | 9839482 A1 | 9/1998 |
| WO | 9951642 A1 | 10/1999 |
| WO | 9958572 A1 | 11/1999 |
| WO | 0014257 A1 | 3/2000 |
| WO | 0162908 A2 | 8/2001 |
| WO | 2004044004 A2 | 5/2004 |
| WO | 2005100402 A1 | 10/2005 |
| WO | 2005116646 A1 | 12/2005 |
| WO | 2006029879 A2 | 3/2006 |
| WO | 2006044908 A2 | 4/2006 |
| WO | 2006076594 A2 | 7/2006 |
| WO | 2008118017 A2 | 10/2008 |
| WO | 2008134046 A1 | 11/2008 |
| WO | 2009051555 A2 | 4/2009 |
| WO | 2009072003 A2 | 6/2009 |
| WO | 2009089004 A1 | 7/2009 |
| WO | 2010033140 A2 | 3/2010 |
| WO | 2011143545 A1 | 11/2011 |
| WO | 2012013913 A1 | 2/2012 |
| WO | 2012129514 A1 | 9/2012 |
| WO | 2013039889 A1 | 3/2013 |
| WO | 2013041865 A1 | 3/2013 |
| WO | 2013071154 A1 | 5/2013 |
| WO | 2013123061 A1 | 8/2013 |
| WO | 2013126726 A1 | 8/2013 |
| WO | 2013151666 A2 | 10/2013 |
| WO | 2013165690 A1 | 11/2013 |
| WO | 2013166321 A1 | 11/2013 |
| WO | 2014018863 A1 | 1/2014 |
| WO | 2014031687 A1 | 2/2014 |
| WO | 2014055668 A1 | 4/2014 |
| WO | 2014138449 A1 | 9/2014 |
| WO | 2014165818 A2 | 10/2014 |
| WO | 2015103072 A1 | 7/2015 |
| WO | 2015136072 A1 | 9/2015 |
| WO | 2016069283 A1 | 5/2016 |
| WO | 2016085904 A1 | 6/2016 |
| WO | 2016154047 A2 | 9/2016 |
| WO | 2016154246 A1 | 9/2016 |
| WO | 2016187508 A2 | 11/2016 |
| WO | 2016191246 A2 | 12/2016 |
| WO | 2016201124 A2 | 12/2016 |
| WO | 2017046198 A1 | 3/2017 |
| WO | 2017089756 A1 | 6/2017 |
| WO | 2017106638 A1 | 6/2017 |
| WO | 2017124001 A2 | 7/2017 |

(56)                    References Cited

FOREIGN PATENT DOCUMENTS

| | | | |
|---|---|---|---|
| WO | 2017156178 A1 | 9/2017 |
| WO | 2017173321 A1 | 10/2017 |
| WO | 2017184590 A1 | 10/2017 |
| WO | 2017189254 A1 | 11/2017 |
| WO | 2017196432 A1 | 11/2017 |
| WO | 2018164637 A1 | 9/2018 |
| WO | 2018195357 A1 | 10/2018 |
| WO | 2018227030 A1 | 12/2018 |
| WO | 2019007974 A1 | 1/2019 |
| WO | 2019036688 A1 | 2/2019 |
| WO | 2019046316 A1 | 3/2019 |
| WO | 2019050994 A1 | 3/2019 |
| WO | 2019075112 A1 | 4/2019 |
| WO | 2019075392 A1 | 4/2019 |
| WO | 2019133853 A1 | 7/2019 |
| WO | 2019168984 A1 | 9/2019 |
| WO | 2020037302 A1 | 2/2020 |
| WO | 2020160189 A1 | 8/2020 |
| WO | 2020236792 A1 | 11/2020 |
| WO | 2021092094 A1 | 5/2021 |
| WO | 2021168355 A1 | 8/2021 |
| WO | 2022026772 A1 | 2/2022 |
| WO | 2022082030 A2 | 4/2022 |
| WO | 2022155503 A1 | 7/2022 |

OTHER PUBLICATIONS

International Search Report and Written Opinion in PCT/US2022/012573, mailed May 13, 2022, 11 pages.

Invitation to Pay Additional Fees in PCT/US2019/046967, mailed Nov. 27, 2019, 2 pages.

Jin et al. "Establishment of cancer/testis antigen profiling based on clinicopathological characteristics in resected pathological stage III non-small cell lung cancer." Cancer management and research (2018): 2031-2046.

Kerry et al. "Interplay between TCR affinity and necessity of coreceptor ligation: high-affinity peptide-MHC/TCR interaction overcomes lack of CD8 engagement." The Journal of Immunology 171.9 (2003): 4493-4503.

Kessels et al. "Changing T cell specificity by retroviral T cell receptor display." Proceedings of the National Academy of Sciences 97.26 (2000): 14578-14583.

Kipriyanov et al. "Bispecific tandem diabody for tumor therapy with improved antigen binding and pharmacokinetics." Journal of molecular biology 293.1 (1999): 41-56.

Klebanoff et al. "Sorting through subsets: which T-cell populations mediate highly effective adoptive immunotherapy?." Journal of immunotherapy 35.9 (2012): 651-660.

Kohler et al. "Continuous cultures of fused cells secreting antibody of predefined specificity." nature 256.5517 (1975): 495-497.

Koste et al. "T-cell receptor transfer into human T cells with ecotropic retroviral vectors." Gene therapy 21.5 (2014): 533-538.

Kuball et al. "Facilitating matched pairing and expression of TCR chains introduced into human T cells." Blood 109.6 (2007): 2331-2338.

Kuball et al. "Increasing functional avidity of TCR-redirected T cells by removing defined N-glycosylation sites in the TCR constant domain." Journal of Experimental Medicine 206.2 (2009): 463-475.

Labrijn et al. "Efficient generation of stable bispecific IgG1 by controlled Fab-arm exchange." Proceedings of the National Academy of Sciences 110.13 (2013): 5145-5150.

Lafleur et al. "Monoclonal antibody therapeutics with up to five specificities: functional enhancement through fusion of target-specific peptides." MAbs. vol. 5. No. 2. Taylor & Francis (2013): 208-218.

Lazar et al. "Engineered antibody Fc variants with enhanced effector function." Proceedings of the National Academy of Sciences 103.11 (2006): 4005-4010.

Lefranc at al. "Human Gm, Km, and Am allotypes and their molecular characterization: a remarkable demonstration of poly-morphism." Immunogenetics: Methods and Applications in Clinical Practice. Totowa, NJ: Humana Press, 2012. 635-680.

Legut et al. "CRISPR-mediated TCR replacement generates superior anticancer transgenic T cells." Blood, The Journal of the American Society of Hematology 131.3 (2018): 311-322.

Li et al. "Increasing the safety and efficacy of chimeric antigen receptor T cell therapy." Protein & cell 8.8 (2017): 573-589.

Li et al. "RSEM: accurate transcript quantification from RNA-Seq data with or without a reference genome." BMC bioinformatics 12.1 (2011): 323.

Lloyd et al. "Modelling the human immune response: performance of a 1011 human antibody repertoire against a broad panel of therapeutically relevant antigens." Protein Engineering, Design & Selection 22.3 (2009): 159-168.

Lonsdale et al. "The genotype-tissue expression (GTEx) project." Nature genetics 45.6 (2013): 580-585.

Luimstra et al. "A flexible MHC class I multimer loading system for large-scale detection of antigen-specific T cells." Journal of Experimental Medicine 215.5 (2018): 1493-1504.

Lupton et al. "Dominant positive and negative selection using a hygromycin phosphotransferase-thymidine kinase fusion gene." Molecular and Cellular Biology 11.6 (1991): 3374-3378.

Manuri et al. "piggyBac transposon/transposase system to generate CD19-specific T cells for the treatment of B-lineage malignancies." Human gene therapy 21.4 (2010): 427-437.

Marcinkowski et al. "Cancer targeting by TCR gene-engineered T cells directed against Kita-Kyushu Lung Cancer Antigen-1." Journal for immunotherapy of cancer 7.1 (2019): 229.

Marks et al. "By-passing immunization: human antibodies from V-gene libraries displayed on phage." Journal of molecular biology 222.3 (1991): 581-597.

Mckinney, P. "Brain tumours: incidence, survival, and aetiology." Journal of Neurology, Neurosurgery & Psychiatry 75.suppl 2 (2004): ii12-ii17.

Merchant et al. "An efficient route to human bispecific IgG." Nature biotechnology 16.7 (1998): 677-681.

Meyer et al. "New insights in Type I and II CD 20 antibody mechanisms-of-action with a panel of novel CD 20 antibodies." British Journal of Haematology 180.6 (2018): 808-820.

Moon et al. "Expression of a functional CCR2 receptor enhances tumor localization and tumor eradication by retargeted human T cells expressing a mesothelin-specific chimeric antibody receptor." Clinical cancer research 17.14 (2011): 4719-4730.

Moore et al. "A novel bispecific antibody format enables simultaneous bivalent and monovalent co-engagement of distinct target antigens." MAbs. vol. 3. No. 6. Taylor & Francis (2011): 546-557.

Moore et al. "Application of dual affinity retargeting molecules to achieve optimal redirected T-cell killing of B-cell lymphoma." Blood, The Journal of the American Society of Hematology 117.17 (2011): 4542-4551.

Moretti et al. "BEAT® the bispecific challenge: a novel and efficient platform for the expression of bispecific IgGs." BMC Proceedings. vol. 7. No. Suppl 6. London: BioMed Central, 2013.

Morrison et al. "Chimeric human antibody molecules: mouse antigen-binding domains with human constant region domains." Proceedings of the National Academy of Sciences 81.21 (1984): 6851-6855.

Mosaad, Y. "Clinical role of human leukocyte antigen in health and disease." Scandinavian journal of immunology 82.4 (2015): 283-306.

Mullen et al. "Transfer of the bacterial gene for cytosine deaminase to mammalian cells confers lethal sensitivity to 5-fluorocytosine: a negative selection system." Proceedings of the National Academy of Sciences 89.1 (1992): 33-37.

Murphy et al. (2017). Janeway's Immunobiology (9th ed.). Ch. 4, "Antigen Recognition by B-cell and T-cell Receptors," pp. 139-172. New York: Garland Science.

Nih, "New T-Cell Immunotherapy that targets Aggressive Epithelial Tumors," National Institutes of Health, 2017 [retrieved on Apr. 28, 2020]. Retrieved from the Internet: <https://www.ott.nih.gov/technology/e-153-2016/>, 2 pages.

Ochi et al. "Novel adoptive T-cell immunotherapy using a WT1-specific TCR vector encoding silencers for endogenous TCRs shows

(56)        References Cited

OTHER PUBLICATIONS marked antileukemia reactivity and safety." Blood, The Journal of the American Society of Hematology 118.6 (2011): 1495-1503.
Office Action in CN201980060989.6, mailed Apr. 29, 2024, 7 pages.
Office Action in CN201980060989.6, mailed Jan. 11, 2025, 2 pages.
Office Action in CN201980060989.6, mailed Aug. 13, 2025, 6 pages.
Office Action in EP19849564.0, mailed Apr. 7, 2022, 3 pages.
Office Action in EP20748612.7, mailed Sep. 27, 2022, 4 pages.
Office Action in EP20748612.7, mailed Feb. 24, 2023, 1 page.
Office Action in EP21756615.7, mailed Mar. 7, 2024, 1 page.
Office Action in EP21850618.6, mailed Jul. 30, 2024, 4 pages.
Office Action in EP21850618.6, mailed Dec. 17, 2024, 1 page.
Office Action in EP22740170.0, mailed May 30, 2025, 1 page.
Office Action in IL280890, mailed Jun. 7, 2022, 3 pages.
Office Action in IL320680, mailed May 13, 2025, 3 pages.
Office Action in U.S. Appl. No. 17/269,246, mailed Mar. 7, 2025, 119 pages.
Oganesyan et al. "Structural characterization of a human Fc fragment engineered for lack of effector functions." Biological Crystallography 64.6 (2008): 700-704.
Okamoto et al. "A promising vector for TCR gene therapy: differential effect of siRNA, 2A peptide, and disulfide bond on the introduced TCR expression." Molecular therapy Nucleic acids 1 (2012).
Olsen et al. "TANTIGEN: a comprehensive database of tumor T cell antigens." Cancer Immunology, Immunotherapy 66.6 (2017): 731-735.
Oxford, "Treating," Oxford English Dictionary, 2025, [retrieved on Feb. 24, 2025]. Retrieved from the Internet: <URL: https://www.oed.com/dictionary/treat>, 1 page.
Paret et al. "CXorf61 is a target for T cell based immunotherapy of triple-negative breast cancer." Oncotarget 6.28 (2015): 25356-25367.
Park et al. "Treating cancer with genetically engineered T cells." Trends in biotechnology 29.11 (2011): 550-557.
Paul, W. Fundamental Immunology. "(textbook)," Fv Structure and Diversity in Three Dimensions" pp. 292-295." (1993).
PCT/US2020/015736, filed Jan. 29, 2020, 534 pages.
Petkova et al. "Enhanced half-life of genetically engineered human IgG1 antibodies in a humanized FcRn mouse model: potential application in humorally mediated autoimmune disease." International immunology 18.12 (2006): 1759-1769.
Pino et al. "The Skyline Ecosystem: Informatics for Quantitative Mass Spectrometry Proteomics," HHS Public Access, Author Manuscript, Mass Spectrom Rev. (2019): 1-32.
Pluckthun et al. "New protein engineering approaches to multivalent and bispecific antibody fragments." Immunotechnology 3.2 (1997): 83-105.
Pluckthun, A. "Antibodies from *Escherichia coli*." The Pharmacology of Monoclonal Antibodies. Berlin, Heidelberg: Springer Berlin Heidelberg, 1994. 269-315.
Queen et al. "A humanized antibody that binds to the interleukin 2 receptor." Proceedings of the National Academy of Sciences 86.24 (1989): 10029-10033.
Quintarelli et al. "Co-expression of cytokine and suicide genes to enhance the activity and safety of tumor-specific cytotoxic T lymphocytes." Blood, The Journal of the American Society of Hematology 110.8 (2007): 2793-2802.
Rader et al. "A phage display approach for rapid antibody humanization: designed combinatorial V gene libraries." Proceedings of the National Academy of Sciences 95.15 (1998): 8910-8915.
Ravetch et al. "Fc receptors." Annual review of immunology 9 (1991): 457-492.
Riddell et al. "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington." Human gene therapy 3.3 (1992): 319-338.

Ridgway et al. "'Knobs-into-holes' engineering of antibody CH3 domains for heavy chain heterodimerization." Protein Engineering, Design and Selection 9.7 (1996): 617-621.
Rodenko et al. "Class I major histocompatibility complexes loaded by a periodate trigger." Journal of the American Chemical Society 131.34 (2009): 12305-12313.
Roth et al. "Reprogramming human T cell function and specificity with non-viral genome targeting." Nature 559.7714 (2018): 405-409.
Rothe et al. "Anticalin® proteins as therapeutic agents in human diseases." BioDrugs 32.3 (2018): 233-243.
Rothenberg et al. "Improving the evaluation of new cancer treatments: challenges and opportunities." Nature Reviews Cancer 3.4 (2003): 303-309.
Rudikoff et al. "Single amino acid substitution altering antigen-binding specificity." Proceedings of the National Academy of Sciences 79.6 (1982): 1979-1983.
Sadelain et al. "The basic principles of chimeric antigen receptor design." Cancer discovery 3.4 (2013): 388-398.
Saini et al. "Dipeptides catalyze rapid peptide exchange on MHC class I molecules." Proceedings of the National Academy of Sciences 112.1 (2015): 202-207.
Saini et al. "Dipeptides promote folding and peptide binding of MHC class I molecules." Proceedings of the National Academy of Sciences 110.38 (2013): 15383-15388.
Sebestyen et al. "Human TCR that incorporate CD3ζ induce highly preferred pairing between TCRα and β chains following gene transfer." The Journal of Immunology 180.11 (2008): 7736-7746.
Shapiro et al. "Single-cell sequencing-based technologies will revolutionize whole-organism science." Nature Reviews Genetics 14.9 (2013): 618-630.
Sharma et al. "Efficient sleeping beauty DNA transposition from DNA minicircles." Molecular therapy Nucleic acids 2 (2013).
Silacci et al. "Linker length matters, fynomer-Fc fusion with an optimized linker displaying picomolar IL-17A inhibition potency." Journal of Biological Chemistry 289.20 (2014): 14392-14398.
Silverman et al. "Multivalent avimer proteins evolved by exon shuffling of a family of human receptor domains." Nature biotechnology 23.12 (2005): 1556-1561.
Smith et al. "A novel, native-format bispecific antibody triggering T-cell killing of B-cells is robustly active in mouse tumor models and cynomolgus monkeys." Scientific reports 5.1 (2015): 17943.
Staerz et al. "Hybrid antibodies can target sites for attack by T cells." Nature 314.6012 (1985): 628-631.
Steinberger et al. "Generation and characterization of a recombinant human CCR5-specific antibody: A phage display approach for rabbit antibody humanization." Journal of Biological Chemistry 275.46 (2000): 36073-36078.
Stevanovic et al. "Landscape of immunogenic tumor antigens in successful immunotherapy of virally induced epithelial cancer." Science 356.6334 (2017): 200-205.
Stewart et al. "The role of Fc gamma receptors in the activity of immunomodulatory antibodies for cancer." Journal for Immuno Therapy of Cancer 2.1 (2014): 29.
Strop et al. "Generating bispecific human IgG1 and IgG2 antibodies from any antibody pair." Journal of molecular biology 420.3 (2012): 204-219.
Terakura et al. "Generation of CD19-chimeric antigen receptor modified CD8+ T cells derived from virus-specific central memory T cells." Blood, The Journal of the American Society of Hematology 119.1 (2012): 72-82.
Thirdborough et al. "Vaccination with DNA encoding a single-chain TCR fusion protein induces anticlonotypic immunity and protects against T-cell lymphoma." Cancer research 62.6 (2002): 1757-1760.
Thompson et al. "Preventing the spontaneous modification of an HLA-A2-restricted peptide at an N-terminal glutamine or an internal cysteine residue enhances peptide antigenicity." Journal of Immunotherapy 27.3 (2004): 177-183.
Todorovska et al. "Design and application of diabodies, triabodies and tetrabodies for cancer targeting." Journal of immunological methods 248.1-2 (2001): 47-66.
Torikai et al. "A foundation for universal T-cell based immunotherapy: T cells engineered to express a CD19-specific chimeric-antigen-

(56)            References Cited

OTHER PUBLICATIONS receptor and eliminate expression of endogenous TCR." Blood, The Journal of the American Society of Hematology 119.24 (2012): 5697-5705.

Torikai et al. "HLA and TCR Knockout by Zinc Finger Nucleases: Toward "off-the-Shelf" Allogeneic T-Cell Therapy for CD19+ Malignancies." Blood 116.21 (2010): 3766.

Non-Final Office Action for copending U.S. Appl. No. 18/300,747, dated Nov. 19, 2025, 67 pages.

GenCore version 6.5.2, Copyright © 1993-2025; Biocceleration Ltd., citation BGN95135; Sequence 124, Publication No. WO2019133851A1 (Year: 2019).

Emanuel et al. "A fibronectin scaffold approach to bispecific inhibitors of epidermal growth factor receptor and insulin-like growth factor-I receptor." MAbs. vol. 3. No. 1. Taylor & Francis (2011): 38-48.

Eng et al. "A deeper look into Come—-implementation and features." Journal of the American Society for Mass Spectrometry 26.11 (2015): 1865-1874.

Extended European Search Report in EP20748612.7, mailed Feb. 7, 2023, 12 pages.

Extended European Search Report in EP21756615.7, mailed Feb. 19, 2024, 6 pages.

Extended European Search Report in EP21850618.6, mailed Nov. 29, 2024, 12 pages.

Extended European Search Report in EP21881209.7, mailed Nov. 8, 2024, 7 pages.

Extended European Search Report in EP22740170.0, mailed May 12, 2025, 9 pages.

Fedorov et al. "PD-1- and CTLA-4-based inhibitory chimeric antigen receptors (iCARs) divert off-target immunotherapy responses." Science translational medicine 5.215 (2013): 215ra172-215ra172.

Fernandez, L. "Prokaryotic expression of antibodies and affibodies." Current opinion in biotechnology 15.4 (2004): 364-373.

Fitzgerald et al. "Improved tumour targeting by disulphide stabilized diabodies expressed in Pichia pastoris." Protein Engineering, 10(10) (1997): 1221-1225.

Frattini et al. "The integrated landscape of driver genomic alterations in glioblastoma." Nature genetics 45.10 (2013): 1141-1149.

Fukuyama et al. "Expression of KK-LC-1, a cancer/testis antigen, at non-tumour sites of the stomach carrying a tumour." Scientific reports 8.1 (2018): 6131.

Fukuyama et al. "Identification of a new cancer/germline gene, KK-LC-1, encoding an antigen recognized by autologous CTL induced on human lung adenocarcinoma." Cancer research 66.9 (2006): 4922-4928.

Futawatari et al. "Early gastric cancer frequently has high expression of KK-LC-1, a cancer-testis antigen." World Journal of Gastroenterology 23.46 (2017): 8200.

Garboczi et al. "HLA-A2-peptide complexes: refolding and crystallization of molecules expressed in *Escherichia coli* and complexed with single antigenic peptides." Proceedings of the National Academy of Sciences 89.8 (1992): 3429-3433.

Gazzano-Santoro et al. "A non-radioactive complement-dependent cytotoxicity assay for anti-CD20 monoclonal antibody." Journal of immunological methods 202.2 (1997): 163-171.

Geyer et al. "[13] Selection of genetic agents from random peptide aptamer expression libraries." Methods in enzymology. vol. 328. Academic Press, 2000. 171-208.

Godin et al. "Microfluidics and photonics for Bio-System-on-a-Chip: A review of advancements in technology towards a microfluidic flow cytometry chip." Journal of biophotonics 1.5 (2008): 355-376.

Goding, J.W., Monoclonal Antibodies: Principles and Practice 3rd ed. (1986) Academic Press, San Diego, CA.

Govers et al. "T cell receptor fused to CD3ζ: transmembrane domain of CD3ζ prevents TCR mis-pairing, whereas complete CD3ζ directs functional TCR expression." The Open Gene Therapy Journal 4.1 (2011): 11-22.

Gramer et al. "Production of stable bispecific IgG1 by controlled Fab-arm exchange: scalability from bench to large-scale manufacturing by application of standard approaches." MAbs. vol. 5. No. 6. Taylor & Francis (2013): 962-972.

Graversen et al. "Mutational Analysis of Affinity and Selectivity of Kringle-Tetranectin Interaction: Grafting Novel Kringle Affinity Onto The Tetranectin Lectin Scaffold." Journal of Biological Chemistry 275.48 (2000): 37390-37396.

Griffioen et al. "Retroviral transfer of human CD20 as a suicide gene for adoptive T-cell therapy." haematologica 94.9 (2009): 1316-1320.

Grotenbreg et al. "Discovery of CD8+ T cell epitopes in Chlamydia trachomatis infection through use of caged class I MHC tetramers." Proceedings of the National Academy of Sciences 105.10 (2008): 3831-3836.

Gruber et al. "Efficient tumor cell lysis mediated by a bispecific single chain antibody expressed in *Escherichia coli.*" The journal of immunology 152.11 (1994): 5368-5374.

Gunasekaran et al. "Enhancing antibody Fc heterodimer formation through electrostatic steering effects: applications to bispecific molecules and monovalent IgG." Journal of Biological Chemistry 285.25 (2010): 19637-19646.

Haga-Friedman et al. "Incorporation of transmembrane hydrophobic mutations in the TCR enhance its surface expression and T cell functional avidity." The Journal of Immunology 188.11 (2012): 5538-5546.

Hegde et al. "The surprising complexity of signal sequences." Trends in biochemical sciences 31.10 (2006): 563-571.

Hellstrom et al. "Antitumor effects of L6, an IgG2a antibody that reacts with most human carcinomas." Proceedings of the National Academy of Sciences 83.18 (1986): 7059-7063.

Hellstrom et al. "Strong antitumor activities of IgG3 antibodies to a human melanoma-associated ganglioside." Proceedings of the National Academy of Sciences 82.5 (1985): 1499-1502.

Hinton et al. "An engineered human IgG1 antibody with longer serum half-life." The Journal of Immunology 176.1 (2006): 346-356.

Hippisley-Cox et al. "Development and validation of risk prediction equations to estimate future risk of heart failure in patients with diabetes: a prospective cohort study." BMJ open 5.9 (2015): 1-25.

Holland et al. "Specificity of bispecific T cell receptors and antibodies targeting peptide-HLA." The Journal of clinical investigation 130.5 (2020): 2673-2688.

Holliger et al. ""Diabodies": small bivalent and bispecific antibody fragments." Proceedings of the National Academy of Sciences 90.14 (1993): 6444-6448.

Hsu et al. "Cytokine-independent growth and clonal expansion of a primary human CD8+ T-cell clone following retroviral transduction with the IL-15 gene." Blood, The Journal of the American Society of Hematology 109.12 (2007): 5168-5177.

Hsu et al. "Primary human T lymphocytes engineered with a codon-optimized IL-15 gene resist cytokine withdrawal-induced apoptosis and persist long-term in the absence of exogenous cytokine." The Journal of Immunology 175.11 (2005): 7226-7234.

Huang et al. "DNA transposons for modification of human primary T lymphocytes." Methods Mol Biol 506 (2009): 115-126.

Huang et al. "Systematic and integrative analysis of large gene lists using DAVID bioinformatics resources." Nature protocols 4.1 (2009): 44-57.

Hudecek et al. "Receptor affinity and extracellular domain modifications affect tumor recognition by ROR1-specific chimeric antigen receptor T cells." Clinical cancer research 19.12 (2013): 3153-3164.

Hudson et al. "Engineered antibodies." Nature medicine 9.1 (2003): 129-134.

International Preliminary Report on Patentability in PCT/US2018/046997, mailed Feb. 20, 2020, 11 pages.

International Preliminary Report on Patentability in PCT/US2018/067931, mailed Jul. 9, 2020, 14 pages.

International Preliminary Report on Patentability in PCT/US2019/046967, mailed Jan. 21, 2020, 9 pages.

International Preliminary Report on Patentability in PCT/US2020/015736, mailed Aug. 12, 2021, 12 pages.

International Preliminary Report on Patentability in PCT/US2021/018912, mailed Sep. 1, 2022, 7 pages.

(56) References Cited

OTHER PUBLICATIONS

International Preliminary Report on Patentability in PCT/US2021/043796, mailed Feb. 9, 2023, 9 pages.

International Preliminary Report on Patentability in PCT/US2021/055261, mailed Apr. 27, 2023, 12 pages.

International Preliminary Report on Patentability in PCT/US2022/012573, mailed Jul. 27, 2023, 9 pages.

International Search Report and Written Opinion in PCT/US2018/046997, mailed Dec. 20, 2018, 22 pages.

International Search Report and Written Opinion in PCT/US2018/067931, mailed Apr. 30, 2019, 22 pages.

Aalberse et al. "IgG4 breaking the rules." Immunology 105.1 (2002): 9-19.

Abelin et al. "Complementary IMAC enrichment methods for HLA-associated phosphopeptide identification by mass spectrometry." Nature protocols 10.9 (2015): 1308-1318.

Ahmed et al. "TCR-mimic bispecific antibodies targeting LMP2A show potent activity against EBV malignancies." JCI insight 3.4 (2018): e97805.

Alonso-Camino et al. "CARbodies: human antibodies against cell surface tumor antigens selected from repertoires displayed on T cell chimeric antigen receptors." Molecular Therapy Nucleic Acids 2 (2013).

Amore et al. "Development of a hypersensitive periodate-cleavable amino acid that is methionine-and disulfide-compatible and its application in MHC exchange reagents for T cell characterisation." Chembiochem 14.1 (2013): 123-131.

An et al. "Construction of a new anti-CD19 chimeric antigen receptor and the anti-leukemia function study of the transduced T cells." Oncotarget 7.9 (2016):10638-10649.

Armour et al. "Differential binding to human FcγRIIa and FcγRIIb receptors by human IgG wildtype and mutant antibodies." Molecular immunology 40.9 (2003): 585-593.

Armour et al. "Recombinant human IgG molecules lacking Fcγ receptor I binding and monocyte triggering activities." European journal of immunology 29.8 (1999): 2613-2624.

Atwell et al. "Stable heterodimers from remodeling the domain interface of a homodimer using a phage display library." Journal of molecular biology 270.1 (1997): 26-35.

Bakker et al. "Conditional MHC class I ligands and peptide exchange technology for the human MHC gene products HLA-A1,-A3,-A11, and-B7." Proceedings of the National Academy of Sciences 105.10 (2008): 3825-3830.

Bassani-Sternberg et al. "Mass spectrometry of human leukocyte antigen class I peptidomes reveals strong effects of protein abundance and turnover on antigen presentation*[S]." Molecular & Cellular Proteomics 14.3 (2015): 658-673.

Benlalam et al. "Identification of five new HLA-B* 3501-restricted epitopes derived from common melanoma-associated antigens, spontaneously recognized by tumor-infiltrating lymphocytes." The Journal of Immunology 171.11 (2003): 6283-6289.

Bialer et al. "Selected murine residues endow human TCR with enhanced tumor recognition." The Journal of Immunology 184.11 (2010): 6232-6241.

Binz et al. "Engineering novel binding proteins from nonimmunoglobulin domains." Nature biotechnology 23.10 (2005): 1257-1268.

Borrok et al. "An "Fc-Silenced" IgG1 format with extended half-life designed for improved stability." Journal of Pharmaceutical Sciences 106.4 (2017): 1008-1017.

Brash et al. "Strontium phosphate transfection of human cells in primary culture: stable expression of the simian virus 40 large-T-antigen gene in primary human bronchial epithelial cells." Molecular and cellular biology 7.5 (1987): 2031-2034.

Bruggemann et al. "Comparison of the effector functions of human immunoglobulins using a matched set of chimeric antibodies." The Journal of experimental medicine 166.5 (1987): 1351-1361.

Cassett et al. "A peptide mimetic of an anti-CD4 monoclonal antibody by rational design." Biochemical and biophysical research communications 307.1 (2003): 198-205.

Cavalieri et al. "Human T lymphocytes transduced by lentiviral vectors in the absence of TCR activation maintain an intact immune competence." Blood 102.2 (2003): 497-505.

Cereghino et al. "New selectable marker/auxotrophic host strain combinations for molecular genetic manipulation of Pichia pastoris." Gene 263.1-2 (2001): 159-169.

Chames et al. "TCR-like human antibodies expressed on human CTLs mediate antibody affinity-dependent cytolytic activity." The Journal of Immunology 169.2 (2002): 1110-1118.

Chang et al. "A general method for facilitating heterodimeric pairing between two proteins: application to expression of alpha and beta T-cell receptor extracellular segments." Proceedings of the National Academy of Sciences 91.24 (1994): 11408-11412.

Chang et al. "Conditional ligands for A sian HLA variants facilitate the definition of CD 8+ T-cell responses in acute and chronic viral diseases." European journal of immunology 43.4 (2013): 1109-1120.

Chang et al. "Opportunities and challenges for TCR mimic antibodies in cancer therapy." Expert opinion on biological therapy 16.8 (2016): 979-987.

Chicaybam et al. "An efficient low cost method for gene transfer to T lymphocytes." PloS one 8.3 (2013): e60298.

Choo et al. "Bioorthogonal cleavage and exchange of major histocompatibility complex ligands by employing azobenzene-containing peptides." Angewandte Chemie International Edition 53.49 (2014): 13390-13394.

Clarke et al. "Multispecific antibody development platform based on human heavy chain antibodies." Frontiers in immunology 9 (2019): 3037.

Clynes et al. "Fc receptors are required in passive and active immunity to melanoma." Proceedings of the National Academy of Sciences 95.2 (1998): 652-656.

Cohen et al. "Enhanced antitumor activity of murine-human hybrid T-cell receptor (TCR) in human lymphocytes is associated with improved pairing and TCR/CD3 stability." Cancer research 66.17 (2006): 8878-8886.

Cohen et al. "Enhanced antitumor activity of T cells engineered to express T-cell receptors with a second disulfide bond." Cancer research 67.8 (2007): 3898-3903.

Cohen et al. "Recombinant antibodies with MHC-restricted, peptide-specific, T-cell receptor-like specificity: new tools to study antigen presentation and TCR-peptide-MHC interactions." Journal of Molecular Recognition 16.5 (2003): 324-332.

Coloma et al. "Design and production of novel tetravalent bispecific antibodies." Nature biotechnology 15.2 (1997): 159-163.

Cooper et al. "T-cell clones can be rendered specific for CD19: Toward the selective augmentation of the graft-versus-B-lineage leukemia effect." Blood, The Journal of the American Society of Hematology 101.4 (2003): 1637-1644.

Craddock et al. "Enhanced tumor trafficking of GD2 chimeric antigen receptor T cells by expression of the chemokine receptor CCR2b." Journal of immunotherapy 33.8 (2010): 780-788.

Cragg et al. "Antibody specificity controls in vivo effector mechanisms of anti-CD20 reagents." Blood 103.7 (2004): 2738-2743.

Cragg et al. "Complement-mediated lysis by anti-CD20 mAb correlates with segregation into lipid rafts." Blood, The Journal of the American Society of Hematology 101.3 (2003): 1045-1052.

Database GenBank: 4PRN_A, "Chain A, Hla Class I Histocompatibility Antigen, B-35 Alpha Chain," Accession No. 4PRN_A, Jun. 18, 2014 [retrieved on Apr. 28, 2024]. Retrieved from the Internet: <URL: https://www.ncbi.nlm.nih.gov/protein/618855286>, 3 pages.

Database GenBank: AGP00831.1, "immunoglobulin A heavy chain variable region, partial [*Homo sapiens*]," Accession No. AGP00831, Jul. 7, 2013 [retrieved on Apr. 8, 2022]. Retrieved from the Internet: <https://www.ncbi.nlm.nih.gov/protein/AGP00831.1>, 2 pages.

Database UniProt: A0A1D3TZM3_HUMAN, "MHC class I antigen {ECO:0000313 | EMBL:SCQ05563.1}," Accession No. A0A1D3TZM3, Nov. 30, 2016 [retrieved on Mar. 7, 2022]. Retrieved from the internet: <URL: https://www.uniprot.org/uniprot/A0A1D3TZM3.txt?version=5>, 2 pages.

Database UniProt: A0A357ARF6_9FIRM, "SGL domain-containing protein," Accession No. A0A357ARF6, Nov. 7, 2018

(56) References Cited

OTHER PUBLICATIONS

[retrieved on Mar. 1, 2021]. Retrieved from the internet: <URL: https://www.uniprot.org/uniprot/A0A357ARF6>, 3 pages.
Database UniProt: CD28_HUMAN, "Full=T-cell-specific surface glycoprotein CD28," Accession No. P10747, Jul. 1, 1989 [retrieved on Apr. 29, 2020]. Retrieved from the internet: <URL: https://www.uniprot.org/uniprot/P10747.txt>, 8 pages.
Database UniProt: O19626_HUMAN, "B-3501 {ECO:0000313|EMBL:AAA19925.1}," Accession No. O19626, Jan. 1, 1998 [retrieved on Dec. 9, 2019]. Retrieved from the internet: <URL: https://www.uniprot.org/uniprot/O19626.txt?version=113>, 6 pages.
Database UniProt: TNR9_HUMAN, "Full=Tumor necrosis factor receptor superfamily member 9," Accession No. Q07011, Feb. 1, 1995 [retrieved on Apr. 29, 2020]. Retrieved from the internet: <URL: https://www.uniprot.org/uniprot/Q07011.txt>, 6 pages.
Davila et al. "CD19 CAR-targeted T cells induce long-term remission and B Cell Aplasia in an immunocompetent mouse model of B cell acute lymphoblastic leukemia." PloS one 8.4 (2013): e61338.
Davis et al. "SEEDbodies: fusion proteins based on strand-exchange engineered domain (SEED) CH3 heterodimers in an Fc analogue platform for asymmetric binders or immunofusions and bispecific antibodies." Protein Engineering, Design & Selection 23.4 (2010): 195-202.
De Pascalis et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Dhanik et al. "In-silico discovery of cancer-specific peptide-HLA complexes for targeted therapy." BMC bioinformatics 17.1 (2016): 286.
Doerr, A. "Mass spectrometry-based targeted proteomics." Nature methods 10.1 (2013): 23.
Doppalapudi et al. "Chemical generation of bispecific antibodies." Proceedings of the National Academy of Sciences 107.52 (2010): 22611-22616.
Edwards et al. "The remarkable flexibility of the human antibody repertoire; isolation of over one thousand different antibodies to a single protein, BLyS." Journal of molecular biology 334.1 (2003): 103-118.
Traunecker et al. "Bispecific single chain molecules (Janusins) target cytotoxic lymphocytes on HIV infected cells." The EMBO Journal 10.12 (1991): 3655-3659.
Turtle et al. "Engineered T cells for anti-cancer therapy." Current opinion in immunology 24.5 (2012): 633-639.
Tutt et al. "Trispecific F (ab') 3 derivatives that use cooperative signaling via the TCR/CD3 complex and CD2 to activate and redirect resting cytotoxic T cells." Journal of immunology (Baltimore, Md.: 1950) 147.1 (1991): 60-69.
U.S. Appl. No. 17/426,627, filed Sep. 16, 2022, 404 pages.
U.S. Appl. No. 17/820,434, filed Aug. 17, 2022, 120 pages.
U.S. Appl. No. 18/018,400, filed Jul. 27, 2023, 374 pages.
U.S. Appl. No. 18/300,747, filed Apr. 14, 2023, 136 pages.
U.S. Appl. No. 19/284,186, filed Jul. 29, 2025, 325 pages.
U.S. Appl. No. 19/284,312, filed Jul. 29, 2025, 214 pages.
Vajdos et al. "Comprehensive functional maps of the antigen-binding site of an anti-ErbB2 antibody obtained with shotgun scanning mutagenesis." Journal of molecular biology 320.2 (2002): 415-428.
Van Tendeloo et al. "High-level transgene expression in primary human T lymphocytes and adult bone marrow CD34+ cells via electroporation-mediated gene delivery." Gene therapy 7.16 (2000): 1431-1437.
Verhoeyen et al. "Lentiviral vector gene transfer into human T cells." Genetic modification of hematopoietic stem cells: methods and protocols. Totowa, NJ: Humana Press, 2009. 97-114.
Vita et al. "The immune epitope database (IEDB) 3.0." Nucleic acids research 43.D1 (2015): D405-D412.

Von Kreudensnein et al. "Improving biophysical properties of a bispecific antibody scaffold to aid developability: quality by molecular design." MAbs. vol. 5. No. 5. Taylor & Francis (2013): 646-54.
Wang et al. "Identification of T-cell receptors targeting KRAS-mutated human tumors." Cancer immunology research 4.3 (2016): 204-214.
Wang et al. "Immune targets and neoantigens for cancer immunotherapy and precision medicine." Cell research 27.1 (2017): 11-37.
Wang et al. "Phenotypic and functional attributes of lentivirus-modified CD19-specific human CD8+ central memory T cells manufactured at clinical scale." Journal of immunotherapy 35.9 (2012): 689-701.
Wieczorek et al. "Major histocompatibility complex (MHC) class I and MHC class II proteins: conformational plasticity in antigen presentation." Frontiers in immunology 8 (2017): 292.
Wigler et al. "Transfer of purified herpes virus thymidine kinase gene to cultured mouse cells." Cell 11.1 (1977): 223-232.
Willemsen et al. "Grafting primary human T lymphocytes with cancer-specific chimeric single chain and two chain TCR." Gene therapy 7.16 (2000): 1369-1377.
Willemsen et al. "Selection of human antibody fragments directed against tumor T-cell epitopes for adoptive T-cell therapy." Cytometry Part A 73.11 (2008): 1093-1099.
Wines et al. "The IgG Fc contains distinct Fc receptor (FcR) binding sites: the leukocyte receptors FcγRI and FcγRIIa bind to a region in the Fc distinct from that recognized by neonatal FcR and protein A." The Journal of Immunology 164.10 (2000): 5313-5318.
Winter et al. "Man-made antibodies." Nature 349.6307 (1991): 293-299.
Wong et al. "Novel antibody-like single-chain TCR antibody Fc fusion protein." The Journal of Immunology 198. Supplement_1 (2017): 120-9.
Wozniak-Knopp et al. "Introducing antigen-binding sites in structural loops of immunoglobulin constant domains: Fc fragments with engineered HER2/neu-binding sites and antibody properties." Protein Engineering, Design & Selection 23.4 (2010): 289-297.
Wu et al. "Adoptive T-cell therapy using autologous tumor-infiltrating lymphocytes for metastatic melanoma: current status and future outlook." The Cancer Journal 18.2 (2012): 160-175.
Wu et al. "Fab-based bispecific antibody formats with robust biophysical properties and biological activity." MAbs. vol. 7. No. 3. Taylor & Francis, 2015, 14 pages.
Wu et al. "Remote control of therapeutic T cells through a small molecule-gated chimeric receptor." Science 350.6258 (2015): aab4077.
Yin et al. "Aglycosylated antibodies and antibody fragments produced in a scalable in vitro transcription-translation system." MAbs. vol. 4. No. 2. Taylor & Francis (2012): 217-225.
Zahnd et al. "A designed ankyrin repeat protein evolved to picomolar affinity to Her2." Journal of molecular biology 369.4 (2007): 1015-1028.
Zarling et al. "Identification of class I MHC-associated phosphopeptides as targets for cancer immunotherapy." Proceedings of the National Academy of Sciences 103.40 (2006): 14889-14894.
Zhang et al. "Transgenic TCR expression: comparison of single chain with full-length receptor constructs for T-cell function." Cancer gene therapy 11.7 (2004): 487-496.
Zhukovsky et al. "A phase I study of an anti-CD30 x Anti-CD16A bispecific Tandab antibody, AFM13, in patients with relapsed or refractory Hodgkin lymphoma." Blood 122.21 (2013): 5116.
An et al. "IgG2m4, an engineered antibody isotype with reduced Fc function." MAbs. vol. 1. No. 6. Taylor & Francis, 2009, 572-579.
Carlring et al. "A novel redox method for rapid production of functional bi-specific antibodies for use in early pilot studies." PLoS One 6.7 (2011): 1-8.
Muydermans et al. "Recognition of antigens by single-domain antibody fragments: the superfluous luxury of paired domains." Trends in biochemical sciences 26.4 (2001): 230-235.
Weatherill et al. "Towards a universal disulphide stabilised single chain Fv format: importance of interchain disulphide bond location and vL-vH orientation." Protein Engineering, Design & Selection 25.7 (2012): 321-329.

(56)                    References Cited

OTHER PUBLICATIONS

Database DrugBank: DB00075, "Muromonab," Accession No. DB00075, 2005 [retrieved on Sep. 12, 2025]. Retrieved from the Internet: <URL: https://go.drugbank.com/drugs/DB00075>, 11 pages.
Database GSRS: J43DL56H6M, "Foralumab," Record No. J43DL56H6M, 2005 [retrieved on Sep. 12, 2025]. Retrieved from the Internet: <URL: https://gsrs.ncats.nih.gov/ginas/app/ui/substances/J43DL56H6M>, 1 page.
Mertens, N. "Tribodies: fab-scfv fusion proteins as a platform to create multifunctional pharmaceuticals." Bispecific antibodies. Berlin, Heidelberg: Springer Berlin Heidelberg, 2011. 135-149.
Office Action in U.S. Appl. No. 17/426,627, mailed Sep. 16, 2025, 13 pages.
Office Action in U.S. Appl. No. 19/284,312, mailed Sep. 22, 2025, 15 pages.
First Examination Report received from the EP Patent Office in European Application No. EP 20748612.7 dated Oct. 28, 2025.
Galluzzi, et al., "Trial Watch: Monoclonal antibodies in cancer therapy", OncoImmunology 1(1): 23-37, (2012).
Kabat, "Sequences of Proteins of Immunological Interest", vol. 1, 5th Edition, pp. 670-699 (1991).
Liu et al., "A Molecular Basis for the Interplay between T Cells, Viral Mutants, and Human Leukocyte Antigen Micropolymorphism," The Journal of Biologcal Chemistry, vol. 289, No. 24, pp. 16688-15598, Jun. 13, 2014.
Robbie, et al., "A Novel Investigational Fc-Modified Humanized Monoclonal Antibody, Motavizumab-YTE, Has an Extended Half-Life in Healthy Adults", Antimicrobial Agents Chemother. vol. 57, No. 12, pp. 6147-6153 (2013).
Final Office Action for copending U.S. Appl. No. 17/269,246, dated Nov. 20, 2025.
U.S. Appl. No. 17/269,246, filed Feb. 17, 2021, 256 pages.
GenCore version 6.5.2, Copyright © 1993-2025; Biocceleration Ltd., citation Sequence 248, Publication No. US20220213194A1 (Year: 2020).
Non-Final Office Action for copending U.S. Appl. No. 17/820,434, dated Jan. 15, 2026, 75 pages.

Second ABR
(against target 1)

Fab
(against target 2)

CH2 domains

CH3 domains

First ABR
(against target 1)

Fc region

Format 4
Dual scFv Conformation

Format 4          Format 5          Format 6

Instability of Format 4

FIG. 5

L1 = L2 = 10 amino acids

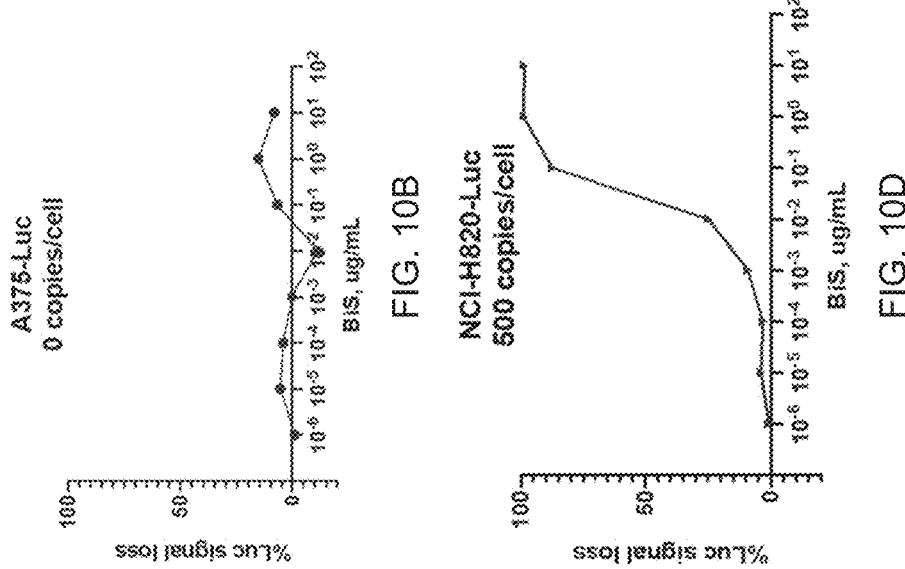
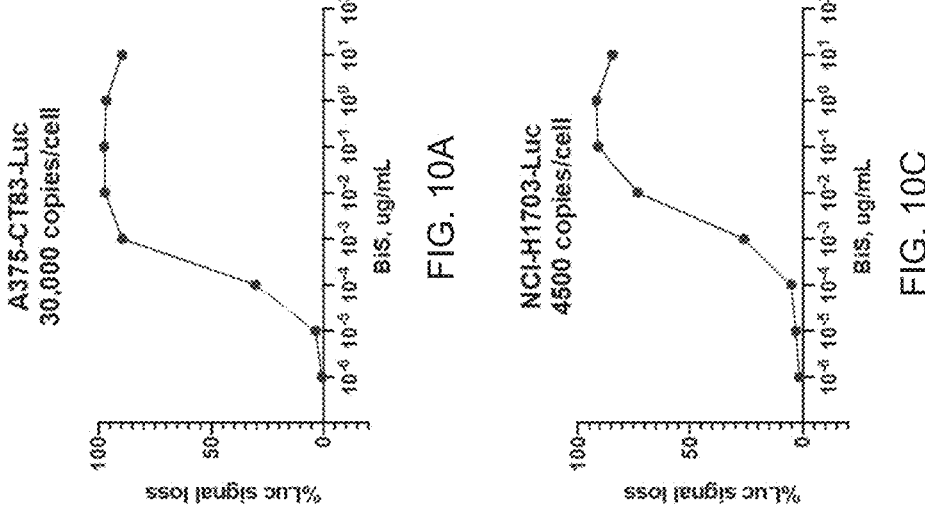

*E07 sequence liabilities (Tier 2)*

VH

QVQLVQSGAEVKKPGASVKVSCKASGFTFTNYLIHWVRQAPGQGLEWMGWINPNSGGTNYAQRL

QGRVTMTRDTSTSTVYMELSSLRSEDTAVYYCARDYGAGNDYWGQGTLVTVSS

VL

DIQMTQSPSSLSASVGDRVTITCRASQEIRRWLAWYQQKPGKAPKLLIYAASNLQSGVPSRFSGSG

SGTDFTLTISSLQPEDFATYYCQQSYSTPYTFGQGTKLEIK

× Oxidation
△ Deamidation
○ Hydrolysis
▧ Cleavage
CDR (Kabat)

FIG. 11

*hOKT3a sequence liabilities (Tier 2)*

VH

QVQLVQSGAEVKKPGASVKVSCKASGYTFTRYTMHWVRQAPGQGLEWMGYINPSRGYTNYNQK

FKDRVTLTTDKSSSTAYMELSSLRSEDTAVYYCARYYDDHYSLDYWGQGTLVTVSS

VL

DIQMTQSPSSLSASVGDRVTITCSASSSVSYMNWYQQKPGKAPKRLIYDTSKLASGVPSRFSGSG

SGTDFTLTISSLQPEDFATYYCQQWSSNPFTFGQGTKLEIK

× Oxidation
△ Deamidation
○ Hydrolysis
▦ Cleavage
CDR (Kabat)

FIG. 12

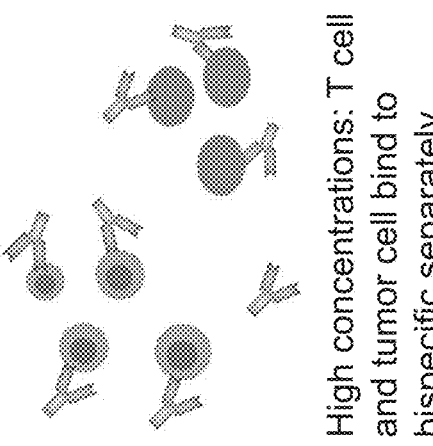
High concentrations: T cell and tumor cell bind to bispecific separately
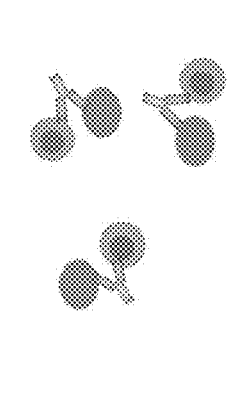
Trimer formation
FIG. 19
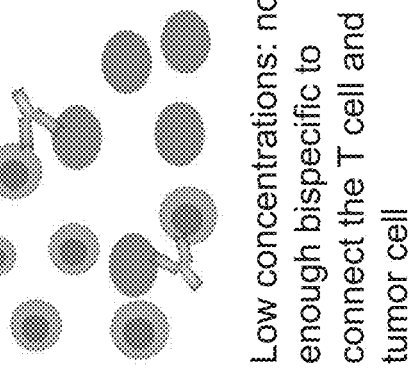
Low concentrations: not enough bispecific to connect the T cell and tumor cell

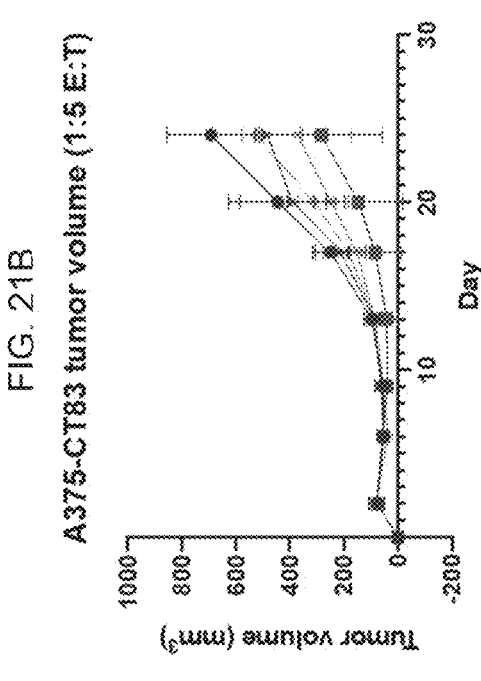
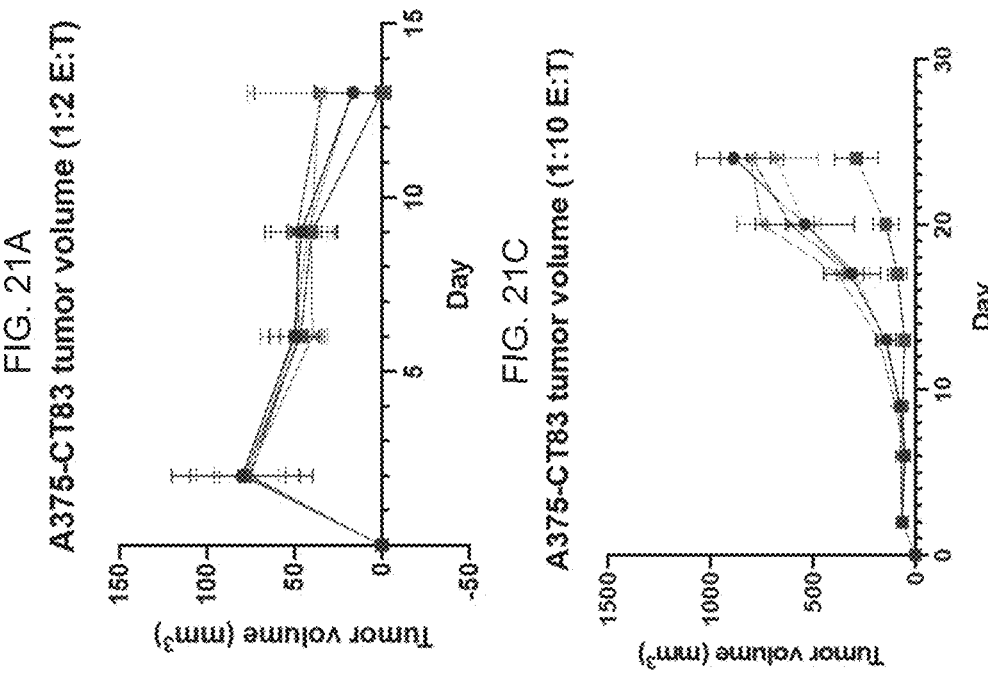
FIG. 21A
A375-CT83 tumor volume (1:2 E:T)
FIG. 21B
A375-CT83 tumor volume (1:5 E:T)
FIG. 21C
A375-CT83 tumor volume (1:10 E:T)
4 ug 41-E07
0.8 ug 41-E07
0.16 ug 41-E07
0.032 ug 41-E07
0 ug 41-E07

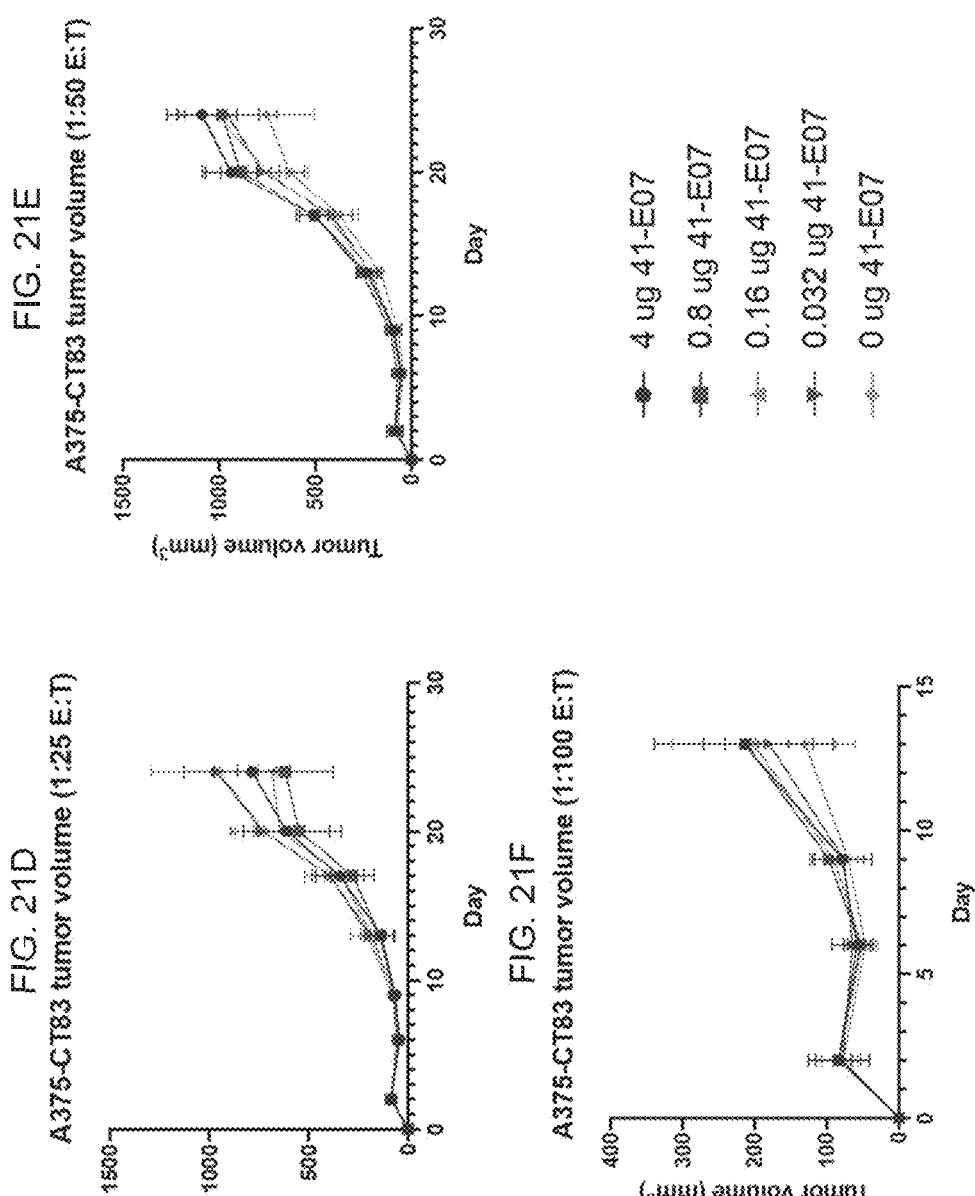

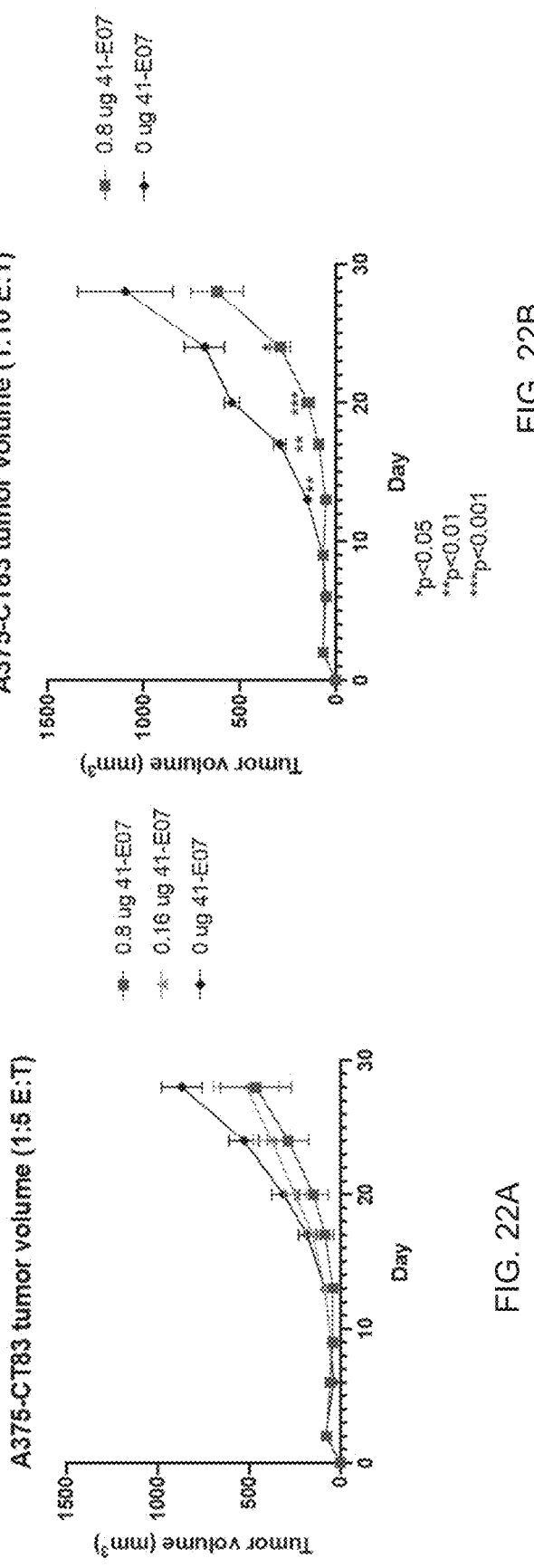

FIG. 28

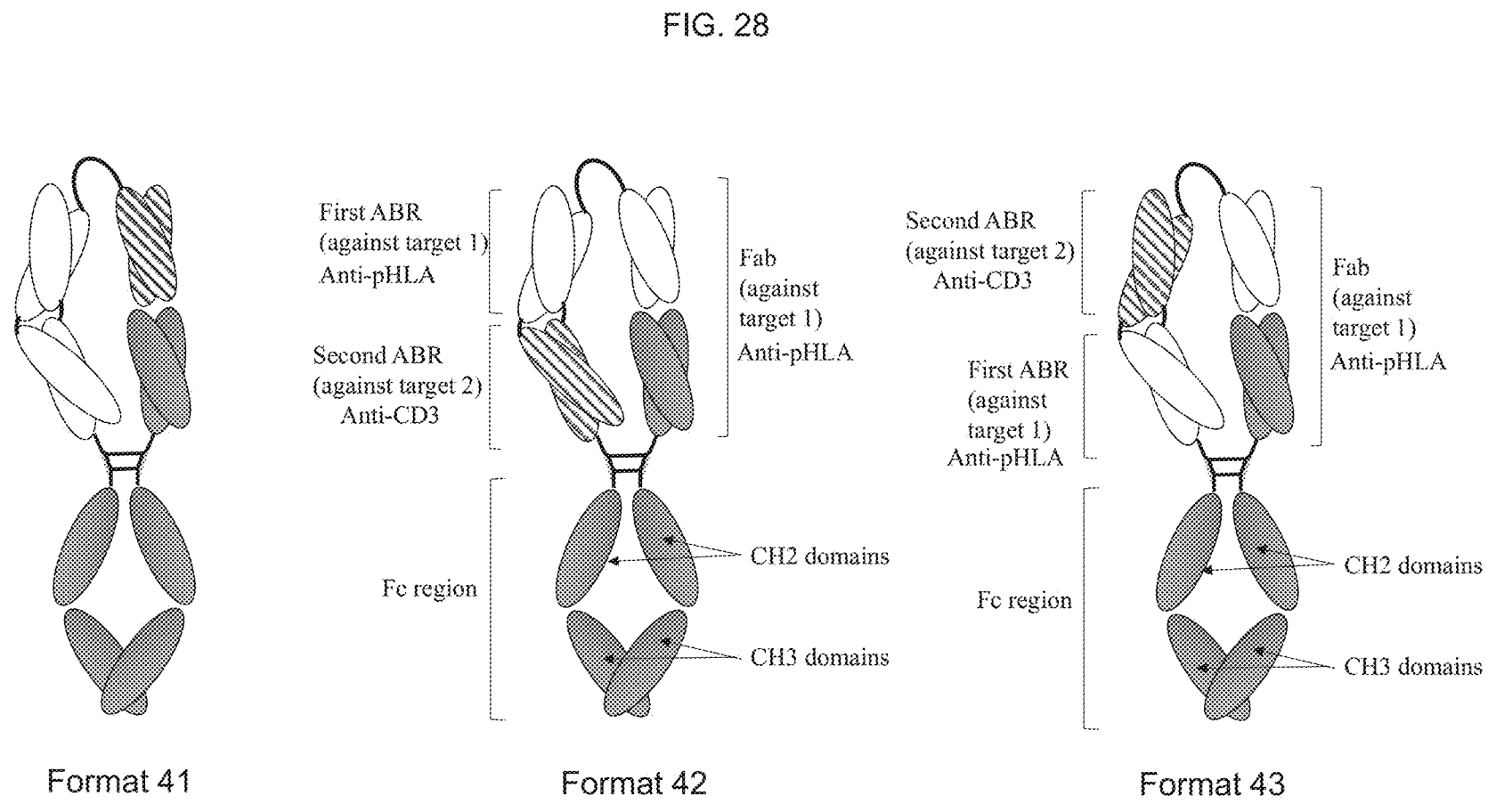

Format 43

Fab (against target 1) Anti-pHLA

CH2 domains

CH3 domains

Second ABR (against target 2) Anti-CD3

First ABR (against target 1) Anti-pHLA

Fc region

Format 42

Fab (against target 1) Anti-pHLA

CH2 domains

CH3 domains

First ABR (against target 1) Anti-pHLA

Second ABR (against target 2) Anti-CD3

Fc region

Format 41

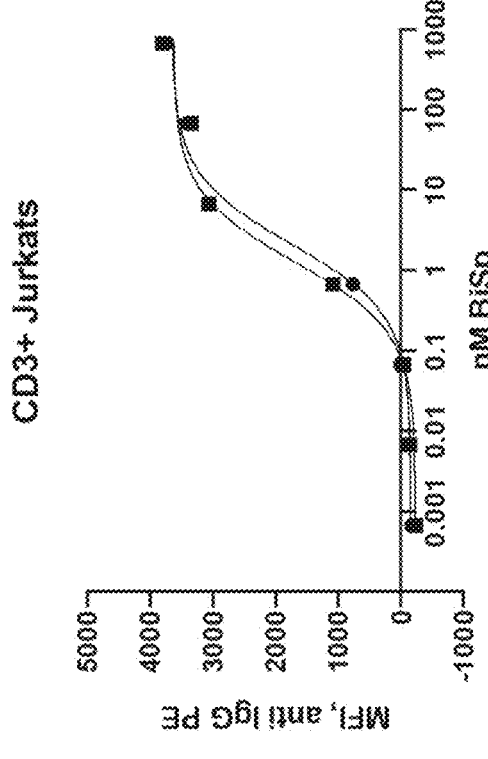
CD3+ Jurkats
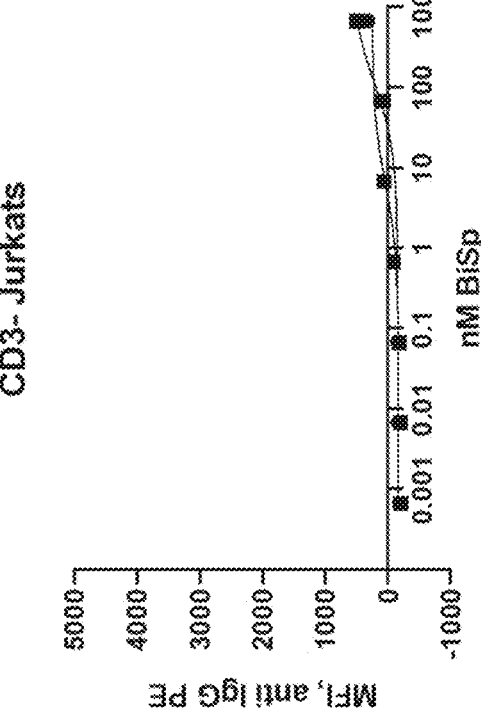
CD3- Jurkats
FIG. 30
41-E07 hUCHT1v9
43-E07 hUCHT1v9

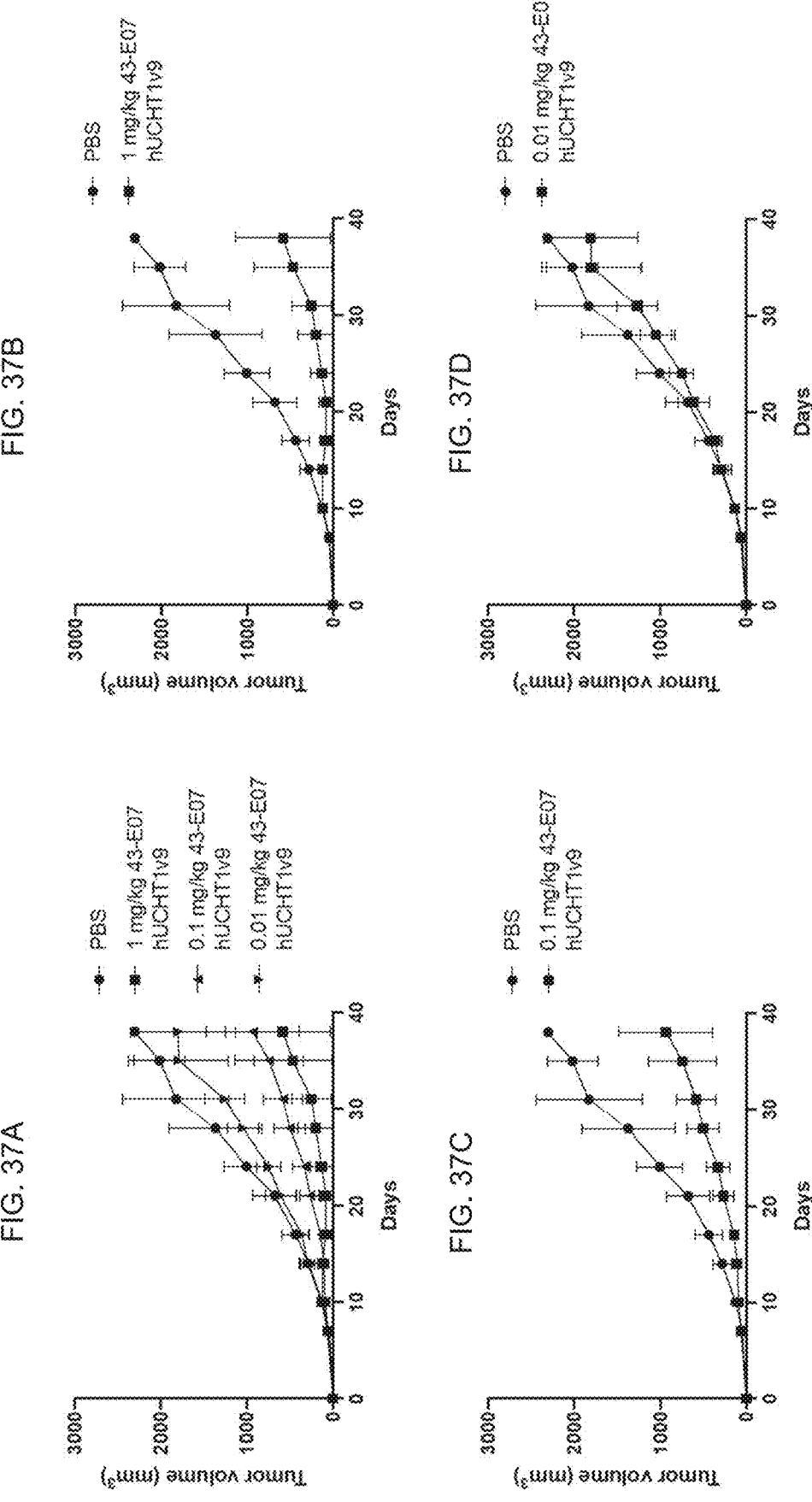

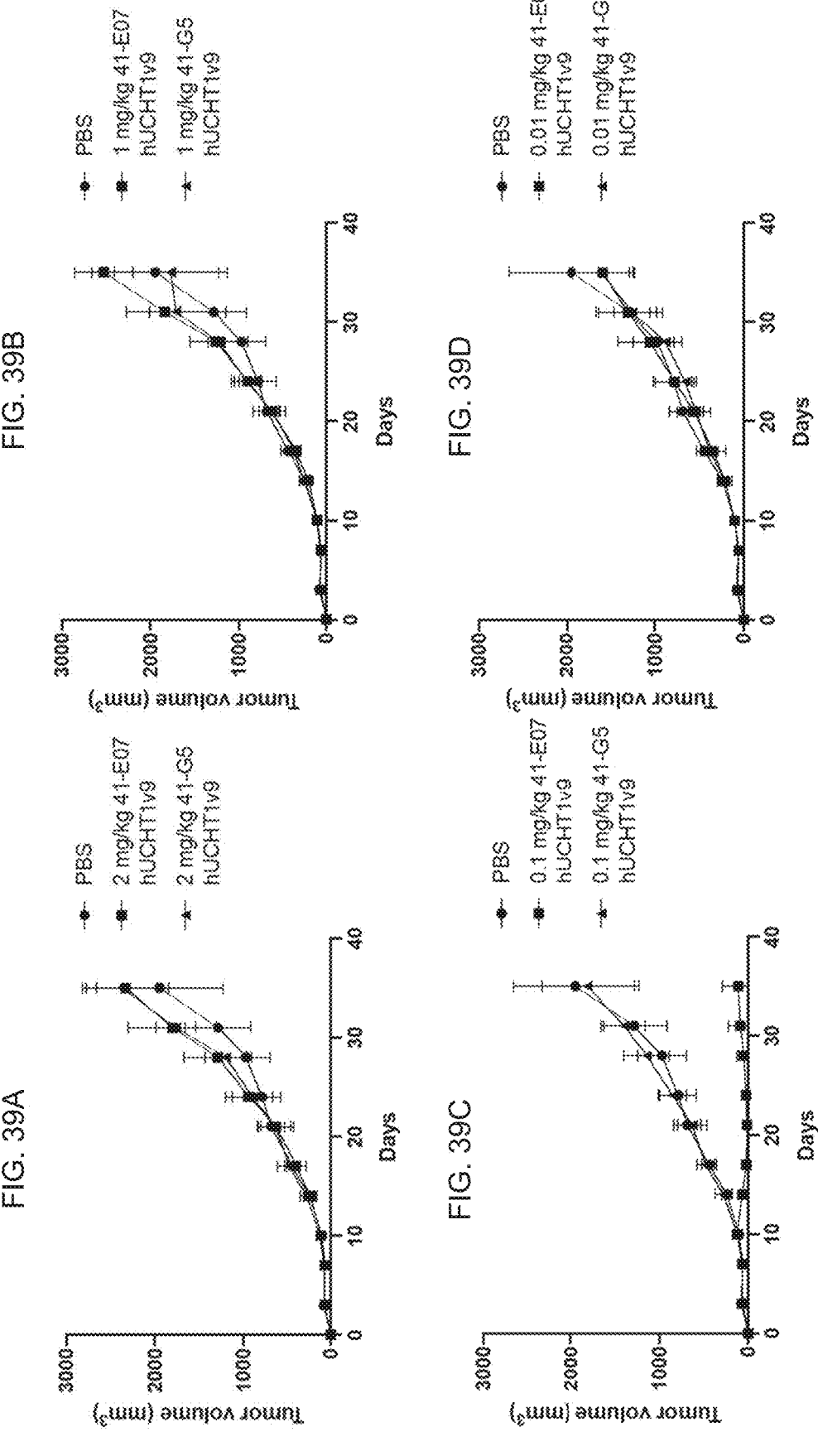

FIG. 40A

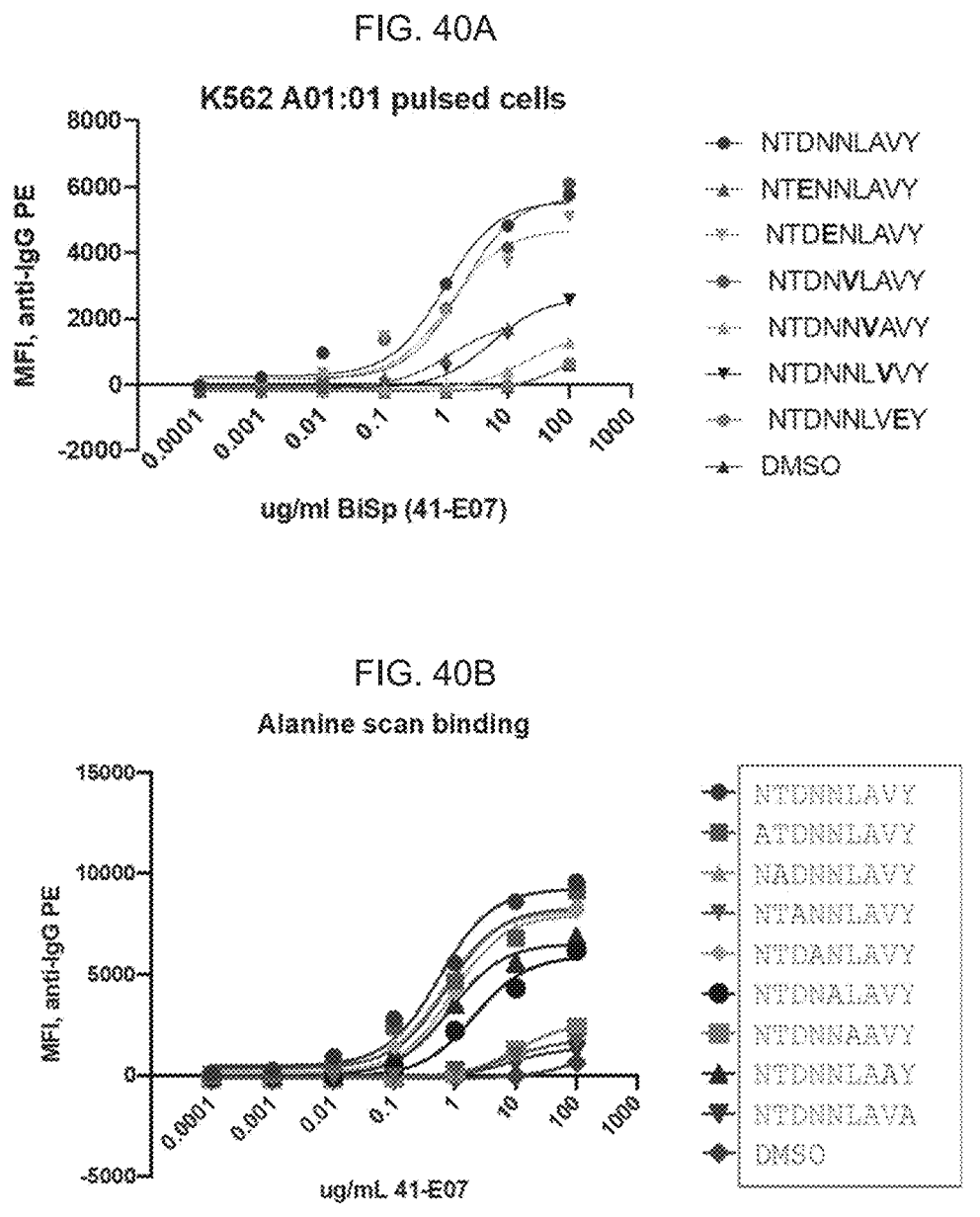

K562 A01:01 pulsed cells

- NTDNNLAVY
- NTENNLAVY
- NTDENLAVY
- NTDNVLAVY
- NTDNNVAVY
- NTDNNLVVY
- NTDNNLVEY
- DMSO

FIG. 40B

Alanine scan binding

- NTDNNLAVY
- ATDNNLAVY
- NADNNLAVY
- NTANNLAVY
- NTDANLAVY
- NTDNALAVY
- NTDNNAAVY
- NTDNNLAAY
- NTDNNLAVA
- DMSO

Pulsed K562 binding

NTDNNLAVY pulsed A01:01 K562s
ETDNNIVVY pulsed A01:01 K562s
PTDENLARY pulsed A01:01 K562s
NTDNLLTEY pulsed A01:01 K562s
unpulsed A01:01 K562s
NTDNNLAVY pulsed A02:01 K562s
AIFPGAVPAA pulsed A02:01 K562s
unpulsed A02:01 K562s
NTDNNLAVY pulsed B35:01 K562s
EVDPIGHVY pulsed B35:01 K562s
unpulsed B35:01 K562s FIG. 42A
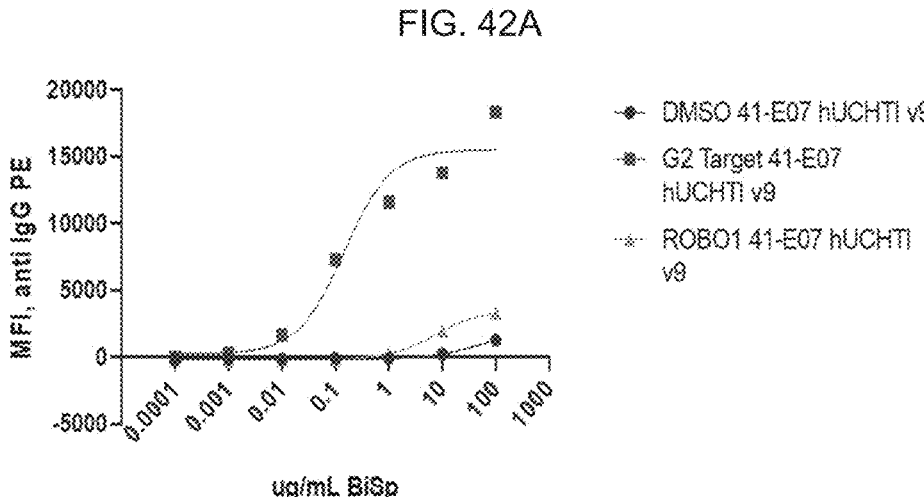
FIG. 42B
41-E07 binding to g2-pHLA
(41-E07 purity by HPLC is 97%)
(G2-pHLA purity by HPLC is 100%)
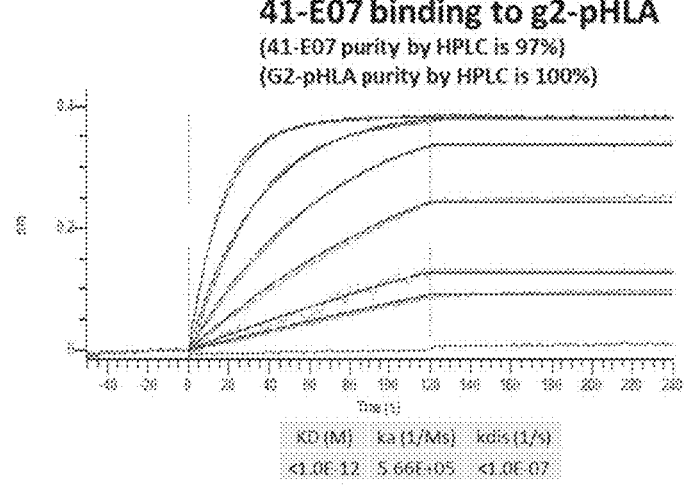
41-E07 binding to Robo pHLA
(Robo purity by HPLC is 100%)
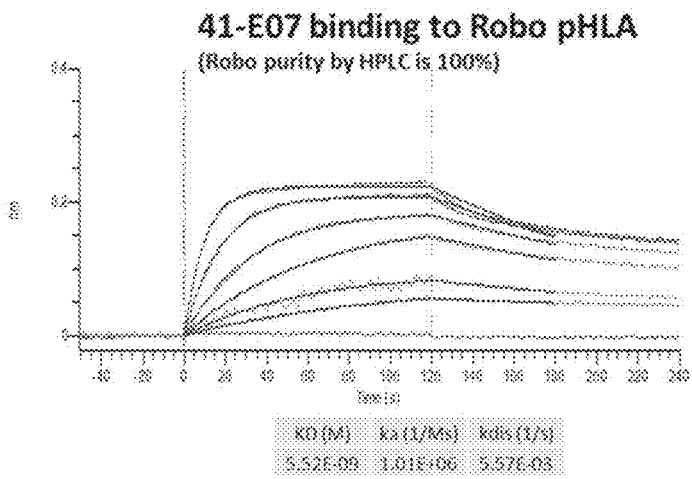

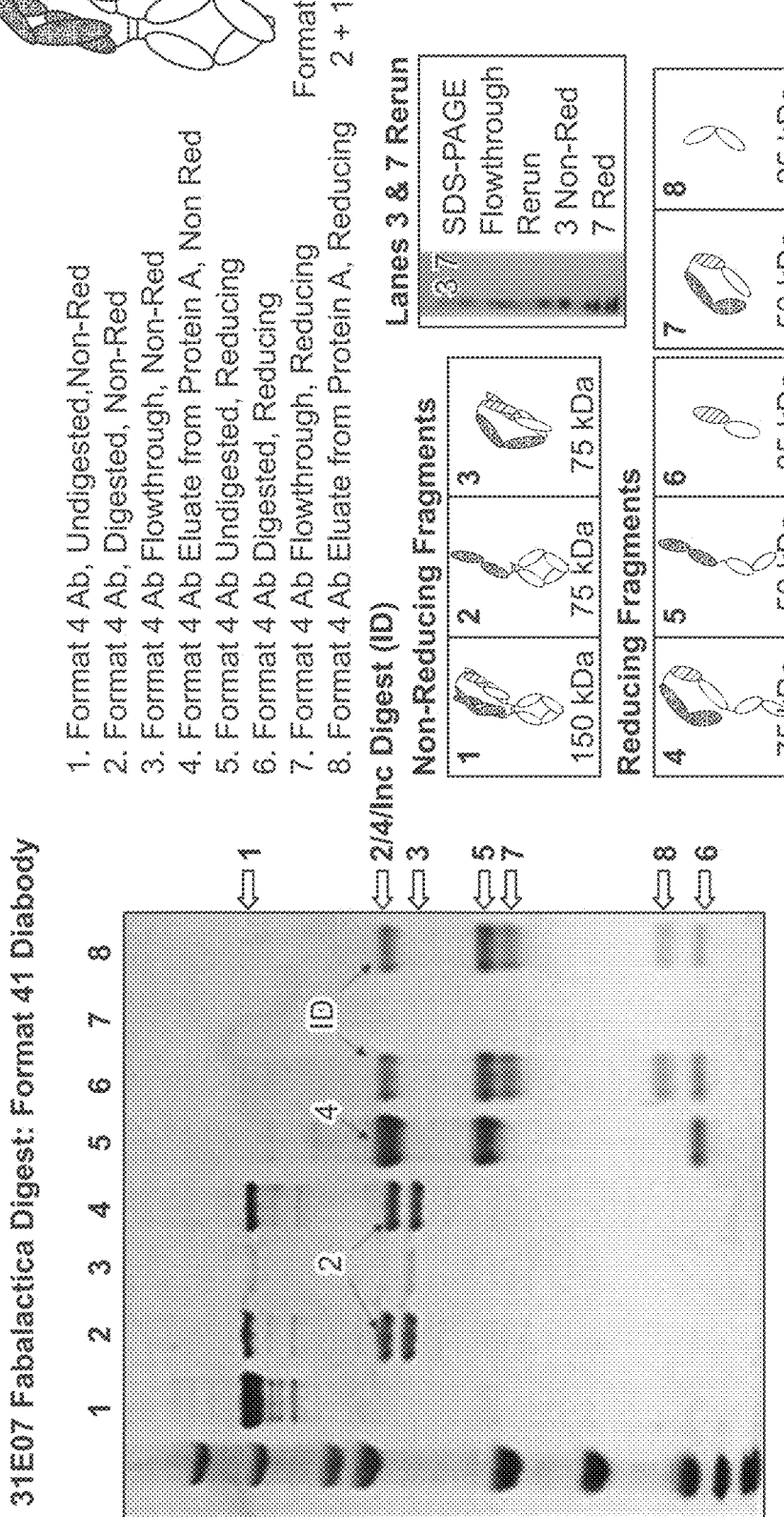

Format 41
2 + 1

1. Format 4 Ab, Undigested, Non-Red
2. Format 4 Ab, Digested, Non-Red
3. Format 4 Ab Flowthrough, Non-Red
4. Format 4 Ab Eluate from Protein A, Non Red
5. Format 4 Ab Undigested, Reducing
6. Format 4 Ab Digested, Reducing
7. Format 4 Ab Flowthrough, Reducing
8. Format 4 Ab Eluate from Protein A, Reducing 2/4/Inc Digest (ID)
Non-Reducing Fragments

| 1 | 2 | 3 |
|---|---|---|
| 150 kDa | 75 kDa | 75 kDa |

Reducing Fragments

| 4 | 5 | 6 |
|---|---|---|
| 75 kDa | 50 kDa | 25 kDa |

| 7 | 8 |
|---|---|
| 50 kDa | 25 kDa |

Lanes 3 & 7 Rerun

SDS-PAGE
Flowthrough
Rerun
3 Non-Red
7 Red

31E07 Fabalactica Digest: Format 41 Diabody

FIG. 43A

The absence of bands in Lanes 3 and 7 (Protein A flowthrough material was run under non-reducing and reducing conditions) confirmed the formation of diabody. See the rerun of the gel of Lanes 3 and 7 to confirm.

Instability of Format Antibodies

Format 4

Dual scFv Form
(Faster SEC migration)

Format 4

Diabody Conformation
(Slower SEC migration)

"Standard" Format 4, two separate scFvs (dual scFv)
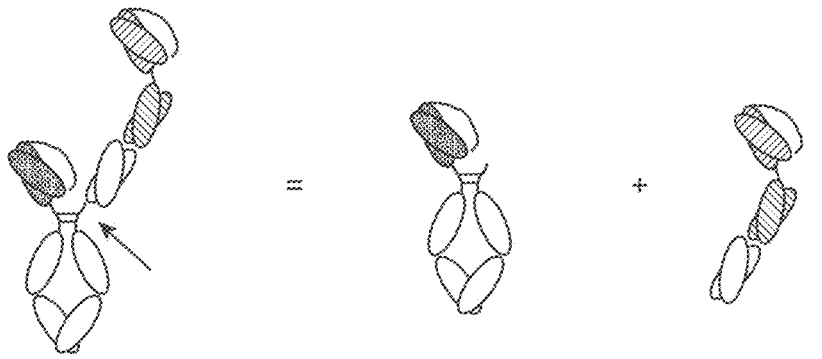
Diabody conformation
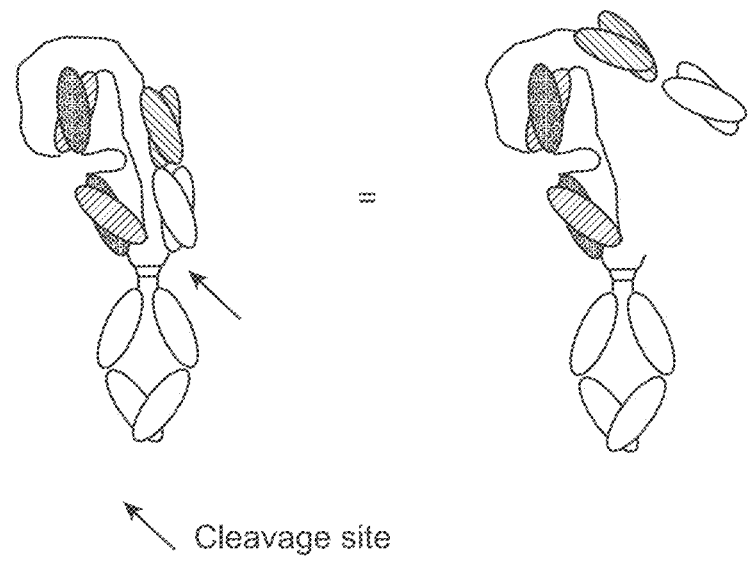
Cleavage site
FIG. 45A

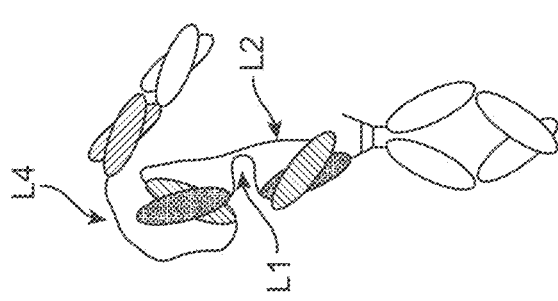
Diabody (linkers not to scale)
Cleaved Fab side
Extended conformation
Faster SEC migration
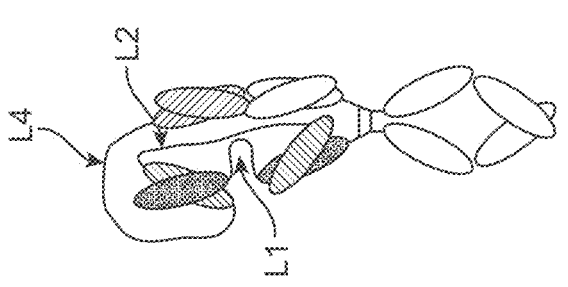
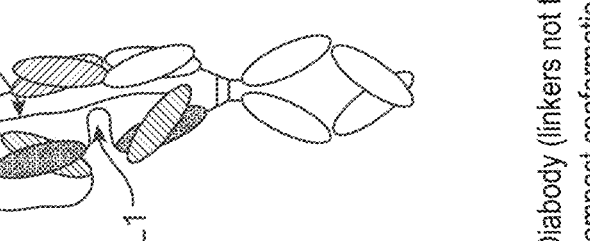
Diabody (linkers not to scale)
compact conformation
Slower SEC migration
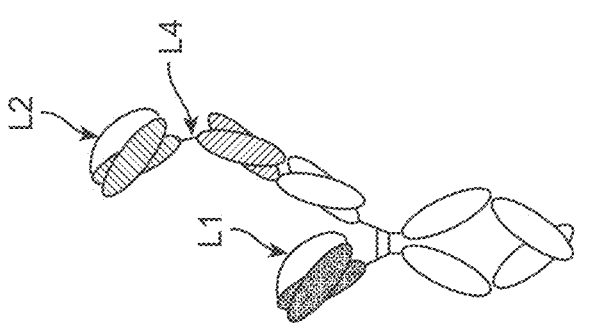
Dual scFv
Extended conformation
Faster SEC migration
FIG. 46

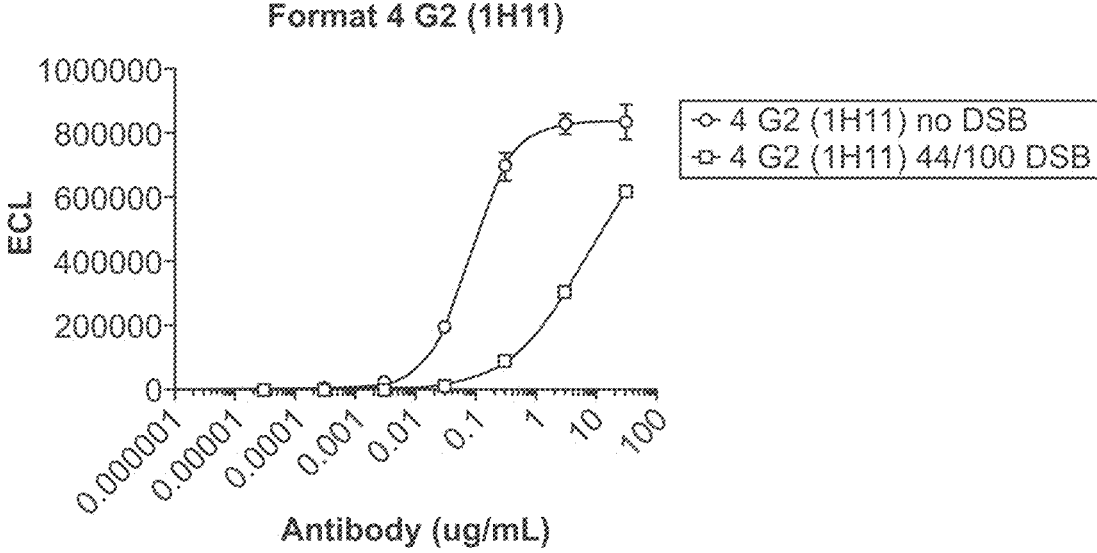
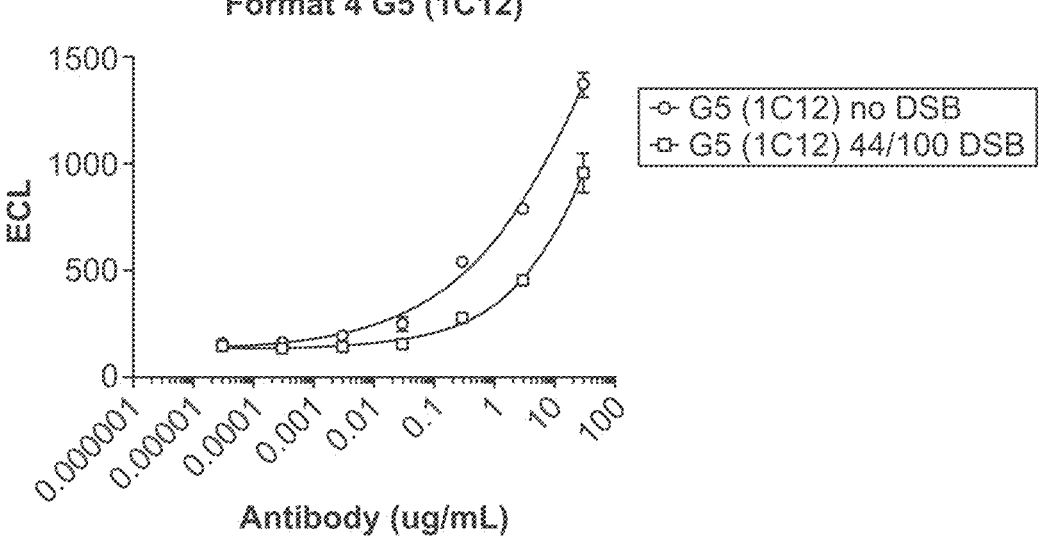
FIG. 53

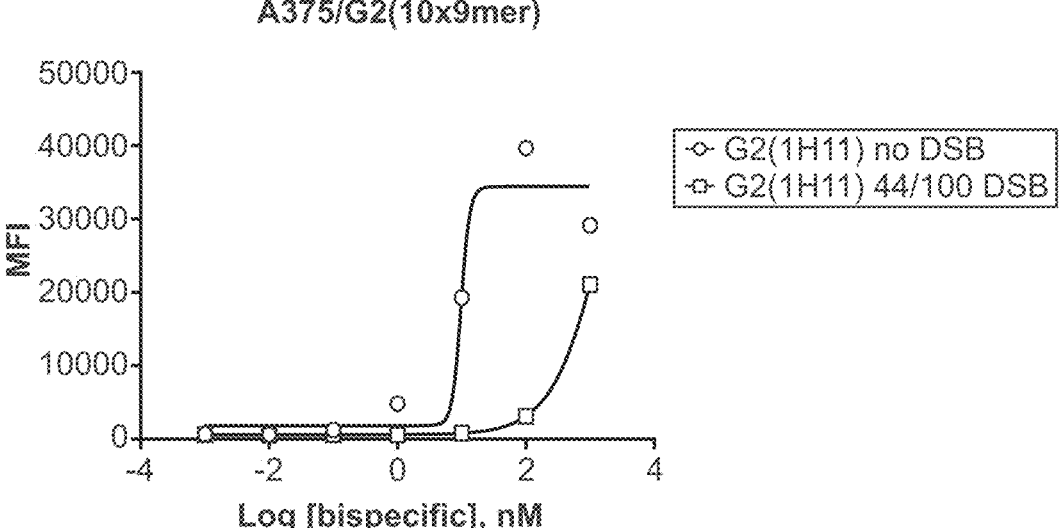
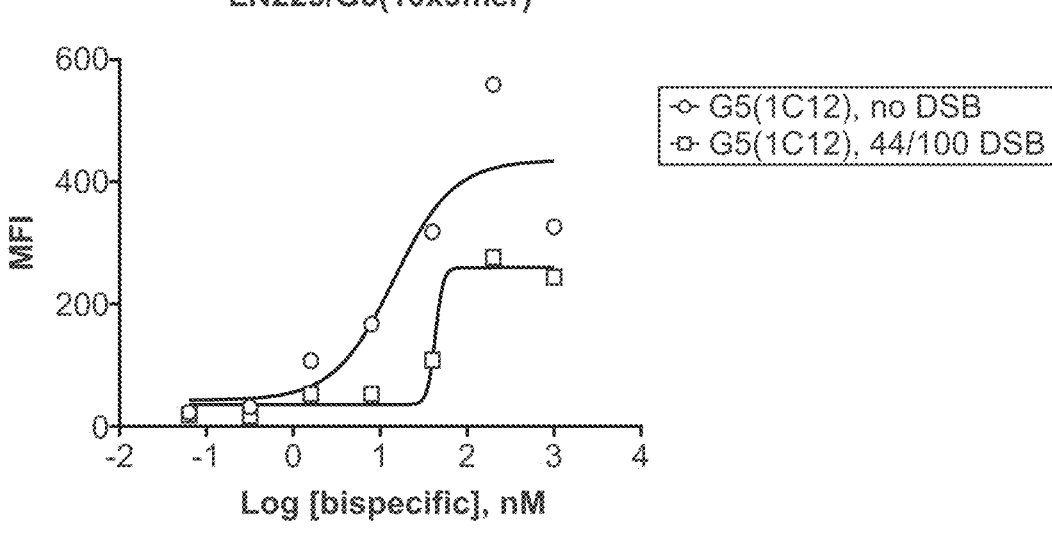
FIG. 54

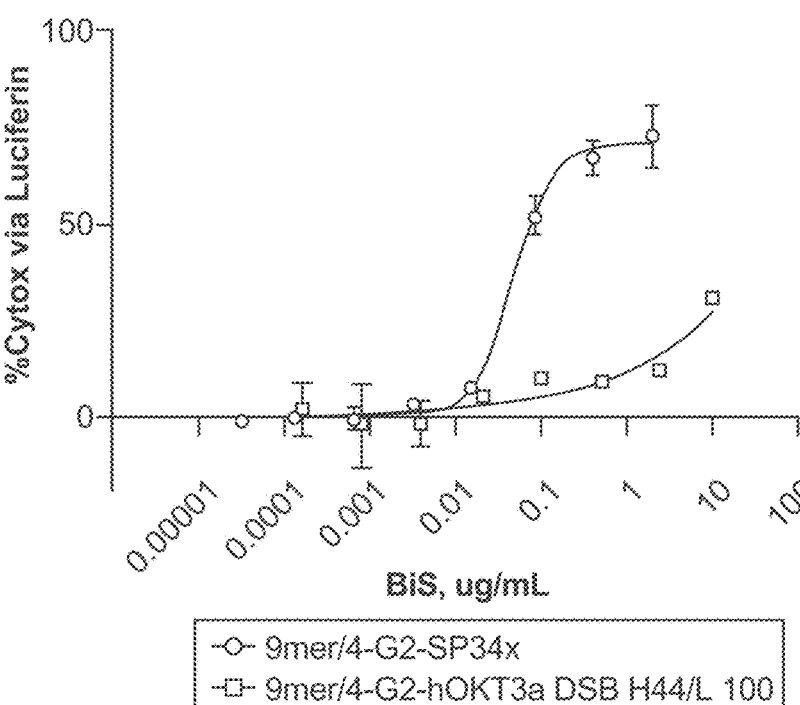
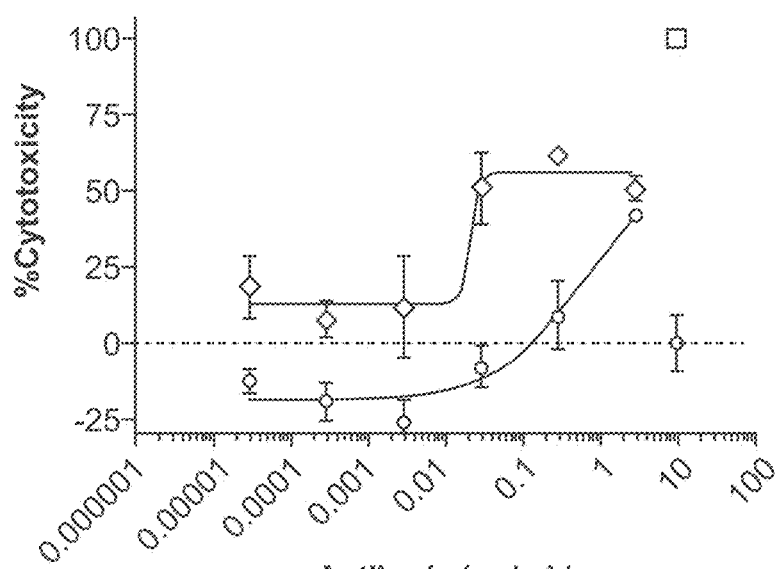
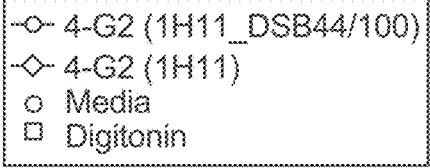
FIG. 55

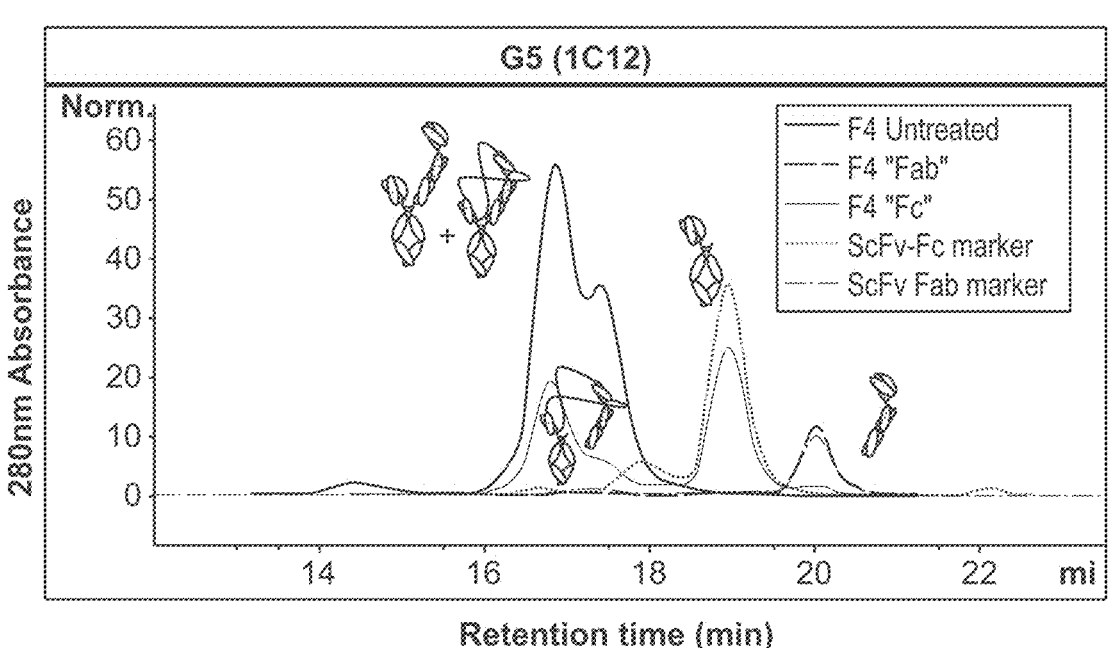
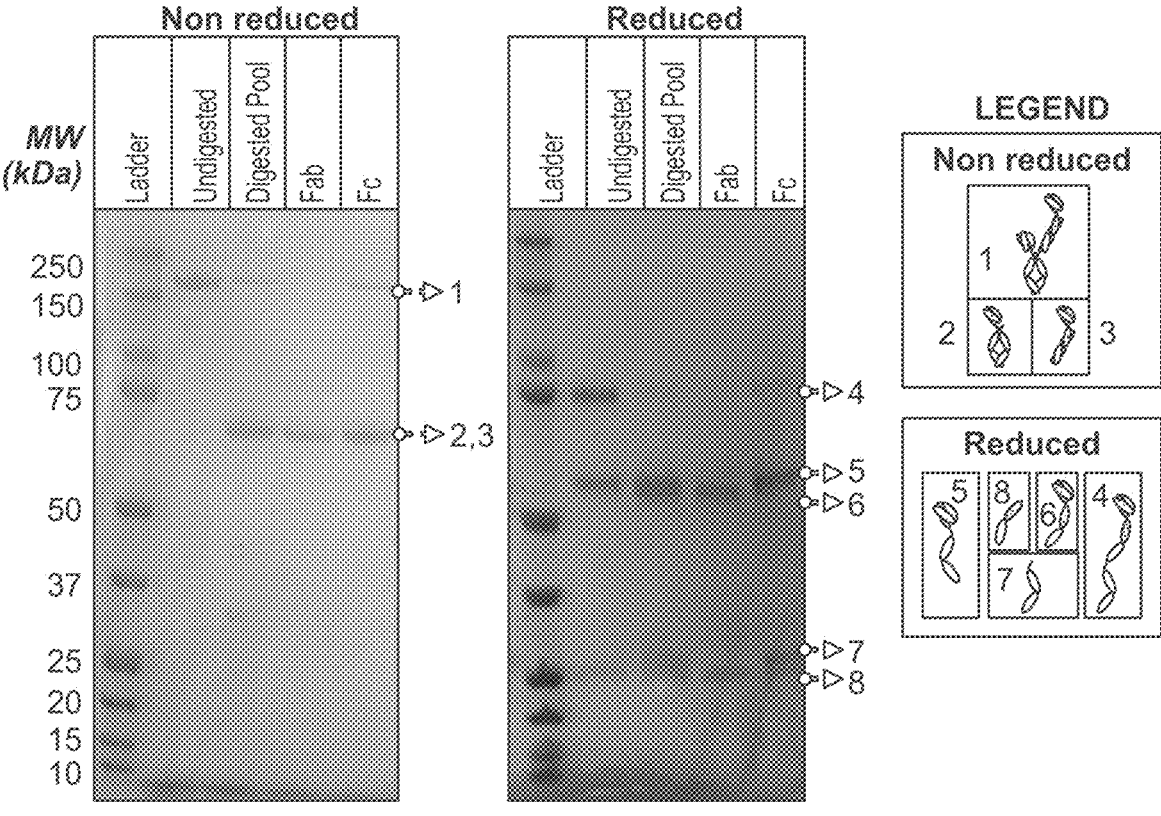
FIG. 56

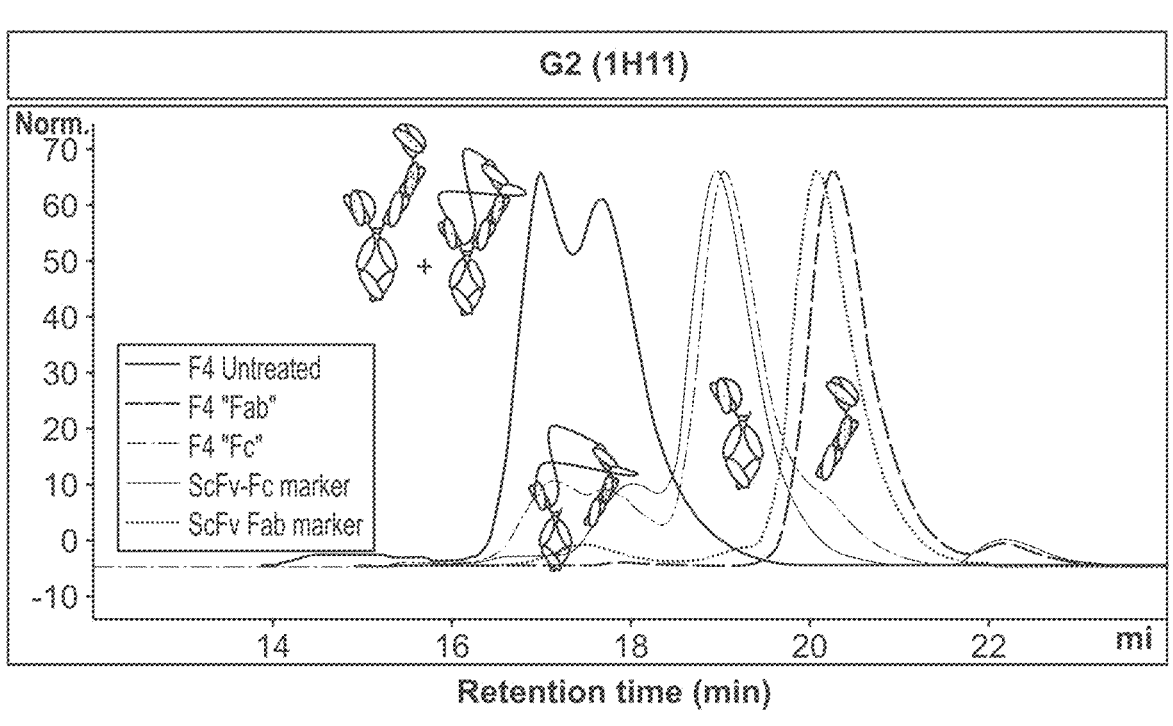
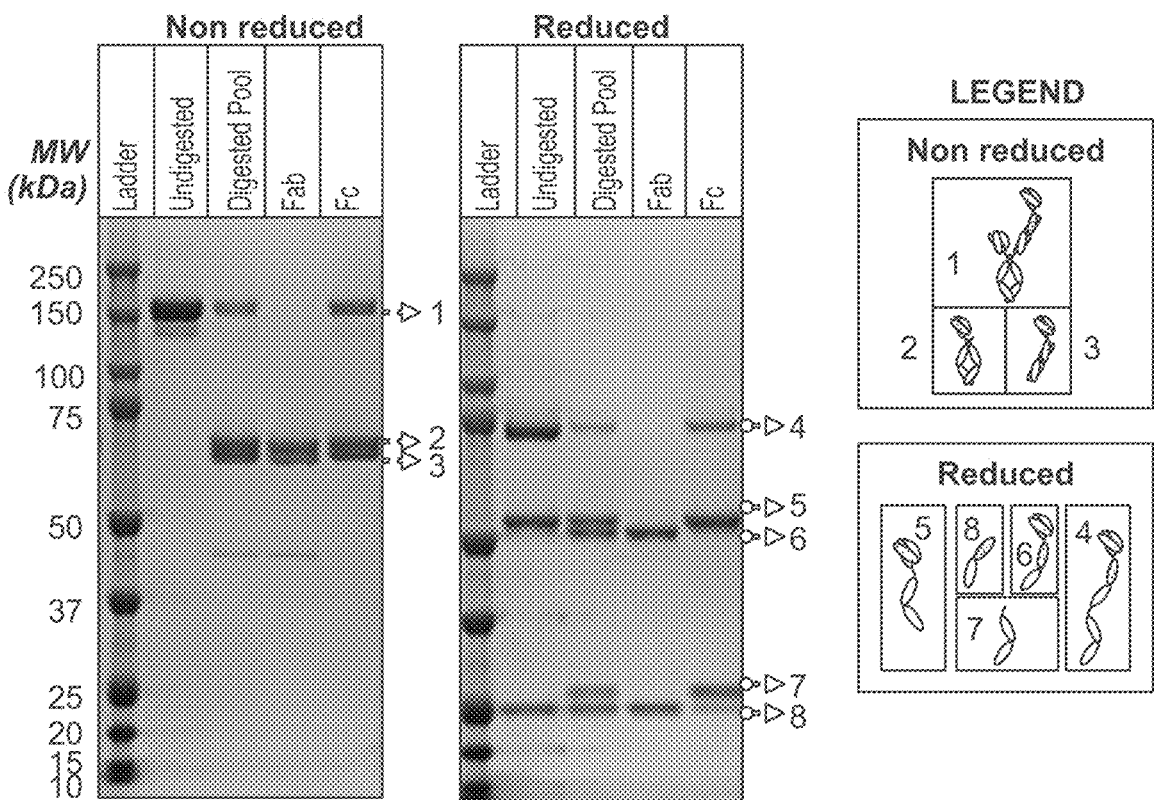
FIG. 57

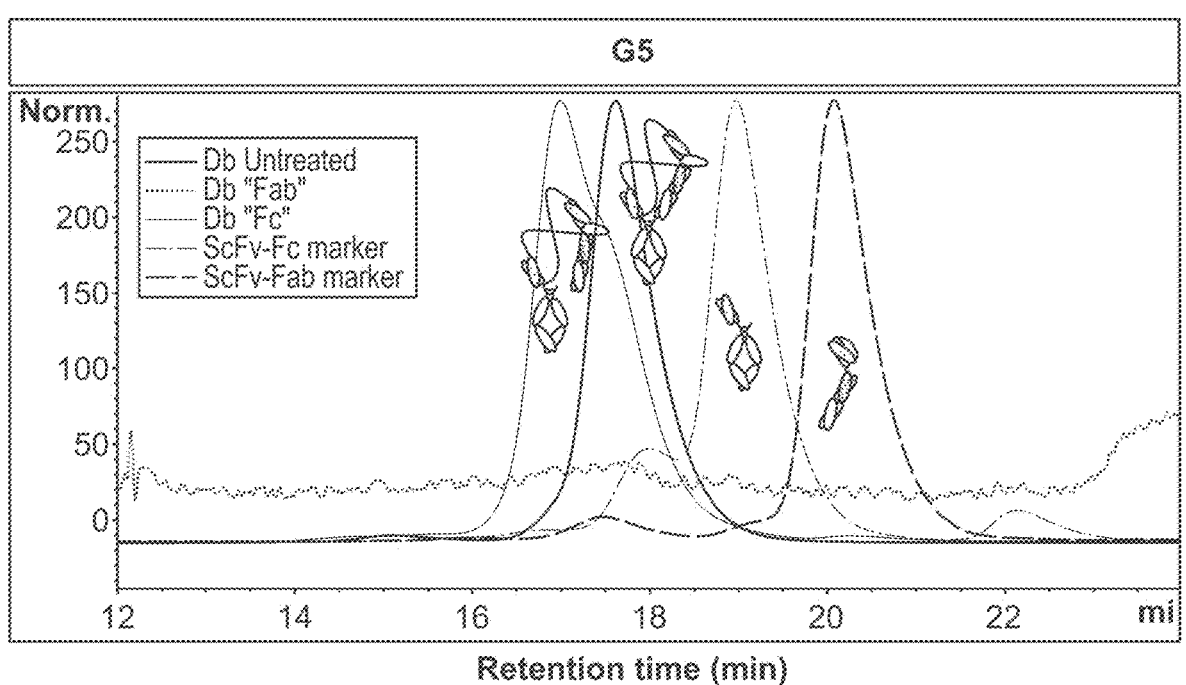
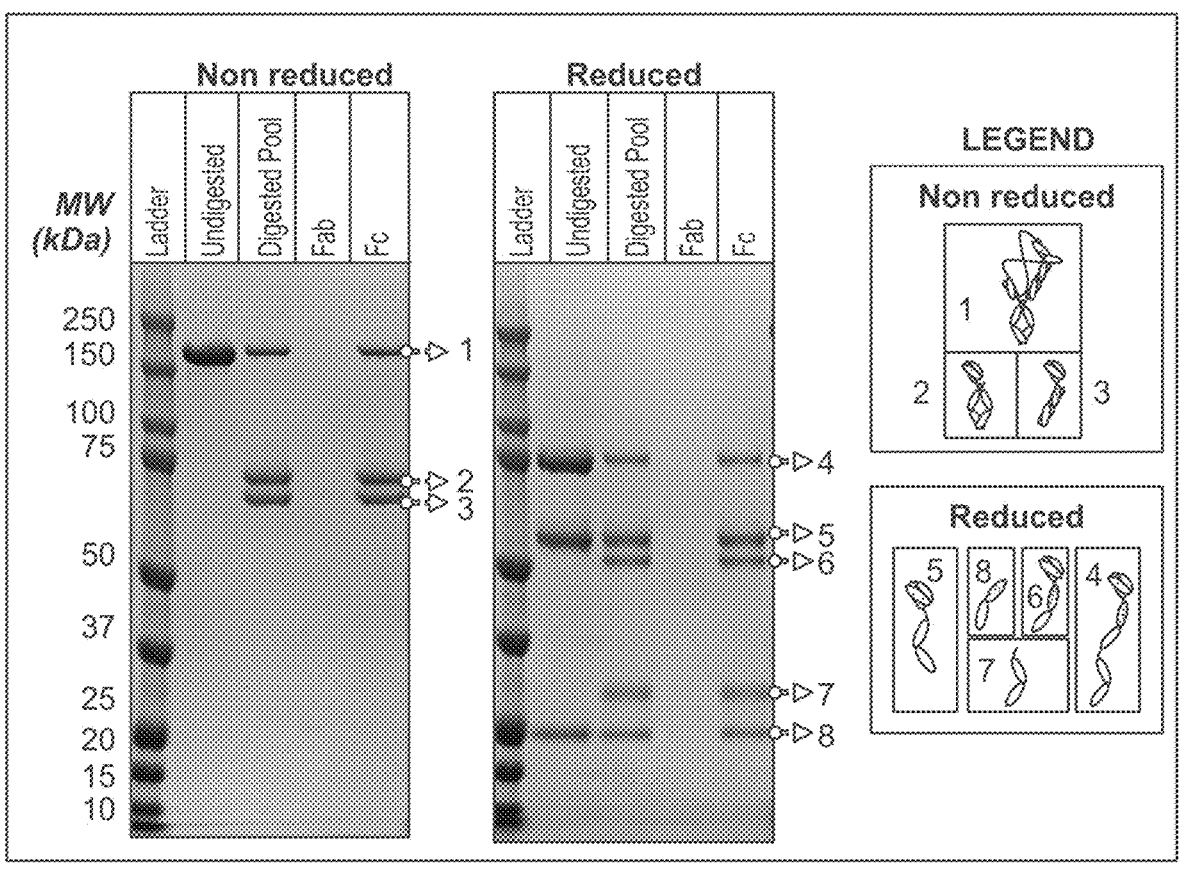
FIG. 58

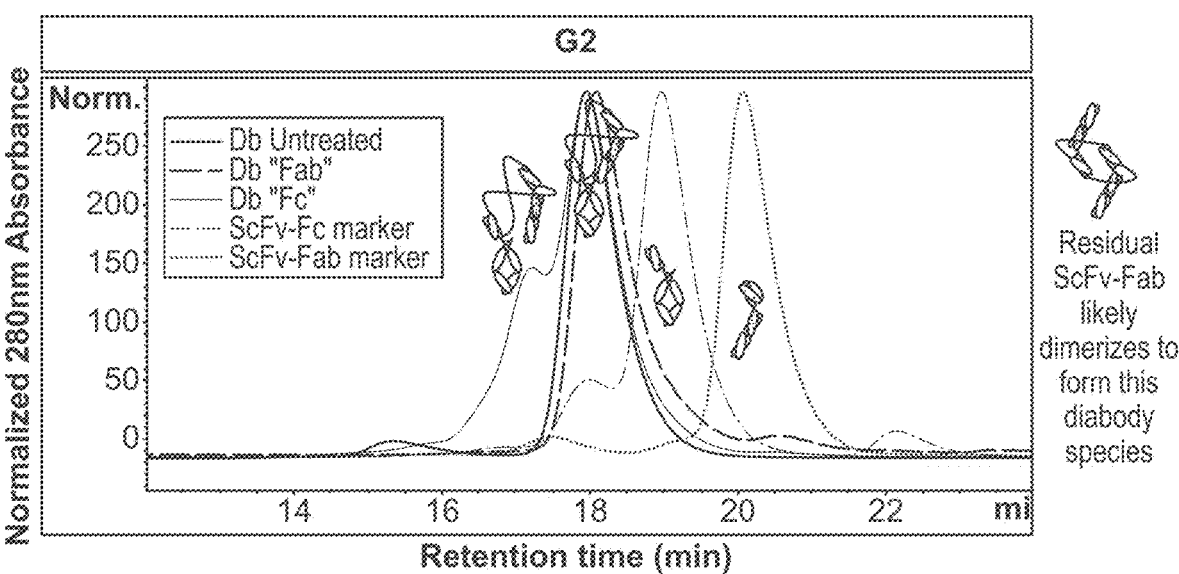
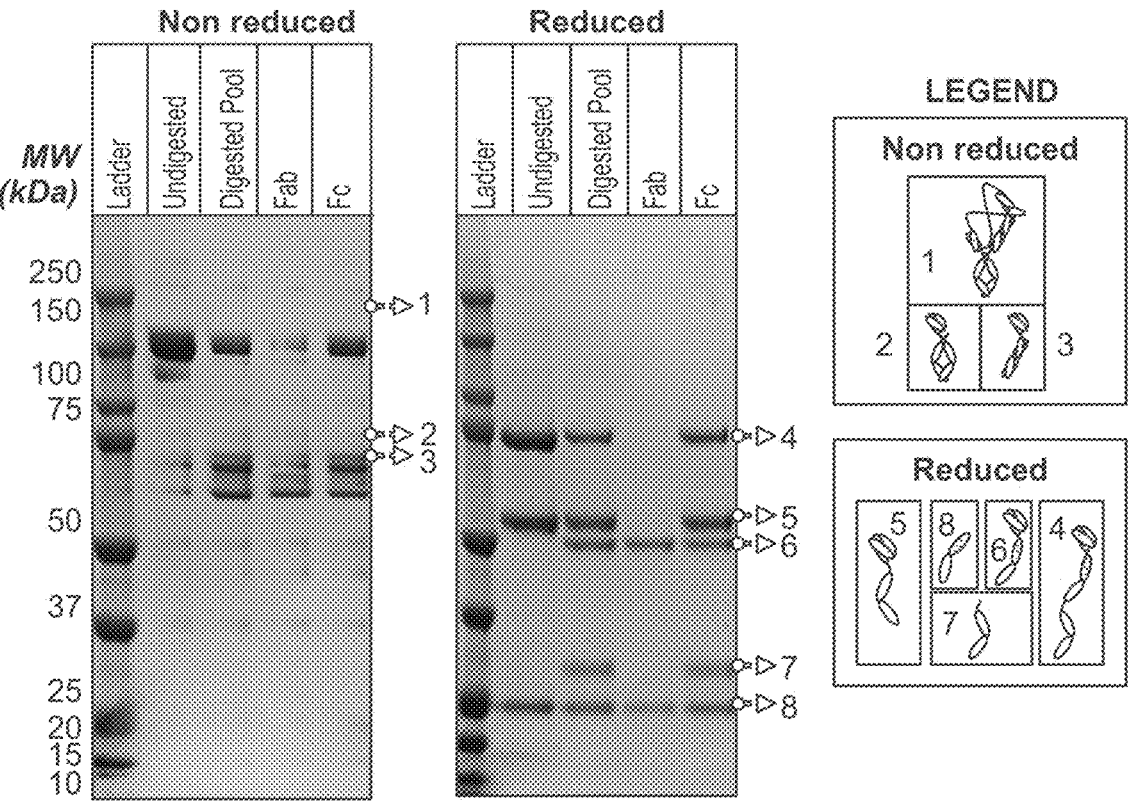
FIG. 59

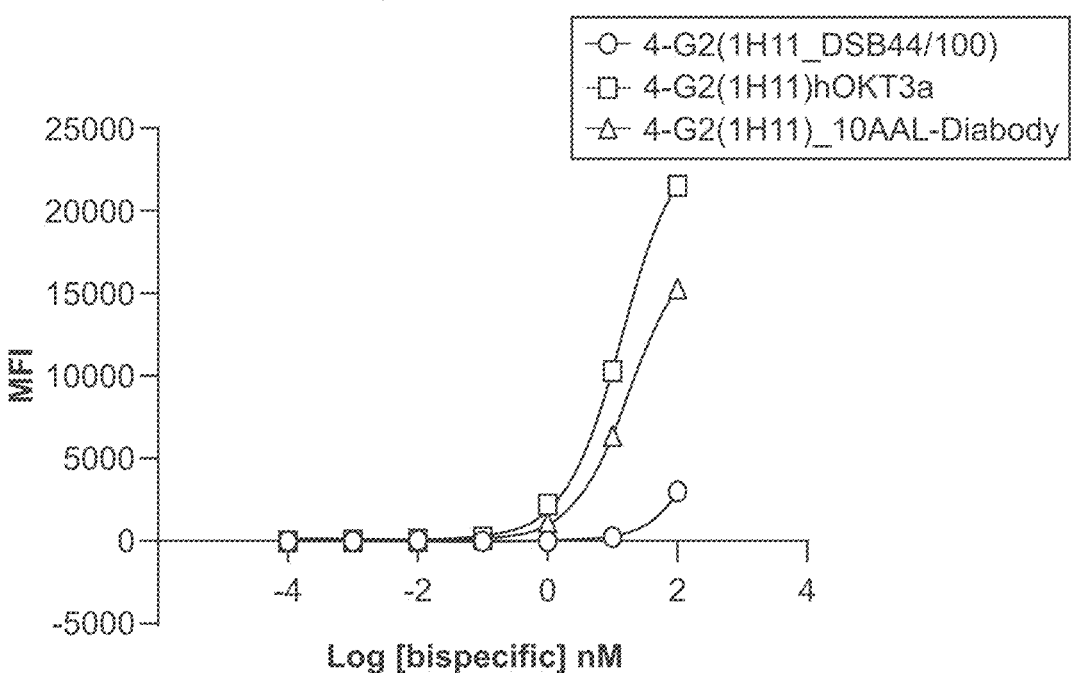
A375-G2-9mer
- -O- 4-G2(1H11_DSB44/100)
- -□- 4-G2(1H11)hOKT3a
- -△- 4-G2(1H11)_10AAL-Diabody
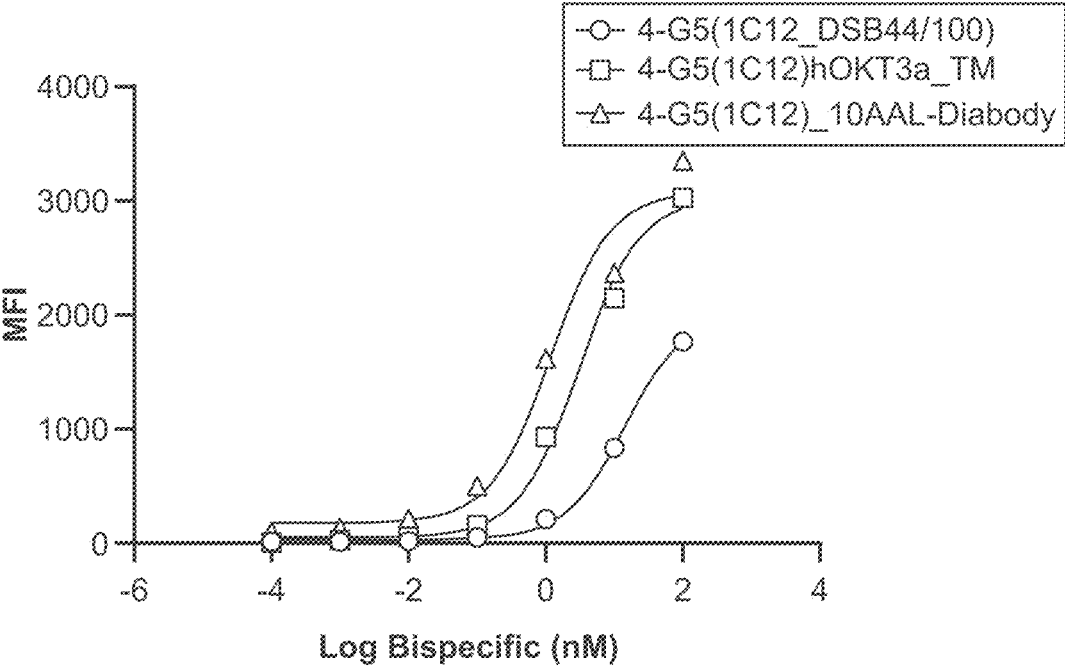
LN229-G5-9mer
- -O- 4-G5(1C12_DSB44/100)
- -□- 4-G5(1C12)hOKT3a_TM
- -△- 4-G5(1C12)_10AAL-Diabody
FIG. 62

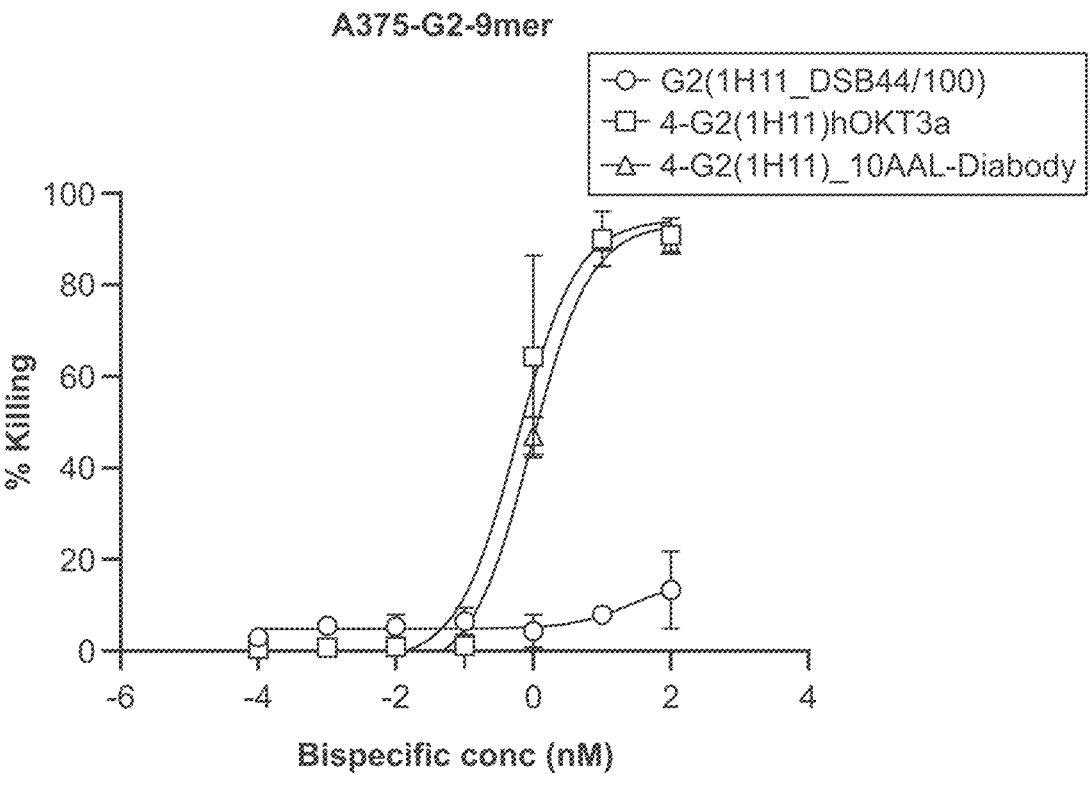
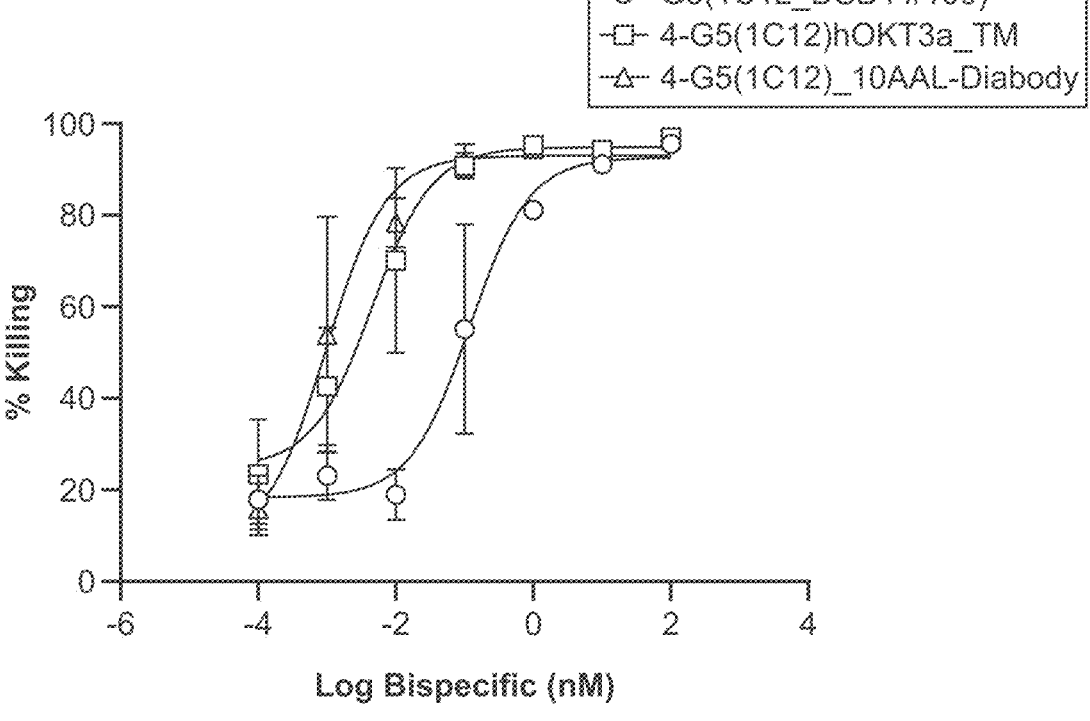
FIG. 63

Covalent diabodies
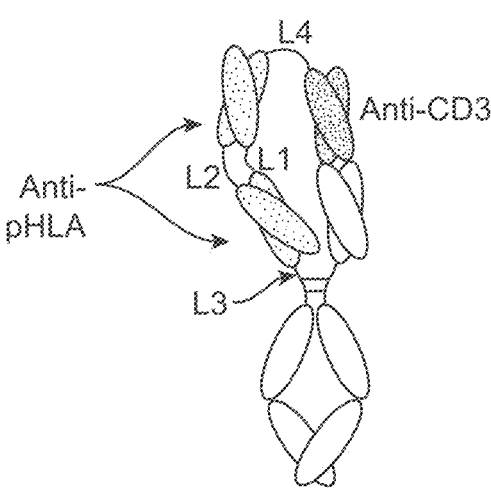
Original Diabody
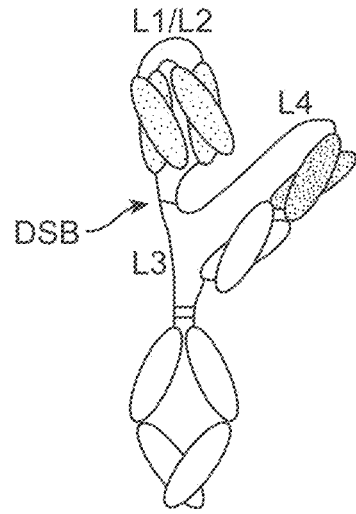
Covalent Diabodies
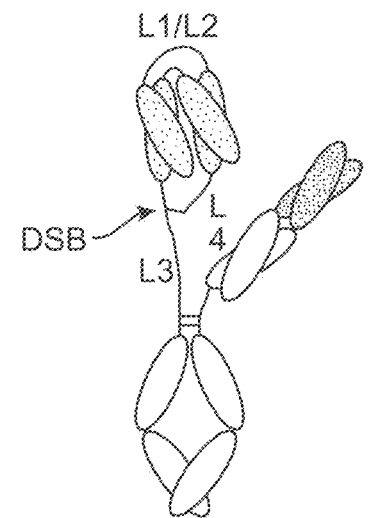
4-Chain Covalent Diabodies
FIG. 64

1

MULTI-SPECIFIC ANTIBODIES AND METHODS OF USE

CROSS REFERENCE TO RELATED APPLICATIONS

This application is a continuation of International Application No. PCT/US2022/012573, filed Jan. 14, 2022, which claims the benefit of U.S. Provisional Application No. 63/137,702, filed Jan. 14, 2021, which is hereby incorporated in its entirety by reference.

SEQUENCE LISTING

The instant application contains a Sequence Listing which has been submitted via PatentCenter and is hereby incorporated by reference in its entirety. Said XML copy, created on Aug. 1, 2023, is named GSO-099WOC1_SL.txt, and is 213,200 bytes in size.

BACKGROUND

Specific antigen recognition is essential for antibodies to function in the adaptive immune system. The specificity of antibodies and antibody fragments for a particular antigen or antigens makes antibodies desirable therapeutic agents. Antibodies and antibody fragments can be used to target specific tissues, for example, tumor tissue or infected tissue, thereby minimizing potential side effects of non-specific targeting. Thousands of antigens are capable of eliciting responses, each almost exclusively directed to the particular antigen which elicited it.

Major histocompatibility complex class I molecules are expressed on the surface of virtually all nucleated cells in the body and are dimeric molecules comprising a transmembrane heavy chain, comprising the peptide antigen binding cleft, and a smaller extracellular chain termed beta2-microglobulin. MHC class I molecules present peptides derived from the degradation of cytosolic proteins by the proteasome, a multi-unit structure in the cytoplasm, (Niedermann G., 2002. Curr Top Microbiol Immunol. 268:91-136; for processing of bacterial antigens, refer to Wick M J, and Ljunggren H G., 1999. Immunol Rev. 172:153-62). Cleaved peptides are transported into the lumen of the endoplasmic reticulum (ER) by the transporter associated with antigen processing (TAP) where they are bound to the groove of the assembled class I molecule, and the resultant MHC/peptide complex is transported to the cell membrane to enable antigen presentation to T lymphocytes (Yewdell J W., 2001. Trends Cell Biol. 11:294-7; Yewdell J W. and Bennink J R., 2001. Curr Opin Immunol. 13:13-8). Alternatively, cleaved peptides can be loaded onto MHC class I molecules in a TAP-independent manner and can also present extracellularly-derived proteins through a process of cross-presentation. As such, a given MHC/peptide complex presents a novel protein structure on the cell surface that can be targeted by a novel antigen-binding protein (e.g., antibodies or TCRs) once the identity of the complex's structure (peptide sequence and MHC subtype) is determined.

Tumor cells can express antigens and may display such antigens on the surface of the tumor cell. Such tumor-associated antigens can be used for development of novel immunotherapeutic reagents for the specific targeting of tumor cells. For example, tumor-associated antigens can be used to identify therapeutic antigen binding proteins, e.g., antibodies or antigen-binding fragments thereof.

Normal cells also display restricted peptides on their surface. In some cases, restricted peptides displayed by normal cells can have sequence overlap to the tumor-specific antigens. Such sequence-overlapping restricted peptides therefore represent potential off-target liabilities for therapeutic cancer immunotherapy.

Therefore, there exists a need for antigen-binding proteins that selectively bind tumor-specific antigens displayed on the surface of tumor cells, preferably with minimal or no off-target liability.

SUMMARY

Provided herein are antigen binding proteins that specifically bind to KKLC-1 and a cell surface molecule (e.g., CD3) on an effector cell.

In one aspect, provided herein are isolated antigen binding proteins (ABP) that comprises: a first antigen binding region (ABR) and a second ABR that each specifically bind a first target antigen, a Fab that specifically binds an additional target antigen that is distinct from the first target antigen, and an Fc domain, wherein the ABP comprises a first polypeptide, a second polypeptide, and a third polypeptide; wherein the first polypeptide comprises, in an N to C direction, the first ABR-a first hinge-CH2-CH3; wherein the second polypeptide comprises, in an N to C direction, the second ABR-a variable heavy chain (VH) domain of the Fab-a CH1 domain of the Fab-a second hinge-CH2-CH3; wherein the third polypeptide comprises, in an N to C direction, a variable light chain (VL) domain of the Fab-a CL domain of the Fab; wherein the first ABR and second ABR each comprise, in an N to C direction: (i) a VH domain-a VL domain or (ii) a VL domain-VH domain; wherein the VH domain of the first ABR is attached to the VL domain of the first ABR via a first linker; wherein the VH domain of the second ABR is attached to the VL domain of the second ABR via a second linker; wherein the first linker and second linker are each about 5-15 amino acids in length; and wherein the first target antigen is an HLA-PEPTIDE target comprising an HLA-restricted peptide complexed with an HLA Class I molecule, wherein the HLA Class I molecule is HLA subtype HLA-A*01:01 and the HLA-restricted peptide comprises the sequence NTDNNLAVY (SEQ ID NO: 214); and wherein the VH domains of the first and second ABRs each comprise complementarity-determining regions (CDR) H1 (CDR-H1), CDR-H2, and CDR-H3 comprising the sequences set forth in SEQ ID NOS:18, 19, and 20, respectively and wherein the VL comprises CDR-L1, CDR-L2, and CDR-L3 comprising the sequences set forth in SEQ ID NOS:21, 22, and 23, respectively.

In one aspect, provided herein are isolated antigen binding proteins (ABP) that comprises: a first antigen binding region (ABR) the specifically binds a first target antigen and a second ABR that specifically binds a second target antigen, a Fab that specifically binds an additional target antigen that is distinct from the first target antigen, and an Fc domain, wherein the ABP comprises a first polypeptide, a second polypeptide, and a third polypeptide; wherein the first polypeptide comprises, in an N to C direction, a variable heavy chain (VH) domain or variable light chain (VL) domain of the first ABR-a VH domain or a VL domain of the second ABR-a first hinge-CH2-CH3; wherein the second polypeptide comprises, in an N to C direction, the VH domain or VL domain of the second ABR-the VH domain or VL domain of the first ABR-a VH domain of the Fab-a CH1 domain of the Fab-a second hinge-CH2-CH3, wherein the third polypeptide comprises, in an N to C direction, a VL domain of the Fab-a CL domain of the Fab; wherein the VH domain or VL domain of the first ABR of the first polypeptide is attached to the VL domain or VH domain of the second ABR of the first polypeptide via a first linker; wherein the VH domain or VL domain of the second ABR of the second polypeptide is attached to the VL domain or VH domain of the first ABR via a second linker; wherein the first linker and second linker are each about 5-15 amino acids in length.

In some embodiments, the first target antigen is an HLA-PEPTIDE target comprising an HLA-restricted peptide complexed with an HLA Class I molecule, wherein the HLA Class I molecule is HLA subtype HLA-A*01:01 and the HLA-restricted peptide comprises the sequence NTDNN-LAVY (SEQ ID NO: 214); and wherein the VH domains of the first and/or second ABRs each comprise complementarity-determining regions (CDR) H1 (CDR-H1), CDR-H2, and CDR-H3 comprising the sequences set forth in SEQ ID NOS:18, 19, and 20, respectively and wherein the VL comprises CDR-L1, CDR-L2, and CDR-L3 comprising the sequences set forth in SEQ ID NOS:21, 22, and 23, respectively.

In some embodiments, the first linker and second linker are each individually 5, 6, 7, 8, 9, 10, 11, 12, 13, 14 or 15 amino acids in length.

In some embodiments, the first linker and second linker are each individually 5-15, 5-14, 5-13, 5-12, 5-11, 5-10, 5-9, 5-8, 5-7, 5-6, 6-15, 6-14, 6-13, 6-12, 6-11, 6-10, 6-9, 6-8, 6-7, 7-15, 7-14, 7-13, 7-12, 7-11, 7-10, 7-9, 7-8, 8-15, 8-14, 8-13, 8-12, 8-11, 8-10, 8-9, 9-15, 9-14, 9-13, 9-12, 9-11 or 9-10 amino acids in length.

In some embodiments, the first linker and second linker are each individually 5-11 amino acids in length.

In some embodiments, the first linker and second linker each consist of 5, 6, 7, 8, 9, 10 or 11 amino acids.

In some embodiments, the first linker and second linker each consist of 5, 8 or 10 amino acids.

In some embodiments, the first linker and second linker each consist of 10 amino acids.

In some embodiments, the additional target antigen is CD3.

In some embodiments, the VH and VL domains of the Fab comprise CDR-H1, CDR-H2, CDR-H3, CDR-L1, CDR-L2, and CDR-L3 comprising the sequences set forth in SEQ ID NOS: 36, 37, 38, 39, 40, and 41; 26, 27, 28, 29, 30, and 31; or 42, 43, 44, 45, 46, and 47 respectively.

In some embodiments, the VH of the first and second ABRs comprises the sequence set forth in SEQ ID NO: 6 and wherein the VL of the first and second ABR comprises the sequence set forth in SEQ ID NO: 4.

In some embodiments, the VH and VL of the Fab comprises the sequence set forth in SEQ ID NOS: 32 and 33; 24 and 25; or 34 and 35, respectively.

In some embodiments, the first polypeptide comprises the sequence set forth in SEQ ID NO: 55.

In some embodiments, the first polypeptide comprises the sequences set forth in SEQ ID NO: 55 and 48.

In some embodiments, the second polypeptide comprises the sequence set forth in SEQ ID NOs: 55.

In some embodiments, the second polypeptide comprises the sequences set forth in SEQ ID NOs: 55 and 51, 49, or 53.

In some embodiments, the third polypeptide comprises the sequence set forth in SEQ ID NOs: 52, 50, or 54.

In some embodiments, the first polypeptide comprises the sequence set forth in SEQ ID NO: 55 and 48, the second polypeptide comprises the sequence set forth in SEQ ID NO: 55 and 51, and the third polypeptide comprises the sequence set forth in SEQ ID NOs: 52.

In some embodiments, the VH domain of the first ABR comprise complementarity-determining regions (CDR) H1 (CDR-H1), CDR-H2, and CDR-H3 comprising the sequences set forth in SEQ ID NOs: 18, 19, and 20, respectively, and wherein the VL comprises CDR-L1, CDR-L2, and CDR-L3 comprising the sequences set forth in SEQ ID NOs: 21, 22, and 23, respectively.

In some embodiments, the VH domain of the second ABR comprise CDR-H1, CDR-H2, CDR-H3 comprising the sequences set forth in SEQ ID NOS: 36, 37, and 38; 26, 27, and 28; or 42, 43, and 44, respectively, and wherein the VL comprises CDR-L1, CDR-L2, and CDR-L3 comprising the sequences set forth in SEQ ID NOS: 39, 40, and 41; 29, 30, and 31; or 45, 46, and 47, respectively.

In some embodiments, the VH and VL domains of the Fab comprise CDR-H1, CDR-H2, CDR-H3, CDR-L1, CDR-L2, and CDR-L3 comprising SEQ ID NOS: 18, 19, 20, 21, 22, and 23, respectively.

In some embodiments, the VH of the first ABR comprises SEQ ID NO:6 and wherein the VL of the first ABR comprises SEQ ID NO:4.

In some embodiments, the VH of the second ABR comprises SEQ ID NO: 32, 24, or 34 and wherein the VL of the second ABR comprises SEQ ID NO: 33, 25, or 35.

In some embodiments, the first polypeptide comprises the sequence set forth in SEQ ID NO: 48 and 58 or 59.

In some embodiments, the second polypeptide comprises the sequence set forth in SEQ ID NO: 56 and 58 or 59.

In some embodiments, the third polypeptide comprises the sequence set forth in SEQ ID NO: 57.

In some embodiments, the first polypeptide comprises the sequence set forth in SEQ ID NO: 48 and 58 or 59, the second polypeptide comprises the sequence set forth in SEQ ID NO: 56 and 58 or 59, and wherein the third polypeptide comprises the sequence set forth in SEQ ID NO: 57.

In some embodiments, the first linker and second linker each consist of (GGGGS)N, wherein N=1-3 (SEQ ID NO: 215).

In some embodiments, the first linker and second linker each consist of (GSGGG)N, wherein N=2 (SEQ ID NO: 216).

In some embodiments, the first linker and second linker each comprise glycine, serine, or glycine and serine amino acids.

In some embodiments, the first linker and second linker each consist of glycine and serine amino acids.

In some embodiments, the VH domain of the first ABR interacts with the VL domain of the second ABR.

In some embodiments, the VL domain of the first ABR interacts with the VH domain of the second ABR.

In some embodiments, the VL domain of the first ABR interacts with the VH domain of the second ABR and wherein the VH domain of the first ABR interacts with the VL domain of the second ABR.

In some embodiments, the interaction of the VL domain of the first ABR with the VH domain of the second ABR and the interaction of the VH domain of the first ABR with the VL domain of the second ABR results in a circularized conformation.

In one aspect, provided herein are isolated antigen binding proteins (ABP) that comprises: (a) a first antigen binding site that specifically binds to a human leukocyte antigen (HLA)-PEPTIDE target, wherein the HLA-PEPTIDE target comprises an HLA-restricted peptide complexed with an HLA Class I molecule, wherein the HLA-restricted peptide is located in the peptide binding groove of an α1/α2 heterodimer portion of the HLA Class I molecule, wherein the HLA Class I molecule is HLA subtype HLA-A*01:01 and the HLA-restricted peptide comprises the sequence NTDNNLAVY (SEQ ID NO: 214); and (b) a second antigen binding site that specifically binds to a CD3 target on an effector cell; wherein the first antigen binding site comprises a variable heavy chain domain (VH) and a variable light chain domain (VL), wherein the VH of the first antigen binding site comprises complementarity-determining regions (CDR) H1 (CDR-H1), CDR-H2, and CDR-H3 comprising SEQ ID NOS: 18, 19, and 20, respectively and wherein the VL comprises a CDR-L1, CDR-L2, and CDR-L3 comprising SEQ ID NOS: 21, 22, and 23, respectively.

In some embodiments, the second antigen binding site comprises a VH and a VL, wherein the VH and VL comprise a CDR-H1, CDR-H2, CDR-H3, CDR-L1, CDR-L2, and CDR-L3 comprising SEQ ID NOS: 36, 37, 38, 39, 40, and 41; 26, 27, 28, 29, 30, and 31; or 42, 43, 44, 45, 46, and 47, respectively.

In some embodiments, the VH and VL of the first antigen binding site comprises SEQ ID NOS: 6 and 4, respectively.

In some embodiments, the VH and VL of the second antigen binding site comprises SEQ ID NOS: 32 and 33, respectively.

In some embodiments, the effector cell is a T cell or an NK cell.

In some embodiments, the ABP binds the HLA-PEPTIDE target with greater affinity as compared to an off-target HLA-PEPTIDE comprising an off-target restricted peptide complexed with an HLA Class I molecule.

In some embodiments, contacting the ABP with cancer cells results in at least 20%, 30%, 40%, 50%, 60%, 70%, 80%, 90% or 95% cytotoxicity.

In some embodiments, the cytotoxicity that results from the ABP contacting cancer cells is greater than a reference antigen binding protein.

In some embodiments, the cancer cells have an A*01: 01_NTDNNLAVY (SEQ ID NO: 214) copy number of less than about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, about 20000, about 30000, and about 40000 copies/cell.

In some embodiments, the cancer cells have an A*01: 01_NTDNNLAVY (SEQ ID NO: 214) copy number of about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, about 20000, about 30000, and about 40000 copies/cell.

In some embodiments, contacting the ABP with a tumor results in a reduction in tumor growth, relative to before contacting the ABP with a tumor.

In some embodiments, contacting the ABP with a tumor results in decreased tumor volume relative to contacting with a reference antigen binding protein.

In some embodiments, the ABP comprises an antibody or antigen-binding fragment thereof.

In some embodiments, the antigen binding protein is linked to a scaffold, optionally wherein the scaffold comprises serum albumin or Fc, optionally wherein Fc is human Fc and is an IgG (IgG1, IgG2, IgG3, IgG4), an IgA (IgA1, IgA2), an IgD, an IgE, or an IgM.

In some embodiments, the antigen binding protein is linked to a scaffold via a linker, optionally wherein the linker is a peptide linker, optionally wherein the peptide linker is a hinge region of a human antibody.

In some embodiments, the antigen binding protein comprises an Fv fragment, a Fab fragment, a F(ab')2 fragment, a Fab' fragment, an scFv fragment, an scFv-Fc fragment, and/or a single-domain antibody or antigen binding fragment thereof.

In some embodiments, the antigen binding protein comprises a single-domain antibody fragment.

In some embodiments, the antigen binding protein comprises an scFv fragment.

In some embodiments, the antigen binding protein comprises an VHH fragment.

In some embodiments, the antigen binding protein comprises an antibody.

In some embodiments, the antigen binding protein is a monoclonal antibody.

In some embodiments, the antigen binding protein is a humanized, human, or chimeric antibody.

In some embodiments, the antigen binding protein is multispecific, optionally bispecific.

In some embodiments, the antigen binding protein binds greater than one antigen or greater than one epitope on a single antigen.

In some embodiments, the antigen binding protein comprises a heavy chain constant region of a class selected from IgG, IgA, IgD, IgE, and IgM.

In some embodiments, the antigen binding protein comprises a heavy chain constant region of the class human IgG and a subclass selected from IgG1, IgG4, IgG2, and IgG3.

In some embodiments, the antigen binding protein comprises a modified Fc, optionally wherein the modified Fc comprises one or more mutations that extend half-life, optionally wherein the one or more mutations that extend half-life is YTE.

In some embodiments, a sequence comprising the CH2-CH3 domains of the first polypeptide is distinct from a sequence comprising the CH2-CH3 domains of the second polypeptide.

In some embodiments, the APB comprises a variant CH2-CH3 domain.

In some embodiments, the variant CH2-CH3 domain comprises a modification that alters an affinity of the ABP for an Fc receptor as compared to an ABP with a non-variant Fc region.

In some embodiments, the variant CH2-CH3 domain comprises one or more amino acid substitutions that reduce at least one Fc effector function.

In some embodiments, the variant CH2-CH3 domain comprises one or more amino acid substitutions that reduce binding to an Fc receptor on the cell surface of an effector cell.

In some embodiments, the Fc receptor on the cell surface of an effector cell is selected from: FcγRI; FcγRIIA; FcγRIIB1; FcγRIIB2; FcγRIIIA; and FcγRIIIB receptors.

In some embodiments, the Fc effector function that is reduced comprises one or more functions selected from: complement-dependent cytotoxicity (CDC), antibody-dependent cellular cytotoxicity (ADCC), and complement fixation.

In some embodiments, the one or more amino acid substitutions is selected from: L234, L235, P331, L234F, L235E, and P331S, according to the EU numbering system.

In some embodiments, the variant CH2-CH3 domain comprises the amino acid substitutions of L234F, L235E, and P331S, according to the EU numbering system.

In some embodiments, the variant CH2-CH3 domain of the first polypeptide comprises a knob-in-hole modification.

In some embodiments, the variant CH2-CH3 domain of the second polypeptide comprises a knob-in-hole modification.

In some embodiments, one CH2-CH3 domain-bearing chain of the ABP comprises a T366W mutation, and the other CH2-CH3 domain-bearing chain of the ABP comprises a T366S, L368A, and Y407V mutation, according to EU numbering.

In some embodiments, the APB comprises an S354C and T366W mutation in one CH2-CH3 domain and a Y349C, T366S, L368A and Y407V mutation in the other CH2-CH3 domain, according to EU numbering.

In some embodiments, one CH2-CH3 domain comprises a H435, Y436, H435R, Y436F, or H435R_Y436F mutation, according to EU numbering.

In some embodiments, the variant CH2-CH3 domain comprises a set of mutations that renders homodimerization electrostatically unfavorable but heterodimerization favorable.

In some embodiments, the first hinge comprises a C220S mutation, according to EU numbering.

In some embodiments, the antigen binding protein is a portion of a chimeric antigen receptor (CAR) comprising: an extracellular portion comprising the antigen binding protein; and an intracellular signaling domain.

In one aspect, provided herein are isolated polynucleotides or sets of polynucleotides encoding the antigen binding protein as disclosed herein or an antigen-binding portion thereof.

In one aspect, provided herein are vectors or sets of vectors comprising the polynucleotide or set of polynucleotides as disclosed herein.

In one aspect, provided herein are host cells comprising the polynucleotide or set of polynucleotides as disclosed herein or the vector or set of vectors as disclosed herein, optionally wherein the host cell is CHO or HEK293, or optionally wherein the host cell is a T cell.

In one aspect, provided herein are methods of producing an antigen binding protein comprising expressing the antigen binding protein with the host cell as disclosed herein and isolating the expressed antigen binding protein.

In one aspect, provided herein are pharmaceutical compositions comprising the antigen binding protein as disclosed herein and a pharmaceutically acceptable excipient.

In one aspect, provided herein are methods of increasing an immune response in a subject, comprising administering to the subject the ABP as disclosed herein or a pharmaceutical composition as disclosed herein, optionally wherein the subject has cancer.

In some embodiments, the cancer is selected from a solid tumor and a hematological tumor.

In some embodiments, the cancer is selected from: esophageal cancer, gastric adenocarcinoma, lung adenocarcinoma, and lung squamous cancer.

In one aspect, provided herein are methods of treating cancer in a subject, comprising administering to the subject an effective amount of the antigen binding protein as disclosed herein or a pharmaceutical composition as disclosed herein.

In some embodiments, the cancer is selected from a solid tumor and a hematological tumor.

In some embodiments, the cancer is selected from: esophageal cancer, gastric adenocarcinoma, lung adenocarcinoma, and lung squamous cancer.

In some embodiments, the cancer expresses or is predicted to express the HLA-PEPTIDE target.

In some embodiments, the method comprises, prior to the administering, determining or having determined the presence of any one or more of the HLA-PEPTIDE target, the restricted peptide of the HLA-PEPTIDE target, and the HLA molecule of the HLA-PEPTIDE target in a biological sample obtained from the subject.

In some embodiments, the biological sample is a blood sample or a tumor sample.

In some embodiments, the blood sample is a plasma or serum sample.

In some embodiments, after having determined the presence of the HLA-PEPTIDE target, restricted peptide, or HLA in the biological sample obtained from the subject, administering to the subject an ABP that selectively binds to the HLA-PEPTIDE antigen.

In one aspect, provided herein are kits comprising the antigen binding protein as disclosed herein or a pharmaceutical composition as disclosed herein and instructions for use.

BRIEF DESCRIPTION OF THE SEVERAL VIEWS OF THE DRAWINGS

These and other features, aspects, and advantages of the present invention will become better understood with regard to the following description, and accompanying drawings, where:

Figure 5:
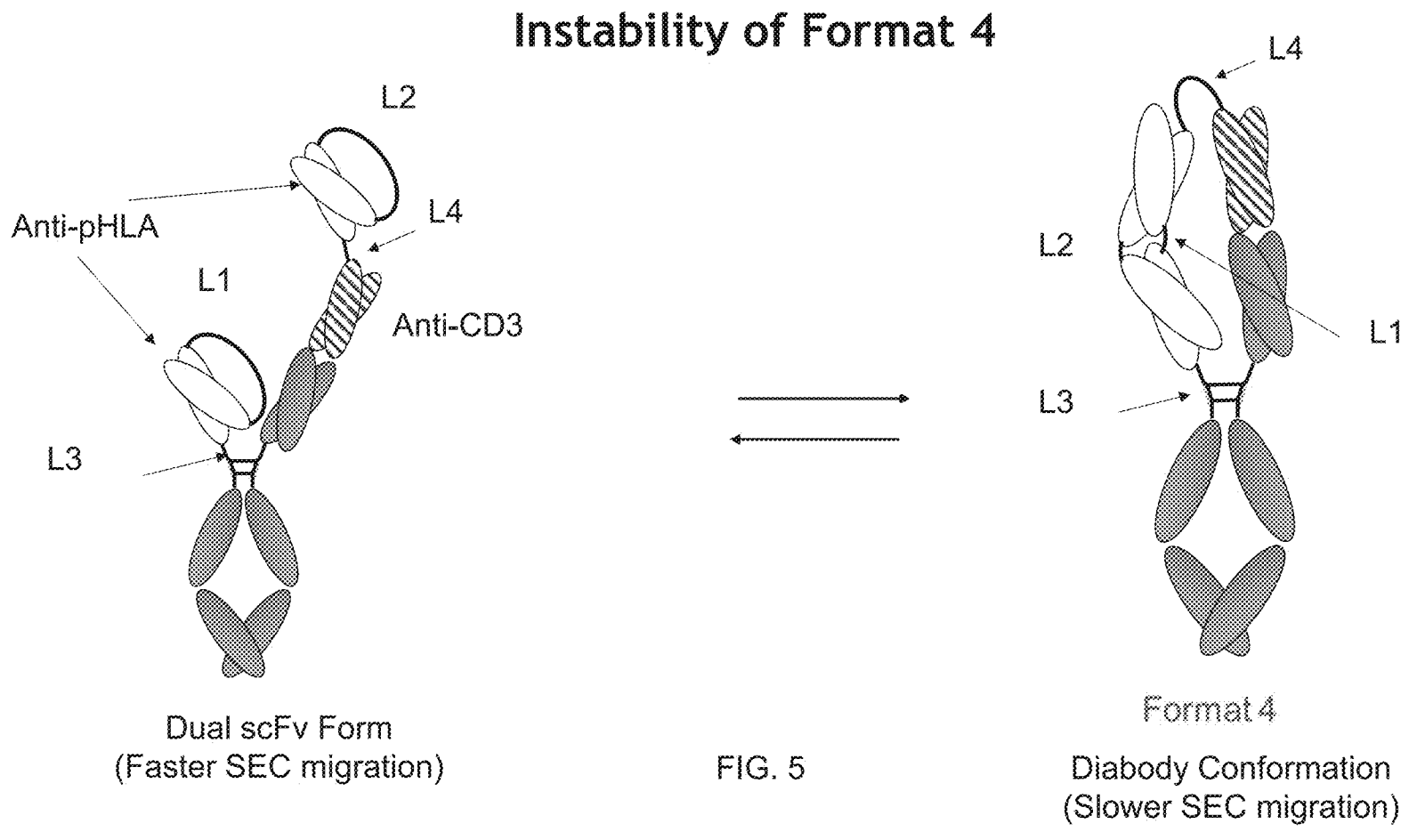

FIG. 5 depicts the equilibrium/unstable conformation state that the Format 4 antibody can exist in when in solution, which can depend on linker length and/or other types of modifications to the antibody.

FIG. 10A shows the cytotoxicity measurements of cells having the indicated target antigen copy number levels when contacted with the E07-CD3 diabody. FIG. 10B shows the cytotoxicity measurements of cells having the indicated target antigen copy number levels when contacted with the E07-CD3 diabody. FIG. 10C shows the cytotoxicity measurements of cells having the indicated target antigen copy number levels when contacted with the E07-CD3 diabody. FIG. 10D shows the cytotoxicity measurements of cells having the indicated target antigen copy number levels when contacted with the E07-CD3 diabody FIG. 11 depicts the VH and VL sequences for the E07 clone with protein liabilities shown. FIG. 11 discloses SEQ ID NOS 235 and 4, respectively, in order of appearance.

FIG. 12 depicts the VH and VL sequences for the hOKT3a clone with protein liabilities shown. FIG. 12 discloses SEQ ID NOS 24 and 25, respectively, in order of appearance.

FIG. 15 discloses SEQ ID NOS 214 and 204-206, respectively, in order of appearance.

FIG. 19 shows the correlation between the drug (E07-CD3 diabody) concentration and trimer formation.

FIG. 21A shows the tumor volume measurements from the indicated effector:target (E:T) ratio and E07-CD3 diabody dose levels. FIG. 21B shows the tumor volume measurements from the indicated effector:target (E:T) ratio and E07-CD3 diabody dose levels. FIG. 21C shows the tumor volume measurements from the indicated effector:target (E:T) ratio and E07-CD3 diabody dose levels. FIG. 21D shows the tumor volume measurements from the indicated effector:target (E:T) ratio and E07-CD3 diabody dose levels. FIG. 21E shows the tumor volume measurements from the indicated effector:target (E:T) ratio and E07-CD3 diabody dose levels. FIG. 21F shows the tumor volume measurements from the indicated effector:target (E:T) ratio and E07-CD3 diabody dose levels.

FIG. 22A depicts the tumor volume measurements from the indicated E:T ratios and E07-CD3 diabody dose levels. FIG. 22B depicts the tumor volume measurements from the indicated E:T ratios and E07-CD3 diabody dose levels

FIG. 28 provides schematics of Format 43 antibodies.

FIG. 30 shows binding of the 41-E07 hUCHT1v9 or 43-E07 hUCHT1 v9 antibodies to CD3– and CD3+ Jurkat cells.

FIG. 37A shows tumor volume in mice treated with 0.01 mg/kg, 0.1 mg/kg, or 1 mg/kg of the indicated antibody. FIG. 37B shows tumor volume in mice treated with 1 mg/kg of the indicated antibody. FIG. 37C shows tumor volume in mice treated with 0.1 mg/kg of the indicated antibody. FIG. 37D shows tumor volume in mice treated with 0.01 mg/kg of the indicated antibody.

FIG. 39A shows tumor volume in mice treated with 2 mg/kg of the indicated antibody. FIG. 39B shows tumor volume in mice treated with 1 mg/kg of the indicated antibody. FIG. 39C shows tumor volume in mice treated with 0.1 mg/kg of the indicated antibody. FIG. 39D shows tumor volume in mice treated with 0.01 mg/kg of the indicated antibody.

FIG. 40A shows binding of the 41-E07 hOKT3a antibody to cells pulsed with the indicated peptide complex. FIG. 40A discloses SEQ ID NOS 214 and 128-133, respectively, in order of appearance. FIG. 40B shows binding of the 41-E07 hOKT3a antibody to cells pulsed with the indicated peptide complex. FIG. 40B discloses SEQ ID NOS 214 and 120-127, respectively, in order of appearance.

FIG. 41 discloses SEQ ID NOS 214, 204-206, 214, 236, 214, and 233, respectively, in order of appearance.

FIG. 42A shows binding of the 41-E07 UCHT1v9 antibody to cells expressing the indicated peptide complex. FIG. 42B shows binding of the 41-E07 UCHT1v9 antibody to the G2-pHLA complex or the ROBO1 pHLA complex.

FIG. 43A shows the SDS-PAGE results from the FabA-LACTICA digestion of the format 41 diabody. FIG. 43A shows the SDS-PAGE results from the FabALACTICA digestion of the control Format 3 antibody.

Figure 44A:
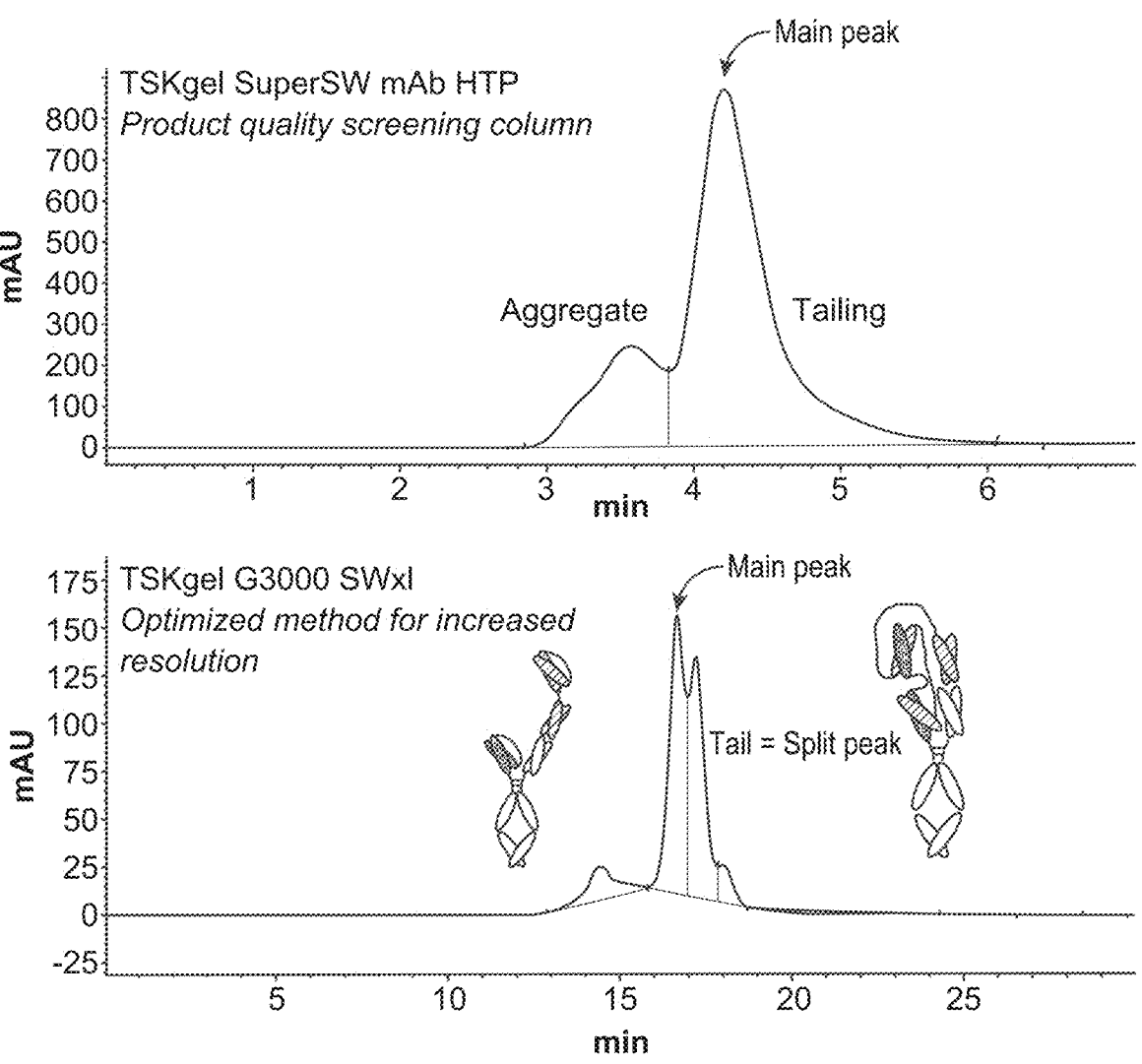
Figure 44B:
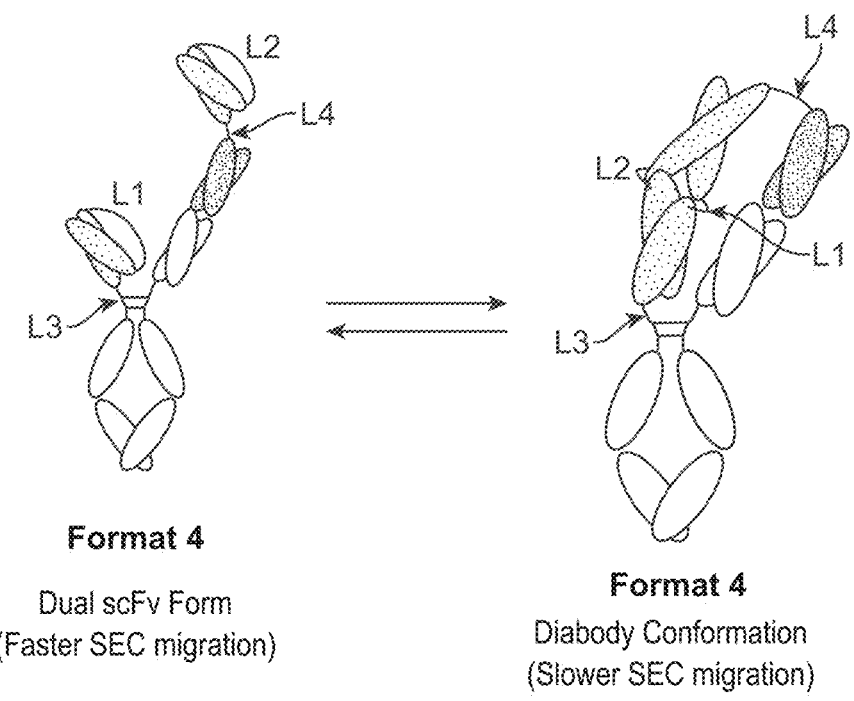

FIG. 44A shows SEC-HPLC results from a product quality screening of antibodies using a TSKgel SuperSW mAb HTP column (top panel), where a peak tailing between 4.5-5.5 minutes suggested presence of an additional antibody moiety that either interacts more with the SEC column, or is more compacted and thus migrates slower than the main antibody conformation. FIG. 44A also shows SEC-HPLC results from a TSKgel G3000SWx1 column (bottom panel) which resolved the tailing into a "split peak." FIG. 44B includes a schematic showing two conformations of Format 4 antibodies that may exist in solution: dual scFv and diabody conformation.

Figure 45B:
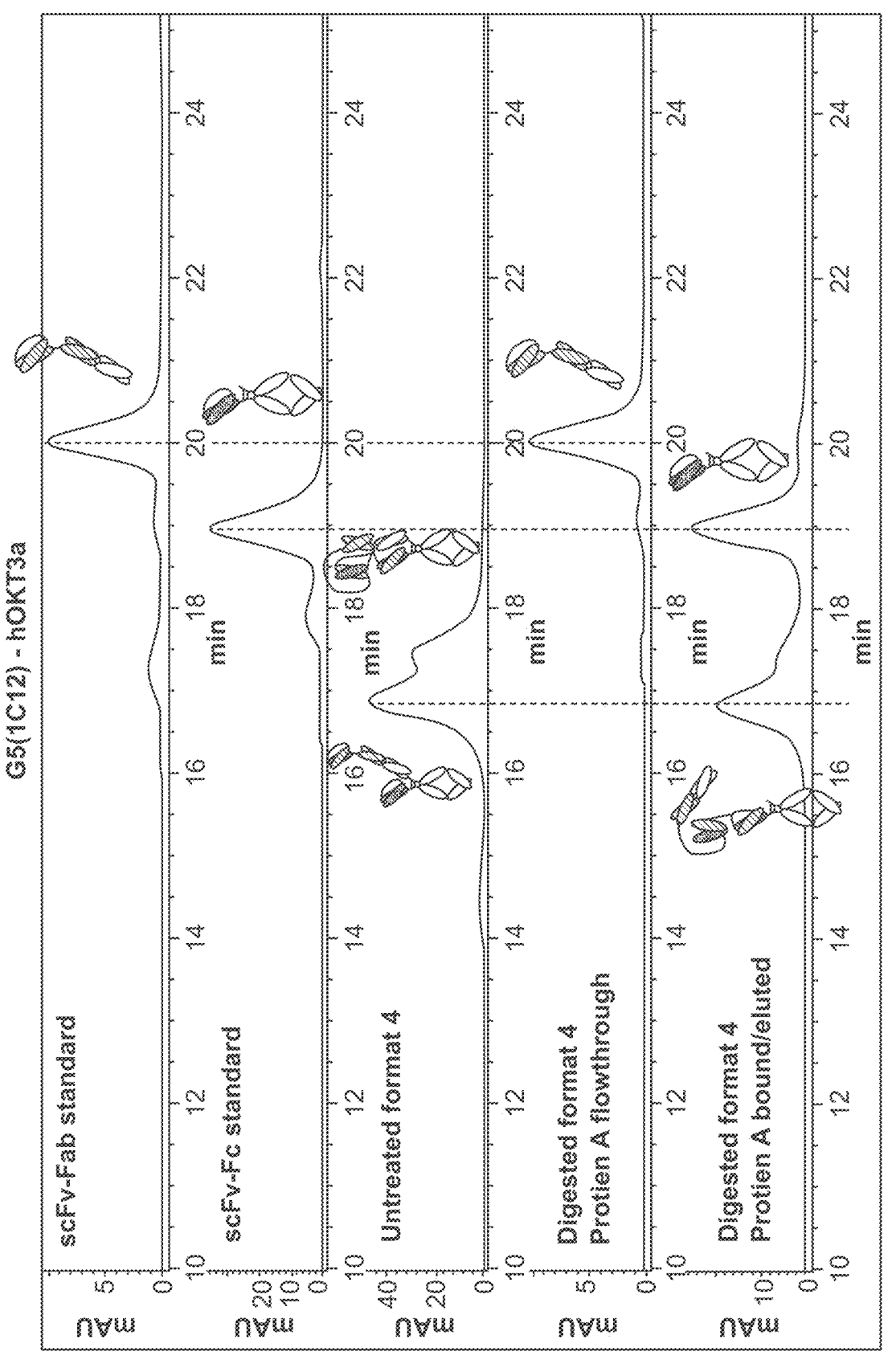

FIG. 45A shows expected protein digestion fragments of "standard" Format 4 antibodies and a "diabody" isomer of Format 4. FIG. 45B shows SEC-HPLC results from a FabALACTICA digestion experiment, where Format 4 antibodies were treated with a cysteine protease that digests human IgG1 at one specific site in the upper hinge (KSCDKT/HTCPPC (SEQ ID NO: 211)).

FIG. 46 includes a schematic representation of the undigested Format 4 "dual scFv" conformation (left), the diabody conformation without digestion (middle), and the diabody conformation after proteolytic digestion (right).

Figure 47:
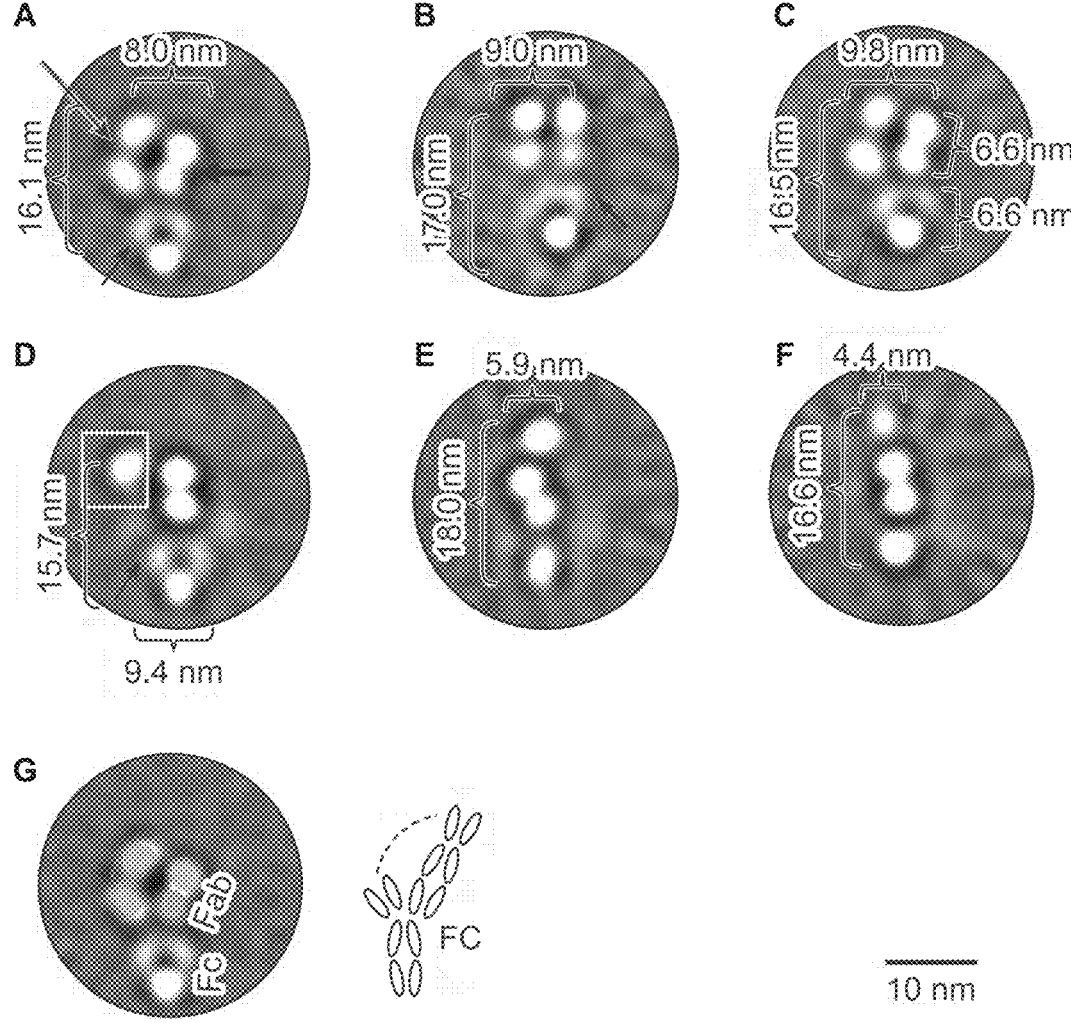

FIG. 47 shows results from an electron microscopy study of a representative Format 4 antibody, Format 4-hOKT3-G5(1C12).

Figure 48:
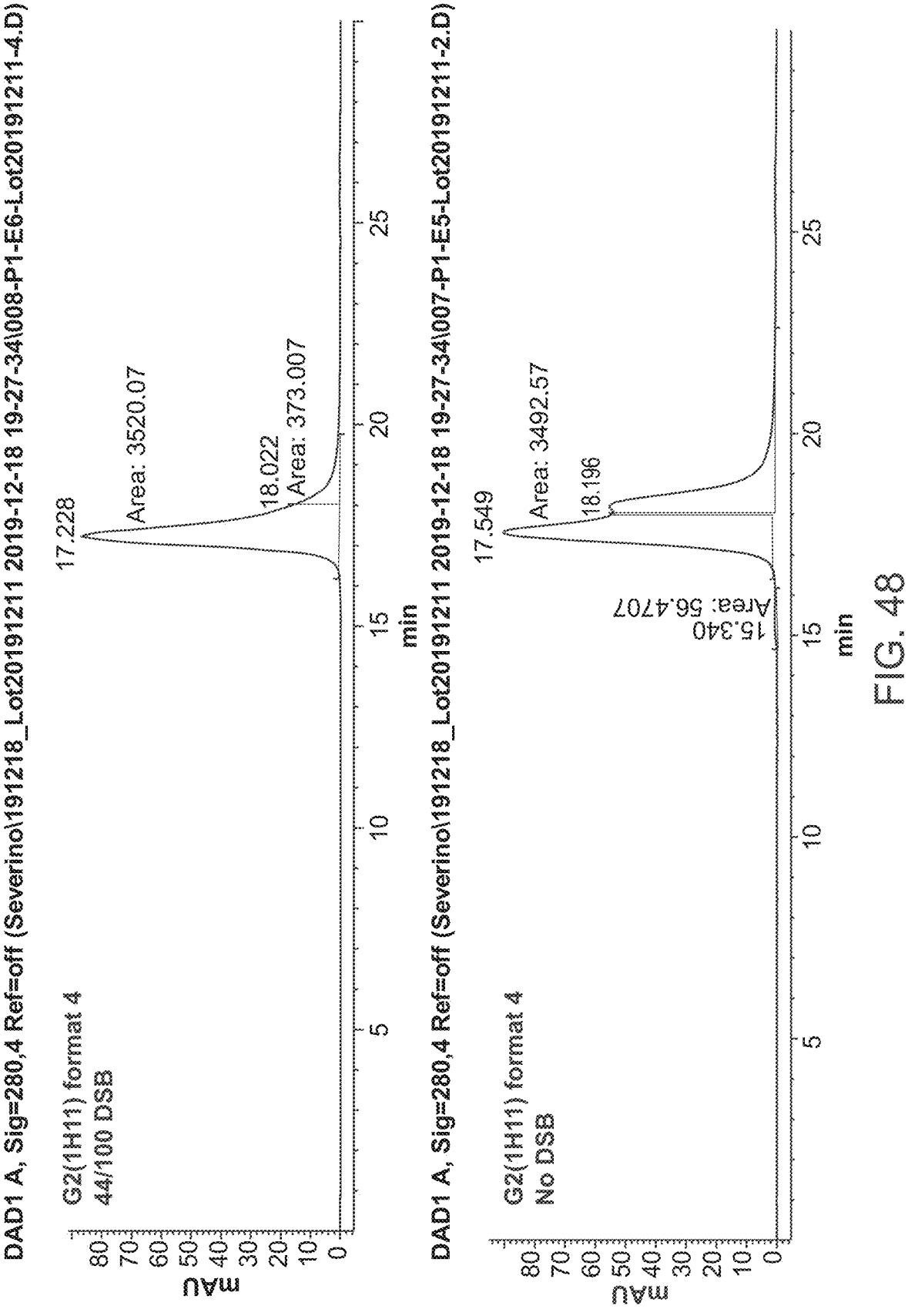

FIG. 48 includes SEC-HPLC chromatograms from a Format 4 G2(1H11) bispecific antibody with an engineered VH44/VL100 disulfide bond (top panel), and without the engineered disulfide bond (bottom panel).

Figure 49:
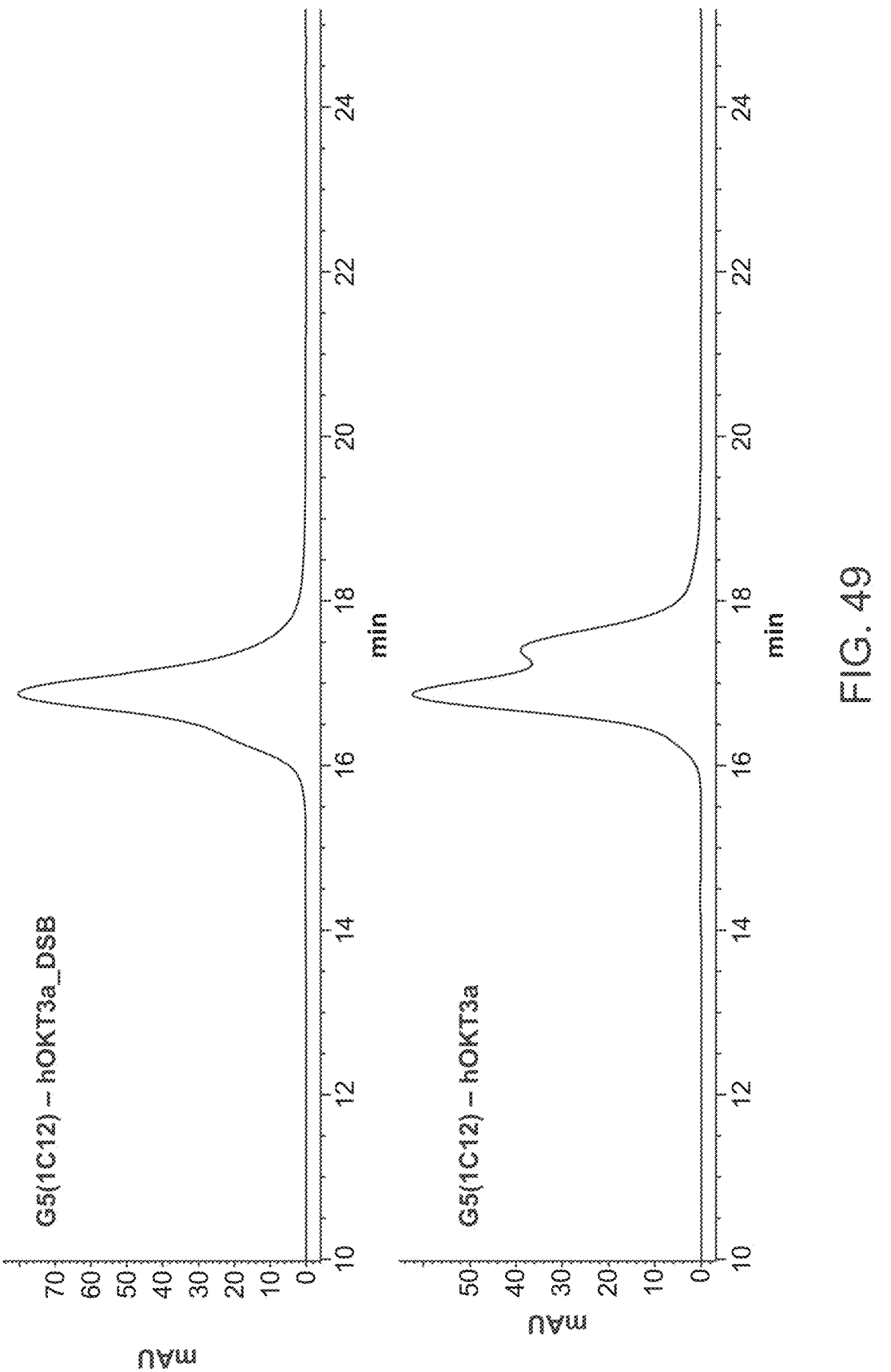

FIG. 49 includes SEC-HPLC chromatograms from a Format 4 G5(1C12) bispecific antibody with an engineered VH44/VL100 disulfide bond (top panel), and without the engineered disulfide bond (bottom panel).

Figure 50A:
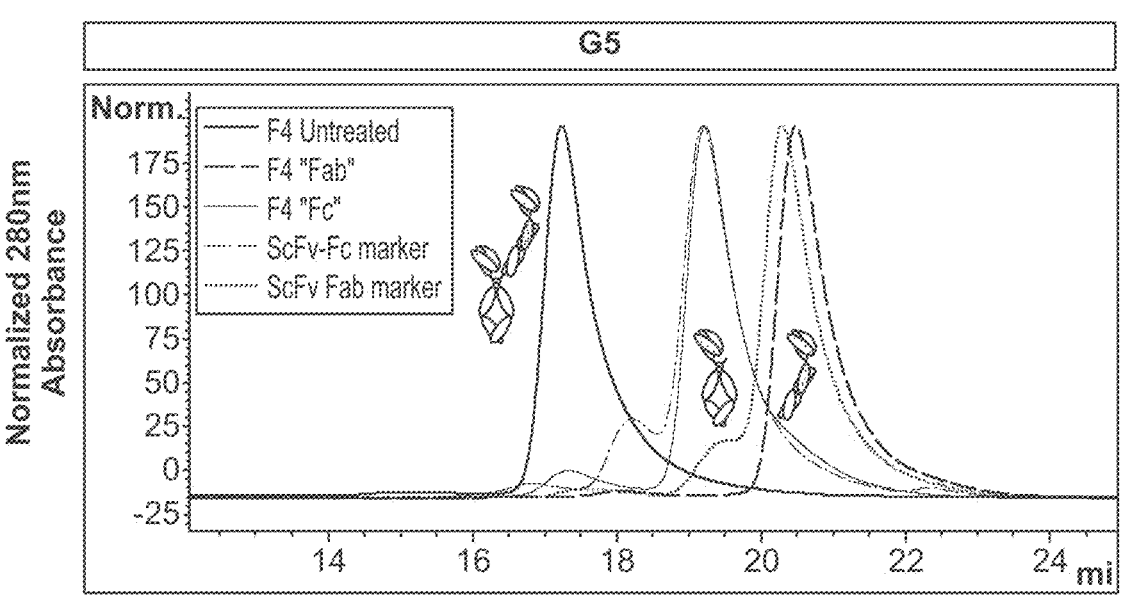
Figure 50B:
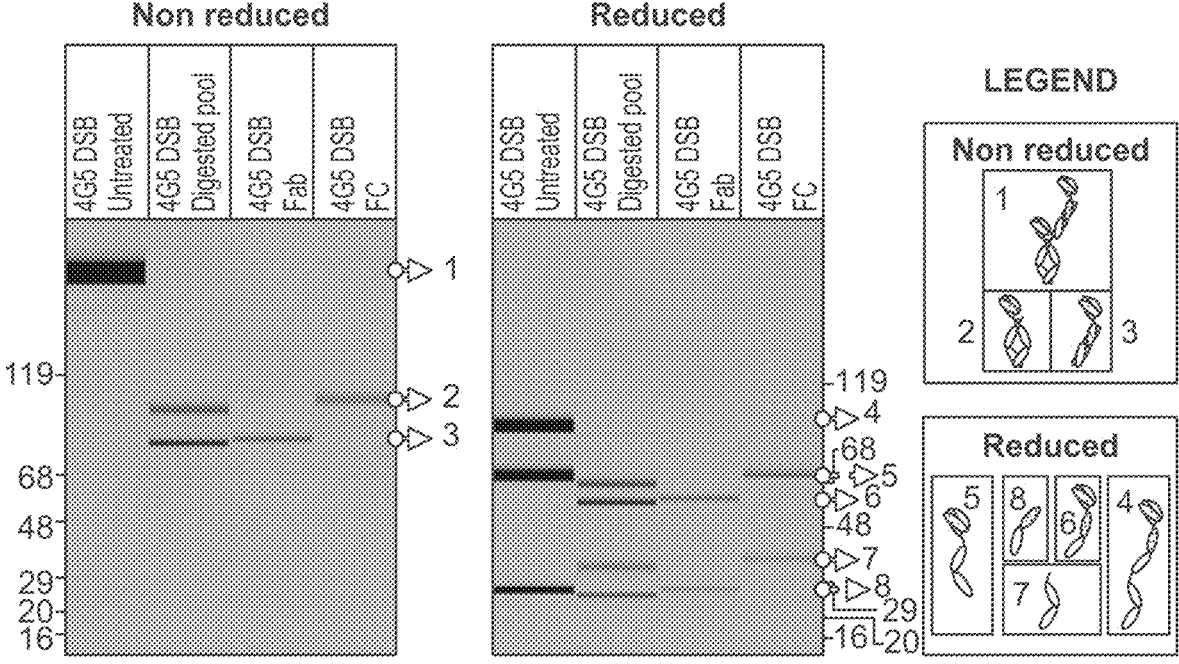

FIG. 50A includes overlayed SEC-HPLC chromatograms for digested Format 4 G5(1C12) bispecific antibody with an engineered VH44/VL100 disulfide bond. FIG. 50B includes reduced and non-reduced gels (CE-SDS) for digested Format 4 G5(1C12) bispecific antibody with an engineered VH44/VL100 disulfide bond.

Figure 51A:
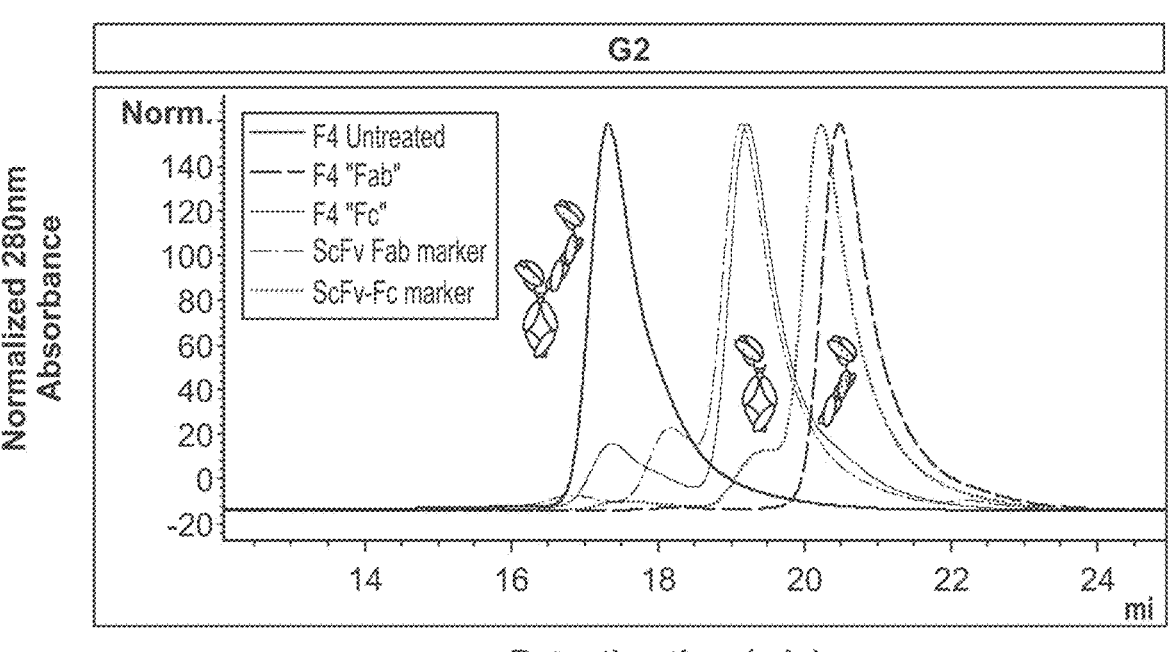
Figure 51B:
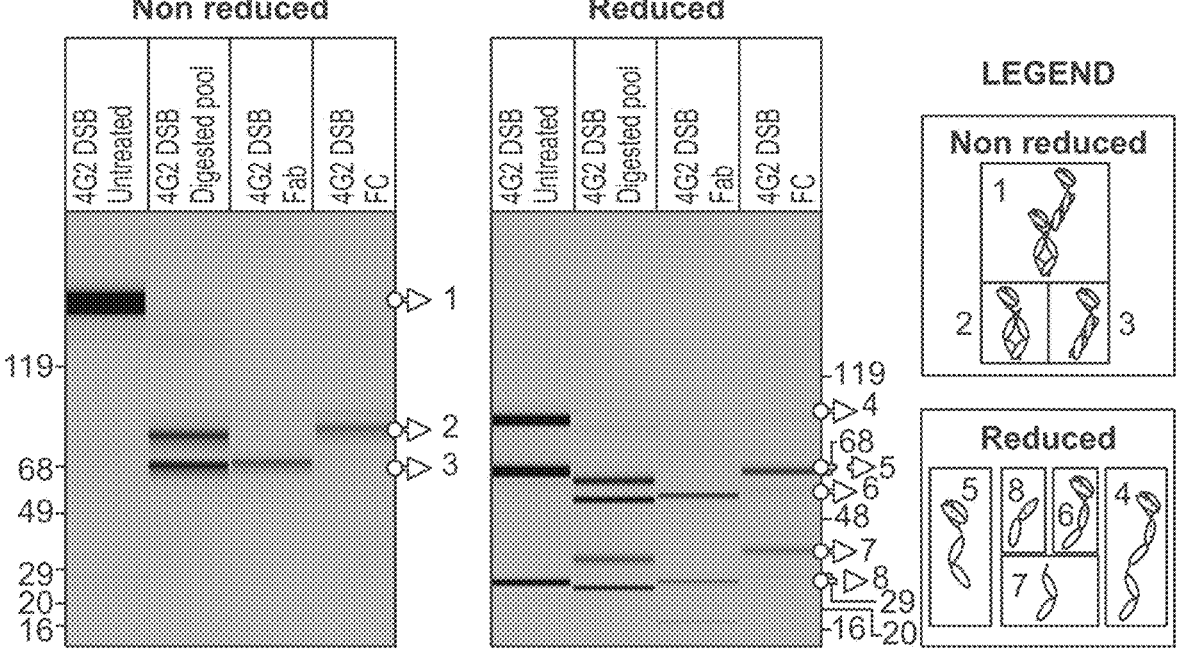

FIG. 51A includes overlayed SEC-HPLC chromatograms for digested Format 4 G2(1H11) bispecific antibody with an engineered VH44/VL100 disulfide bond. FIG. 51B includes reduced and non-reduced gels (CE-SDS) for digested Format 4 G2(1H11) bispecific antibody with an engineered VH44/VL100 disulfide bond.

Figure 52:
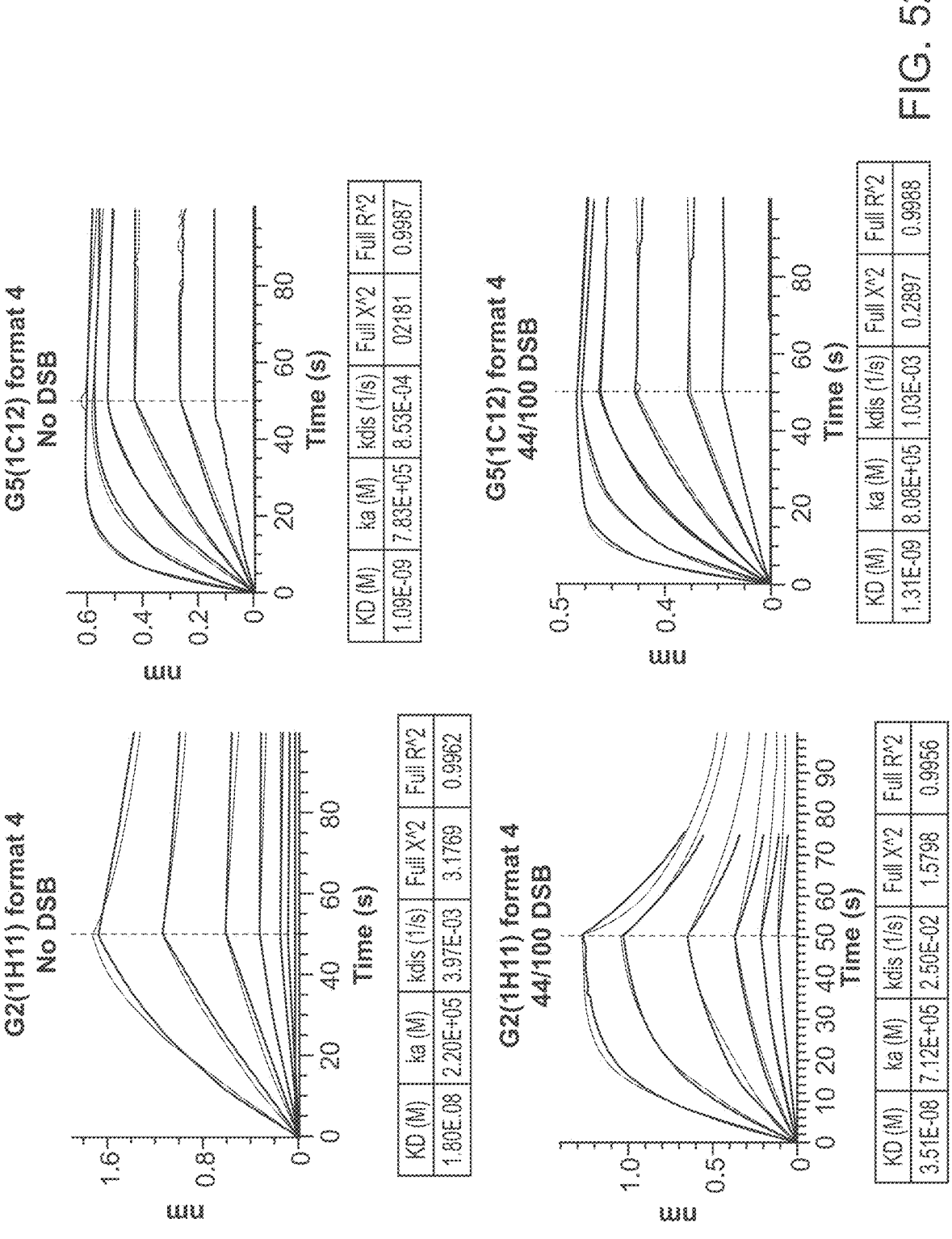

FIG. 52 includes plots showing the BLI results from representative bispecific Format 4 antibodies with and without the engineered VH44/VL100 disulfide bond.

FIG. 53 includes plots showing MSD results from representative bispecific Format 4 antibodies with and without the engineered VH44/VL100 disulfide bond.

FIG. 54 includes plots showing cell binding results from representative bispecific Format 4 antibodies with and without the engineered VH44/VL100 disulfide bond.

FIG. 55 includes plots showing 2D cytotoxicity and spheroid toxicity results from representative G2 Format 4 antibodies with and without the engineered VH44/VL100 disulfide bond.

FIG. 56 includes overlayed SEC-HPLC chromatograms and reduced and non-reduced gels (SDS-PAGE) from digestion of a Format 4 G5(1C12) ABP having a non-shortened linker.

FIG. 57 includes overlayed SEC-HPLC chromatograms and reduced and non-reduced gels (SDS-PAGE) from digestion of a Format 4 G2(1H11) ABP having a non-shortened linker.

FIG. 58 includes overlayed SEC-HPLC chromatograms and reduced and non-reduced gels (SDS-PAGE) from digestion of a Format 4 G5(1C12) ABP having shortened first and second linkers (10 amino acids long).

FIG. 59 includes overlayed SEC-HPLC chromatograms and reduced and non-reduced gels (SDS-PAGE) from digestion of a Format 4 G2(1H11) ABP having shortened first and second linkers (10 amino acids long).

Figure 60:
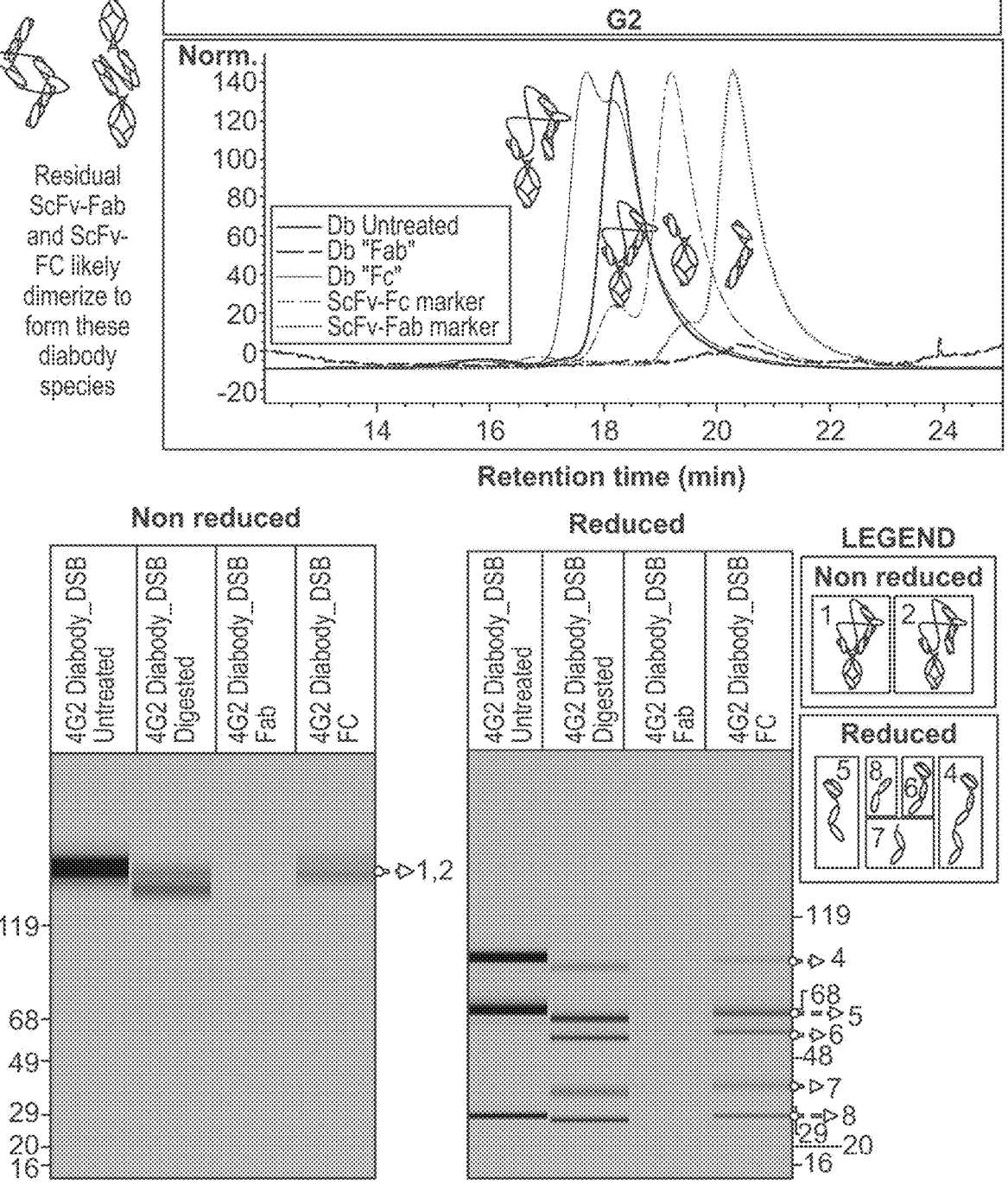

FIG. 60 includes an SEC-HPLC plot and reduced and non-reduced gels (CE-SDS) from digestion of a Format 4 G2(1H11) ABP having (i) shortened first and second linkers (10 amino acids long) and (ii) engineered VH44/VL100 disulfide bond.

Figure 61:
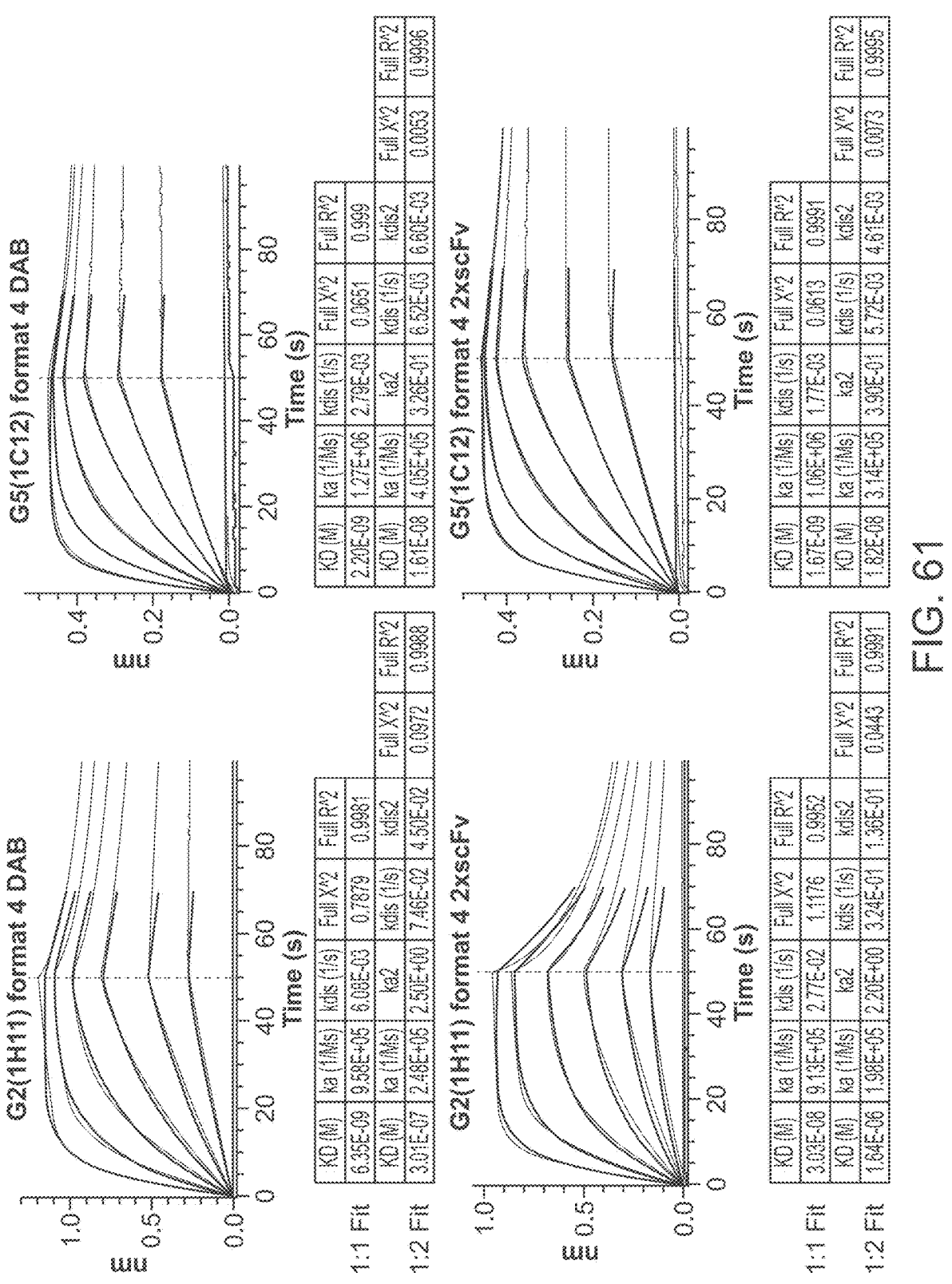

FIG. 61 includes plots showing the BLI results from representative bispecific Format 4 antibodies with ("DAB") and without (2×scFv) shortened first and second linkers (10 amino acids long).

FIG. 62 shows the cell binding results from the indicated G2 and G5 Format 4 ABPs.

FIG. 63 shows the cytotoxicity results for the indicated G2 and G5 Format 4 ABPs.

FIG. 64 includes schematic of Format 4 diabody constructs with disulfide bridge stabilization outside variable domains.

DETAILED DESCRIPTION

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise. For example, a multispecific ABP "comprising a diabody" includes a multispecific ABP "consisting of a diabody" and a multispecific ABP "consisting essentially of a diabody."

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s)±one standard deviation of that value(s).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antigen binding protein" or "ABP" is used herein in its broadest sense and includes certain types of molecules comprising one or more antigen-binding domains that specifically bind to an antigen or epitope.

In some embodiments, the ABP comprises an antibody. In some embodiments, the ABP consists of an antibody. In some embodiments, the ABP consists essentially of an antibody. An ABP specifically includes intact antibodies (e.g., intact immunoglobulins), antibody fragments, ABP fragments, and multispecific antibodies. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment. In some embodiments, a CAR comprises an ABP provided herein. An "HLA-PEPTIDE ABP," "anti-HLA-PEPTIDE ABP," or "HLA-PEPTIDE-specific ABP" is an ABP, as provided herein, which specifically binds to the antigen HLA-PEPTIDE. An ABP includes proteins comprising one or more antigen-binding domains that specifically bind to an antigen or epitope via a variable region, such as a variable region derived from a B cell (e.g., antibody).

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain (VH) regions capable of specifically binding the antigen, single chain antibody fragments, including single chain variable fragments (scFv), and single domain antibodies (e.g., sdAb, sdFv, nanobody, camelid VHH, engineered or evolved human VH that does not require pairing to VL for solubility or activity) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

"Reference antigen binding protein" or "reference ABP" refers to an ABP that, for example, having specificity for a target antigen other than HLA-PEPTIDE target, wherein the HLA Class I molecule is HLA-A*01:01 and the HLA-restricted peptide comprises the sequence NTDNNLAVY (SEQ ID NO: 214). In some embodiments, a reference ABP refers to an ABP having specificity for an HLA-PEPTIDE target, wherein the HLA Class I molecule is HLA-A*01:01 and the HLA-restricted peptide comprises the sequence NTDNNLAVY (SEQ ID NO: 214), however the same ABP has affinity for validate OTLAs (see Examples). In some embodiments, a reference ABP is a Format 4 ABP having an L1 linker and/or L2 linker of a length outside of the range 10-15. In some embodiments, a reference ABP refers to a Format 4 ABP having an L1 linker and/or L2 linker less than 10 amino acids or less than 9 amino acids. In some embodiments, a reference ABP refers to a Format 4 ABP having an L1 linker and/or L2 linker greater than 15 amino acids.

As used herein, "variable region" refers to a variable nucleotide sequence that arises from a recombination event, for example, it can include a V, J, and/or D region of an immunoglobulin.

The term "antigen-binding domain" means the portion of an ABP that is capable of specifically binding to an antigen or epitope. One example of an antigen-binding domain is an antigen-binding domain formed by an antibody $V_H$-$V_L$ dimer of an ABP. Another example of an antigen-binding domain is an antigen-binding domain formed by diversification of certain loops from the tenth fibronectin type III domain of an Adnectin. An antigen-binding domain can include antibody CDRs 1, 2, and 3 from a heavy chain in that order; and antibody CDRs 1, 2, and 3 from a light chain in that order.

The antibody $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three antibody CDRs and four FRs, arranged in the following order (from N-terminus to C-terminus): FR1-CDR1-FR2-CDR2-FR3-CDR3-FR4. The antibody CDRs are involved in antigen binding, and influence antigen specificity and binding affinity of the ABP. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, β, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of an antibody CDR can be determined by one of skill in the art using any of a number of known numbering schemes, including those described by Kabat et al., supra ("Kabat" numbering scheme): Al-Lazikani et al., 1997, *J. Mol. Biol.*, 273:927-

948 ("Chothia" numbering scheme): MacCallum et al., 1996, *J. Mol. Biol.* 262:732-745 ("Contact" numbering scheme): Lefranc et al., *Dev. Comp. Immunol.,* 2003, 27:55-77 ("IMGT" numbering scheme); and Honegge and Pluckthun, *J. Mol. Biol.,* 2001, 309:657-70 ("AHo" numbering scheme): each of which is incorporated by reference in its entirety.

Table A provides the positions of antibody LCDR1, LCDR2, LCDR3, HCDR1, HCDR2, and HCDR3 as identified by the Kabat and Chothia schemes. For HCDR1, residue numbering is provided using both the Kabat and Chothia numbering schemes.

Antibody CDRs may be assigned, for example, using ABP numbering software, such as Abnum, available at www.bioinf.org.uk/abs/abnum/, and described in Abhinandan and Martin, *Immunology,* 2008, 45:3832-3839, incorporated by reference in its entirety.

TABLE A

| Residues in CDRs according to Kabat and Chothia numbering schemes | | |
|---|---|---|
| CDR | Kabat | Chothia |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an ABP heavy chain constant region (e.g., as reported in Kabat et al., supra). Unless stated otherwise, the EU numbering scheme is used to refer to residues in ABP heavy chain constant regions described herein.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

An "ABP fragment" comprises a portion of an intact ABP, such as the antigen-binding or variable region of an intact ABP. ABP fragments include, for example, Fv fragments, Fab fragments, F(ab')$_2$ fragments, Fab' fragments, scFv (sFv) fragments, and scFv-Fc fragments. ABP fragments include antibody fragments. Antibody fragments can include Fv fragments, Fab fragments, F(ab')$_2$ fragments, Fab' fragments, scFv (sFv) fragments, and scFv-Fc fragments "Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length ABP.

"F(ab')$_2$" fragments contain two Fab' fragments joined, near the hinge region, by disulfide bonds. F(ab')$_2$ fragments may be generated, for example, by recombinant methods or by pepsin digestion of an intact ABP. The F(ab') fragments can be dissociated, for example, by treatment with ß-mercaptoethanol.

"Single-chain Fv" or "sFv" or "scFv" fragments comprise a VH domain and a VL domain in a single polypeptide chain. The VH and VL are generally linked by a peptide linker. See Plückthun A. (1994). Any suitable linker may be used. In some embodiments, the linker is a (GGGGS)$_n$ (SEQ ID NO: 217). In some embodiments, n=1, 2, 3, 4, 5, or 6. See ABPs from *Escherichia coli.* In Rosenberg M. & Moore G. P. (Eds.), *The Pharmacology of Monoclonal ABPs* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "Fc region" or "Fc" refers to the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.,* 2010, 125:S41-52, incorporated by reference in its entirety. The Fc region may be a naturally occurring Fc region, or an Fc region modified as described in the art or elsewhere in this disclosure.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an ABP. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD3 (e.g., Tetranectins), Fynomers, and (LDLR-A module) (e.g., Avimers). Additional information on alternative scaffolds is provided in Binz et al., *Nat. Biotechnol.,* 2005 23:1257-1268: Skerra, *Current Opin. in Biotech.,* 2007 18:295-304; and Silacci et al., *J. Biol. Chem.,* 2014, 289:14392-14398: each of which is incorporated by reference in its entirety. An alternative scaffold is one type of ABP.

A "multispecific ABP" is an ABP that comprises two or more different antigen-binding domains that collectively specifically bind two or more different epitopes. The two or more different epitopes may be epitopes on the same antigen (e.g., a single HLA-PEPTIDE molecule expressed by a cell) or on different antigens (e.g., different HLA-PEPTIDE molecules expressed by the same cell, or a HLA-PEPTIDE molecule and a non-HLA-PEPTIDE molecule). In some aspects, a multispecific ABP binds two different epitopes (i.e., a "bispecific ABP"). In some aspects, a multispecific ABP binds three different epitopes (i.e., a "trispecific ABP").

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

As used, the term "diabody" refers to a dimerized antigen binding region (ABR) comprising a heavy chain variable domain ($V_H$) and a light chain variable domain ($V_L$). Diabodies have two antigen binding sites and can be bispecific or monospecific. (See, for example, Holliger and Winter, Cancer Immunol Immunother, 1997, 45:128-130 and Proc. Natl. Acad. Sci. USA, 1993, 90:6444-6448, each of which is incorporated by reference in its entirety).

As used, the term "interacts" refers to the non-covalent pairing of VH and VL sequences either within an scFv or between a VH domain and VL domain of an ABR or set of ABRs, e.g., to form an antigen binding site. It is also contemplated that the VH domain from a first ABR can interact with the VL domain from another ABR. For example, in FIG. 4A, in each of the ABRs, a $V_H$ is shown interacting with a $V_L$ from the same polypeptide (intramolecular interaction). In the diabody of FIG. 5 (right), a $V_H$ from the first ABR (in the first polypeptide) is shown interacting with a $V_L$ from the second ABR (in the second polypeptide), while a $V_L$ from the first ABR (in the first polypeptide) is shown interacting with a $V_H$ from the second ABR (in the second polypeptide). These noncovalent interactions that facilitate the pairing can consist of hydrophobic, electrostatic, and van der Waals interactions. Further, in some embodiments, these noncovalent interactions may be stabilized by introduction of 2 Cys residues to form a disulfide bond (DSB) holding VH and VL together covalently. In some embodiments, this involves a Cys introduced in VH at position 44 according to Kabat numbering and a second Cys at VL100 according to Kabat numbering.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

As used, the term "tumor antigen" refers to refers to an antigen or portion thereof expressed only by a tumor or at a level that is higher than that expressed by normal tissue. In some embodiments, tumor antigens are exclusively expressed on tumor cells. In some embodiments, the presence or expression of a tumor antigen on normal cells is negligible. In some embodiments, these tumor antigens are expressed in a significantly higher amount on tumor cells than on normal cells. In some embodiments, the tumor antigen is an HLA-PEPTIDE.

As used, the term "target antigen" refers to an antigen or portion thereof capable of stimulating an immune response and/or being bound by a binding domain of an immune cell. Target antigens can be bound by the antigen binding site of an antibody or antibody fragment. The term target antigen encompasses, for example, cell surface molecules present on effector cells such as T cells or NK cells. In some embodiments, the target antigen is CD3. The term target antigen also encompasses tumor antigens, as described supra.

"T cells" refer to a type of lymphocyte that naturally expresses a T-cell receptor on its cell surface and plays a central role in the immune response (e.g., immune-related cell death). They differentiate into several distinct types of T cells (e.g., helper, regulatory, or cytotoxic T cells, and memory T cells). Effector T cells, for example, refer to the subset of cytotoxic T cells which are actively involved in eliminating (e.g., killing) different types of cells that are infected with pathogens, or are otherwise damaged or dysfunctional.

"Natural killer cells" or "NK cells" are a component of the innate immune system and make up approximately 15% of circulating lymphocytes. NK cells infiltrate virtually all tissues, killing target cells by means similar to cytotoxic T cells—i.e., via cytolytic granules that contain perforin and granzymes as well as via death receptor pathways. Activated NK cells also secrete inflammatory cytokines and chemokines that promote the recruitment of other leukocytes to the target tissue.

As used herein, the term "cytotoxicity" refers to the ability of antibodies, antibody fragments, and ABPs as described herein to mediate or facilitate cell death or elimination through an effector cell of the immune system (e.g., T cells and/or NK cells). For example, the term "cytotoxicity" can refer to a process by which an ABP binds an effector cell (e.g., an anti-CD3 binding domain of the ABP binds to CD3 present on an effector cell (e.g., a T cell)) and a tumor antigen binding domain of the ABP binds a target cell expressing an antigen such as a tumor antigen (e.g., a pHLA binding domain binds to a target cell expressing pHLA). Thereafter, the effector cell facilitates cell death and/or destruction (e.g., via apoptosis or lysis) of the target cell. Cytotoxic T cells, for example, can destroy the target cell through release of various molecules such as cytokines, perforin, granzymes, and proteases, which cause the target cell to undergo cell death (e.g., apoptosis). In some embodiments, the term cytotoxicity also encompasses antibody-dependent cellular cytotoxicity (also referred to as antibody-dependent cell-mediated cytotoxicity), which is an immune defense mechanism whereby effector cells of the immune system actively lyse a target cell. It is typically driven by Fc bind to Fc receptors.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule. In some aspects, the affinity of a HLA-PEPTIDE ABP for a non-target molecule is less than about 50% of the affinity for HLA-PEPTIDE. In some aspects, the affinity of a HLA-PEPTIDE ABP for a non-target molecule is less than about 40% of the affinity for HLA-PEPTIDE. In some aspects, the affinity of a HLA-PEPTIDE ABP for a non-target molecule is less than about 30% of the affinity for HLA-PEPTIDE. In some aspects, the affinity of a HLA-PEPTIDE ABP for a non-target molecule is less than about 20% of the affinity for HLA-PEPTIDE. In some aspects, the affinity of a HLA-PEPTIDE ABP for a non-target molecule is less than about 10% of the affinity for HLA-PEPTIDE. In some aspects, the affinity of a HLA-PEPTIDE ABP for a non-target molecule is less than about 1% of the affinity for HLA-PEPTIDE. In some aspects, the affinity of a HLA-PEPTIDE ABP for a non-target molecule is less than about 0.1% of the affinity for HLA-PEPTIDE.

The term "$k_d$" ($sec^{-1}$), as used herein, refers to the dissociation rate constant of a particular ABP-antigen interaction. This value is also referred to as the $k_{off}$ value.

The term "$k_a$" ($M^{-1} \times sec^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D = k_d / k_a$. In some embodiments, the affinity of an ABP is described in terms of the $K_D$ for an interaction between such ABP and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular ABP-antigen interaction. $K_A = k_d / k_d$.

An "immunoconjugate" is an ABP conjugated to one or more heterologous molecule(s), such as a therapeutic (cytokine, for example) or diagnostic agent.

"Fc effector functions" refer to those biological activities mediated by the Fc region of an ABP having an Fc region, which activities may vary depending on isotype. Examples of ABP effector functions include C1q binding to activate complement dependent cytotoxicity (CDC), Fc receptor binding to activate ABP-dependent cellular cytotoxicity (ADCC), and ABP dependent cellular phagocytosis (ADCP).

When used herein in the context of two or more ABPs, the term "competes with" or "cross-competes with" indicates that the two or more ABPs compete for binding to an antigen (e.g., HLA-PEPTIDE).

The term "epitope" means a portion of an antigen that specifically binds to an ABP. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an ABP binds can be determined using known techniques for epitope determination such as, for example, testing for ABP binding to HLA-PEPTIDE variants with different point-mutations, or to chimeric HLA-PEPTIDE variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

In some embodiments, the VH and VL of the antibody binding regions (ABRs) in the ABPs of the present disclosure are at least about 90%, about 91%, about 92%, about 93%, about 94%, about 95%, about 96%, about 97%, about 98%, about 99%, about 100% identical to the VH and VL for 31E07 (Table 19). In some embodiments, the VH and VL of the Fab region in the ABP of the present disclosure are at least about 90%, about 91%, about 92%, about 93%, about 94%, about 95%, about 96%, about 97%, about 98%, about 99%, about 100% identical to the VH and VL for hOKT3a (Table 21).

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 10, 15 and 16 are, in some embodiments, considered conservative substitutions for one another.

TABLE B

| Selected groups of amino acids that are considered conservative substitutions for one another, in certain embodiments. | |
| --- | --- |
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE C

| Additional selected groups of amino acids that are considered conservative substitutions for one another, in certain embodiments. | |
| --- | --- |
| Group 1 | A, S, and T |
| Group 2 | D and E |
| Group 3 | N and Q |
| Group 4 | R and K |
| Group 5 | I, L, and M |
| Group 6 | F, Y, and W |

TABLE D

| Further selected groups of amino acids that are considered conservative substitutions for one another, in certain embodiments. | |
| --- | --- |
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, NY. An ABP generated by making one or more conservative substitutions of amino acid residues in a parent ABP is referred to as a "conservatively modified variant."

The term "amino acid" refers to the twenty common naturally occurring amino acids. Naturally occurring amino acids include alanine (Ala: A), arginine (Arg: R), asparagine (Asn: N), aspartic acid (Asp: D), cysteine (Cys: C): glutamic acid (Glu: E), glutamine (Gln: Q), Glycine (Gly: G); histidine (His; H), isoleucine (Ile; I), leucine (Leu: L), lysine (Lys: K), methionine (Met: M), phenylalanine (Phe: F), proline (Pro: P), serine (Ser; S), threonine (Thr: T), tryptophan (Trp: W), tyrosine (Tyr: Y), and valine (Val: V).

The term "protein liability" refers to a possible chemical modification at a particular amino acid, or sequence of amino acids, in a protein that could lead to alterations of biophysical and/or biological properties.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an ABP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an ABP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The terms "nucleic acids" and "polynucleotides" may be used interchangeably herein to refer to polymeric form of nucleotides of any length, either deoxyribonucleotides or ribonucleotides, or analogs thereof. Polynucleotides can include, but are not limited to coding or non-coding regions of a gene or gene fragment, loci (locus) defined from linkage analysis, exons, introns, messenger RNA (mRNA), cDNA, recombinant polynucleotides, branched polynucleotides, plasmids, vectors, isolated DNA, isolated RNA, nucleic acid probes, and primers. A polynucleotide may comprise modified nucleotides, such as methylated nucleotides and nucleotide analogs. Exemplary modified nucleotides include, e.g., 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthioN6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

Formats, Dual ScFv Conformation and Diabody Conformation in ABPs

This application is related to PCT/US2020/015736, filed on Jan. 29, 2020, published as WO2020160189A1; U.S. application Ser. No. 17/426,627, filed Jul. 28, 2021; and PCT/US2021/043796, filed on Jul. 29, 2021, each of which are hereby incorporated by reference in their entirety for all purposes.

The inventors of the present disclosure identified that antibodies (e.g., Format 4 antibodies) can exist in two conformations: (i) dual scFv (Format 4) and (ii) diabody conformation (Format 41). In solution, these antibodies may exist in equilibrium between the two conformations and these two conformations may have different relative properties. For example, the two conformations in a solution may differ in terms of, but not limited to, antibody affinity to a target (e.g., to tumor-associated antigens, receptors expressed on tumor cells, receptors highly expressed on tumor cells, pHLA, etc.), cytotoxicity to diseased cells, pharmacokinetic profiles, immunogenicity, stimulation of anti-drug antibodies, etc. The present disclosure identifies modifications, as described herein, to drive the antibodies towards a single conformation, i.e., either dual scFv conformation or diabody conformation.

Figures 4A, 4B:
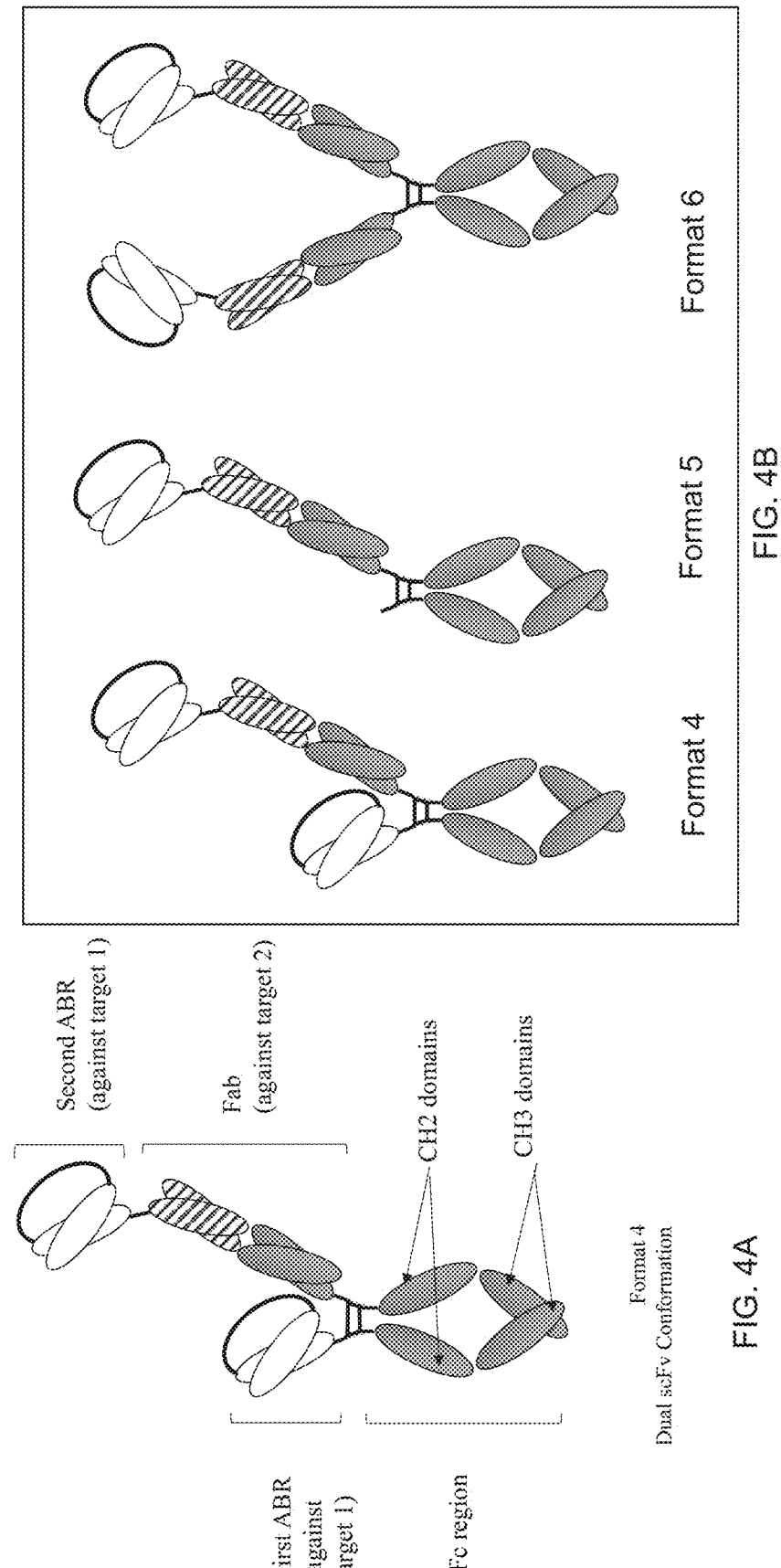
FIG. 4A depicts a Format 4 antibody in dual scFv conformation.
FIG. 4B depicts Format 4, 5, and 6 antibody structures.

Provided herein are Format 4 antibodies, as shown in FIG. 4A. A Format 4 antibody can be described as an ABP comprising three polypeptides, wherein the first polypeptide comprises, in an N→C direction, a first ABR (antigen binding region), a first hinge, a CH2 domain and a CH3 domain. The second polypeptide comprises, in an N→C direction, a VH domain of a Fab region, a CH1 domain of a Fab region, a second hinge, a CH2 domain, and a CH3 domain. The third polypeptide comprises a light chain comprising, in an N→C direction, a VL domain of the Fab region and a CL domain of the Fab region. The first and second ABRs each comprise a VH domain and a VL domain. A second ABR is attached, directly or indirectly, to the N-terminus of the second polypeptide or the third polypeptide. The first and second ABRs each comprise in an N→C direction: (i) a VH domain-a VL domain or (ii) a VL domain-VH domain. In some embodiments, the VH and VL domains of the first ABR interact with each other (shown in FIG. 4A). In some embodiments, the VH and VL domains of the second ABR interact with each other (shown in FIG. 4A). The hinge-CH2-CH3 domains on the first and second polypeptide constitute the Fc region of the ABP. This ABP is referred to herein as a Format 4 antibody in extended conformation, dual scFv conformation or 2×scFv conformation. (See FIG. 4A).

In some embodiments, a Format 4 antibody can be described as an ABP comprising three polypeptides, wherein the first polypeptide comprises, in an N→C direction, a first ABR (antigen binding region), a first hinge, a CH2 domain and a CH3 domain. The second polypeptide comprises, in an N→C direction, a second ABR, a VH domain of a Fab region, a CH1 domain of a Fab region, a second hinge, a CH2 domain, and a CH3 domain. The third polypeptide comprises a light chain comprising, in an N→C direction, a VL domain of the Fab region and a CL domain of the Fab region. The first and second ABRs each comprise a VH domain and a VL domain. The first and second ABRs each comprise in an N→C direction: (i) a VH domain-a VL domain or (ii) a VL domain-VH domain. In some embodiments, the VH and VL domains of the first ABR interact with each other (shown in FIG. 4A). In some embodiments, the VH and VL domains of the second ABR interact with each other (shown in FIG. 4A). The hinge-CH2-CH3 domains on the first and second polypeptide constitute the Fc region of the ABP. This ABP is referred to herein as a Format 4 antibody in extended conformation, dual scFv conformation or 2×scFv conformation. (See FIG. 4A).

In some embodiments, the first ABR comprises, in an N→C direction, a VH domain of the first ABR and a VL domain of the first ABR. In some embodiments, the first ABR comprises, in an N→C direction, a VL domain of the first ABR and a VH domain of the first ABR. In some embodiments, the second ABR comprises, in an N→C direction, a VH domain of the second ABR and a VL domain of the second ABR. In some embodiments, the second ABR comprises in an N→C direction, a VL domain of the second ABR and a VH domain of the second ABR.

In certain embodiments, wherein the ABP is a Format 4 antibody in extended conformation, the ABPs each comprise a first ABR and a second ABR that each specifically bind an epitope of a first target antigen (e.g., G2), a Fab that specifically binds an epitope of an additional target antigen (e.g., a cell surface molecule on an effector cell, e.g. CD3) that is distinct from the first target antigen, and an Fc domain, wherein the ABP comprises a first polypeptide, a second polypeptide, and a third polypeptide, wherein the first polypeptide comprises, in an N→C direction, a first ABR-a hinge-CH2-CH3, wherein the second polypeptide comprises, in an N→C direction, a second ABR-a VH domain of the Fab-a CH1 domain of the Fab-a hinge-CH2-CH3, and wherein the third polypeptide comprises, in an N→C direction, a VL domain of the Fab-a CL domain of the Fab. The VH domain of the first ABR is attached to the VL domain of the first ABR via a first linker (e.g. see L1 of the 2×scFv form in FIG. 5) and the VH domain of the second ABR is attached to the VL domain of the second ABR via a second linker (e.g., see L2 of the 2×scFv form in FIG. 5). Additional linkers shown in FIG. 5 are linker 3 (L3) and linker 4 (L4). L3 attaches the first ABR to the Fc domain. L4 attaches the second ABR to the Fab.

In some embodiments, the first target antigen is an HLA-PEPTIDE target. In some embodiments, the additional target antigen is expressed on an effector cell (e.g. T cells or NK cells). In some embodiments, the additional target antigen is a cell surface molecule expressed on an effector cells (e.g. T cells or NK cells). In some embodiments, the cell surface molecule is CD3, optionally CD3ε.

The present disclosure also provides ABPs comprising three polypeptides, wherein the first polypeptide comprises, in an N→C direction, a first ABR, a first hinge, a CH2 domain, and a CH3 domain. The second polypeptide comprises, in an N→C direction, a second ABR, a VH domain of a Fab region, a CH1 domain of a Fab region, a second hinge, a CH2 domain, and a CH3 domain. The third polypeptide comprises a light chain comprising, in an N→C direction, a VL domain of the Fab region and a CL domain of the Fab region. In this conformation of ABP, the VH domain of the first ABR interacts with the VL domain of the second ABR, while the VH domain of the second ABR interacts with the VL domain of the first ABR, thereby forming a diabody (see FIG. 5). The hinge-CH2-CH3 domains on the first and second polypeptide constitute the Fc region of the ABP. This ABP is referred to herein as a Format 4 antibody in compact conformation or diabody conformation. The diabody conformation is also referred to herein as "circularized conformation" and is shown in FIG. 5.

In some embodiments, the first ABR comprises, in an N→C direction, a VH domain of the first ABR and a VL domain of the first ABR. In some embodiments, the first ABR comprises, in an N→C direction, a VL domain of the first ABR and a VH domain of the first ABR. In some embodiments, the second ABR comprises, in an N→C direction, a VH domain of the second ABR and a VL domain of the second ABR. In some embodiments, the second ABR comprises in an N→C direction, a VL domain of the second ABR and a VH domain of the second ABR.

In certain embodiments, wherein the ABP is a Format 4 antibody in diabody conformation, the VH domain of the first ABR is attached to the VL domain of the second ABR via a first linker (e.g., L1 of the diabody form in FIG. 5) and the VH domain of the second ABR is attached to the VL domain of the first ABR via a second linker (e.g., L2 of the diabody form in FIG. 5).

Also described herein, are Format 5 and Format 6 antibodies, as shown in FIG. 4B and described in International Application No. PCT/US2015/033076, which is incorporated by reference in its entirety.

In some embodiments, Format 4 antibodies exist in equilibrium between two conformations: (i) an extended conformation referred to as dual scFv (or 2×scFv) conformation, and (ii) compact conformation (or diabody conformation).

When a Format 4 antibody is in the dual scFv conformation (shown in FIG. 4A), the VH of the first ABR interacts (pairs) with the VL of the first ABR and the VH of the second ABR interacts with the VL of the second ABR. Alternatively, when the Format 4 antibody is in compact conformation (or diabody conformation), the VH of the first ABR interacts (pairs) with the VL of the second ABR, while the VH of the second ABR interacts with the VL of the first ABR and forms a diabody.

Format 41 antibodies (shown in FIG. 8A) exist stably in diabody conformation in solution (i.e. they do not form dual scFv conformation in solution or there is a negligible fraction that will form dual scFv conformation) and they have shortened L1 and L2 linkers. In some embodiments, the shortened L1 and L2 linkers in Format 41 antibodies can range from 5-15 amino acids in length. In some embodiments, the L1 and L2 linkers consist of 5, 6, 7, 8, 9, 10, 11, 12, 13, 14 or 15 amino acids. In some embodiments, the L1 and L2 linkers consist of 5, 8 or 10 amino acids. In some embodiments, the L1 and L2 linkers consist of 5, 8 or 10 amino acids. In some embodiments, the L1 and L2 linkers consist of 5, 6, 7, 8, 9 or 10 amino acids. In some embodiments, the L1 and L2 linkers consist of a range of amino acids selected from: 5-15, 5-14, 5-13, 5-12, 5-11, 5-10, 5-9, 5-8, 5-7, 5-6, 6-15, 6-14, 6-13, 6-12, 6-11, 6-10, 6-9, 6-8, 6-7, 7-15, 7-14, 7-13, 7-12, 7-11, 7-10, 7-9, 7-8, 8-15, 8-14, 8-13, 8-12, 8-11, 8-10, 8-9, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, 13-15, and 13-14 amino acids in length. In some embodiments, the L1 an L2 linkers consist of less than 5, 6, 7, 8, 9, 10, 11, 12, 13, 14 or 15 amino acids.

Described herein is an isolated ABP comprising a first antigen binding region (ABR) and a second ABR that each specifically bind a first target antigen, a Fab that specifically binds an additional target antigen that is distinct from the first target antigen, and an Fc domain, wherein the ABP comprises a first polypeptide, a second polypeptide, and a third polypeptide, wherein the first polypeptide comprises, in an N→C direction, the first ABR-a first hinge-CH2-CH3, wherein the second polypeptide comprises, in an N→C direction, the second ABR-a variable heavy (VH) domain of the Fab-a CH1 domain of the Fab-a hinge-CH2-CH3, wherein the third polypeptide comprises, in an N→C direction, a variable light chain (VL) domain of the Fab-a CL domain of the Fab; wherein the first ABR and second ABR each comprise, in an N→C direction: (i) a VH domain-a VL domain or (ii) a VL domain-VH domain; wherein the VH domain of the first ABR is attached to the VL domain of the first ABR via a first linker; wherein the VH domain of the second ABR is attached to the VL domain of the second ABR via a second linker; and wherein the first linker and second linker are each about 5-15 amino acids in length.

It is also contemplated that the first and second linker are of different lengths (number of amino acids). See Hudson, P. J., and Kortt, A. A., *Journal of immunological methods* 231.1-2 (1999): 177-189, which is incorporated by reference in its entirety.

Examples of diabodies described in the art are provided in Hollinger et al., *Proc. Natl. Acad. Sci. USA*, 1993, 90:6444-6448; Olafsen, T. et al. *Protein Eng Des Sel.*, 2004, 17(1): 21-27; Wu, A. et al. *Protein Engineering*, 2001, 14(2): 1025-1033; Asano et al., 2004, *Abstract 3P-683, J. Biochem.* 76(8):992; Takemura, S. et al. *Protein Eng.*, 2000, 13(8): 583-588; Baeuerle, P. A. et al. *Cancer Res.*, 2009, 69(12): 4941-4944; U.S. Pat. No. 7,129,330; and International Application No. PCT/US2015/033076, each of which is incorporated by reference in its entirety.

Exemplary sequences of Format 41 diabodies are provided in Table 23. Table 23 provides the linker-Fc sequence of an exemplary first polypeptide chain, minus the first ABR sequence (SEQ ID NO: 48); the linker-Fab-Fc sequence of an exemplary second polypeptide with an OKT3, UCHT1v9 or SP34 CD3 binding fragment (SEQ ID NOs: 49, 51, 53); and the light chain of an exemplary OKT3, UCHT1v9 or SP34 CD3 binding fragment (SEQ ID NOS: 50, 52, 54). The 31E07 ABR (scFv format) is provided as SEQ ID NO: 55. In some embodiments, the first polypeptide comprises the sequence as set forth in SEQ ID NO: 55. In some embodiments, the first polypeptide comprises the sequence as set forth in SEQ ID NOs: 55 and 48. In some embodiments, the second polypeptide comprises the sequence as set forth in SEQ ID NO: 51, 49, or 53. In some embodiments, the second polypeptide comprises the sequence as set forth in SEQ ID NO: 55 and one of 51, 49, or 53. In some embodiments, the second polypeptide comprises the sequence as set forth in SEQ ID NO: 55 and 51. In some embodiments, the third polypeptide comprises the sequence as set forth in SEQ ID NO: 52, 50, or 54. In some embodiments, the isolated ABP comprising a first antigen binding region (ABR) and a second ABR that each specifically bind a first target antigen, a Fab that specifically binds an additional target antigen that is distinct from the first target antigen, and an Fc domain comprises the sequences as set forth in SEQ ID NOs: 48, 49, 50, and 55; 48, 51, 52, and 55, or 48, 53, 54, and 55. In some embodiments, the isolated ABP comprising a first antigen binding region (ABR) and a second ABR that each specifically bind a first target antigen, a Fab that specifically binds an additional target antigen that is distinct from the first target antigen, and an Fc domain comprises the sequences as set forth in SEQ ID NOs: 48, 51, 52, and 55.

Described herein is an isolated ABP comprising a first antigen binding region (ABR) and a second ABR that each specifically bind distinct target antigens, (e.g., a first target antigen and a second target antigen wherein the second target antigen is distinct from the first target antigen), a Fab that specifically binds the first target antigen, and an Fc domain, wherein the ABP comprises a first polypeptide, a second polypeptide, and a third polypeptide, wherein the first polypeptide comprises, in an N→C direction, a variable heavy chain (VH) domain or variable light chain (VL) domain of the second ABR-a VH domain or the VL domain of the first ABR—a first hinge—CH2-CH3, wherein the second polypeptide comprises, in an N→C direction, the VH domain or VL domain of the first ABR—the VH or VL of the second ABR—the VH domain of the Fab-a CH1 domain of the Fab-a second hinge-CH2-CH3, wherein the third polypeptide comprises, in an N→C direction, the VL domain of the Fab-a CL domain of the Fab; wherein the first ABR and second ABR each comprise: (i) a VH domain-a VL domain or (ii) a VL domain-VH domain; wherein the VH domain or VL domain of the first ABR is attached to the VL domain or VH domain of the second ABR via a first linker; wherein the VH domain or VL domain of the second ABR is attached to the VL domain or VH domain of the first ABR via a second linker; and wherein the first linker and second linker are each about 5-15 amino acids in length.

The VH or VL domain of the first ABR on the first polypeptide interacts with the VL or VH domain of the first ABR on the second polypeptide to form a complete ABR molecule. The VH or VL domain of the second ABR on the first polypeptide interacts with the VL or VH domain of the second ABR on the second polypeptide to form a complete ABR molecule. The first ABR binds a first target antigen and the second ABR binds a second target antigen that is distinct from the first target antigen. The Fab binds an additional target antigen that can be the first target antigen and is distict from the second antigen target.

The VH or VL domain of the first ABR on the first polypeptide interacts with the VL or VH domain of the first ABR on the second polypeptide to form a complete ABR molecule. The VH or VL domain of the second ABR on the first polypeptide interacts with the VL or VH domain of the second ABR on the second polypeptide to form a complete ABR molecule. The first ABR binds a first target antigen and the second ABR binds a second target antigen that is distinct from the first target antigen. The Fab binds the first target antigen.

Exemplary sequences of Format 43 antibodies as described in the paragraph above are provided in Table 25.

Table 25 provides the sequence of an exemplary first polypeptide chain comprising the linker-Fc (SEQ ID NO: 48); the linker-Fab-Fc sequence of an exemplary second comprising the VH domains of the E07 antigen binding fragment (SEQ ID NO: 56); the light chain of an exemplary 31E07 antibody (SEQ ID NO: 57); and the mixed ABR comprising the VH or VL of the E07 antigen binding fragment and the VL or VH of the UCHTIV9 CD3 binding fragment (SEQ ID NOs: 58 and 59). In some embodiments, the first polypeptide comprises the sequence as set forth in SEQ ID NO: 48. In some embodiments, the first polypeptide comprises the sequence as set forth in SEQ ID NO: 48 and one of 58 or 59. In some embodiments, the second polypeptide comprises the sequence as set forth in SEQ ID NO: 56. In some embodiments, the second polypeptide comprises the sequence as set forth in SEQ ID NO: 56 and one of 58 or 59. In some embodiments, the third polypeptide comprises the sequence as set forth in SEQ ID NO: 57. In some embodiments, the isolated ABP comprising a first antigen binding region (ABR) that specifically binds a first target antigen and a second ABR that specifically bind a second target antigen, a Fab that specifically binds the first target antigen, and an Fc domain comprises the sequences as set forth in SEQ ID NOs: 48, 56, 57, 58, and 59.

In some aspects, provided herein are isolated antigen binding proteins (ABP) that comprises: a first antigen binding region (ABR) the specifically binds a first target antigen and a second ABR that specifically binds a second target antigen, a Fab that specifically binds an additional target antigen that is distinct from the first target antigen, and an Fc domain, wherein the ABP comprises a first polypeptide, a second polypeptide, and a third polypeptide; wherein the first polypeptide comprises, in an N→C direction, a variable heavy chain (VH) domain or variable light chain (VL) domain of the first ABR-a VH domain or a VL domain of the second ABR-a first hinge-CH2-CH3; wherein the second polypeptide comprises, in an N→C direction, the VH domain or VL domain of the second ABR-the VH domain or VL domain of the first ABR-a VH domain of the Fab-a CH1 domain of the Fab-a second hinge-CH2-CH3, wherein the third polypeptide comprises, in an N→C direction, a VL domain of the Fab-a CL domain of the Fab; wherein the VH domain or VL domain of the first ABR of the first polypeptide is attached to the VL domain or VH domain of the second ABR of the first polypeptide via a first linker; wherein the VH domain or VL domain of the second ABR of the second polypeptide is attached to the VL domain or VH domain of the first ABR via a second linker; wherein the first linker and second linker are each about 5-15 amino acids in length; wherein the first target antigen is an HLA-PEPTIDE target comprising an HLA-restricted peptide complexed with an HLA Class I molecule, wherein the HLA Class I molecule is HLA subtype HLA-A*01:01 and the HLA-restricted peptide comprises the sequence NTDNN-LAVY (SEQ ID NO: 214); and wherein the VH domains of the first ABR and Fab each comprise complementarity-determining regions (CDR) H1 (CDR-H1), CDR-H2, and CDR-H3 comprising SEQ ID NOS: 18, 19, and 20, respectively and wherein the VL domain of the first ABR comprises CDR-L1, CDR-L2, and CDR-L3 comprising SEQ ID NOS:21, 22, and 23, respectively.

Described herein is an isolated ABP comprising a first antigen binding region (ABR) and a second ABR that each specifically bind distinct target antigens, (e.g., a first target antigen and a second target antigen wherein the second target antigen is distinct from the first target antigen), a Fab that specifically binds the first target antigen, and an Fc domain, wherein the ABP comprises a first polypeptide, a second polypeptide, and a third polypeptide, wherein the first polypeptide comprises, in an N→C direction, a variable heavy chain (VH) domain or variable light chain (VL) domain of the first ABR—a VH domain or the VL domain of the second ABR—a first hinge—CH2-CH3, wherein the second polypeptide comprises, in an N→C direction, the VH domain or VL domain of the second ABR—the VH domain or VL domain of the first ABR—the VH domain of the Fab-a CH1 domain of the Fab-a second hinge-CH2-CH3, wherein the third polypeptide comprises, in an N→C direction, the VL domain of the Fab-a CL domain of the Fab; wherein the first ABR and second ABR each comprise: (i) a VH domain-a VL domain or (ii) a VL domain-VH domain; wherein the VH domain or VL domain of the first ABR is attached to the VL domain or VH domain of the second ABR via a first linker; wherein the VH domain or VL domain of the second ABR is attached to the VL domain or VH domain of the first ABR via a second linker; and wherein the first linker and second linker are each about 5-15 amino acids in length.

The VH or VL domain of the first ABR on the first polypetide interacts with the VL or VH domain of the first ABR on the second polypetide to form a complete ABR molecule. The VH or VL domain of the second ABR on the first polypetide interacts with the VL or VH domain of the second ABR on the second polypetide to form a complete ABR molecule. The first ABR binds a first target antigen and the second ABR binds a second target antigen that is distinct from the first target antigen. The Fab binds an additional target antigen that can be the first target antigen and is distict from the second antigen target.

Exemplary sequences of Format 42 antibodies as described in the paragraph above are provided in Table 24. Table 24 provides the linker-Fc sequence of an exemplary first polypeptide chain (SEQ ID NO: 48); the linker-Fab-Fc sequence of an exemplary second polypeptide with a Fab comprising the VH domains of the E07 antigen binding fragment (SEQ ID NO: 56); and the light chain of the E07 antibody (SEQ ID NO: 57). Table 24 also provides the mixed ABR sequence comprising the VH or VL of the E07 antigen binding fragment and the VL or VH of the UCHTIv9 CD3 binding fragment (SEQ ID NO: 59 and 58). In some embodiments, the first polypeptide comprises the sequence as set forth in SEQ ID NO: 48 and 59 or 58. In some embodiments, the second polypeptide comprises the sequence as set forth in SEQ ID NO: 56 and 59 or 58. In some embodiments, the third polypeptide comprises the sequence as set forth in SEQ ID NO: 58. In some embodiments, the isolated ABP comprising a first antigen binding region (ABR) that specifically binds a first target antigen and a second ABR that specifically bind a second target antigen, a Fab that specifically binds the first target antigen, and an Fc domain comprises the sequences as set forth in SEQ ID NOs: 48, 56, 57, 58, and 59.

Linkers

Various linkers are contemplated for use in the ABPs described herein, particularly between the variable domains (variable heavy and variable light domains), between the variable regions and N-terminus of the VH domain of the Fab, and/or between the variable regions and hinge of the first polypeptide. In some embodiments, the linker is a polypeptide linker. In some embodiments, the amino acids in the polypeptide linker are selected with properties that confer flexibility and resist cleavage from proteases (e.g., glycine and serine). In some embodiments, the polypeptide linker comprises one or more glycine and/or serine residues.

In some embodiments, the linker includes one or more glycines. In some embodiments, the linker includes one or more serines. In some embodiments, the linker comprises or consists of glycines and serines. In some embodiments, the linker comprises or consists of a $(GS)_n$ (SEQ ID NO: 218), $(GGS)_n$ (SEQ ID NO: 219), $(GGGS)_n$ (SEQ ID NO: 220), $(GGSG)_n$ (SEQ ID NO: 221), $(GGSGG)_n$ (SEQ ID NO: 222), and $(GGGGS)_n$ (SEQ ID NO: 223) sequence, wherein n is 1, 2, 3, 4, 5, 6, 7, 8, 9, 10, 11, 12, 13, 14, 15, 16, 17, 18, 19, or 20. In some embodiments, the linker comprises or consists of a $(GGGGS)_n$ (SEQ ID NO: 223) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2, or 3. Any combination of glycines and serines in the linker is contemplated. In some embodiments, the linker comprises or consists of a $(GSGGG)_n$ (SEQ ID NO: 224), $(GGSGG)_n$ (SEQ ID NO: 222) or $(GGGSG)_n$ (SEQ ID NO: 225) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2 or 3. In some embodiments, the linker comprises or consists of a $(GGGGG)_n$ (SEQ ID NO: 226) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2, or 3. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20. In some embodiments, n is 1-5; 1-4, 1-3, 1-2, 2-5, 2-4, 2-3, 3-5, 3-4, or 4-5. In some embodiments, n is 1-3. In some embodiments, n is 2-3.

In some embodiments, the VH domain of the first ABR is attached to the VL domain of the second ABR via a first linker ("L1" in FIG. 5); wherein the VH domain of the second ABR is attached to the VL domain of the second ABR via a second linker ("L2" in FIG. 5) and the first and second linkers are polypeptide linkers. In some embodiments, the first and second linkers each consist of $(GGGGS)_N$, wherein N=1-3 (SEQ ID NO: 215). In some embodiments, the first and second linkers each consist of $(GGGGS)_N$, wherein N=2 (SEQ ID NO: 111).

Figure 8A:
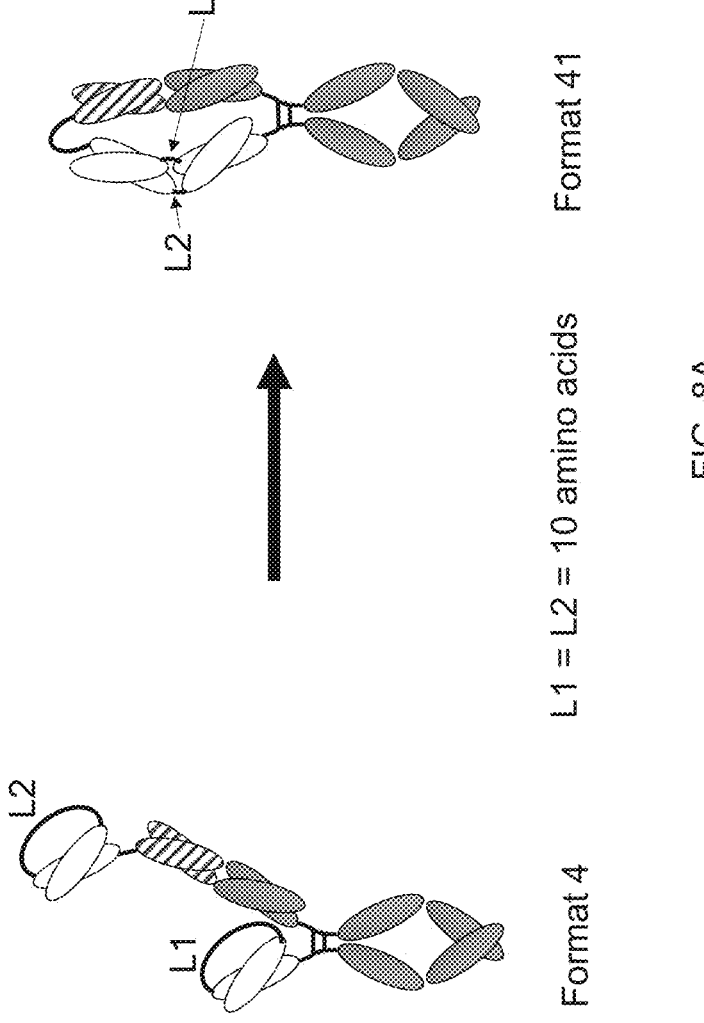
FIG. 8A depicts the stable conformation that resulted from shortening the L1 and L2 linkers to 10 amino acids.

In some embodiments, wherein the VH domain of the first ABR is attached to the VL domain of the second ABR via a first linker ("L1" in FIG. 5), wherein the VH domain of the second ABR is attached to the VL domain of the second ABR via a second linker ("L2" in FIG. 5), wherein the first and second linkers each consist of $(GGGGS)_N$, and wherein $_N$=2 (SEQ ID NO: 111), the resulting conformation is a Format 41 antibody having a diabody conformation (see FIG. 8A).

The present disclosure provides methods of producing a multispecific ABP with a diabody conformation, by creating a Format 4 antibody having shortened linkers between the VH and VL domains of the ABRs, wherein a shortened linker is a peptide linker having less than 16 amino acids (e.g., $(GGGGS)_N$, wherein $_N$=1-3 (SEQ ID NO: 215)), optionally having greater than 4 amino acids or optionally having 5-10 amino acids.

In some embodiments, the present disclosure provides methods of producing a multispecific ABP with a diabody conformation by creating a Format 41 antibody having shortened linkers between the VH and VL domains of the ABRs, wherein a shortened linker is a peptide linker having 10 amino acids. In some embodiments, the 10 amino-acid peptide linker is (GGGGS)$_2$ (SEQ ID NO: 111). One of ordinary skill in the art would appreciate that (GGGGS)$_2$ (SEQ ID NO: 111) can also be referred to as GGGGSGGGGS (SEQ ID NO: 111) or (G4S)$_2$ (SEQ ID NO: 111).

In some embodiments, the present disclosure provides methods of producing an ABP with a diabody conformation by creating a Format 4 antibody having shortened linkers between the VH and VL domains of the ABRs, wherein a shortened linker is a peptide linker having 10 amino acids. In some embodiments, the 10 amino-acid peptide linker is (GGGGS)$_2$ (SEQ ID NO: 111). One of ordinary skill in the art would appreciate that (GGGGS)$_2$ (SEQ ID NO: 111) can also be referred to as GGGGSGGGGS (SEQ ID NO: 111) or (G4S)$_2$ (SEQ ID NO: 111).

Introduction of a shortened linker, as described supra, at the first linker (L1 in FIG. 5) and second linker (L2 in FIG. 5) can shift the equilibrium of 2×scFv-conformed antibodies and diabody conformed antibody towards a higher proportion of diabody conformed antibodies. (See Examples).

Stabilizing Dual scFv Conformation with Disulfide Bonds (DSBs)

The present disclosure provides compostions of APBs internal disulfide bonds (internal DSB) that stabilize the 2×scFv conformation of Format 4 APBs. As used herein, the term "internal DSB" refers to a DSB resulting from cysteines present in an ABP, e.g., in certain variable domains of the ABP.

In some embodiments, the ABP is a Format 4 antibody, wherein the VH domain of the first ABR is attached to the VL domain of the first ABR via a first linker (L1 in FIG. 5): wherein the VH domain of the second ABR is attached to the VL domain of the second ABR via a second linker (L2 in FIG. 5); wherein the VL domain of the first ABR is attached to the hinge in the first polypeptide via a third linker (L3 in FIG. 5); wherein the VL domain of the second ABR is attached to the N-terminus of the second polypeptide or the third polypeptide via a fourth linker (L4 in FIG. 5). In some embodiments, the first linker and the second linker each comprise 20 amino acids. In some embodiments, the first linker and the second linker each comprise 14 amino acids. For example, the first and second linker can each consist of 14, 15, 16, 17, 18, 19, 20, 21, 22, 23, 24, 25, 26, 27, 28, 29 or 30 amino acids. The first and second linker can consist of (GGGGS)$_N$, wherein $_N$=3-10 (SEQ ID NO: 227). The first and second linker can consist of (GGGGS)$_N$, wherein $_N$=4 (SEQ ID NO: 228). In some embodiments, the third linker and the fourth linker each consist of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids. In some embodiments, the third linker and the fourth linker each consist of 10 amino acids. For example, the third and fourth linker can consist of (GGGGS)$_N$, wherein $_N$=2 (SEQ ID NO: 111). In such embodiments, the ABPs exist at an equilibrium between the extended conformation of Format 4 antibody and the diabody conformation of Format 4 antibody.

In some embodiments, when the first and second linker comprise 20 amino acids (optionally comprise 14, 15, or 16 amino acids), the VH domain of the first ABR and/or second ABR further comprises a cysteine (Cys) at amino acid residue 44 of the VH domain according to the Kabat numbering system and wherein the VL domain of the first ABR and/or second ABR comprises a cysteine residue at amino acid residue 100 of the VL domain according to the Kabat numbering system (referred to as H44-L100 in reference to the VH ("H") and VL ("L") domains of the ABRs). By introducing Cys residues at both of these positions, a disulfide bond (DSB) forms that stabilizes the VH/VL interactions within each ABR. This reduces the probability that the two ABRs of the Format 4 antibodies interact to form the alternative diabody conformation. (See Examples). As a result, the 2×scFv conformation is "stabilized". In some embodiments, this results in the absence of diabody-conformed ABPs or a negligible amount of diabody-conformed ABPs.

Other internal disulfide bonds are contemplated in the present ABPs. Non-limiting examples of other disulfide bridge mutations/positions are H105-L43, H110b-L49, H100-L50 and H101-L46. See Weatherill, E. E., et al., *Protein Engineering, Design & Selection* 25.7 (2012): 321-329, which is incorporated by reference in its entirety. Additional potential DSBs that are useful in the ABPs described herein can be calculated using computational modeling.

In some embodiments, in these ABPs with internal DSBs, the first ABR and second ABR bind to an HLA-peptide target with a dissociation constant ($K_D$) less than or equal to 100 nM, as measured by surface plasmon resonance (SPR) technology (e.g., BIACORE®), biolayer interferometry (e.g., FORTEBIO®) or other methods known in the art for measuring affinity. In some embodiments, the first ABR and second ABR bind to an HLA-peptide target with a dissociation constant ($K_D$) less than or equal to about 80 nM, about 82 nM, about 84 nM, about 86 nM, about 88 nM, about 90 nM, about 92 nM, about 94 nM, about 96 nM, about 98 nM, about 100 nM, about 102 nM, about 104 nM, about 106 nM, about 108 nM, about 110 nM, about 112 nM, about 114 nM, about 116 nM, about 118 nM, about 120 nM, as measured by surface plasmon resonance (SPR) technology (e.g., BIACORE®), biolayer interferometry (e.g., FORTEBIO®) or other methods known in the art for measuring affinity. In some embodiments, the antibody that binds to an HLA peptide target has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M).

In some embodiments, in these ABPs with internal DSBs, the Fab binds to a cell surface molecule on an effector cell (e.g. a CD3 target) with a dissociation constant ($K_D$) less than or equal to 500 nM, preferably 20-100 nM, as measured by surface plasmon resonance (SPR) technology (e.g., BIACORE®), biolayer interferometry (e.g., FORTEBIO®) or other methods known in the art for measuring affinity. In some embodiments, the antibody that binds to CD3 target has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M).

In some embodiments, the ABP binds to HLA-peptide targets (e.g. in vitro) at a higher affinity than a reference ABP. In some embodiment, the ABP binds to HLA-peptide targets (e.g. in vitro) at a the same affinity or a lower affinity than a reference ABP. In some embodiments, the ABP binds to HLA-peptide targets (e.g. in vitro) at a the same affinity or a lower affinity than a reference ABP, but has greater product homogeneity and/or stability. Stability, as used here, refers to drug stability as known in the art (e.g., stability in terms of long term storage, serum stability, through freeze-thaw cycle stability, etc.). Stability, as used here, refers to drug stability as known in the art (e.g., stability in terms of long term storage, serum stability, through freeze-thaw cycle stability, etc.). In some embodiments, the ABP binds to a CD3 target on cells at a higher affinity than a reference ABP. In some embodiments, the ABP binds to a CD3 target on cells at a the same or a lower affinity than a reference ABP. In some embodiments, the ABP binds to a CD3 target on cells at a the same or a lower affinity than a reference ABP, but as greater product homogeneity and/or stability. Stability, as used here, refers to drug stability as known in the art (e.g., stability in terms of long term storage, serum stability, through freeze-thaw cycle stability, etc.). As used herein, the term "reference ABP" can refer to a Format 4 antibody similar to the ABP, but without the internal DSB(s). In some embodiments, the reference ABP refers to another monospecific ABP, a Format 3 antibody (as disclosed in International application No. PCT/US2020/15736, incorporated by reference in its entirety), a Format 5 antibody (as shown in FIG. 4B and as disclosed in International application No. PCT/US2020/015736, incorporated by reference in its entirety), a Format 6 antibody (as shown in FIG. 4B), a different type of bispecific or multispecific antibody.

In some embodiments, an ABP described herein having at least one internal DSB results in cytotoxicity once the ABP contacts a cell expressing a tumor antigen (e.g. HLA-peptide). In some embodiments, contacting the ABP with cancer cells results in at least about 10%, 20%, 30%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, cytotoxicity. In some embodiments, a concentration of 0.1 nM, 1 nM, 5 nM or 10 nM of the ABP is sufficient to result in that cytotoxicity upon contacting the ABP with a cancer cell that expresses a tumor antigen (e.g., HLA-peptide) and an effector cell.

In some embodiments, an ABP described herein results in greater cytotoxicity than a reference ABP, as described supra. In some embodiments, an ABP results in similar cytotoxicity to a reference ABP or less cytotoxicity than a reference ABP, as described supra. In some embodiments, the ABP described herein results in similar cytotoxicity to a reference ABP (or less cytotoxicity), but has greater product homogeneity and/or stability. Stability, as used here, refers to drug stability as known in the art (e.g., stability in terms of long term storage, serum stability, through freeze-thaw cycle stability, etc.).

Non-limiting examples of cancer cells that express tumor antigen (e.g. HLA-peptide) include A375 cells and LN229 cells.

Stabilizing Diabodies with Disulfide Bonds and Shortened Linkers

As described supra, the introduction of shortened linkers at the first linker of the first ABR and second linker of the second ABR of the Format 4 antibodies drives diabody formation. In addition, the introduction of an internal DSB can stabilize diabody formation. This benefit of combining the shortened linker with internal DSBs is most notable when the ABP type "breathes" and is prone to fall apart under non-reduced denaturing conditions during proteolytic digestion. As used, the term "breathing" refers to large-scale movements of secondary structures, subunits or domains or the rapid association and disassociation of antibody domains. The introduction of DSBs in the protein can reduces this breathing. (See Makowski L, et al., *J Mol Biol.* 2008: 375(2):529-546, which is incorporated herein by reference in its entirety).

In some embodiments, where the ABP comprises a first linker and a second linker that are each a shortened linker, as described supra, the VH domain of the first ABR and/or second ABR further comprises a cysteine (Cys) at amino acid residue 44 of the VH domain according to the Kabat numbering system and wherein the VL domain of the first ABR and/or second ABR comprises a cysteine residue at amino acid residue 100 of the VL domain according to the Kabat numbering system. The cysteine mutations that form this disulfide bond are herein referred to as "H44/L100," "VH44/VL100," "DSB44/100," "H44-L100" or any other term known in the art to describe that mutation. By introducing Cys residues at both of these positions, a disulfide bond (DSB) forms that stabilizes the diabody conformation. This reduces the probability that the complexes or fragments will dissociate under non-reducing denaturing conditions during proteolytic digestion (See Examples). As a result, the diabody conformation is "stabilized". In some embodiments, this results in the absence of 2×scFv-conformed ABPs or a negligible amount of 2×scFv-conformed ABPs.

In some embodiments, in these ABPs that combine the shortened first and second linkers with internal DSBs, the first ABR and second ABR bind to an HLA-peptide target with a dissociation constant ($K_D$) less than or equal to 100 nM, as measured by surface plasmon resonance (SPR) technology (e.g., BIACORE®), biolayer interferometry (e.g., FORTEBIO®) or other methods known in the art for measuring affinity. In some embodiments, the first ABR and second ABR bind to an HLA-peptide target with a dissociation constant ($K_D$) less than or equal to about 80 nM, about 82 nM, about 84 nM, about 86 nM, about 88 nM, about 90 nM, about 92 nM, about 94 nM, about 96 nM, about 98 nM, about 100 nM, about 102 nM, about 104 nM, about 106 nM, about 108 nM, about 110 nM, about 112 nM, about 114 nM, about 116 nM, about 118 nM, about 120 nM, as measured by surface plasmon resonance (SPR) technology (e.g., BIACORE®), biolayer interferometry (e.g., FORTEBIO®) or other methods known in the art for measuring affinity. In some embodiments, the antibody that binds to an HLA peptide target has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M).

In some embodiments, in these ABPs that combine the shortened first and second linkers with internal DSBs, the Fab binds to CD3 target with a dissociation constant ($K_D$) less than or equal to 500 nM, preferably 20-100 nM, as measured by surface plasmon resonance (SPR) technology (e.g., BIACORE®), biolayer interferometry (e.g., FORTEBIO®) or other methods known in the art for measuring affinity. In some embodiments, the antibody that binds to CD3 target has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M).

In some embodiments, the ABP binds to HLA-peptide targets (e.g. in vitro) at a higher affinity than a reference ABP. In some embodiment, the ABP binds to HLA-peptide targets (e.g. in vitro) at a the same affinity or a lower affinity than a reference ABP. In some embodiments, the ABP binds to HLA-peptide targets (e.g. in vitro) at a the same affinity or a lower affinity than a reference ABP, but has greater product homogeneity and/or stability. Stability, as used here, refers to drug stability as known in the art (e.g., stability in terms of long term storage, serum stability, through freeze-thaw cycle stability, etc.). In some embodiments, the ABP binds to a CD3 target on cells at a higher affinity than a reference ABP. In some embodiments, the ABP binds to a CD3 target on cells at a the same or a lower affinity than a reference ABP. In some embodiments, the ABP binds to a CD3 target on cells at a the same or a lower affinity than a reference ABP, but as greater product homogeneity and/or stability. Stability, as used here, refers to drug stability as known in the art (e.g., stability in terms of long term storage, serum stability, through freeze-thaw cycle stability, etc.). As used herein, the term "reference ABP" can refer to a Format 4 antibody similar to the ABP, but without the internal DSB(s) and/or the shortened first and second linkers. In some embodiments, the reference ABP refers to another monospecific ABP, a Format 3 antibody (as as disclosed in International application No. PCT/US2020/15736, incorporated by reference in its entirety), a Format 5 antibody (as shown in FIG. 4B and as disclosed in International application No. PCT/US2020/15736, incorporated by reference in its entirety), a Format 6 antibody (as shown in FIG. 4B), a different type of bispecific or multispecific antibody.

In some embodiments, the ABP described herein has similar affinity to CD3 and/or pHLA to a reference ABP, but has greater product homogeneity and/or stability. Stability, as used here, refers to drug stability as known in the art (e.g., stability in terms of long term storage, serum stability, through freeze-thaw cycle stability, etc.).

In some embodiments, an ABP described herein having shortened first and second linkers and internal DSBs results in cytotoxicity once the ABP contacts a cell expressing a tumor antigen (e.g. HLA-peptide) and an effector cell. In some embodiments, contacting the ABP with cancer cells results in at least about 10%, 20%, 30%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, cytotoxicity. In some embodiments, a concentration of 0.1 nM, 1 nM, 5 nM or 10 nM of the ABP is sufficient to result in that cytotoxicity upon contacting the ABP with the a cancer cell that expresses a tumor antigen (e.g., HLA-peptide) and an effector cell.

In some embodiments, an ABP described herein results in greater cytotoxicity than a reference ABP, as described supra. In some embodiments, an ABP results in similar cytotoxicity to a reference ABP or less cytotoxicity than a reference ABP, as described supra. In some embodiments, the ABP described herein results in similar cytotoxicity to a reference ABP (or less cytotoxicity), but has greater product homogeneity and/or stability. Stability, as used here, refers to drug stability as known in the art (e.g., stability in terms of long term storage, serum stability, through freeze-thaw cycle stability, etc.).

Non-limiting examples of cancer cells that express tumor antigen (e.g. HLA-peptide) include A375 cells and LN229 cells.

External DSBs

It is also contemplated that the ABPs described supra comprise an external DSB in place of or in addition to the internal DSBs. In some embodiments, this external DSB confers the same benefits as the internal DSBs (e.g. homogeneity, stability, affinity to target antigens, cytotoxicity, etc.). As used, the term "external DSB" refers to DSBs that result from Cys residues outside of the ABRs, for example in linkers 3 and 4, in the Fab region or in the Fc region of the ABPs. Non-limiting examples of cysteine mutations that result in external DSBs in the ABPs described herein are provided in Table 17 and 18 (see Examples).

In some embodiments, the introduction of external DSBs stabilizes a Format 4 ABP, as described herein, in either the 2×scFv conformation or the diabody conformation. In some embodiments, the introduction of an external DSB increases the affinity of the ABP comprising that external DSB to a target antigen (e.g. pHLA, CD3) relative to a reference ABP. In some embodiments, the affinity of the ABP with the external DSB(s) is similar to that of the reference ABP, but the ABP having the external DSB(s) exhibits greater product homogeneity and/or stability. Stability, as used here, refers to drug stability as known in the art (e.g., stability in terms of long term storage, serum stability, through freeze-thaw cycle stability, etc.).

In some embodiments, the introduction of an external DSB in an ABP increases the cytotoxicity of the ABP relative to a reference ABP. For example, when the ABP having an external DSB contacts a cancer cell or a virally-infected cell, in the presence of an effector cell, the contacting results in greater cytotoxicity than a reference ABP. In some embodiments, the cytotoxicity of the ABP with the external DSB(s) is similar or lower compared to that of the reference ABP, but the ABP having the external DSB(s) exhibits greater product homogeneity and/or stability. Stability, as used here, refers to drug stability as known in the art (e.g., stability in terms of long term storage, serum stability, through freeze-thaw cycle stability, etc.).

As used herein, the term "reference ABP" refers to a Format 4 ABP lacking an external DSB or having a different number of external DSBs than the ABP claimed or as disclosed herein. In some embodiments, the reference ABP refers to another monospecific ABP, a Format 3 antibody (see International application No. PCT/US2020/15736, incorporated by reference in its entirety), a Format 5 antibody (see FIG. 4B and as disclosed in International application No. PCT/US2020/15736, incorporated by reference in its entirety), a Format 6 antibody (as shown in FIG. 4B), a different type of bispecific or multispecific antibody.

In some embodiments, the ABP having an external DSB is a covalent diabody or 4-chain covalent diabody (e.g., as shown in FIG. 64; see Examples).

Cluster of Differentiation 3 (CD3)

In some embodiments, the present disclosure provides an antigen binding protein (ABPs) comprising variable regions (e.g., in the Fab region) that bind to a cell surface molecule present on T cells, for example, cluster of differentiation 3 (CD3). CD3 is a protein complex and T cell co-receptor that is involved in activating both the cytotoxic T cell (CD8+ naive T cells) and T helper cells (CD4+ naive T cells). As used herein, the term "cluster of differentiation 3" or "CD3" refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3θ or CD3γ), as well as any form of CD3 that results from processing in the cell. The term also encompasses naturally occurring variants of CD3, including, for example, splice variants or allelic variants. CD3 includes, for example, human CD3θ protein (NCBI RefSeq No: NP_000724), which is 207 amino acids in length, and human CD3γ protein (NCBI RefSeq No: NP_000064), which is 182 amino acids in length.

HLA-PEPTIDE ABPs

Provided herein are ABPs, e.g., ABPs that specifically bind to an HLA-PEPTIDE target, wherein the HLA-PEPTIDE target comprises an HLA-restricted peptide complexed with an HLA Class I molecule, wherein the HLA-restricted peptide is located in the peptide binding groove of an α1/α2 heterodimer portion of the HLA Class I molecule, and wherein the HLA-PEPTIDE target corresponds to tumor-specific gene product KKLC-1.

In some embodiments of the HLA-PEPTIDE target, the HLA Class I molecule is HLA-A*01:01 and the HLA-restricted peptide comprises the sequence NTDNNLAVY (SEQ ID NO: 214). In some embodiments, the HLA Class I molecule is HLA-A*01:01 and the HLA-restricted peptide consists essentially of the sequence NTDNNLAVY (SEQ ID NO: 214). In some embodiments, the HLA Class I molecule is HLA-A*01:01 and the HLA-restricted peptide consists of the sequence NTDNNLAVY (SEQ ID NO: 214).

In some embodiments, the ABP is an ABP that selectively binds HLA-PEPTIDE target A*01:01_NTDNNLAVY (SEQ ID NO: 214). HLA-PEPTIDE target A*01:01 NTDNN-LAVY (SEQ ID NO: 214), also referred to herein as "G2", refers to an HLA-PEPTIDE target comprising the HLA-restricted peptide NTDNNLAVY (SEQ ID NO: 214) complexed with the HLA Class I molecule A*01:01, wherein the HLA-restricted peptide is located in the peptide binding groove of an α1/α2 heterodimer portion of the HLA Class I molecule. In some embodiments, the restricted peptide is from tumor-specific gene product KKLC-1.

The HLA-PEPTIDE target may be expressed on the surface of any suitable target cell including a tumor cell.

In some embodiments, the ABP does not bind HLA class I in the absence of the HLA-restricted peptide. In some embodiments, the ABP does not bind the HLA-restricted peptide in the absence of human MHC class I. In some embodiments, the ABP binds tumor cells presenting human MHC class I being complexed with the HLA-restricted peptide. In some embodiments, the HLA restricted peptide is a tumor antigen characterizing the cancer.

An ABP can bind to each portion of an HLA-PEPTIDE complex (i.e., HLA and peptide representing each portion of the complex), which when bound together form a novel target and protein surface for interaction with and binding by the ABP, distinct from a surface presented by the peptide alone or HLA subtype alone. Generally the novel target and protein surface formed by binding of HLA to peptide does not exist in the absence of each portion of the HLA-PEPTIDE complex.

In some embodiments, an ABP specific for HLA-PEPTIDE target A*01:01_NTDNNLAVY (SEQ ID NO: 214) (G2) selectively binds G2 with greater affinity as compared to an off-target HLA-PEPTIDE complex. The off-target HLA-PEPTIDE complex may comprise an off-target restricted peptide complexed with an HLA Class I molecule, wherein the HLA-restricted peptide is located in the peptide binding groove of an α1/α2 heterodimer portion of the HLA Class I molecule.

In some embodiments, the HLA Class I molecule of the off-target HLA-PEPTIDE is HLA subtype A*01:01.

In some embodiments, the restricted peptide of the off-target HLA-PEPTIDE comprises a sequence that has no more than 5 amino acid mismatches from the G2 target restricted peptide NTDNNLAVY (SEQ ID NO: 214).

In some embodiments, the restricted peptide of the off-target HLA-PEPTIDE is 5-14 amino acids in length. In some embodiments, the restricted peptide of the off-target HLA-PEPTIDE is 7-12 amino acids in length. In some embodiments, the restricted peptide of the off-target HLA-PEPTIDE is 8-10 amino acids in length. In some embodiments, the restricted peptide of the off-target HLA-PEPTIDE is 9 amino acids in length.

In some embodiments, the restricted peptide of the off-target HLA-PEPTIDE is expressed in normal human tissue as indicated by the public GTEx database.

In some embodiments, the restricted peptide of the off-target HLA-PEPTIDE is derived from the gene product PTS, DSG3, DSG4, KDM7A, or ICE1. In particular embodiments, the restricted peptide of the off-target HLA-PEPTIDE is derived from the gene product PTS.

In some embodiments, the restricted peptide of the off-target HLA-PEPTIDE comprises the sequence ETDN-NIVVY (SEQ ID NO: 204), YTDNWLAVY (SEQ ID NO: 152), GTDNWLAQY (SEQ ID NO: 203), PTDENLARY (SEQ ID NO: 205), or NTDNLLTEY (SEQ ID NO: 206). In some embodiments, the restricted peptide of the off-target HLA-PEPTIDE consists essentially of the sequence ETDN-NIVVY (SEQ ID NO: 204), YTDNWLAVY (SEQ ID NO: 152), GTDNWLAQY (SEQ ID NO: 203), PTDENLARY (SEQ ID NO: 205), or NTDNLLTEY (SEQ ID NO: 206). In some embodiments, the restricted peptide of the off-target HLA-PEPTIDE consists of the sequence ETDNNIVVY (SEQ ID NO: 204), YTDNWLAVY (SEQ ID NO: 152), GTDNWLAQY (SEQ ID NO: 203), PTDENLARY (SEQ ID NO: 205), or NTDNLLTEY (SEQ ID NO: 206).

In some embodiments, the off-target HLA-PEPTIDE is HLA-A*01:01_ETDNNIVVY (SEQ ID NO: 204), HLA-A*01:01_YTDNWLAVY (SEQ ID NO: 152), HLA-A*01:01_GTDNWLAQY (SEQ ID NO: 203), HLA-A*01:01_PT-DENLARY (SEQ ID NO: 205), or HLA-A*01:01_NTDNLLTEY (SEQ ID NO: 206).

In some embodiments, the ABP binds to the HLA-PEPTIDE target with more than 10-fold, 20-fold, 50-fold stronger affinity as compared to the off-target HLA-PEPTIDE. In some embodiments, the ABP binds to the HLA-PEPTIDE target with 100×-10,000× stronger affinity as compared to the off-target HLA-PEPTIDE.

In particular embodiments, the ABP binds to the HLA-PEPTIDE target with more than 10-fold, 20-fold, 50-fold stronger affinity as compared to the off-target HLA-PEP-TIDE A*01:01_ETDNNIVVY (SEQ ID NO: 204). In particular embodiments, the ABP binds to the HLA-PEPTIDE target with 100×-10,000× stronger affinity as compared to the off-target HLA-PEPTIDE A*01:01_ETDNNIVVY (SEQ ID NO: 204).

In some embodiments, the ABP exhibits little or weak binding to the off-target HLA-PEPTIDE. For example, in some embodiments, the ABP binds to the off-target HLA-PEPTIDE with a Kd that is at least 1 M or higher, 5 μM or higher, 10 μM or higher, 20 μM or higher, 50 μM or higher, 100 μM or higher, or 1000 μM or higher.

In particular embodiments, the ABP binds to the off-target HLA-PEPTIDE A*01:01_ETDNNIVVY (SEQ ID NO: 204) with a Kd that is at least 1 μM or higher, 5 μM or higher, 10 μM or higher, 20 μM or higher, 50 μM or higher, 100 μM or higher, or 1000 μM or higher.

In some embodiments, the ABP does not exhibit detectable binding to the off-target HLA-PEPTIDE. In some embodiments, the ABP does not bind to the off-target HLA-PEPTIDE.

In some embodiments, the ABP does not exhibit detectable binding to the off-target HLA-PEPTIDE A*01:01_ETDNNIVVY (SEQ ID NO: 204). In some embodiments, the ABP does not bind to the off-target HLA-PEPTIDE A*01:01_ETDNNIVVY (SEQ ID NO: 204).

The ABP can be capable of specifically binding a complex comprising the HLA-PEPTIDE target, e.g., derived from a tumor. In some embodiments, the ABP does not bind HLA in an absence of the HLA-restricted peptide derived from the tumor. In some embodiments, the ABP does not bind the HLA-restricted peptide derived from the tumor in an absence of HLA. In some embodiments, the ABP binds a complex comprising HLA and HLA-restricted peptide when naturally presented on a cell such as a tumor cell.

In some embodiments, an ABP provided herein modulates binding of the HLA-PEPTIDE to one or more ligands of the HLA-PEPTIDE.

Also provided herein is an ABP is an ABP that competes with an illustrative ABP disclosed herein. In some aspects, the ABP that competes with the illustrative ABP provided herein binds the same epitope as an illustrative ABP provided herein.

In some aspects, provided herein are ABPs referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs. In some embodiments, a variant is derived from any of the sequences provided herein, wherein one or more conservative amino acid substitutions are made. In some embodiments, a variant is derived from any of the sequences provided herein, wherein one or more nonconservative amino acid substitutions are made. Conservative amino acid substitutions are described herein. Exemplary nonconservative amino acid substitutions include those described in J Immunol. 2008 May 1:180(9): 6116-31, which is hereby incorporated by reference in its entirety. In preferred embodiments, the non-conservative amino acid substitution does not interfere with or inhibit the biological activity of the functional variant. In yet more preferred embodiments, the non-conservative amino acid substitution enhances the biological activity of the functional variant, such that the biological activity of the functional variant is increased as compared to the parent ABP.

In some embodiments, either the first ABR or the second ABR binds to an additional target antigen that is not an HLA-Peptide target. In some embodiments, either the first ABR and the second ABR binds to an additional target antigen.

The first ABR, second ABR, and Fab can be referred to as three different binders. In some of such embodiments, one of the binders binds to CD3. In some embodiments, the other two binders bind to an HLA-PEPTIDE target (different or the same). In alternate embodiments, one binder binds to CD3, a second binder binds to an HLA-peptide target, and a third binder binds to a receptor on a effector cells (e.g., T cell) that is not CD3, for example, CD28. In some embodiments, where two binders bind to a receptor on an effector cell (e.g., T cell), one but not both binders will bind CD3. Without being bound by theory or mechanism, this is to avoid overstimulation of the T cells.

Sequences of Exemplary ABPs

The ABP specific for A*01:01_NTDNNLAVY (SEQ ID NO: 214) may comprise one or more sequences, as described in further detail below.

CDRs

The ABP specific for A*01:01_NTDNNLAVY (SEQ ID NO: 214) may comprise one or more antibody complementarity determining region (CDR) sequences, e.g., may comprise three heavy chain CDRs (HCDR1, HCDR2, HCDR3) and three light chain CDRs (LCDR1, LCDR2, LCDR3). For example, the ABP specific for A*01:01_NTDNNLAVY (SEQ ID NO: 214) may comprise one or more antibody complementarity determining region (CDR) sequences from the clone designated C11, D5, or E07 (Table 20).

The ABP specific for A*01:01_NTDNNLAVY (SEQ ID NO: 214) may comprise a particular HCDR3 sequence. In some embodiments, the ABP comprises the HCDR3 from the clone designated C11, D5, or E07 (Table 20).

The ABP specific for A*01:01_NTDNNLAVY (SEQ ID NO: 214) may comprise a particular light chain CDR3 sequence. The LCDR3 sequence may be selected from the clone designated C11, D5, or E07 (Table 20).

The ABP specific for A*01:01_NTDNNLAVY (SEQ ID NO: 214) may comprise a particular heavy chain CDR3 (HCDR3) sequence and a particular light chain CDR3 (LCDR3) sequence. In some embodiments, the ABP comprises the HCDR3 and the LCDR3 from the clone designated C11, D5, or E07 (Table 20).

The ABP specific for A*01:01_NTDNNLAVY (SEQ ID NO: 214) may comprise all six CDRs from the clone designated C11, D5, or E07 (Table 20).

In some embodiments, an ABP provided herein comprises a CDR-H3 of SEQ ID NO: 20, a CDR-H2 of SEQ ID NO: 19, a CDR-H1 of SEQ ID NO: 18, a CDR-L3 of SEQ ID NO: 23, a CDR-L2 of SEQ ID NO: 22, and a CDR-L1 of SEQ ID NO: 21. In some embodiments, an ABP provided herein comprises a CDR-H3 of SEQ ID NO: 9, a CDR-H2 of SEQ ID NO: 8, a CDR-H1 of SEQ ID NO: 7, a CDR-L3 of SEQ ID NO: 11, a CDR-L2 of SEQ ID NO: 10, and a CDR-L1 of SEQ ID NO: 21. In some embodiments, an ABP provided herein comprises a CDR-H3 of SEQ ID NO: 14, a CDR-H2 of SEQ ID NO: 13, a CDR-H1 of SEQ ID NO: 12, a CDR-L3 of SEQ ID NO: 23, a CDR-L2 of SEQ ID NO: 22, and a CDR-L1 of SEQ ID NO: 21. In some embodiments, an ABP provided herein comprises a CDR-H3 of SEQ ID NO: 17, a CDR-H2 of SEQ ID NO: 16, a CDR-H1 of SEQ ID NO: 15, a CDR-L3 of SEQ ID NO: 11, a CDR-L2 of SEQ ID NO: 10, and a CDR-L1 of SEQ ID NO: 21. In some embodiments, the CDR-H3 has at least about 50%, 75%, 80%, 85%, 90%, or 95% identity with a CDR-H3 of SEQ ID NO: 20, 17, 14, or 9, the CDR-H2 has at least about 50%, 75%, 80%, 85%, 90%, or 95% identity with a CDR-H2 of SEQ ID NO: 19, 16, 13, or 8, the CDR-H1 has at least about 50%, 75%, 80%, 85%, 90%, or 95% identity with a CDR-H1 of SEQ ID NO: 18, 15, 12, or 7, the CDR-L3 has at least about 50%, 75%, 80%, 85%, 90%, or 95% identity with a CDR-L3 of SEQ ID NO: 23 or 11, the CDR-L2 has at least about 50%, 75%, 80%, 85%, 90%, or 95% identity with a CDR-L2 of SEQ ID NO: 22 or 10, and the CDR-L1 has at least about 50%, 75%, 80%, 85%, 90%, or 95% identity with a CDR-L1 of SEQ ID NO: 21. In some embodiments, the CDR-H3 is a CDR-H3 of SEQ ID NO: 20, 17, 14, or 9, with up to 1, 2, 3, 4, 5, 6, 7, or 8 amino acid substitutions; the CDR-H2 is a CDR-H2 of SEQ ID NO: 19, 16, 13, or 8, with up to 1, 2, 3, 4, 5, 6, 7, or 8 amino acid substitutions; the CDR-H1 is a CDR-H1 of SEQ ID NO: 18, 15, 12, or 7, with up to 1, 2, 3, 4, or 5 amino acid substitutions; the CDR-L3 is a CDR-L3 of SEQ ID NO: 23 or 11, with up to 1, 2, 3, 4, or 5 amino acid substitutions; the CDR-L2 is a CDR-L2 of SEQ ID NO: 22 or 10, with up to 1, 2, 3, or 4 amino acid substitutions; and the CDR-L1 is a CDR-L1 of SEQ ID NO: 21 with up to 1, 2, 3, 4, 5, or 6 amino acid substitutions.

The CD3 antibody or antigen binding fragment may comprise three heavy chain CDRs (HCDR1, HCDR2, HCDR3) and three light chain CDRs (LCDR1, LCDR2, LCDR3). For example, the CD3 antibody or antigen binding fragment may comprise one or more antibody complementarity determining region (CDR) sequences from the clone designated OKT3, UCHT1v9 or SP34 (Table 21).

In some embodiments, a CD3 antibody or antigen binding fragment provided herein comprises a CDR-H3 of SEQ ID NO: 38, a CDR-H2 of SEQ ID NO: 37, a CDR-H1 of SEQ ID NO: 36, a CDR-L3 of SEQ ID NO: 41, a CDR-L2 of SEQ ID NO: 40, and a CDR-L1 of SEQ ID NO: 39. In some embodiments, a CD3 antibody or antigen binding fragment provided herein comprises a CDR-H3 of SEQ ID NO: 44, a CDR-H2 of SEQ ID NO: 43, a CDR-H1 of SEQ ID NO: 42, a CDR-L3 of SEQ ID NO: 47, a CDR-L2 of SEQ ID NO: 46, and a CDR-L1 of SEQ ID NO: 45. In some embodiments, a CD3 antibody or antigen binding fragment provided herein comprises a CDR-H3 of SEQ ID NO: 28, a CDR-H2 of SEQ ID NO: 27, a CDR-H1 of SEQ ID NO: 26, a CDR-L3 of SEQ ID NO: 31, a CDR-L2 of SEQ ID NO: 30, and a CDR-L1 of SEQ ID NO: 29. In some embodiments, the CDR-H3 has at least about 50%, 75%, 80%, 85%, 90%, or 95% identity with a CDR-H3 of SEQ ID NO: 38, 44, or 28, the CDR-H2 has at least about 50%, 75%, 80%, 85%, 90%, or 95% identity with a CDR-H2 of SEQ ID NO: 37, 43, or 27, the CDR-H1 has at least about 50%, 75%, 80%, 85%, 90%, or 95% identity with a CDR-H1 of SEQ ID NO: 36, 42, or 26, the CDR-L3 has at least about 50%, 75%, 80%, 85%, 90%, or 95% identity with a CDR-L3 of SEQ ID NO: 41, 47, or 31, the CDR-L2 has at least about 50%, 75%, 80%, 85%, 90%, or 95% identity with a CDR-L2 of SEQ ID NO: 40, 46, or 30, and the CDR-L1 has at least about 50%, 75%, 80%, 85%, 90%, or 95% identity with a CDR-L1 of SEQ ID NO: 39, 45, or 29. In some embodiments, the CDR-H3 is a CDR-H3 of SEQ ID NO: 38, 44, or 28, with up to 1, 2, 3, 4, 5, 6, 7, or 8 amino acid substitutions; the CDR-H2 is a CDR-H2 of SEQ ID NO: 37, 43, or 27, with up to 1, 2, 3, 4, 5, 6, 7, or 8 amino acid substitutions; the CDR-H1 is a CDR-H1 of SEQ ID NO: 36, 42, or 26, with up to 1, 2, 3, 4, or 5 amino acid substitutions; the CDR-L3 is a CDR-L3 of SEQ ID NO: 41, 47, or 31, with up to 1, 2, 3, 4, or 5 amino acid substitutions; the CDR-L2 is a CDR-L2 of SEQ ID NO: 40, 46, or 30, with up to 1, 2, 3, or 4 amino acid substitutions; and the CDR-L1 is a CDR-L1 of SEQ ID NO: 39, 45, or 29 with up to 1, 2, 3, 4, 5, or 6 amino acid substitutions.

VH and VL

The ABP specific for A*01:01_NTDNNLAVY (SEQ ID NO: 214) may comprise a particular VL sequence. The VL sequence may be from the clone designated C11, D5, or E07 (Table 19).

The ABP specific for A*01:01_NTDNNLAVY (SEQ ID NO: 214) may comprise a VH sequence. The VH sequence may be from the clone designated C11, D5, or E07 (Table 19).

In some embodiments, an ABP provided herein comprises a VH sequence selected from SEQ ID NOs: 6, 1, 3, or 5. In some embodiments, an ABP provided herein comprises a VH sequence of SEQ ID NO: 6. In some embodiments, an ABP provided herein comprises a VH sequence of SEQ ID NO: 1. In some embodiments, an ABP provided herein comprises a VH sequence of SEQ ID NO: 3. In some embodiments, an ABP provided herein comprises a VH sequence of SEQ ID NO: 5.

In some embodiments, the VH sequence has at least 70%, 80%, or 90% identity with SEQ ID NO: 1, wherein any variation from SEQ ID NO: 1 does not occur within CDR-H1, CDR-H2, or CDR-H3. In some embodiments, the VH sequence has at least 70%, 80%, or 90% identity with SEQ ID NO: 6, wherein any variation from SEQ ID NO: 6 does not occur within CDR-H1, CDR-H2, or CDR-H3. In some embodiments, the VH sequence has at least 70%, 80%, or 90% identity with SEQ ID NO: 3, wherein any variation from SEQ ID NO: 3 does not occur within CDR-H1, CDR-H2, or CDR-H3. In some embodiments, the VH sequence has at least 70%, 80%, or 90% identity with SEQ ID NO: 5, wherein any variation from SEQ ID NO: 5 does not occur within CDR-H1, CDR-H2, or CDR-H3.

In some embodiments, an antibody provided herein comprises a VH sequence having at least about 50%, 60%, 70%, 80%, 90%, 95%, or 99% identity to SEQ ID NO: 1. In some embodiments, an antibody provided herein comprises a VH sequence having at least about 50%, 60%, 70%, 80%, 90%, 95%, or 99% identity to SEQ ID NO: 3. In some embodiments, an antibody provided herein comprises a VH sequence having at least about 50%, 60%, 70%, 80%, 90%, 95%, or 99% identity to SEQ ID NO: 6. In some embodiments, an antibody provided herein comprises a VH sequence having at least about 50%, 60%, 70%, 80%, 90%, 95%, or 99% identity to SEQ ID NO: 5.

In some embodiments, an antibody provided herein comprises a VH sequence provided in SEQ ID NOs: 1, 3, 5, or 6, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an ABP thereof provided herein comprises a VL sequence selected from SEQ ID NOs: 4 or 2. In some embodiments, an ABP provided herein comprises a VL sequence of SEQ ID NO: 4. In some embodiments, an antibody provided herein comprises a VL sequence of SEQ ID NO: 2.

In some embodiments, the VL sequence has at least 70%, 80%, or 90% identity with SEQ ID NO: 4, wherein any variation from SEQ ID NO: 4 does not occur within CDR-L1, CDR-L2, or CDR-L3. In some embodiments, the VL sequence has at least 70%, 80%, or 90% identity with SEQ ID NO: 2, wherein any variation from SEQ ID NO: 2 does not occur within CDR-L1, CDR-L2, or CDR-L3.

In some embodiments, an ABP provided herein comprises a VL sequence having at least about 50%, 60%, 70%, 80%, 90%, 95%, or 99% identity to SEQ ID NO: 4. In some embodiments, an antibody provided herein comprises a VL sequence having at least about 50%, 60%, 70%, 80%, 90%, 95%, or 99% identity to SEQ ID NO: 2.

In some embodiments, an ABP provided herein comprises a VL sequence provided in SEQ ID NOs: 4 or 2, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, a CD3 antibody or antigen binding fragment provided herein comprises a VH sequence selected from SEQ ID NOs: 32, 24, or 34. In some embodiments, a CD3 antibody or antigen binding fragment provided herein comprises a VH sequence of SEQ ID NO: 32. In some embodiments, a CD3 antibody or antigen binding fragment provided herein comprises a VH sequence of SEQ ID NO: 24. In some embodiments, a CD3 antibody or antigen binding fragment provided herein comprises a VH sequence of SEQ ID NO: 34.

In some embodiments, the CD3 antibody or antigen binding fragment VH sequence has at least 70%, 80%, or 90% identity with SEQ ID NO: 32, 24, or 34, wherein any variation from SEQ ID NO: 32, 24, or 34 does not occur within CDR-H1, CDR-H2, or CDR-H3.

In some embodiments, a CD3 antibody or antigen binding fragment provided herein comprises a VH sequence having at least about 50%, 60%, 70%, 80%, 90%, 95%, or 99% identity to SEQ ID NO: 32, 24, or 34.

In some embodiments, a CD3 antibody or antigen binding fragment provided herein comprises a VH sequence provided in SEQ ID NOs: 32, 24, or 34, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, a CD3 antibody or antigen binding fragment thereof provided herein comprises a VL sequence selected from SEQ ID NOs: 33, 25, or 35. In some embodiments, an ABP provided herein comprises a VL sequence of SEQ ID NO: 33.

In some embodiments, the CD3 antibody or antigen binding fragment VL sequence has at least 70%, 80%, or 90% identity with SEQ ID NO: 33, wherein any variation from SEQ ID NO: 33 does not occur within CDR-L1, CDR-L2, or CDR-L3.

In some embodiments, a CD3 antibody or antigen binding fragment provided herein comprises a VL sequence having at least about 50%, 60%, 70%, 80%, 90%, 95%, or 99% identity to SEQ ID NO: 33, 25, or 35.

In some embodiments, a CD3 antibody or antigen binding fragment provided herein comprises a VL sequence provided in SEQ ID NOs: 33, 25, or 35, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VH-VL Combinations

The ABP specific for A*01:01_NTDNNLAVY (SEQ ID NO: 214) may comprise a particular VH sequence and a particular VL sequence. In some embodiments, the ABP specific for A*01:01_NTDNNLAVY (SEQ ID NO: 214) comprises the VH sequence and the VL sequence from the clone designated C11, D5, or E07 (Table 19).

In some embodiments, an ABP provided herein comprises a VH sequence selected from SEQ ID NOs: 6, 1, 3, or 5; and a VL sequence selected from SEQ ID NOs: 2 or 4. In some embodiments, an antibody provided herein comprises a VH sequence of SEQ ID NO: 6 and a VL sequence of SEQ ID NO: 4. In some embodiments, an antibody provided herein comprises a VH sequence of SEQ ID NO: 1 and a VL sequence of SEQ ID NO: 2. In some embodiments, an antibody provided herein comprises a VH sequence of SEQ ID NO: 3 and a VL sequence of SEQ ID NO: 4. In some embodiments, an antibody provided herein comprises a VH sequence of SEQ ID NO: 5 and a VL sequence of SEQ ID NO: 2.

In some embodiments, a CD3 antibody or antigen binding fragment thereof provided herein comprises a VH sequence selected from SEQ ID NOs: 32, 24, or 34; and a VL sequence selected from SEQ ID NOs: 33, 25, or 35. In some embodiments, an antibody provided herein comprises a VH sequence of SEQ ID NO: 32 and a VL sequence of SEQ ID NO: 33. In some embodiments, an antibody provided herein comprises a VH sequence of SEQ ID NO: 24 and a VL sequence of SEQ ID NO: 25. In some embodiments, an antibody provided herein comprises a VH sequence of SEQ ID NO: 34 and a VL sequence of SEQ ID NO: 35.

Fc Region and Variants

An Fc region (also referred to herein as an Fc domain) can be an integral part of an antibody or Fc-fusion molecule, and can play a role in mediating effector functions such as, e.g., antibody-dependent cell-mediated cytotoxicity (ADCC), complement dependent cytotoxicity (CDC), opsonization and transcytosis.

In certain embodiments, a multispecific ABP provided herein comprises an Fc region (e.g., a CH2-CH3 domain). An Fc region can be wild-type or a variant thereof. A "wild-type Fc" or "wild-type CH2-CH3 domain" refers to one comprising an amino acid sequence identical to the amino acid sequence of an Fc region found in nature. For example, wild-type human Fc regions include a wild-type-sequence human IgG1 Fc region (non-A and A allotypes): wild-type-sequence human IgG2 Fc region: wild-type sequence human IgG3 Fc region; and wild-type-sequence human IgG4 Fc region, as well as naturally occurring variants thereof. In certain embodiments, an ABP provided herein comprises an Fc region with one or more amino acid substitutions, insertions, or deletions in comparison to a naturally occurring Fc region. In some aspects, such substitutions, insertions, or deletions yield ABP with altered stability, glycosylation, or other characteristics. In some aspects, such substitutions, insertions, or deletions yield a glycosylated ABP.

A "variant Fc region," "engineered Fc region" or "variant CH2-CH3 domain" comprises an amino acid sequence that differs from that of a native-sequence Fc region by virtue of at least one, relative amino acid modification, e.g., one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

The term "Fc-region-comprising ABP" refers to an ABP that comprises an Fc region. The C-terminal lysine (residue 447 according to the EU numbering system) of the Fc region may be removed, for example, during purification of the ABP or by recombinant engineering the nucleic acid encoding the ABP. Accordingly, an ABP having an Fc region can comprise an ABP with or without K447.

In some aspects, the Fc region (e.g., the CH2-CH3 domain) of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, an ABP provided herein has one or more mutations to reduce an effector function. For example, an ABP may have mutations in the Fc of human IgG1 that result in reduced, substantial loss or complete loss of the ABP binding to CD64, CD32A, CD16 and C1q (FcγRI, FcγRII, FcγRIII and C1q) relative to an unmodified version of the Fc. In some embodiments, an ABP provided herein comprises a variant CH2-CH3 domain comprising one or more amino acid substitutions that reduce binding to an Fc receptor on the cell surface of an effector cell, e.g., FcγRI; FcγRIIA; FcγRIIB1; FcγRIIIB2; FcγRIIIA; FcγRIIIB receptors. In some embodiments, the reduced effector functions can include one or more of reduced complement-dependent cytotoxicity (CDC), reduced antibody-dependent cellular cytotoxicity (ADCC), and reduced complement fixation. These modifications to the Fc can prevent multispecific ABPs from causing target cell death (e.g., T cell death) or, e.g., unwanted cytokine secretion. The modification(s) can also help reduce inter-individual variation in patient response to an ABP provided herein. Disabling productive Fc receptor engagement by reducing binding to one or more Fc receptors other than FcRn, where the Fc receptor binds monomeric IgG and/or multimeric immune complexes, can restore activity to the antibody and provide an improved therapeutic profile.

Examples of Fc effector functions that can be reduced through modification include, without limitation: ability to activate classical complement; ADCC; opsonization; ability to bind FcγRI (CD64) at, e.g., a high affinity of $1 \times 10^{-9}$ M; ability to bind FcγRIIIa,b (CD16), e.g., at an affinity $5 \times 10^{-5}$ M or higher; and ability to bind FcγRIIa,b (CD32), e.g., at an affinity of $2 \times 10^{-6}$ M or higher. Properties of antibodies having reduced effector function via Fc silencing are described, for example, in An et al. *mAbs* vol. 1,6 (2009): 572-9 and Wang, et al. *Protein & cell* 9.1 (2018): 63-73, the relevant disclosures of each of which are herein incorporated by reference.

In some embodiments, the ABP comprises a variant CH2-CH3 domain comprising one or more amino acid substitutions which reduce Fc effector functions. In some embodiments, the one or more amino acid substitutions are in the CH2 domain at one or more of EU index positions:

234, 235, and/or 331. In some embodiments, the one or more amino acid substitutions are in the CH2 domain at EU index positions: 234, 235, and 331. In some embodiments, the one or more amino acid substitutions are selected from: L234F, L235E, and P331S, according to the EU numbering system. In some embodiments, the variant CH2-CH3 domain comprises the amino acid substitutions of L234F, L235E, and P331S (dubbed "TM" modifications or mutations), according to the EU numbering system.

Binding of IgG to the FcγRs or C1q depends on residues located in the hinge region and the CH2 domain. Substitutions in human IgG1 or IgG2 residues at positions 233-236 and IgG4 residues at positions 327, 330 and 331 have been shown to greatly reduce ADCC and CDC. The triple amino acid substitution L234A, L235A, and G237A largely eliminates FcγR and complement effector functions (see, for example, U.S. Pat. No. 9,644,025, the relevant disclosures of which are herein incorporated by reference). The LALA variant, L234A/L235A, also has significantly reduced FcγR binding; as does E233P/L234V/L235A/G236+A327G/A330S/P331S. See, for example, Armour et al. (1999) *Eur J Immunol.* 29(8):2613-24. The set of mutations: K322A, L234A and L235A are sufficient to almost completely abolish FcγR and C1q binding.

Additional modifications to silence the Fc region or reduce effector function may include three amino acid substitutions in the CH2 region to reduce FcγRI binding at EU index positions 234, 235, and 237 (see Duncan et al., (1988) *Nature* 332:563). Two amino acid substitutions in the complement C1q binding site at EU index positions 330 and 331 reduce complement fixation (see Tao et al., *J. Exp. Med.* 178:661 (1993) and Canfield and Morrison, *J. Exp. Med.* 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 *Eur J Immunol.* 29(8): 2613-24; and Shields R L. et al., 2001. *J Biol Chem.* 276(9):6591-604).

Additional mutations that reduce binding to FcγR include, without limitation, modification of the glycosylation on asparagine 297 of the Fc domain, which is known to be required for optimal FcR interaction. For example known amino acid substitutions include N297 mutations, for example N297A/Q/D/H/G/C, which changes result in the loss of a glycosylation site on the protein. Enzymatically deglycosylated Fc domains, recombinantly expressed antibodies in the presence of a glycosylation inhibitor and the expression of Fc domains in bacteria have a similar loss of glycosylation and consequent binding to FcγRs.

Additional examples of Fc silencing are known to those of ordinary skill in the art and are provided, for example, in U.S. Pat. No. 10,611,842, the relevant disclosures of which are herein incorporated by reference.

As used herein, a "silenced Fc" or "silenced CH2-CH3 domain" refers to one that has been mutagenized to retain activity with respect to, for example, prolonging serum half-life through interaction with, e.g., FcRn, or while retaining its PK profile, but which has reduced or absent binding to one or more other Fc receptor(s), including without limitation a human FcγR as listed supra.

In some embodiments, the Fc region or CH2-CH3 domain of an ABP provided herein is a human IgG4 Fc region comprising one or more of the hinge stabilizing mutations S228P and L235E, according to EU numbering. See Aalberse et al., *Immunology,* 2002, 105:9-19, incorporated by reference in its entirety. In some embodiments, the IgG4 Fc region comprises one or more of the following mutations:

E233P, F234V, and L235A, according to EU numbering. See Armour et al., *Mol. Immunol.,* 2003, 40:585-593, incorporated by reference in its entirety. In some embodiments, the IgG4 Fc region comprises a deletion at position G236.

In some embodiments, the Fc region or CH2-CH3 domain of an ABP provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A), according to EU numbering. In some aspects, the ABP comprises a PVA236 mutation. PVA236 means that the amino acid sequence ELLG (SEQ ID NO: 212), from amino acid position 233 to 236 of IgG1 or EFLG (SEQ ID NO: 213) of IgG4, is replaced by PVA, according to EU numbering. See U.S. Pat. No. 9,150,641, incorporated by reference in its entirety.

In some embodiments, the Fc region of an ABP provided herein is modified as described in Armour et al., *Eur. J. Immunol.,* 1999, 29:2613-2624: WO 1999/058572; and/or U.K. patent application Ser. No. 98/099,518: each of which is incorporated by reference in its entirety.

In some embodiments, a sequence comprising the CH2-CH3 domains of the first polypeptide is distinct from a sequence comprising the CH2-CH3 domains of the second polypeptide. In some embodiments, the CH2-CH3 domains of the first polypeptide and/or the CH2-CH3 domains of the second polypeptide comprise a variant CH2-CH3 domain. In some embodiments, the variant CH2-CH3 domain comprises a modification that alters an affinity of the ABP for an Fc receptor as compared to a multispecific ABP with a non-variant CH2-CH3 domain. In some embodiments, the first hinge comprises a C220S mutation, according to EU numbering. In some embodiments, the variant CH2-CH3 domain comprises a human IgG4 Fc region comprising one or more of the hinge stabilizing mutations S228P and L235E, or comprising one or more of the following mutations: E233P, F234V, and L235A, according to EU numbering. In some embodiments, the variant CH2-CH3 domain is a human IgG1 Fc region comprising one or more mutations to reduce Fc receptor binding, optionally wherein the one or more mutations are in residues selected from S228 (e.g., S228A), L234 (e.g., L234A), L235 (e.g., L235A), D265 (e.g., D265A), and N297 (e.g., N297A or N297Q), or optionally wherein the amino acid sequence ELLG (SEQ ID NO: 212), from amino acid position 233 to 236 of IgG1 or EFLG (SEQ ID NO: 213) of IgG4, is replaced by PVA, according to EU numbering. In some embodiments, the variant CH2-CH3 domain is a human IgG2 Fc region comprising one or more of mutations A330S and P331S, according to EU numbering. In some embodiments, the variant CH2-CH3 domain comprises an amino acid substitution at one or more positions selected from 238, 265, 269, 270, 297, 327 and 329, optionally wherein the variant CH2-CH3 domain comprises substitutions at two or more of amino acid positions 265, 269, 270, 297 and 327, optionally wherein the variant CH2-CH3 domain comprises substitution of residues 265 or 297 with alanine, optionally wherein the variant CH2-CH3 domain comprises substitution of residues 265 and 297 with alanine, according to EU numbering In some embodiments, the variant CH2-CH3 domain of an ABP provided herein is a human IgG2 Fc region comprising one or more of mutations A330S and P331S, according to EU numbering.

In some embodiments, the Fc region (variant CH2-CH3 domain) of an ABP provided herein has an amino acid substitution at one or more positions selected from 238, 265, 269, 270, 297, 327 and 329, according to EU numbering. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine, according to EU numbering. See U.S. Pat. No. 7,332,581, incorporated by reference in its entirety. In some embodiments, the ABP comprises an alanine at amino acid position 265. In some embodiments, the ABP comprises an alanine at amino acid position 297.

In certain embodiments, an ABP provided herein comprises an Fc region (a variant CH2-CH3 domain) with one or more amino acid substitutions that reduce at least one Fc effector function. In certain embodiments, an ABP provided herein comprises a CH2-CH3 domain comprising one or more amino acid substitutions that reduce binding to an Fc receptor on the cell surface of an effector cell.

In certain embodiments, the Fc receptor on the cell surface of an effector cell is selected from: FcγRI: FcγRIIA: FcγRIIB1: FcγRIIIB2: FcγRIIIA; and FcγRIIIB receptors. In certain embodiments, the one or more amino acid substitutions is selected from: L234, L235, P331, L234F, L235E, and P331S, according to the EU numbering system. In certain embodiments, the variant CH2-CH3 domain comprises the amino acid substitutions of L234F, L235E, and P331S, according to the EU numbering system. In certain embodiments, the Fc effector function that is reduced comprises one or more functions selected from: complement-dependent cytotoxicity (CDC), antibody-dependent cellular cytotoxicity (ADCC), and complement fixation.

In some embodiments, the variant CH2-CH3 domain comprises one or more amino acid substitutions which improve ADCC, such as a substitution at one or more of positions 298, 333, and 334 of the variant CH2-CH3 domain, or a substitution at one or more of positions 239, 332, and 330 of the variant CH2-CH3 domain, according to EU numbering. In some embodiments, the variant CH2-CH3 domain comprises one or more modifications to increase half-life, optionally wherein the variant CH2-CH3 domain comprises substitutions at one or more of the variant CH2-CH3 domain residues: 238, 250, 256, 265, 272, 286, 303, 305, 307, 311, 312, 314, 317, 340, 356, 360, 362, 376, 378, 380, 382, 413, 424, 428, and 434 of an IgG, according to EU numbering. In some embodiments, the ABP comprises a G1m17,1 allotype.

In certain embodiments, an ABP provided herein comprises a variant CH2-CH3 domain with one or more amino acid substitutions which improve ADCC, such as a substitution at one or more of positions 298, 333, and 334 of the Fc region, according to EU numbering. In some embodiments, an ABP provided herein comprises a variant CH2-CH3 domain with one or more amino acid substitutions at positions 239, 332, and 330, as described in Lazar et al., *Proc. Natl. Acad. Sci. USA,* 2006, 103:4005-4010, incorporated by reference in its entirety, according to EU numbering.

In some embodiments, an ABP provided herein comprises one or more alterations that improves or diminishes C1q binding and/or CDC. See U.S. Pat. No. 6,194,551: WO 99/51642; and Idusogie et al., *J. Immunol.,* 2000, 164:4178-4184; each of which is incorporated by reference in its entirety.

In some embodiments, an ABP provided herein comprises one or more alterations to increase half-life. ABPs with increased half-lives and improved binding to the neonatal Fc receptor (FcRn) are described, for example, in Hinton et al., *J. Immunol.*, 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG, according to EU numbering. In some embodiments, the ABP comprises one or more non-Fc modifications that extend half-life. Exemplary non-Fc modifications that extend half-life are described in, e.g., US20170218078, which is hereby incorporated by reference in its entirety.

In some embodiments, an ABP provided herein comprises a G1m17,1 allotype. Such allotype is described in, e.g., Lefranc G, Lefranc M-P. Gm allotype and Gm haplotypes> Allotypes. In IMGT Repertoire (IG and TR). IMGT®, the international ImMunoGeneTics information System®. www.imgt.org/IMGTrepertoire/Proteins/allotypes/human/IGH/IGHC/G1m_allotypes.html, which is hereby incorporated by reference in its entirety.

In some embodiments, an ABP provided herein comprises one or more variant CH2-CH3 domains as described in U.S. Pat. Nos. 7,371,826 5,648,260, and 5,624,821: Duncan and Winter, *Nature*, 1988, 322:738-740; and WO 94/29351; each of which is incorporated by reference in its entirety.

In some embodiments, the multispecific ABP comprises one or more Fc (CH2-CH3 domain) modifications that promote heteromultimerization. In some embodiments, the Fc modification comprises a knob-in-hole modification. Knob-in-hole modifications are described in, e.g., U.S. Pat. No. 7,695,936, Merchant et al., Nature Biotechnology 1998 July: 16(7):677-81: Ridgway et al., Protein Engineering 1996 July; 9(7):617-21; and Atwell et al., J Mol Biol. 1997 Jul. 4:270(1): 26-35, each of which is incorporated by reference in its entirety.

In some embodiments, the hinge region on the knob side has a C220 mutation, e.g., C220S, according to EU numbering. This C220S mutation is added in the antibody arm that does not have a light-chain because a free Cys can cause challenges with folding.

In some embodiments, one Fc-bearing chain (CH2-CH3 domain) of the multispecific ABP comprises a T366W mutation, and the other Fc-bearing chain (CH2-CH3 domain) of the multispecific ABP comprises a T366S, L368A, and Y407V mutation, according to EU numbering. In some embodiments, the multispecific ABP comprising a knob-in-hole modification further comprises an engineered disulfide bridge in the Fc region. In some embodiments, the engineered disulfide bridge comprises a K392C mutation in one Fc-bearing chain (CH2-CH3 domain) of the multispecific ABP, and a D399C in the other Fc-bearing chain (CH2-CH3 domain) of the multispecific ABP, according to EU numbering. In some embodiments, the engineered disulfide bridge comprises a S354C mutation in one Fc-bearing chain (CH2-CH3 domain) of the multispecific ABP, and a Y349C mutation in the other Fc-bearing chain of the multispecific ABP, according to EU numbering.

In some embodiments, the ABP comprises a T366W mutation, and the other Fc-bearing chain (CH2-CH3 domain) of the ABP comprises a T366S, L368A, and Y407V mutation, according to EU numbering; and the ABP comprises an engineered disulfide bridge, wherein the engineered disulfide bridge comprises a S354C mutation in one Fc-bearing chain (CH2-CH3 domain) of the ABP, and a Y349C mutation in the other Fc-bearing chain (CH2-CH3 domain) of the ABP, according to EU numbering.

In some embodiments, the engineered disulfide bridge comprises a 447C mutation in both Fc-bearing chains of the ABP, which 447C mutations are provided by extension of the C-terminus of a CH3 domain incorporating a KSC tripeptide sequence. In some embodiments, the ABP comprises an S354C and T366W mutation in one Fc-bearing chain and a Y349C, T366S, L368A and Y407V mutation in the other Fc-bearing chain, according to EU numbering.

In some embodiments, the Fc modification comprises a set of mutations described in Von Kreudenstein T S, Escobar-Carbrera E, Lario P I, et al. Improving biophysical properties of a bispecific antibody scaffold to aid developability: quality by molecular design. *MAbs.* 2013:5(5):646-54, which is hereby incorporated by reference in its entirety. In some embodiments, the Fc modification comprises a set of mutations as provided in the following

TABLE E

| (numbering is according to EU numbering). Table E | |
| --- | --- |
| Chain-A | Chain-B |
| F405A_Y407V | T394W |
| F405A_Y407V | T366I_T394W |
| F405A_Y407V | T366L_T394W |
| F405A_Y407V | T366L_K392M_T394W |
| L351Y_F405A_Y407V | T366L_K392M_T394W |
| T350V_L351Y_F405A_Y407V | T350V_T366L_K392M_T394W |
| T350V_L351Y_F405A_Y407V | T350V_T366L_K392L_T394W |

In some embodiments, the Fc modification comprises a set of mutations described in Labrijn A F, et al., Proc Natl Acad Sci USA. 2013 Mar. 26:110(13):5145-50. doi: 10.1073/pnas. In some embodiments, the Fc region is an IgG1 Fc, and the Fc modification comprises a K409R mutation in one Fc-bearing chain and a mutation selected from a Y407, L368, F405, K370, and D399 mutation in the other Fc-bearing chain, according to EU numbering. In some embodiments, the Fc modification comprises a K409R mutation in one Fc-bearing chain and a F405L mutation in the other Fc-bearing chain, according to EU numbering.

In some embodiments, the Fc modification comprises a set of mutations that renders homodimerization electrostatically unfavorable but heterodimerization favorable. An exemplary set of mutations is described in U.S. Pat. No. 8,592,562, and in Gunasekaran K et al., The Journal of Biological Chemistry 285, 19637-19646, doi: 10.1074/jbc.M110.117382, which are each incorporated by reference in its entirety. In some embodiments, the Fc modification comprises a K409D_K392D mutation in one Fc-bearing chain and a D399K_E356K mutation in the other Fc-bearing chain, according to EU numbering.

In some embodiments, the engineered disulfide bridge comprises a K392C mutation in one CH2-CH3 domain (Fc region) of the ABP, and a D399C in the other CH2-CH3 domain (Fc region) of the ABP, according to EU numbering. In some embodiments, the engineered disulfide bridge comprises a S354C mutation in one CH2-CH3 domain of the ABP, and a Y349C mutation in the other CH2-CH3 domain of the ABP, according to EU numbering. In some embodiments, the engineered disulfide bridge comprises a 447C mutation in both CH2-CH3 domains of the ABP, which 447C mutations are provided by extension of the C-terminus of a CH3 domain incorporating a KSC tripeptide sequence, according to EU numbering In some embodiments, the Fc modification comprises a set of mutations described in WO2011143545, which is hereby incorporated by reference in its entirety. In some embodiments, the Fc modification comprises a K409R mutation in one Fc-bearing chain and a L368E or L368D mutation in the other Fc-bearing chain, according to EU numbering. In some embodiments, the Fc modification comprises a set of mutations described in Strop P et al., J. Mol. Biol., 420 (2012), pp. 204-219, which is hereby incorporated by reference in its entirety. In some embodiments, the Fc modification comprises a D221E, P228E, and L368E mutation in one Fc-bearing chain and a D221R, P228R, and K409R in the other Fc-bearing chain, according to EU numbering.

In some embodiments, the Fc modification comprises a set of mutations described in Moore G L, et al., mAbs, 3 (2011), pp. 546-557, which is hereby incorporated by reference in its entirety. In some embodiments, the Fc modification comprises an S364H and F405A mutation in one Fc-bearing chain and a Y349T and T394F mutation in the other Fc-bearing chain, according to EU numbering. In some embodiments, the Fc modification comprises a set of mutations described in U.S. Pat. No. 9,822,186, which is hereby incorporated by reference in its entirety. In some embodiments, the Fc modification comprises an E375Q and S364K mutation in one Fc-bearing chain and a L368D and K370S mutation in the other Fc-bearing chain, according to EU numbering.

In some embodiments, the Fc modification comprises strand-exchange engineered domain (SEED) CH3 heterodimers. Such SEED CH3 heterodimers are described in, e.g., Davis J H et al., Protein Eng Des Sel. 2010 April; 23(4): 195-202. doi: 10.1093/protein/gzp094, which is hereby incorporated by reference in its entirety.

In some embodiments, the Fc modification comprises a modification in the CH3 sequence that affects the ability of the CH3 domain to bind an affinity agent, e.g., Protein A. In some embodiments, one of the variant CH2-CH3 domains is capable of binding Protein A and the other variant CH2-CH3 domain comprises a mutation that reduces binding affinity of such CH2-CH3 domain to Protein A as compared to the first CH2-CH3 domain. Such modifications, and methods of producing multispecific ABPs comprising the modifications, are described in U.S. Pat. No. 8,586,713, US20160024147A1, and Smith E J, et al., Scientific Reports 2015 Dec. 11; 5:17943. doi: 10.1038/srep17943., each of which is hereby incorporated by reference in its entirety. In some embodiments, the Fc modification comprises a H435 and/or Y436 mutation (e.g., H435R and/or Y436F mutation) in at least one Fc-bearing chain, according to EU numbering. In some embodiments, the other Fc-bearing chain does not comprise an amino acid mutation. In some embodiments, the other CH2-CH3 domain comprises a H435, Y436, H435R, Y436F, or H435R_Y436F mutation, according to EU numbering.

Isolated HLA-Peptide Targets

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against class I glycoproteins, while helper T-cells respond mainly against class II glycoproteins.

Human major histocompatibility complex (MHC) class I molecules, referred to interchangeably herein as HLA Class I molecules, are expressed on the surface of nearly all cells. These molecules function in presenting peptides which are mainly derived from endogenously synthesized proteins to, e.g., CD8+ T cells via an interaction with the alpha-beta T-cell receptor. The class I MHC molecule comprises a heterodimer composed of a 46-kDa α chain which is non-covalently associated with the 12-kDa light chain beta-2 microglobulin. The a chain generally comprises α1 and α2 domains which form a groove for presenting an HLA-restricted peptide, and an α3 plasma membrane-spanning domain which interacts with the CD8 co-receptor of T-cells. See, e.g., Kerry S E, Buslepp J, Cramer L A, et al. Interplay between TCR Affinity and Necessity of Coreceptor Ligation: High-Affinity Peptide-MHC/TCR Interaction Overcomes Lack of CD8 Engagement. Journal of immunology (Baltimore, Md: 1950). 2003; 171(9):4493-4503.)

Class I MHC-restricted peptides (also referred to interchangeably herein as HLA-restricted antigens, HLA-restricted peptides, MHC-restricted antigens, restricted peptides, or peptides) generally bind to the heavy chain alpha1-alpha2 groove via about two or three anchor residues that interact with corresponding binding pockets in the MHC molecule. The beta-2 microglobulin chain plays an important role in MHC class I intracellular transport, peptide binding, and conformational stability. For most class I molecules, the formation of a heterotrimeric complex of the MHC class I heavy chain, peptide (self, non-self, and/or antigenic) and beta-2 microglobulin leads to protein maturation and export to the cell-surface.

Binding of a given HLA subtype to an HLA-restricted peptide forms a complex with a unique and novel surface that can be specifically recognized by an ABP such as, e.g., a TCR on a T cell or an antibody or antigen-binding fragment thereof. HLA complexed with an HLA-restricted peptide is referred to herein as an HLA-PEPTIDE or HLA-PEPTIDE target. In some cases, the restricted peptide is located in the α1/α2 groove of the HLA molecule. In some cases, the restricted peptide is bound to the α1/α2 groove of the HLA molecule via about two or three anchor residues that interact with corresponding binding pockets in the HLA molecule.

The HLA-PEPTIDE targets described herein is useful for cancer immunotherapy. In some embodiments, the HLA-PEPTIDE targets identified herein are presented on the surface of a tumor cell. The HLA-PEPTIDE targets identified herein may be expressed by tumor cells in a human subject. The HLA-PEPTIDE targets identified herein may be expressed by tumor cells in a population of human subjects. For example, the HLA-PEPTIDE targets identified herein may be shared antigens which are commonly expressed in a population of human subjects with cancer.

The HLA-PEPTIDE targets identified herein may have a prevalence with an individual tumor type The prevalence with an individual tumor type may be about 0.1%, 0.2%, 0.3%, 0.4%, 0.5%, 0.6%, 0.7%, 0.8%, 0.9%, 1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The prevalence with an individual tumor type may be about 0.1%-100%, 0.2-50%, 0.5-25%, 2-20% or 1-10%.

Preferably, HLA-PEPTIDE targets are not generally expressed in most normal tissues. For example, the HLA- PEPTIDE targets may in some cases not be expressed in tissues in the Genotype-Tissue Expression (GTEx) Project, or may in some cases be expressed only in immune privileged or non-essential tissues. Exemplary immune privileged or non-essential tissues include testis, minor salivary glands, the endocervix, and the thyroid. In some cases, an HLA-PEPTIDE target may be deemed to not be expressed on essential tissues or non-immune privileged tissues if the median expression of a gene from which the restricted peptide is derived is less than 0.5 RPKM (Reads Per Kilobase of transcript per Million mapped reads) across GTEx samples, if the gene is not expressed with greater than 10 RPKM across GTEX samples, if the gene was expressed at >=5 RPKM in no more two samples across all essential tissue samples, or any combination thereof.

Also provided herein are off-target HLA-PEPTIDES. Such off-target HLA-PEPTIDES may be useful for identifying a cancer therapeutic, e.g., an ABP disclosed herein.

HLA-Restricted Peptides

The HLA-restricted peptides of an HLA-PEPTIDE target disclosed herein (referred to interchangeably herein) as "restricted peptides" can be peptide fragments of tumor-specific genes, e.g., cancer-specific genes. Preferably, the cancer-specific genes are expressed in cancer samples. The restricted peptide contemplated herein is from tumor-specific gene product CT83 (Cancer/testis antigen 83; also referred to as KKLC-1). Genes which are aberrantly expressed in cancer samples can be identified through a database. Exemplary databases include, by way of example only, The Cancer Genome Atlas (TCGA) Research Network: cancergenome.nih.gov/; the International Cancer Genome Consortium: dcc.icgc.org/. In some embodiments, the cancer-specific gene has an observed expression of at least 10 RPKM in at least 5 samples from the TCGA database. The cancer-specific gene may have an observable bimodal distribution.

The cancer-specific gene may have an observed expression of greater than 10, 20, 30, 40, 50, 60, 70, 80, 90, or 100 transcripts per million (TPM) in at least one TCGA tumor tissue. See FIGS. 1A and 1B. In some embodiments, the cancer-specific gene has an observed expression of greater than 100 TPM in at least one TCGA tumor tissue. In some cases, the cancer specific gene has an observed bimodal distribution of expression across TCGA samples. Without wishing to be bound by theory, such bimodal expression pattern is consistent with a biological model in which there is minimal expression at baseline in all tumor samples and higher expression in a subset of tumors experiencing epigenetic dysregulation.

Preferably, the cancer-specific gene is not generally expressed in most normal tissues. For example, the cancer-specific gene may in some cases not be expressed in tissues in the Genotype-Tissue Expression (GTEx) Project, or may in some cases be expressed in immune privileged or non-essential tissues. Exemplary immune privileged or non-essential tissues include testis, minor salivary glands, the endocervix, and thyroid. In some cases, an cancer-specific gene may be deemed to not be expressed an essential tissues or non-immune privileged tissue if the median expression of the cancer-specific gene is less than 0.5 RPKM (Reads Per Kilobase of transcript per Million mapped reads) across GTEx samples, if the gene is not expressed with greater than 10 RPKM across GTEx samples, if the gene was expressed at >=5 RPKM in no more two samples across all essential tissue samples, or any combination thereof.

In some embodiments, the cancer-specific gene meets the following criteria by assessment of the GTEx: (1) median GTEx expression in brain, heart, or lung is less than 0.1 transcripts per million (TPM), with no one sample exceeding 5 TPM, (2) median GTEx expression in other essential organs (excluding testis, thyroid, minor salivary gland) is less than 2 TPM with no one sample exceeding 10 TPM.

In some embodiments, the cancer-specific gene is not likely expressed in immune cells generally, e.g., is not an interferon family gene, is not an eye-related gene, not an olfactory or taste receptor gene, and is not a gene related to the circadian cycle (e.g., not a CLOCK, PERIOD, CRY gene).

The restricted peptide preferably may be presented on the surface of a tumor.

The restricted peptides may have a size of about 5, about 6, about 7, about 8, about 9, about 10, about 11, about 12, about 13, about 14, or about 15 amino molecule residues, and any range derivable therein. In particular embodiments, the restricted peptide has a size of about 8, about 9, about 10, about 11, or about 12 amino molecule residues. The restricted peptide may be about 5-15 amino acids in length, preferably may be about 7-12 amino acids in length, or more preferably may be about 8-11 amino acids in length.

A restricted peptide of an off-target HLA-PEPTIDE can be a fragment of a protein expressed in normal, e.g., non-tumor tissue. In some embodiments, a restricted peptide of an off-target HLA-PEPTIDE is indicated as being expressed in normal tissues according to the public GTEX database.

HLA Class I molecules which do not associate with a restricted peptide ligand are generally unstable. Accordingly, the association of the restricted peptide with the α1/α2 groove of the HLA molecule may stabilize the non-covalent association of the β2-microglobulin subunit of the HLA subtype with the α-subunit of the HLA subtype.

Stability of the non-covalent association of the β2-microglobulin subunit of the HLA subtype with the α-subunit of the HLA subtype can be determined using any suitable means. For example, such stability may be assessed by dissolving insoluble aggregates of HLA molecules in high concentrations of urea (e.g., about 8M urea), and determining the ability of the HLA molecule to refold in the presence of the restricted peptide during urea removal, e.g., urea removal by dialysis. Such refolding approaches are described in, e.g., Proc. Natl. Acad. Sci. USA Vol. 89, pp. 3429-3433 April 1992, hereby incorporated by reference in its entirety.

For other example, such stability may be assessed using conditional HLA Class I ligands. Conditional HLA Class I ligands are generally designed as short restricted peptides which stabilize the association of the β2 and α subunits of the HLA Class I molecule by binding to the α1/α2 groove of the HLA molecule, and which contain one or more amino acid modifications allowing cleavage of the restricted peptide upon exposure to a conditional stimulus. Upon cleavage of the conditional ligand, the β2 and α-subunits of the HLA molecule dissociate, unless such conditional ligand is exchanged for a restricted peptide which binds to the α1/α2 groove and stabilizes the HLA molecule. Conditional ligands can be designed by introducing amino acid modifications in either known HLA peptide ligands or in predicted high-affinity HLA peptide ligands. For HLA alleles for which structural information is available, water-accessibility of side chains may also be used to select positions for introduction of the amino acid modifications. Use of conditional HLA ligands may be advantageous by allowing the batch preparation of stable HLA-peptide complexes which may be used to interrogate test restricted peptides in a high throughput manner. Conditional HLA Class I ligands, and methods of production, are described in, e.g., Proc Natl Acad Sci USA. 2008 Mar. 11; 105(10): 3831-3836; Proc Natl Acad Sci USA. 2008 Mar. 11; 105(10): 3825-3830; J Exp Med. 2018 May 7; 215(5): 1493-1504; Choo, J. A. L. et al. Bioorthogonal cleavage and exchange of major histocompatibility complex ligands by employing azobenzene-containing peptides. Angew Chem Int Ed Engl 53, 13390-13394 (2014); Amore, A. et al. Development of a Hypersensitive Periodate-Cleavable Amino Acid that is Methionine- and Disulfide-Compatible and its Application in MHC Exchange Reagents for T Cell Characterisation. ChemBioChem 14, 123-131 (2012); Rodenko, B. et al. Class I Major Histocompatibility Complexes Loaded by a Periodate Trigger. J Am Chem Soc 131, 12305-12313 (2009); and Chang, C. X. L. et al. Conditional ligands for Asian HLA variants facilitate the definition of CD8+ T-cell responses in acute and chronic viral diseases. Eur J Immunol 43, 1109-1120 (2013). These references are incorporated by reference in their entirety.

Accordingly, in some embodiments, the ability of an HLA-restricted peptide described herein to stabilize the association of the β2- and α-subunits of the HLA molecule, is assessed by performing a conditional ligand mediated-exchange reaction and assay for HLA stability. HLA stability can be assayed using any suitable method, including, e.g., mass spectrometry analysis, immunoassays (e.g., ELISA), size exclusion chromatography, and HLA multimer staining followed by flow cytometry assessment of T cells.

Other exemplary methods for assessing stability of the non-covalent association of the β2-microglobulin subunit of the HLA subtype with the α-subunit of the HLA subtype include peptide exchange using dipeptides. Peptide exchange using dipeptides has been described in, e.g., Proc Natl Acad Sci USA. 2013 Sep. 17, 110(38): 15383-8; Proc Natl Acad Sci USA. 2015 Jan. 6, 112(1):202-7, which is hereby incorporated by reference in its entirety.

Provided herein are useful antigens comprising an HLA-PEPTIDE target. The HLA-PEPTIDE targets may comprise a specific HLA-restricted peptide having a defined amino acid sequence complexed with a specific HLA subtype allele.

The HLA-PEPTIDE target or off-target HLA-PEPTIDE may be isolated and/or in substantially pure form. For example, the HLA-PEPTIDE targets or off-target HLA-PEPTIDEs may be isolated from their natural environment, or may be produced by means of a technical process. In some cases, the HLA-PEPTIDE target or off-target HLA-PEPTIDE is provided in a form which is substantially free of other peptides or proteins.

THE HLA-PEPTIDE targets or off-target HLA-PEP-TIDEs may be presented in soluble form, and optionally may be a recombinant HLA-PEPTIDE target complex. The skilled artisan may use any suitable method for producing and purifying recombinant HLA-PEPTIDE targets or off-target HLA-PEPTIDEs. Suitable methods include, e.g., use of E. coli expression systems, insect cells, and the like. Other methods include synthetic production, e.g., using cell free systems. An exemplary suitable cell free system is described in WO2017089756, which is hereby incorporated by reference in its entirety.

Also provided herein are compositions comprising an HLA-PEPTIDE target or off-target HLA-PEPTIDE.

In some cases, the composition comprises an HLA-PEPTIDE target or off-target HLA-PEPTIDE attached to a solid support. Exemplary solid supports include, but are not limited to, beads, wells, membranes, tubes, columns, plates, sepharose, magnetic beads, and chips. Exemplary solid supports are described in, e.g., Catalysts 2018, 8, 92; doi: 10.3390/catal8020092, which is hereby incorporated by reference in its entirety.

The HLA-PEPTIDE target may be attached to the solid support by any suitable methods known in the art. In some cases, the HLA-PEPTIDE target is covalently attached to the solid support.

In some cases, the HLA-PEPTIDE target is attached to the solid support by way of an affinity binding pair. Affinity binding pairs generally involved specific interactions between two molecules. A ligand having an affinity for its binding partner molecule can be covalently attached to the solid support, and thus used as bait for immobilizing Common affinity binding pairs include, e.g., streptavidin and biotin, avidin and biotin; polyhistidine tags with metal ions such as copper, nickel, zinc, and cobalt; and the like.

The HLA-PEPTIDE target may comprise a detectable label.

ABPs Comprising an Antibody or Antigen-Binding Fragment Thereof

In some embodiments, the ABP comprises an antibody or antigen-binding fragment thereof.

In some embodiments, the ABPs provided herein comprise a light chain. In some aspects, the light chain is a kappa light chain. In some aspects, the light chain is a lambda light chain.

In some embodiments, the ABPs provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the ABPs provided herein comprise an antibody fragment. In some embodiments, the ABPs provided herein consist of an antibody fragment. In some embodiments, the ABPs provided herein consist essentially of an antibody fragment. In some aspects, the ABP fragment is an Fv fragment. In some aspects, the ABP fragment is a Fab fragment. In some aspects, the ABP fragment is a $F(ab')_2$ fragment. In some aspects, the ABP fragment is a Fab' fragment. In some aspects, the ABP fragment is an scFv (sFv) fragment. In some aspects, the ABP fragment is an scFv-Fc fragment. In some aspects, the ABP fragment is a fragment of a single domain ABP.

In some embodiments, an ABP fragment provided herein is derived from an illustrative ABP provided herein. In some embodiments, an ABP fragments provided herein is not derived from an illustrative ABP provided herein and may, for example, be isolated de novo according to the methods provided herein for obtaining ABP fragments.

In some embodiments, an ABP fragment provided herein retains the ability to bind the HLA-PEPTIDE target, as measured by one or more assays or biological effects described herein. In some embodiments, an ABP fragment provided herein retains the ability to prevent HLA-PEP-TIDE from interacting with one or more of its ligands, as described herein.

The ABP fragments provided herein may be made by any suitable method, including the illustrative methods described herein or those known in the art. Suitable methods include recombinant techniques and proteolytic digestion of whole ABPs.

In some embodiments, the ABPs provided herein are monoclonal ABPs. Monoclonal ABPs may be obtained, for example, using a hybridoma method or using phage or yeast-based libraries.

DNA encoding the monoclonal ABPs may be readily isolated and sequenced using conventional procedures.

In some embodiments, the ABPs provided herein are polyclonal ABPs.

In some embodiments, the ABPs provided herein comprise a chimeric ABP. In some embodiments, the ABPs provided herein consist of a chimeric ABP. In some embodiments, the ABPs provided herein consist essentially of a chimeric ABP. Chimeric ABPs can be made by any methods known in the art. In some embodiments, a chimeric ABP is made by using recombinant techniques to combine a non-human variable region (e.g., a variable region derived from a mouse, rat, hamster, rabbit, or non-human primate, such as a monkey) with a human constant region.

In some embodiments, the ABPs provided herein comprise a humanized ABP. In some embodiments, the ABPs provided herein consist of a humanized ABP. In some embodiments, the ABPs provided herein consist essentially of a humanized ABP. Humanized ABPs may be generated by replacing most, or all, of the structural portions of a non-human monoclonal ABP with corresponding human ABP sequences.

In some embodiments, the ABPs provided herein comprise a human ABP. In some embodiments, the ABPs provided herein consist of a human ABP. In some embodiments, the ABPs provided herein consist essentially of a human ABP. Human ABPs can be generated by a variety of techniques known in the art, for example by using transgenic animals (e.g., humanized mice), can be derived from phage-display libraries, can be generated by in vitro activated B cells, or can be derived from yeast-based libraries In some embodiments, the ABPs provided herein comprise an alternative scaffold. In some embodiments, the ABPs provided herein consist of an alternative scaffold. In some embodiments, the ABPs provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. The alternative scaffolds provided herein may be made by any suitable method, including the illustrative methods described herein or those known in the art.

Also disclosed herein is an isolated humanized, human, or chimeric ABP that competes for binding to an HLA-PEPTIDE with an ABP disclosed herein.

Also disclosed herein is an isolated humanized, human, or chimeric ABP that binds an HLA-PEPTIDE epitope bound by an ABP disclosed herein.

In certain aspects, an ABP may comprise a human Fc region comprising at least one modification that reduces binding to a human Fc receptor.

It is known that when an ABP is expressed in cells, the ABP is modified after translation. Examples of the post-translational modification include cleavage of lysine at the C terminus of the heavy chain by a carboxypeptidase: modification of glutamine or glutamic acid at the N terminus of the heavy chain and the light chain to pyroglutamic acid by pyroglutamylation: glycosylation: oxidation: deamidation; and glycation, and it is known that such posttranslational modifications occur in various ABPs (See Journal of Pharmaceutical Sciences, 2008, Vol. 97, p. 2426-2447, incorporated by reference in its entirety). In some embodiments, an ABP is an ABP or antigen-binding fragment thereof which has undergone posttranslational modification. Examples of an ABP or antigen-binding fragment thereof which have undergone posttranslational modification include an ABP or antigen-binding fragments thereof which have undergone pyroglutamylation at the N terminus of the heavy chain variable region and/or deletion of lysine at the C terminus of the heavy chain. It is known in the art that such posttranslational modification due to pyroglutamylation at the N terminus and deletion of lysine at the C terminus does not have any influence on the activity of the ABP or fragment thereof (Analytical Biochemistry, 2006, Vol. 348, p. 24-39, incorporated by reference in its entirety).

In some embodiments, the ABPs provided herein are multispecific ABPs.

In some embodiments, a multispecific ABP provided herein binds more than one antigen. In some embodiments, a multispecific ABP binds 2 antigens. In some embodiments, a multispecific ABP binds 3 antigens. In some embodiments, a multispecific ABP binds 4 antigens. In some embodiments, a multispecific ABP binds 5 antigens.

In some embodiments, a multispecific ABP provided herein binds more than one epitope on the HLA-PEPTIDE target. In some embodiments, a multispecific ABP binds 2 epitopes on the HLA-PEPTIDE target. In some embodiments, a multispecific ABP binds 3 epitopes on the HLA-PEPTIDE target.

In some embodiments, the multispecific ABP comprises an antigen-binding domain (ABD) that specifically binds to an HLA-PEPTIDE target disclosed herein and an additional ABD that binds to an additional target antigen.

Many multispecific ABP constructs are known in the art, and the ABPs provided herein may be provided in the form of any suitable multispecific construct.

The multispecific ABPs provided herein may be made by any suitable method, including the illustrative methods described herein or those known in the art.

In certain embodiments, an ABP provided herein comprises an Fc region. An Fc region can be wild-type or a variant thereof. In certain embodiments, an ABP provided herein comprises an Fc region with one or more amino acid substitutions, insertions, or deletions in comparison to a naturally occurring Fc region. In some aspects, such substitutions, insertions, or deletions yield ABP with altered stability, glycosylation, or other characteristics. In some aspects, such substitutions, insertions, or deletions yield a glycosylated ABP.

In some embodiments, the Fc region is a variant Fc region. A "variant Fc region" or "engineered Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

The term "Fc-region-comprising ABP" refers to an ABP that comprises an Fc region. The C-terminal lysine (residue 447 according to the EU numbering system) of the Fc region may be removed, for example, during purification of the ABP or by recombinant engineering the nucleic acid encoding the ABP. Accordingly, an ABP having an Fc region can comprise an ABP with or without K447.

In some aspects, the Fc region of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, an ABP provided herein comprises one or more alterations that improves or diminishes C1q binding and/or CDC.

In some embodiments, an ABP provided herein comprises one or more alterations to increase half-life. In some embodiments, the ABP comprises one or more non-Fc modifications that extend half-life.

In some embodiments, the multispecific ABP comprises one or more Fc modifications that promote heteromultimerization. In some embodiments, the Fc modification comprises a set of mutations that renders homodimerization electrostatically unfavorable but heterodimerization favorable.

In some embodiments, the Fc modification comprises a modification in the CH3 sequence that affects the ability of the CH3 domain to bind an affinity agent, e.g., Protein A.

Among the provided ABPs, e.g., HLA-PEPTIDE ABPs, are receptors. The receptors can include antigen receptors and other chimeric receptors that specifically bind an HLA-PEPTIDE target disclosed herein. The receptor may be a chimeric antigen receptor (CAR).

Also provided are cells expressing the receptors and uses thereof in adoptive cell therapy, such as treatment of diseases and disorders associated with HLA-PEPTIDE expression, including cancer.

The chimeric receptors, such as CARs, generally include an extracellular antigen binding domain that includes, is, or is comprised within, one of the provided anti-HLA-PEPTIDE ABPs such as anti-HLA-PEPTIDE antibodies. Thus, the chimeric receptors, e.g., CARs, typically include in their extracellular portions one or more HLA-PEPTIDE-ABPs, such as one or more antigen-binding fragment, domain, or portion, or one or more antibody variable domains, and/or antibody molecules, such as those described herein. In some embodiments, the CAR includes a HLA-PEPTIDE-binding portion or portions of the ABP (e.g., antibody) molecule, such as a variable heavy (VH) chain region and/or variable light (VL) chain region of the antibody, e.g., an scFv antibody fragment.

In some embodiments, the CAR is a recombinant CAR. The recombinant CAR may be a human CAR, comprising fully human sequences, e.g., natural human sequences.

Also provided are cells such as cells that contain an antigen receptor, e.g., that contains an extracellular domain including an anti-HLA-PEPTIDE ABP (e.g., a CAR), described herein. Also provided are populations of such cells, and compositions containing such cells. In some embodiments, compositions or populations are enriched for such cells, such as in which cells expressing the HLA-PEPTIDE ABP make up at least 1, 5, 10, 20, 30, 40, 50, 60, 70, 80, 90, 91, 92, 93, 94, 95, 96, 97, 98, 99, or more than 99 percent of the total cells in the composition or cells of a certain type such as T cells or CD8+ or CD4+ cells. In some embodiments, a composition comprises at least one cell containing an antigen receptor disclosed herein. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing an ABP comprising a receptor, e.g., a CAR.

Nucleotides, Vectors, Host Cells, and Related Methods

Also provided are isolated nucleic acids encoding HLA-PEPTIDE ABPs, vectors comprising the nucleic acids, and host cells comprising the vectors and nucleic acids, as well as recombinant techniques for the production of the ABPs.

The nucleic acids may be recombinant. The recombinant nucleic acids may be constructed outside living cells by joining natural or synthetic nucleic acid segments to nucleic acid molecules that can replicate in a living cell, or replication products thereof. For purposes herein, the replication can be in vitro replication or in vivo replication.

For recombinant production of an ABP, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Exemplary vectors or constructs suitable for expressing an ABP, e.g., a CAR, antibody, or antigen binding fragment thereof, include, e.g., the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as AGTIO, AGTI 1, AZapII (Stratagene), AEMBL4, and ANMI 149, are also suitable for expressing an ABP disclosed herein.

Illustrative examples of suitable host cells are provided below. These host cells are not meant to be limiting, and any suitable host cell may be used to produce the ABPs provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as Escherichia (E. coli), Enterobacter, Erwinia, Klebsiella, Proteus, Salmonella (S. typhimurium), Serratia (S. marcescens), Shigella, Bacilli (B. subtilis and B. licheniformis), Pseudomonas (P. aeruginosa), and Streptomyces. One useful E. coli cloning host is E. coli 294, although other strains such as E. coli B, E. coli X1776, and E. coli W3110 are also suitable.

In addition to prokaryotes, eukaryotic microbes such as filamentous fungi or yeast are also suitable cloning or expression hosts for HLA-PEPTIDE ABP-encoding vectors. Saccharomyces cerevisiae, or common baker's yeast, is a commonly used lower eukaryotic host microorganism. However, a number of other genera, species, and strains are available and useful, such as Schizosaccharomyces pombe, Kluyveromyces (K. lactis, K. fragilis, K. bulgaricus K. wickeramii, K. waltii, K. drosophilarum, K. thermotolerans, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells: baby hamster kidney (BHK) cells: Chinese hamster ovary (CHO): mouse sertoli cells: African green monkey kidney cells (VERO-76), and the like.

The host cells used to produce the HLA-PEPTIDE ABP may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44: Barnes et al., *Anal. Biochem.*, 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the ABP can be produced intracellularly, in the periplasmic space, or directly secreted into the medium. If the ABP is produced intracellularly, as a first step, the particulate debris, either host cells or lysed fragments, is removed, for example, by centrifugation or ultrafiltration. For example, Carter et al. (*Bio/Technology*, 1992, 10:163-167, incorporated by reference in its entirety) describes a procedure for isolating ABPs which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the ABP is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the ABP may be useful, for example, where the ABP accumulates in a cell as an insoluble aggregate, or where yields from periplasmic expression are low.

Where the ABP is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The ABP composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the ABP. Protein A can be used to purify ABPs that comprise human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the ABP comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the ABP of interest and contaminants may be subjected to low pH hydrophobic interaction chromatography using an elution buffer at a pH between about 2.5 to about 4.5, generally performed at low salt concentrations (e.g., from about 0 to about 0.25 M salt).

Methods of Identifying ABPs

Identification and/or preparation of an ABP described herein may comprise use of an HLA-PEPTIDE target or off-target HLA-PEPTIDE.

Such antigens may comprise intact HLA-PEPTIDE complexes or fragments thereof. Such antigen may be, for example, in the form of isolated protein or a protein expressed on the surface of a cell.

In some embodiments, the HLA-PEPTIDE antigen is a non-naturally occurring variant of HLA-PEPTIDE, such as a HLA-PEPTIDE protein having an amino acid sequence or post-translational modification that does not occur in nature.

In some embodiments, the HLA-PEPTIDE antigen is truncated by removal of, for example, intracellular or membrane-spanning sequences, or signal sequences. In some embodiments, the HLA-PEPTIDE antigen is fused at its C-terminus to a human IgG1 Fc domain or a polyhistidine tag.

ABPs that bind HLA-PEPTIDE can be identified using any method known in the art, e.g., phage display or immunization of a subject.

One method of identifying an antigen binding protein includes binding a target disclosed herein with an antigen binding protein, contacting the antigen binding protein with one or more off-target HLA-PEPTIDEs disclosed herein, and identifying the antigen binding protein if the antigen binding protein does not bind to the one or more off-target HLA-PEPTIDEs. The antigen binding protein can be present in a library comprising a plurality of distinct antigen binding proteins.

In some embodiments, the library is a phage display library. The phage display library can be developed so that it is substantially free of antigen binding proteins that non-specifically bind the HLA of the HLA-PEPTIDE target. The antigen binding protein can be present in a yeast display library comprising a plurality of distinct antigen binding proteins. The yeast display library can be developed so that it is substantially free of antigen binding proteins that non-specifically bind the HLA of the HLA-PEPTIDE target.

In some embodiments, the library is a yeast display library.

Another method of identifying an antigen binding protein can include obtaining at least one HLA-PEPTIDE target: administering the HLA-PEPTIDE target to a subject (e.g., a mouse, rabbit or a llama), optionally in combination with an adjuvant; and isolating the antigen binding protein from the subject.

In some aspects, isolating the antigen binding protein comprises isolating a B cell from the subject that expresses the antigen binding protein. The B cell can be used to create a hybridoma. The B cell can also be used for cloning one or more of its CDRs. The B cell can also be immortalized, for example, by using EBV transformation. Sequences encoding an antigen binding protein can be cloned from immortalized B cells or can be cloned directly from B cells isolated from an immunized subject. A library that comprises the antigen binding protein of the B cell can also be created, optionally wherein the library is phage display or yeast display.

Engineered Cells

Also provided are engineered cells such as cells that contain an antigen receptor, e.g., that contains an extracellular domain including an anti-HLA-PEPTIDE ABP (e.g., a CAR), described herein. Also provided are populations of such cells, and compositions containing such cells. In some embodiments, compositions or populations are enriched for such cells, such as in which cells expressing the HLA-PEPTIDE ABP make up at least 1, 5, 10, 20, 30, 40, 50, 60, 70, 80, 90, 91, 92, 93, 94, 95, 96, 97, 98, 99, or more than 99 percent of the total cells in the composition or cells of a certain type such as T cells or CD8+ or CD4+ cells. In some embodiments, a composition comprises at least one cell containing an antigen receptor disclosed herein. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing an ABP comprising a receptor, e.g., an anti-HLA-PEPTIDE ABP CAR. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MALT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

The cells may be genetically modified to reduce expression or knock out endogenous TCRs. Such modifications are described in Mol Ther Nucleic Acids. 2012 December; 1(12): e63; Blood. 2011 Aug. 11; 118(6):1495-503; Blood. 2012 Jun. 14; 119(24): 5697-5705; Torikai, Hiroki et al "HLA and TCR Knockout by Zinc Finger Nucleases: Toward "off-the-Shelf" Allogeneic T-Cell Therapy for CD19+ Malignancies." Blood 116.21 (2010): 3766; Blood. 2018 Jan. 18; 131(3):311-322. doi: 10.1182/blood-2017-05-787598; and WO2016069283, which are incorporated by reference in their entirety.

The cells may be genetically modified to promote cytokine secretion. Such modifications are described in Hsu C, Hughes M S, Zheng Z, Bray R B, Rosenberg S A, Morgan R A. Primary human T lymphocytes engineered with a codon-optimized IL-15 gene resist cytokine withdrawal-induced apoptosis and persist long-term in the absence of exogenous cytokine. J Immunol. 2005; 175:7226-34; Quintarelli C, Vera J F, Savoldo B, Giordano Attianese G M, Pule M, Foster A E, Co-expression of cytokine and suicide genes to enhance the activity and safety of tumor-specific cytotoxic T lymphocytes. Blood. 2007; 110:2793-802; and Hsu C, Jones S A, Cohen C J, Zheng Z, Kerstann K, Zhou J, Cytokine-independent growth and clonal expansion of a primary human CD8+ T-cell clone following retroviral transduction with the IL-15 gene. Blood. 2007; 109:5168-77.

Mismatching of chemokine receptors on T cells and tumor-secreted chemokines has been shown to account for the suboptimal trafficking of T cells into the tumor microenvironment. To improve efficacy of therapy, the cells may be genetically modified to increase recognition of chemokines in tumor micro environment. Examples of such modifications are described in Moon et al., Expression of a functional CCR2 receptor enhances tumor localization and tumor eradication by retargeted human T cells expressing a mesothelin-specific chimeric antibody receptor. Clin Cancer Res. 2011; 17: 4719-4730; and Craddock et al., Enhanced tumor trafficking of GD2 chimeric antigen receptor T cells by expression of the chemokine receptor CCR2b. J Immunother. 2010; 33: 780-788.

The cells may be genetically modified to enhance expression of costimulatory/enhancing receptors, such as CD28 and 41BB.

Adverse effects of T cell therapy can include cytokine release syndrome and prolonged B-cell depletion. Introduction of a suicide/safety switch in the recipient cells may improve the safety profile of a cell-based therapy. Accordingly, the cells may be genetically modified to include a suicide/safety switch. The suicide/safety switch may be a gene that confers sensitivity to an agent, e.g., a drug, upon the cell in which the gene is expressed, and which causes the cell to die when the cell is contacted with or exposed to the agent. Exemplary suicide/safety switches are described in Protein Cell. 2017 August; 8(8): 573-589. The suicide/safety switch may be HSV-TK. The suicide/safety switch may be cytosine deaminase, purine nucleoside phosphorylase, or nitroreductase. The suicide/safety switch may be RapaCIDe™, described in U.S. Patent Application Pub. No. US20170166877A1. The suicide/safety switch system may be CD20/Rituximab, described in Haematologica. 2009 September; 94(9): 1316-1320. These references are incorporated by reference in their entirety.

The anti-HLA-PEPTIDE ABP CAR may be introduced into the recipient cell as a split receptor which assembles only in the presence of a heterodimerizing small molecule. Such systems are described in Science. 2015 Oct. 16; 350(6258): aab4077, and in U.S. Pat. No. 9,587,020, which are hereby incorporated by reference in its entirety.

In some embodiments, the cells include one or more nucleic acids, e.g., a polynucleotide encoding an anti-HLA-PEPTIDE ABP CAR disclosed herein, wherein the polynucleotide is introduced via genetic engineering, and thereby express recombinant or genetically engineered receptors, e.g., anti-HLA-PEPTIDE ABP CARs, as disclosed herein. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The nucleic acids may include a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

Methods for Engineering Cells with ABPs

Also provided are methods, nucleic acids, compositions, and kits, for expressing the ABPs, including receptors comprising antibodies, and anti-HLA-PEPTIDE ABP CARs, and for producing genetically engineered cells expressing such ABPs. The genetic engineering generally involves introduction of a nucleic acid encoding the recombinant or engineered component into the cell, such as by retroviral transduction, transfection, or transformation.

Preparation of Engineered Cells

In some embodiments, preparation of the engineered cells includes one or more culture and/or preparation steps. The cells for introduction of the HLA-PEPTIDE-ABP, e.g., CAR, can be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

In some embodiments, the cells are incubated and/or cultured prior to or in connection with genetic engineering.

Assays

A variety of assays known in the art may be used to identify and characterize an HLA-PEPTIDE ABP provided herein.

Pharmaceutical Compositions

An ABP, cell, or HLA-PEPTIDE target provided herein can be formulated in any appropriate pharmaceutical composition and administered by any suitable route of administration. Suitable routes of administration include, but are not limited to, the intra-arterial, intradermal, intramuscular, intraperitoneal, intravenous, nasal, parenteral, pulmonary, and subcutaneous routes. These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g, oral, intravenous, cutaneous or subcutaneous, nasal, intramuscular, intraperitoneal routes.

Therapeutic Applications

For therapeutic applications, ABPs and/or cells are administered to a mammal, generally a human, in a pharmaceutically acceptable dosage form such as those known in the art and those discussed above. For example, ABPs and/or cells may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The ABPs also are suitably administered by peritumoral, intralesional, or perilesional routes, to exert local as well as systemic therapeutic effects. The intraperitoneal route may be particularly useful, for example, in the treatment of ovarian tumors.

The ABPs and/or cells provided herein can be useful for the treatment of any disease or condition involving HLA-PEPTIDE. In some embodiments, the disease or condition is a disease or condition that can benefit from treatment with an anti-HLA-PEPTIDE ABP and/or cell. In some embodiments, the disease or condition is a tumor. In some embodiments, the disease or condition is a cell proliferative disorder. In some embodiments, the disease or condition is a cancer.

In some embodiments, the ABPs and/or cells provided herein are provided for use as a medicament. In some embodiments, the ABPs and/or cells provided herein are provided for use in the manufacture or preparation of a medicament. In some embodiments, the medicament is for the treatment of a disease or condition that can benefit from an anti-HLA-PEPTIDE ABP and/or cell. In some embodiments, the disease or condition is a tumor. In some embodiments, the disease or condition is a cell proliferative disorder. In some embodiments, the disease or condition is a cancer.

In some embodiments, provided herein is a method of treating a disease or condition in a subject in need thereof by administering an effective amount of an ABP and/or cell provided herein to the subject. In some aspects, the disease or condition is a cancer.

In some embodiments, provided herein is a method of treating a disease or condition in a subject in need thereof by administering an effective amount of an ABP and/or cell provided herein to the subject, wherein the disease or condition is a cancer, and the cancer is selected from a solid tumor and a hematological tumor. In some embodiments, the cancer is selected from any one of the tumor types shown in FIG. 1B. In some embodiments, the cancer is selected from In some embodiments, provided herein is a method of modulating an immune response in a subject in need thereof, comprising administering to the subject an effective amount of an ABP and/or cell or a pharmaceutical composition disclosed herein. In some embodiments, the modulating of the immune response comprises increasing the immune response. Stimulating the immune response may comprise stimulating an immune response or enhancing an immune response.

In some embodiments of any one of the methods described herein, the presence of an HLA-PEPTIDE target described herein has been detected in the subject or a biological sample obtained from the subject. In some embodiments of any one of the methods described herein, the presence of a restricted peptide of an HLA-PEPTIDE target described herein has been detected in the subject or a biological sample obtained from the subject. In some embodiments of any one of the methods described herein, the presence of the HLA subtype of an HLA-PEPTIDE target described herein has been detected in the subject or a biological sample obtained from the subject. In some embodiments, the method comprises administering an ABP disclosed herein to the subject after having determined the presence of the HLA-PEPTIDE target, restricted peptide, or HLA in the biological sample obtained from the subject.

In some embodiments, contacting the ABP with cancer cells results in at least about 10%, 20%, 30%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% cytotoxicity. In some embodiments, a concentration of 0.1 nM, 1 nM, 5 nM or 10 nM of the ABP is sufficient to result in that cytotoxicity upon contacting the ABP with the a cancer cell that expresses a tumor antigen (e.g., HLA-peptide) and an effector cell.

In some embodiments, the cytotoxicity resulting from contacting an ABP of the present disclosure with a cancer cell is greater than from contacting a cancer cell with a reference ABP.

In some embodiments, the cancer cells have an A*01:01_NTDNNLAVY (SEQ ID NO: 214) copy numbers of less than about 300, about 350, about 400, about 450, about 500, about 550, about 600, about 650, about 700, about 750, about 800, about 850, about 900, about 950, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, about 20000, about 30000, and about 40000 copies/cell.

In some embodiments, the cancer cells have an A*01:01_NTDNNLAVY (SEQ ID NO: 214) copy numbers of less than about 300, about 350, about 400, about 450, about 500, about 550, about 600, about 650, about 700, about 750, about 800, about 850, about 900, about 950, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, about 20000, about 30000, and about 40000 copies/cell.

Diagnostic Methods

Also provided are methods for predicting and/or detecting the presence of a given HLA-PEPTIDE on a cell from a subject. Such methods may be used, for example, to predict and evaluate responsiveness to treatment with an ABP and/or cell provided herein.

In some embodiments, a blood or tumor sample is obtained from a subject and the fraction of cells expressing HLA-PEPTIDE is determined. In some aspects, the relative amount of HLA-PEPTIDE expressed by such cells is determined. The fraction of cells expressing HLA-PEPTIDE and the relative amount of HLA-PEPTIDE expressed by such cells can be determined by any suitable method. In some embodiments, flow cytometry is used to make such measurements. In some embodiments, fluorescence assisted cell sorting (FACS) is used to make such measurement. See Li et al., *J. Autoimmunity*, 2003, 21:83-92 for methods of evaluating expression of HLA-PEPTIDE in peripheral blood.

In some embodiments, detecting the presence of a given HLA-PEPTIDE on a cell from a subject is performed using immunoprecipitation and mass spectrometry. This can be performed by obtaining a tumor sample (e.g., a frozen tumor sample) such as a primary tumor specimen and applying immunoprecipitation to isolate one or more peptides. The HLA alleles of the tumor sample can be determined experimentally or obtained from a third party source. The one or more peptides can be subjected to mass spectrometry (MS) to determine their sequence(s). The spectra from the MS can then be searched against a database. An example is provided in the Examples section below.

In some embodiments, predicting the presence of a given HLA-PEPTIDE on a cell from a subject is performed using a computer-based model applied to the peptide sequence and/or RNA measurements of one or more genes comprising that peptide sequence (e.g., RNA seq or RT-PCR, or nanostring) from a tumor sample. The model used can be as described in international patent application no. PCT/US2016/067159, herein incorporated by reference, in its entirety, for all purposes.

Kits

Also provided are kits comprising an ABP and/or cell provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an ABP provided herein. The label or package insert indicates that the composition is used for treating the selected condition.

In some embodiments, the kit comprises (a) a first container with a first composition contained therein, wherein the first composition comprises an ABP and/or cell provided herein; and (b) a second container with a second composition contained therein, wherein the second composition comprises a further therapeutic agent. The kit in this embodiment can further comprise a package insert indicating that the compositions can be used to treat a particular condition, e.g., cancer.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993): A. L. Lehninger, *Biochemistry* (Worth Publishers, Inc., current addition): Sambrook, et al., *Molecular Cloning: A Laboratory Manual* (2nd Edition, 1989): *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990): Carey and Sundberg *Advanced Organic Chemistry* 3$^{rd}$ *Ed.* (Plenum Press) Vols A and B (1992).

Example 1: Determining Expression Levels of CT83 in Various Tumor Types

Figure 1A:
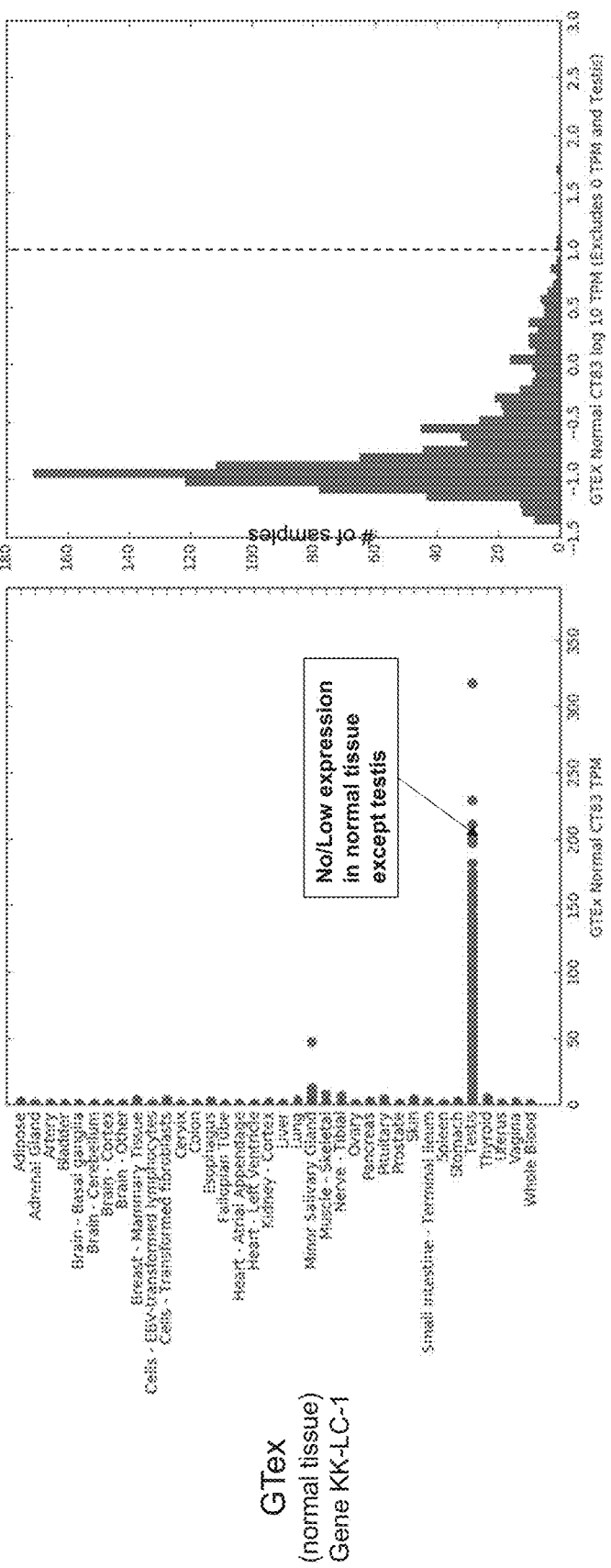
FIG. 1A depicts levels of expression (in transcript per million (TPM)) of the KKLC-1 gene in normal tissue.

CT83 (also referred to as KKLC1) is a cancer testis antigen that is highly expressed in several cancer types. As shown in FIG. 1A and Table 1 there are low (and occasionally negligible) expression levels of CT83 in several normal tissues, with the exception of normal testis tissue.

TABLE 1

Expression levels of CT83 in normal tissue

| Normal Tissue | Median TPM | 95%-tile TPM |
|---|---|---|
| Brain (all GTEx areas) | 0 | 0.08 |
| Adipose | 0 | 0.11 |
| Adrenal Gland | 0 | 0.10 |
| Artery - Aorta | 0 | 0.10 |
| Artery - Coronary | 0 | 0.10 |
| Bladder | 0 | 0.32 |
| Breast - Mammary Tissue | 0 | 0.34 |
| Cervix - Ectocervix | 0.06 | 0.14 |
| Cervix - Endocervix | 0 | 0.13 |
| Colon | 0 | 0.12 |
| Esophagus - Gastroesophageal Junction | 0 | 0.00 |
| Esophagus - Mucosa | 0 | 0.12 |
| Esophagus - Muscularis | 0 | 0.11 |
| Fallopian Tube | 0 | 0.16 |
| Heart - Atrial Appendage | 0 | 0.06 |
| Heart - Left Ventricle | 0 | 0.00 |
| Kidney - Cortex | 0 | 0.15 |

TABLE 1-continued

Expression levels of CT83 in normal tissue

| Normal Tissue | Median TPM | 95%-tile TPM |
|---|---|---|
| Liver | 0 | 0.02 |
| Lung | 0 | 0.32 |
| Minor Salivary Gland | 0.66 | 6.11 |
| Muscle - Skeletal | 0 | 0.08 |
| Nerve - Tibial | 0 | 0.11 |
| Ovary | 0 | 0.12 |
| Pancreas | 0 | 0.10 |
| Pituitary | 0 | 0.13 |
| Prostate | 0 | 0.18 |
| Skin | 0 | 0.12 |
| Small Intestine - Terminal Ileum | 0 | 0.12 |
| Spleen | 0 | 0.00 |
| Stomach | 0 | 0.12 |
| Testis | 74.54 | 163.97 |
| Thyroid | 0 | 0.26 |
| Uterus | 0 | 0.11 |
| Vagina | 0 | 0.24 |
| Whole Blood | 0 | 0.00 |

Figure 1B:
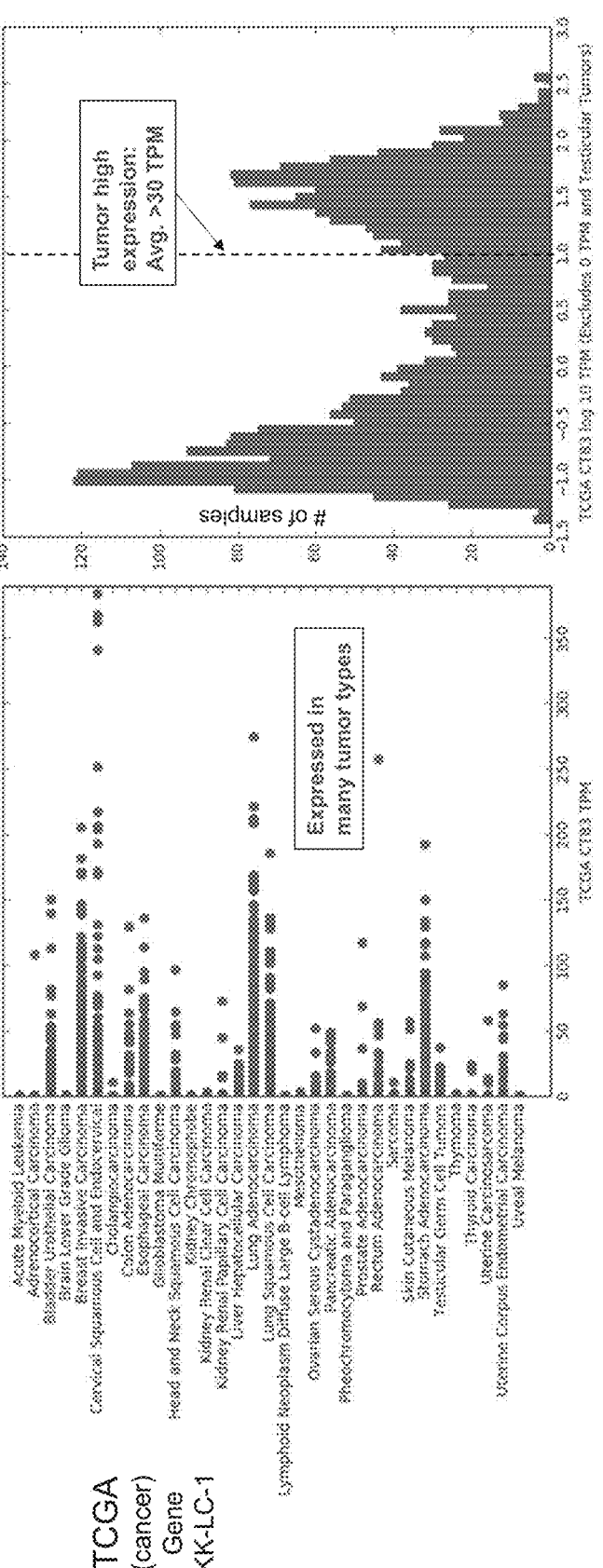
FIG. 1B depicts the levels of expression (in transcript per million (TPM)) of the KKLC-1 gene in the indicated tumor cells.

In contrast, as shown in FIG. 1B, CT83 is highly expressed across several type of tumor tissues, and of the tumor tissue types shown in FIG. 1B, there is an average CT83 transcript per million (TPM) of over 30 TPM.

Figure 2:
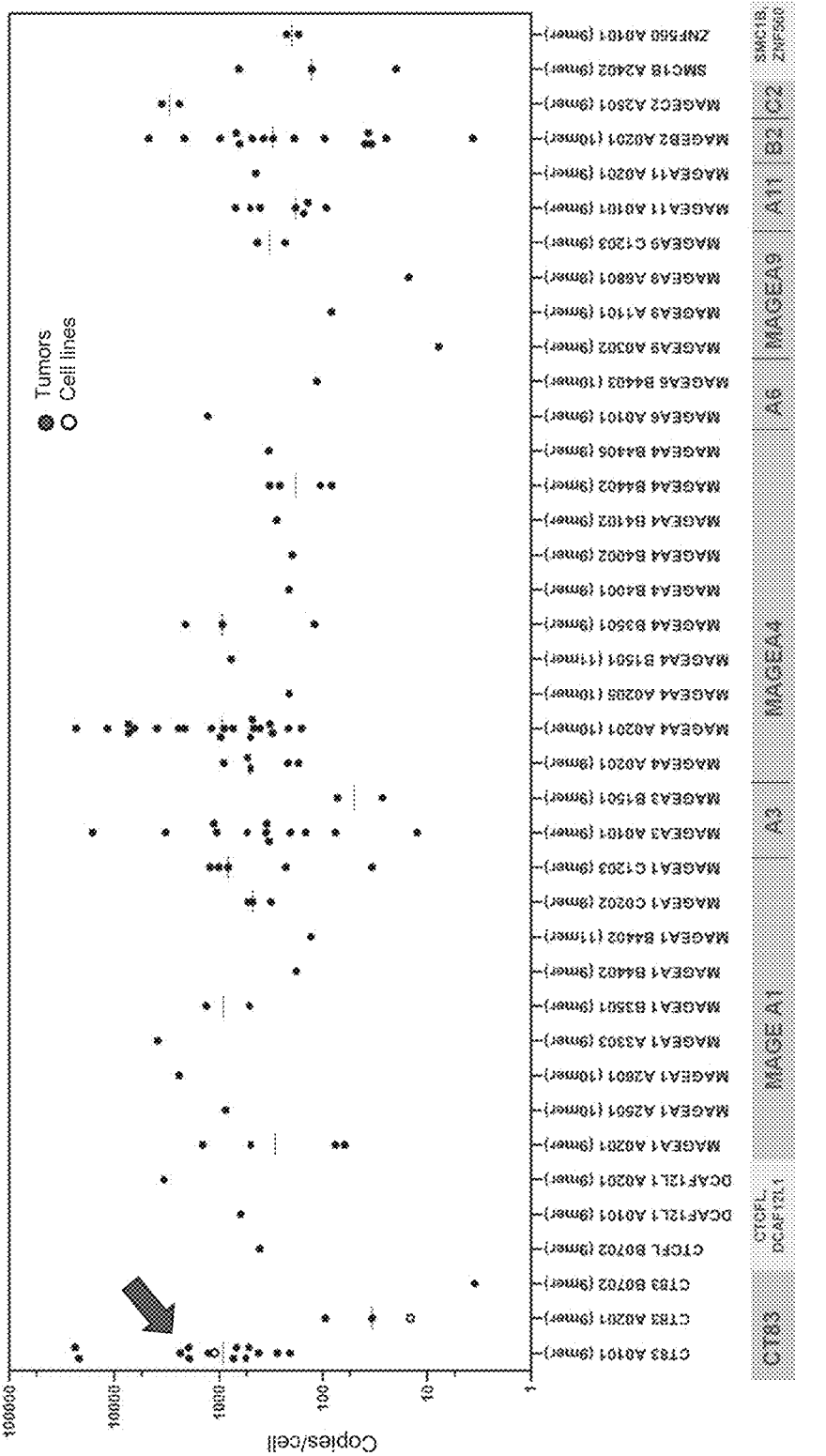
FIG. 2 depicts the copy numbers for tumor antigen targets, e.g., the copy number for *A01:01 target in the CT-83 gene (arrow).

Mass spectrometry was used to determine the copies/cell of various targets within the tumor antigens indicated in FIG. 2. Due to a heavy standard deviation observed at end of the mass spectrometry process, copy numbers were recalculated assuming 20% generic recovery. The results showed that the HLA-PEPTIDE target A*01:01_NTDNNLAVY (SEQ ID NO: 214) (also referred to as G2) was detected in multiple tumor samples at a high median copy number (FIG. 2, arrow). Table 2 shows the mean and median copy numbers measured using mass spectrometry (n=14 tumors) as well as the prevalence of top tumor indications within the United States of America. The mean and median copy numbers reported in Table 2 are corrected copies per cell based on median G2 process recovery of 6% in n=18 tumor/tumor cell lines.

TABLE 2

The calculated copy numbers for A*01:01_ NTDNNLAVY (SEQ ID NO: 214) target and top tumor indications within which CT83 is highly expressed.

| HLA | Gene | Calculated Copies/Cell | Top Tumor indications | Prevalence (US) |
|---|---|---|---|---|
| G2 A*01:01 | CT83 | 13000 mean 3000 median | Esophageal | 10% |
| | | | Gastric Adenocarcinoma | 11% |
| | | | Lung Adenocarcinoma | 9% |
| | | | Lung squamous | 5% |

These results indicate that the G2 target is highly expressed in multiple prevalent cancer types and has a high copy number in these prevalent tumor indications.

Example 2: Identification of Antigen-Binding Proteins (ABPs) that Selectively Bind HLA-PEPTIDE Target A*01:01_NTDNNLAVY (SEQ ID NO: 214) Over Identified G2 Off-Target Liability Peptides To identify lead target sequences against HLA-PEPTIDE target A*01:01_NTDNNLAVY (SEQ ID NO: 214) (G2), two lead molecules: 2H03 (D5) and 2F10 (C11), were selected based on their specificity, affinity, and potency (see, e.g., WO2021168355A1, published Aug. 26, 2021, hereby incorporated by reference in its entirety). To improve the potency, an affinity maturation campaign was carried out on both of these molecules. For the affinity maturation library design, the CDR3 regions of the heavy chains (VH) were randomized to include up to 3 mutations at a time while, CDR1 and CDR2 regions of the heavy chains included single mutations. For the C11_VH library, CDR3 region was randomized using 17 of 20 amino acids (except, Cysteine, Methionine, and Proline). D5_VH affinity maturation library was designed using a tailored in vitro affinity maturation (TiAM) approach.

Figure 3:
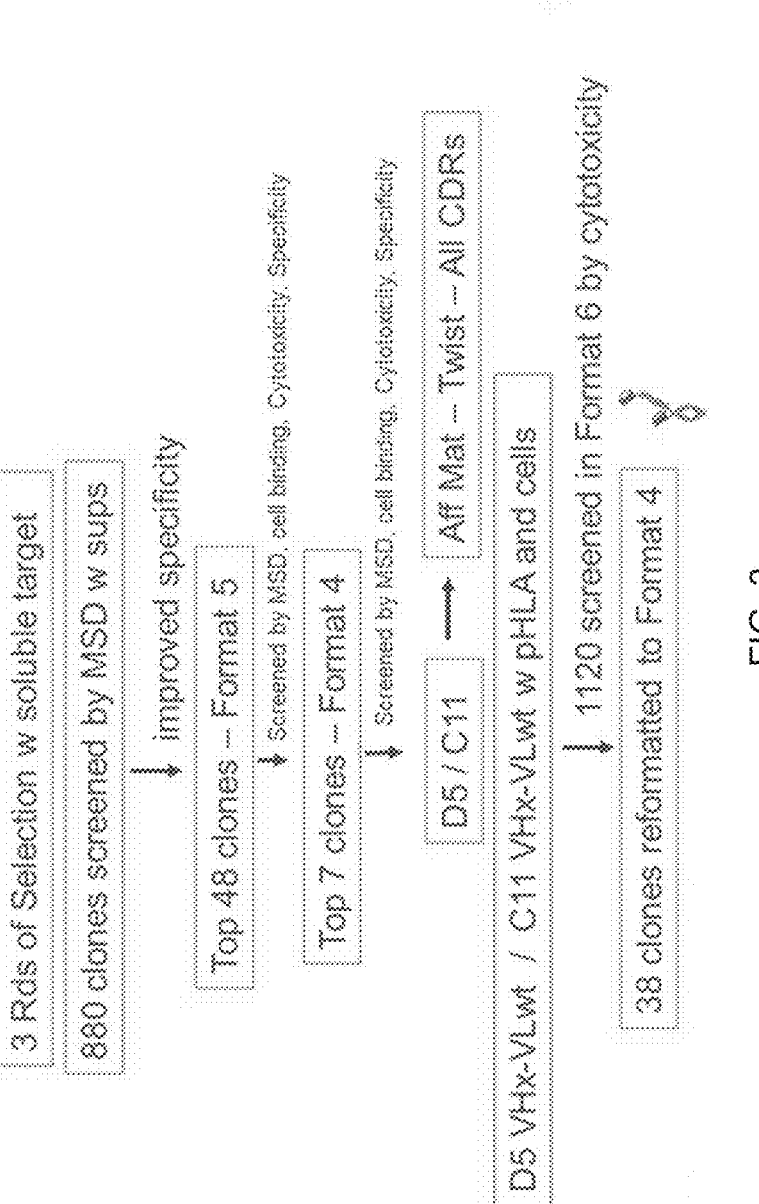
FIG. 3 is a flow chart showing the selection and screening process for identifying lead clones for use in the described antigen binding proteins.

As shown in FIG. 3, through affinity maturation of D5 and C11 and cytotoxicity screening of the randomly mutated clones in Format 6, 38 clones were identified as potential leads and for screening in Format 4.

Construction of Affinity Maturation Libraries

Affinity maturation libraries were synthesized at Twist Biosciences and delivered as double stranded V-gene fragments. To clone these libraries into pADL-23c phagemid vector, gene fragments were PCR amplified using forward (5'-CTCGCGGCCCAGCCGGCCATGG-3' (SEQ ID NO: 229)) and reverse (5'-GTTGGCCTCCCGGGC-CACTAGTTTTGATCTC-3' (SEQ ID NO: 230)) primers. PCR was carried out using Phusion high-fidelity PCR master mix with GC buffer (NEB) using 400 ng of template in 750 μl volume and cycled 25 times at 98° C.-10 sec, 70° C.-3, 72° C.-30 sec. Next, the PCR products as well as pADL-23c phagemid vector were digested using BglI restriction enzyme (NEB) for 4 hours at 37° C. and purified using gel extraction kit (Macherey-Nagel). The digested insert and vector were ligated using T4 DNA ligase (NEB) overnight at 16° C. Ligation reactions were purified using PCR clean-up kit (Macherey-Nagel) before electroporation into TG1 electrocompetent *E. coli* cells (Lucigen). After electroporation, the library was pooled and plated on 2YT media with 100 μg/mL carbenicillin and 2% glucose (2YTCG) agar plates and incubated overnight at 30° C. Serial dilution plates were also generated to determine the electroporation efficiency and to calculate the library size. Following, overnight incubation, plates were scrapped into 2YTCG media, aliquoted, and stored at –80° C.

Packaging of Affinity Maturation Libraries Employing CM13K-Trypsin Sensitive Helper Phage Aliquots of the libraries were thawed and 500 ml of 2YTCG cultures were inoculated with the initial $OD_{600}$=0.1. Cultures were grown at 37° C., 250 rpm until $OD_{600}$ reached 0.5. At that stage, CM13K helper phage were added to the cultures to the multiplicity of infection (MOI) of 10 and incubated at 37° C. without shaking for 30 minutes followed by 30 minutes with vigorous shaking. Cultures were centrifuged and pellets were resuspended in 2YT media with 100 μg/mL carbenicillin and 50 μg/mL kanamycin (2YTCK) medium and incubated at 25° C. overnight. On the following day, cultures were centrifuged and ¼ volume of PEG/NaCl solution was added to the supernatant to precipitate phage particles. After 4 hours of incubation on ice, the mixtures were centrifuged and white pellets containing phage particles were collected and resuspended in PBS. 250 μL of PEG/NaCl was added to the phage solution and incubated on ice for 30 minutes, followed by centrifugation at 18,000×g for 10 minutes. Supernatant was discarded and phage pellets were resuspended in PBS.

Panning of Affinity Maturation Libraries

For each of the affinity maturation libraries, three parallel panning campaigns were carried out. These were a) soluble-soluble panning, b) soluble-cell panning, c) cell-cell panning.

Soluble-Soluble Panning:

For the first-round panning, libraries (1.0E+11) were depleted against 100 nM of a pool of five negative control pHLAs (Table 3) for 1 hour at room temperature with rotation. pHLA bound phage were pulled down using Dyna-bead M-280 streptavidin beads (Life Technologies), and the supernatant (depleted library) was collected for selections.

TABLE 3

| List of G2 target and negative control peptides presented on A*0101 pHLA complex. | | |
|---|---|---|
| Peptide | Peptide Sequence | SEQ ID NO: |
| Target peptide | NTDNNLAVY | 214 |
| Control peptide-1 | YTDNWLAVY | 152 |
| Control peptide-2 | GTDNWLAQY | 203 |
| Control peptide-3 | ETDNNIVVY | 204 |
| Control peptide-4 | PTDENLARY | 205 |
| Control peptide-5 | NTDNLLTEY | 206 |

For selections, the depleted library was incubated with 100 nM of target pHLA complex for 1 hour at room temperature with rotation. Dynabead M-280 streptavidin beads (Life Technologies), blocked in 3% milk/PBS for one hour, were added to the mixture and incubated for one additional hour with rotation. Beads were collected using magnetic separator and any non-specific phages were removed by washing the beads five times with PBS with 0.05% tween-20 (PBST) followed by five additional washes with PBS. To elute the bound phages from the washed beads, 100 μl of freshly prepared 100 μg/mL TPCK-trypsin (NEB) was added and incubated for 15 minutes at room temperature. The eluted phages were then used to infect log growth TG-1 cells ($OD_{600}$=0.5) and after an hour of incubation at 37° C., cells were plated onto 2YTCG agar plates for output titer and bacterial growth for subsequent panning rounds. The next day, cells were scrapped and fresh 5 ml 2YTCG culture was started. Once $OD_{600}$ reached 0.5, phage particles were rescued using CM13K helper phage to a MOI of 10. For the second round of soluble-soluble panning, the process was repeated with lower target pHLA concentration, 50 nM.

Soluble-Cell Panning:

For the first-round of soluble panning, libraries (1.0E+11) were depleted against 100 nM of against a pool of five negative control pHLAs (Table 3) for 1 hour at room temperature with rotation. pHLA bound phage were pulled down using Dynabead M-280 streptavidin beads (Life Technologies), and the supernatant (depleted library) was collected for selections. The depleted library was incubated with 100 nM of target pHLA complex for 1 hour at room temperature with rotation. Dynabead M-280 streptavidin beads (Life Technologies), blocked in 3% milk/PBS for one hour, were added to the mixture and incubated for one additional hour with rotation. Beads were collected using magnetic separator and any non-specific phages were removed by washing the beads five times with PBST followed by five additional washes with PBS. To elute the bound phages from the washed beads, 100 μl of freshly prepared 100 μg/mL TPCK-trypsin (NEB) was added and incubated for 15 minutes at room temperature. The eluted phages were then used to infect log growth TG-1 cells (OD$_{600}$=0.5) and after an hour of incubation at 37° C., cells were plated onto 2YTCG agar plates for output titer and bacterial growth for subsequent panning rounds. Next day, cells were scrapped and fresh 5 ml 2YTCG culture was started. Once OD$_{600}$ reached 0.5, phages were rescued using CM13K helper phage to a MOI of 10.

For the second round, cell panning was carried out using A375 cells overexpressing G2 target peptide. Approximately, 0.5×10$^7$ of K562 cells, pulsed with 5 control peptides (Table 3) and 0.5×10$^7$ of A375-Luciferase cells were incubated with ~10$^{11}$ phage particles from the first round output of soluble panning for 1 hour at 4° C. to deplete the library against cell background. The phage/cell suspension was centrifuged at 500×g for 5 minutes, and the supernatant containing non-bound phage was incubated with 1×10$^7$ of A375 cells overexpressing G2 target for 1 hour at 4° C. The cells were then washed three times with pH 5 buffer (PBS with pH lowered to 5.0 using citric acid), followed by three washes with PBS, pH 7.4. To elute cell bound phage, cells were incubated with 100 μl of freshly prepared 100 μg/mL TPCK-trypsin (NEB) for 15 minutes at room temperature, followed by centrifugation at 500×g for 5 minutes. The phage elute was used to infect 2YCG culture at OD$_{600}$ 0.5 for 1 hour followed by plating cells on onto 2YTCG agar plates.

Cell-Cell Panning:

For the first round for cell panning, approximately, 1.0× 10$^7$ of A375-Luciferase cells were incubated with ~10$^{11}$ phage particles for 1 hour at 4° C. to deplete the library against cell background. The phage/cell suspension was centrifuged at 500×g for 5 minutes, then the supernatant containing non-bound phage was incubated with 1×10$^7$ of A375 cells overexpressing G2 target for 1 hour at 4° C. The cells were then washed three times with pH 5 buffer (PBS with pH lowered to 5.0 using citric acid), followed by three washes with PBS, pH 7.4. To elute cell bound phage, cells were incubated with 100 μl of freshly prepared 100 μg/mL TPCK-trypsin (NEB) for 15 minutes at room temperature, followed by centrifugation at 500×g for 5 minutes. The phage elute was used to infect 2YCG culture at OD$_{600}$ 0.5 for 1 hour followed by plating cells on onto 2YTCG agar plates.

For the second round, approximately, 0.5×10$^7$ of K562 cells, pulsed with 5 control peptide (Table 3) and 0.5×10$^7$ of A375-Luciferase cells were incubated with ~10$^{11}$ phage particles from the first round output for 1 hour at 4° C. to deplete the library against cell background. The phage/cell suspension was centrifuged at 500×g for 5 minutes, then the supernatant containing non-bound phage was incubated with 1×10$^7$ of A375 cells overexpressing G2 target for 1 hour at 4° C. The cells were then washed three times with pH 5 buffer (PBS with pH lowered to 5.0 using citric acid), followed by 3 washes with PBS, pH 7.4. To elute cell bound phage, cells were incubated with 100 μl of freshly prepared 100 μg/mL TPCK-trypsin (NEB) for 15 minutes at room temperature, followed by centrifugation at 500×g for 5 minutes. The phage elute was used to infect 2YCG culture at OD$_{600}$ 0.5 for 1 hour followed by plating cells on onto 2YTCG agar plates.

Example 3: Generation of Bispecific Antibodies that Specifically Bind an HLA-PEPTIDE Target and CD3

Antigen binding domains specific for various combinations of distinct targets were formatted into six bispecific construct designs (also referred to herein as formats). See International Application No. PCT/US2020/15736, which is hereby incorporated by reference in its entirety. For clarity, for designs (formats) #2-#6, the antigen binding domains are attached, directly or indirectly, to an Fc region. Format #3, #4, and #5 optionally comprise knob-hole or other Fc heterodimerization modification(s). Format #2 and #6 optionally comprise WT IgG1 Fc or IgG1 FC with TM mutations (P331S, L234E, L235F) sequences without knob-hole modification(s). In some embodiments, target 1 is the HLA-PEPTIDE target and target 2 is a cell surface molecule present on a T cell or NK cell. In some embodiments, target 2 is CD3. The antigen binding domain specific for CD3 can comprise CDRs or variable regions from any anti-CD3 antibody or antigen binding fragment thereof. In some embodiments, target 2 is CD16. It is contemplated that target 1 is A*01:01_NTDNNLAVY (SEQ ID NO: 214) (G2).

Briefly, bispecific antibodies were generated using standard molecular cloning techniques, including restriction digestion and ligation, gene synthesis, and homology-based cloning methods such as In-fusion (Takara). Positive clones were confirmed by DNA sequencing and used to generate bispecific antibody molecules by transfecting Expi-293 cells (Thermo) according to the manufacturer's protocol. Cultures were harvested and bispecific antibodies were purified from the supernatants using protein A, Kappa-select, or IMAC (GE healthcare) based chromatography methods. If necessary, bispecific antibodies or controls were polished by SEC or mixed-mode (CHT, BIO-RAD) chromatography. Molecules were formulated in PBS by dialysis or desalting chromatography. Molecules were evaluated to confirm high monomer purity (>95%) and low endotoxin (<1 EU/mg) prior to subsequent testing.

Examples of Formats 4, 5, and 6 are shown in FIGS. 4A and 4B. In the screening procedures for a lead anti-CT83 antibody (as outlined in FIG. 3), the first and second ABRs were the G2-targeted clones and the Fab portions were specific for CD3.

Example 4: Modification to Stabilize Conformation of Format 4 Antibodies that Specifically Bind G2 Target and CD3

Figure 6:
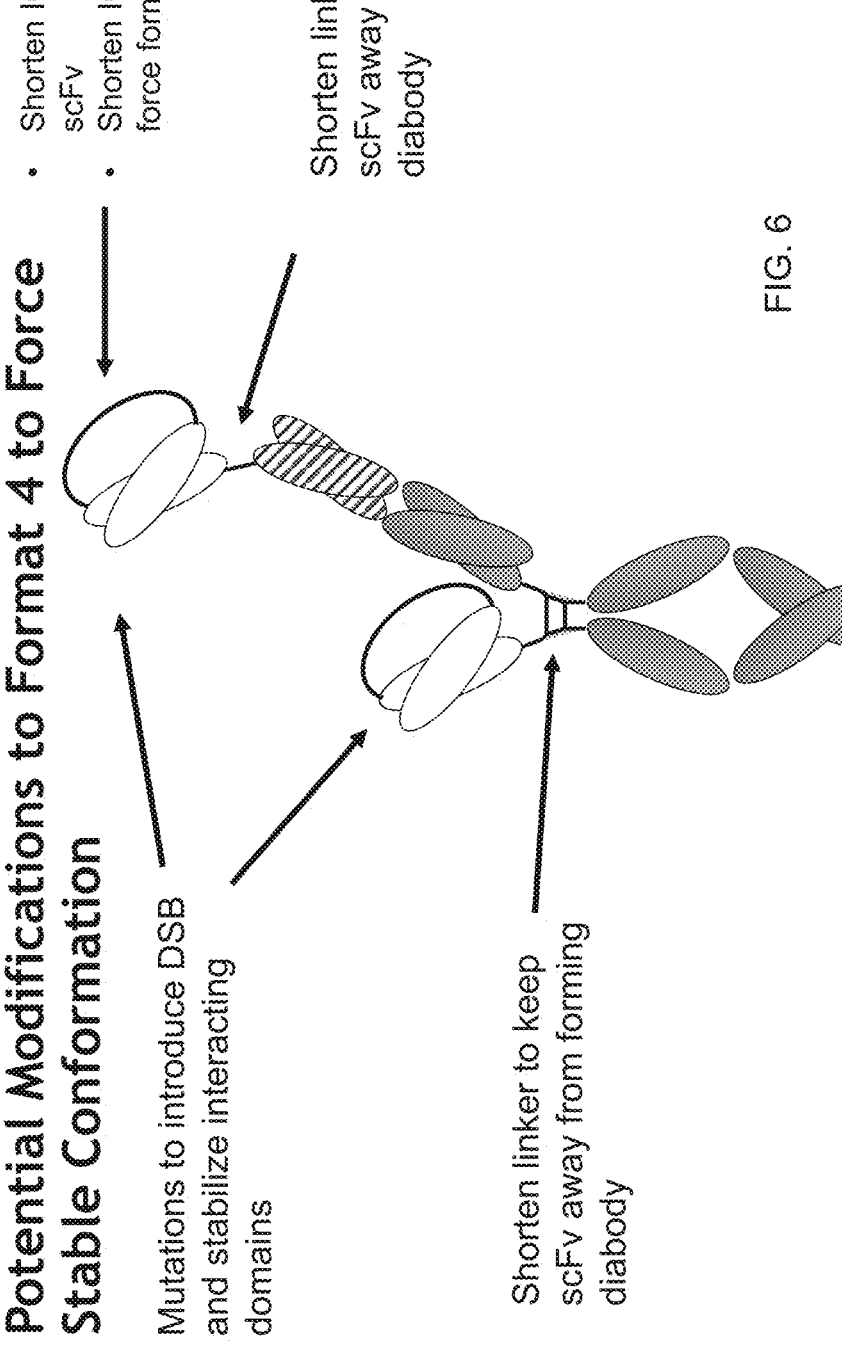
FIG. 6 depicts potential modifications to the Format 4 antibody that may result in stable conformation (either dual-scFv conformation or diabody conformation).

Format 4 antibodies (as shown in FIGS. 4A-5) can exist in two conformations. In solution, Format 4 antibody will be in equilibrium between (1) a dual scFv conformation and (2) a diabody conformation (see FIG. 5). The purpose of this experiment was to identify modifications to the Format 4 antibody that would stabilize the antibody in one conformation when in solution. Groups of Format 4 antibodies targeting G2-pHLA (C11, D5, 52C11, and 31E07 (also referred to as "E07" and affinity matured from D5): see Tables 19 and 20) were generated, each with one type of potential modification for Format-4 stability, as shown in FIG. 6. Examples of the groups of antibodies tested are shown in Table 4. The antibodies were evaluated for stability using size exclusion chromatography (SEC).

TABLE 4

Figure 7A:
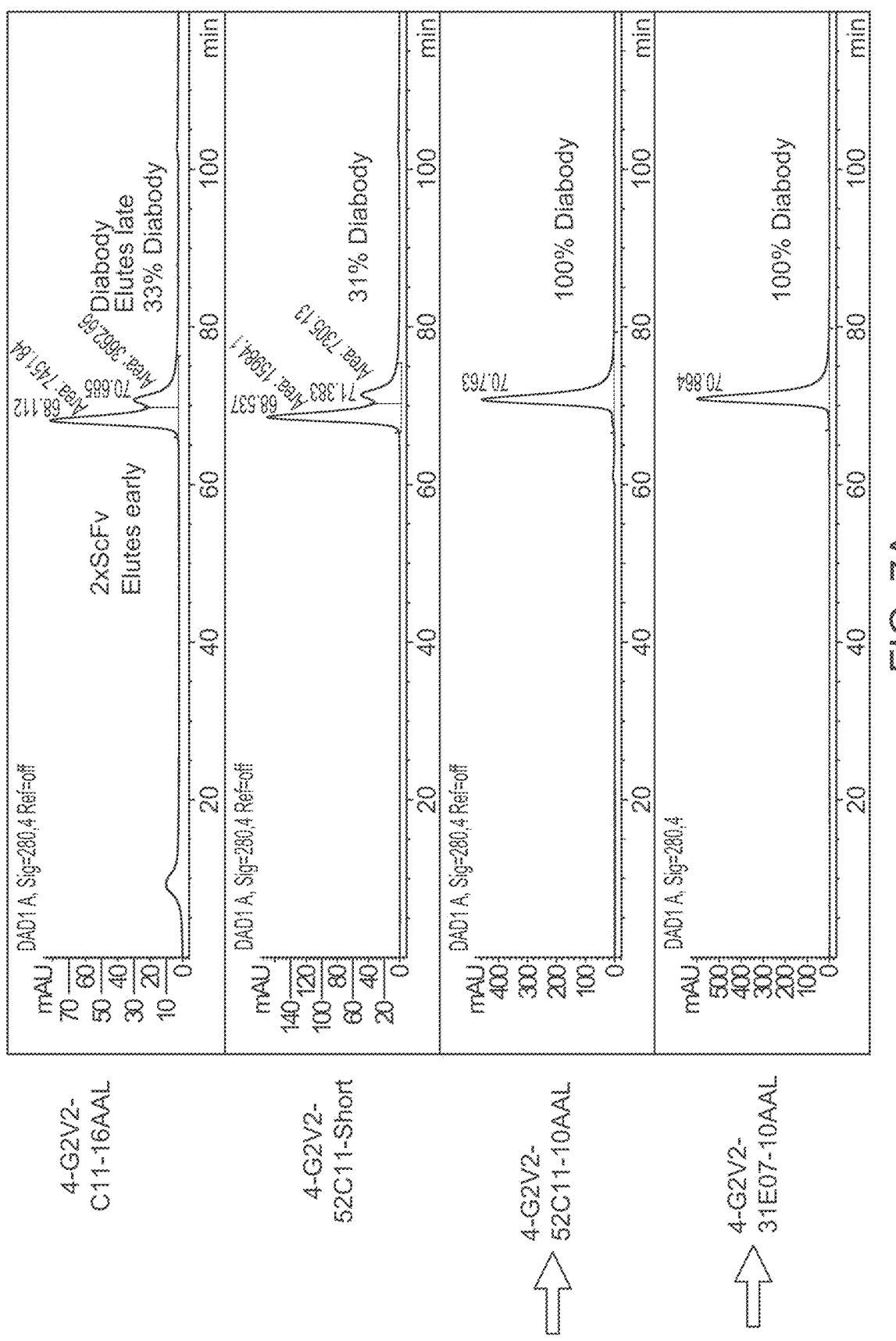
FIGS. 7A and 7B include size exclusion chromatograms of the modified Format 4 antibodies. The two arrows (FIG. 7A) show two antibodies that stably formed diabodies (Format 41 antibody formed). The two antibodies in FIG. 7B also stably formed diabodies.
Figure 7A:
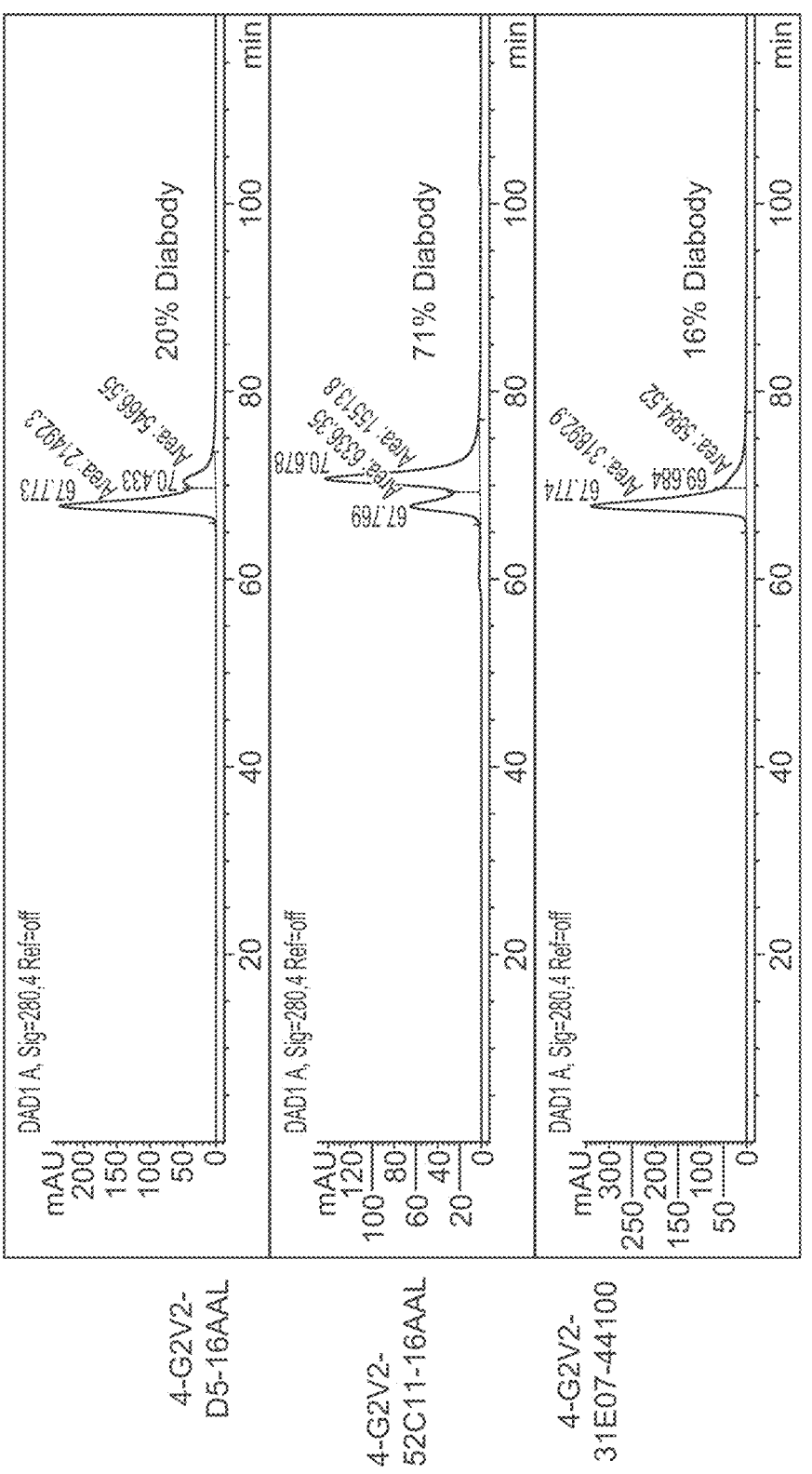
Figure 7B:
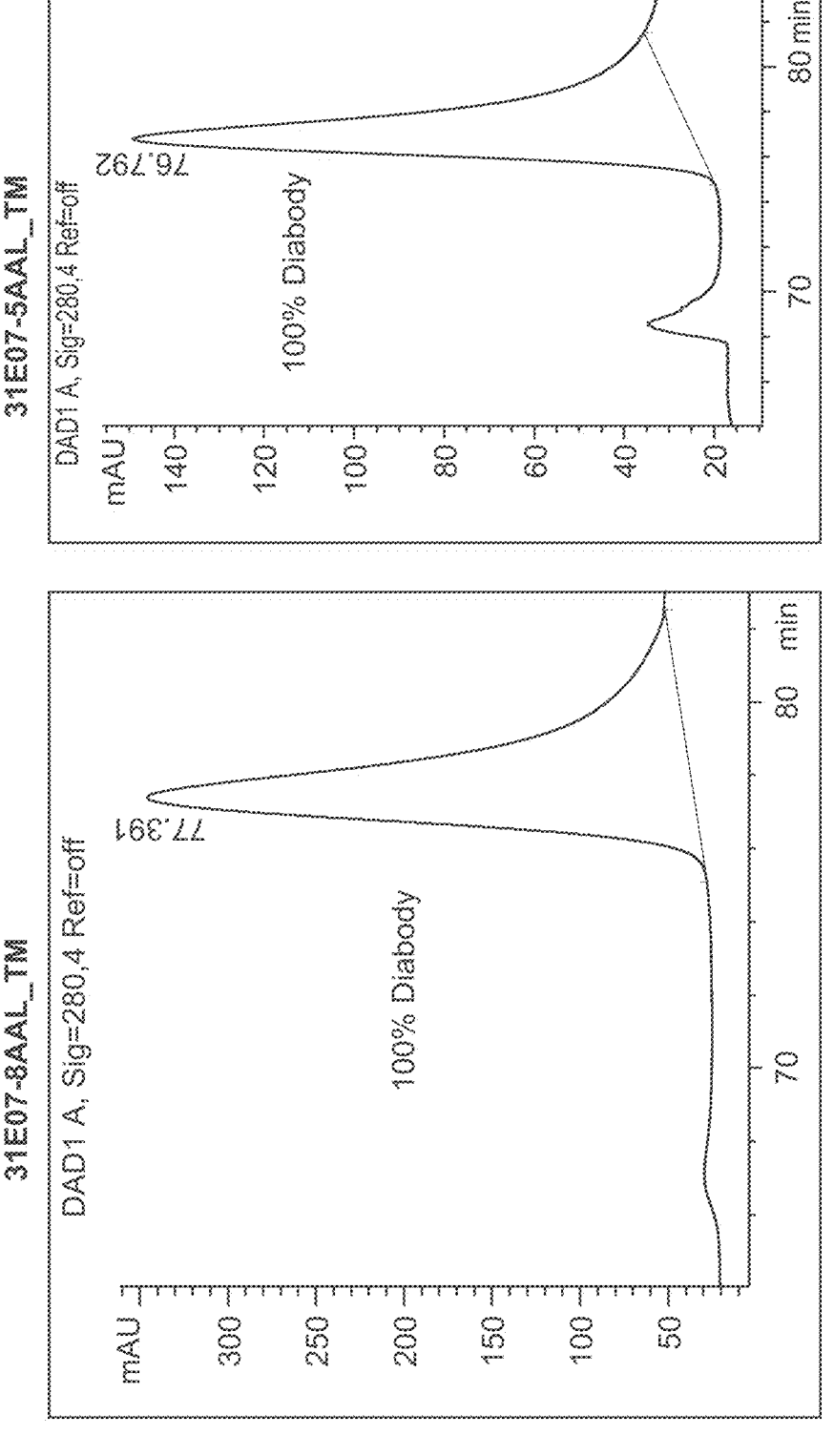

| Modifications tested for stability in Format-4 antibodies. | | |
|---|---|---|
| Format 4 Antibody (see FIGS. 7A-7B) | Anti-pHLA Clone | Modification for Stability |
| 4-G2V2-C11-16AAL | C11 | Shortened ICL; L1 = L2 = 16aa* |
| 4-G2V2-52-C11-Short | C11 | Shortened L3 and L4; L3 = GSGGGG-CP (SEQ ID NO: 237) and L4 = GSGGGG (SEQ ID NO: 231) |
| 4-G2V2-52-C11-10AAL | C11 | Shortened ICL; L1 = L2 = 10aa |
| 4-G2V2-31-E07-10AAL | 31E07 | Shortened ICL; L1 = L2 = 10aa |
| 4-G2V2-D5-16AAL | D5 | Shortened ICL; L1 = L2 = 16aa |
| 4-G2V2-52-C11-16AAL | C11 | Shortened ICL; L1 = L2 = 16aa |
| 4-G2V2-31-E07-44100 | 31E07 | Disulfide bond; cysteines at position 44 in the VH and position 100 in the VL (Kabat) |
| 31-E07-8AAL_TM | 31E07 | Shortened ICL; L1 = L2 = 8aa |
| 31-E07-5AAL_TM | 31E07 | Shortened ICL; L1 = L2 = 5aa |

*aa = amino acids

Size Exclusion Chromatography

Purified bispecific antibody samples (50 ug) were filtered using 0.22 um centrifugal filters (VWR P/N 82031-348) and spun at 4000 g for 1 minute to remove any large particulates. Approximately 40 ug of the filtered samples were then loaded on the Agilent HPLC-SEC with TSKgel G3000SWx1 column (Tosoh P/N 08541) with TSK guard column (Tosoh P/N 08543). An isocratic method using PBS with Calcium and Magnesium (Corning P/N 21-030-CM) as mobile phase was ran over 120 minutes with a flow rate of 0.125 ml/min to ensure good separation of 2×ScFv and diabody species. Responses were detected and recorded using A280 wavelength. The peaks on the chromatogram were manually integrated and the percentage of the diabody species were calculated based on the total peak areas from each sample.

The SEC chromatograms showed that most of the antibody groups had mixed populations of proteins in solution (i.e. unstable with both the dual scFv and diabody conformations present). However, four groups demonstrated a stable conformation: 4-G2V2-52-C11-10AAL, 4-G2V2-31-E07-10AAL, 31-E07-8AAL_TM, and 31-E07-5AAL_TM. These four antibody groups had shortened 5aa (5 amino acid), 8aa or 10aa linkers present at positions L1 and L2 (see FIGS. 7A-8). The four resulting chromatograms showed a single peak resulting from each group, indicating 100% diabody formation (see FIGS. 7A and 7B). The length and compositions of the ABR-region linkers for the 4-G2V2-52-C11-10AAL and 4-G2V2-31-E07-10AAL are shown in Table 5.

TABLE 5

| Linker compositions for the 4-G2V2-52-C11-10AAL and 4-G2V2-31-E07-10AAL | |
|---|---|
| ABR-region Linkers | |
| L1 | (GGGGS)x2 (SEQ ID NO: 111) |
| L2 | (GGGGS)x2 (SEQ ID NO: 111) |
| Knob (L3) | GGGGS-EPKSSDKTHTCP (SEQ ID NO: 232) |
| Hole (L4) | GGGGSGGGGS (SEQ ID NO: 111) |

This format having the shortened 10aa L1 and L2 linkers is referred to as "Format 41" (see FIG. 8A). Following the affinity maturation of D5 and C11, the selected clones were cytotoxicity screened in Format 6 and screened with cell binding to remove any clones that bind off-target pHLAs (see Example 2). From there, 38 of the clones (including E07) were incorporating into Format 41 for further cytotoxicity screening and cell-binding screening (see FIG. 8B).

As described herein, E07-CD3 diabody refers to the Format 41 bispecific antibody with its first and second ABRs comprising the VH and VL sequences for E07 (Table 19) and its Fab comprising the VH and VL for hOKT3a (Table 21).

Fabalactica Digestion to Confirm Diabody Formation

The results showed that shorter amino acid linker length (e.g., 10 amino acids of (G4S)×2 (SEQ ID NO: 111)) is enough to form the diabody confirmation for affinity mature molecules. The format 4 antibodies having a linker length of 10 amino acids without DSB were named "Format 41" antibodies. Their formation of diabody was confirmed by FabALACTICA digestion experiment, using the proteolysis by FabALACTICA methods described herein.

Figure 43B:
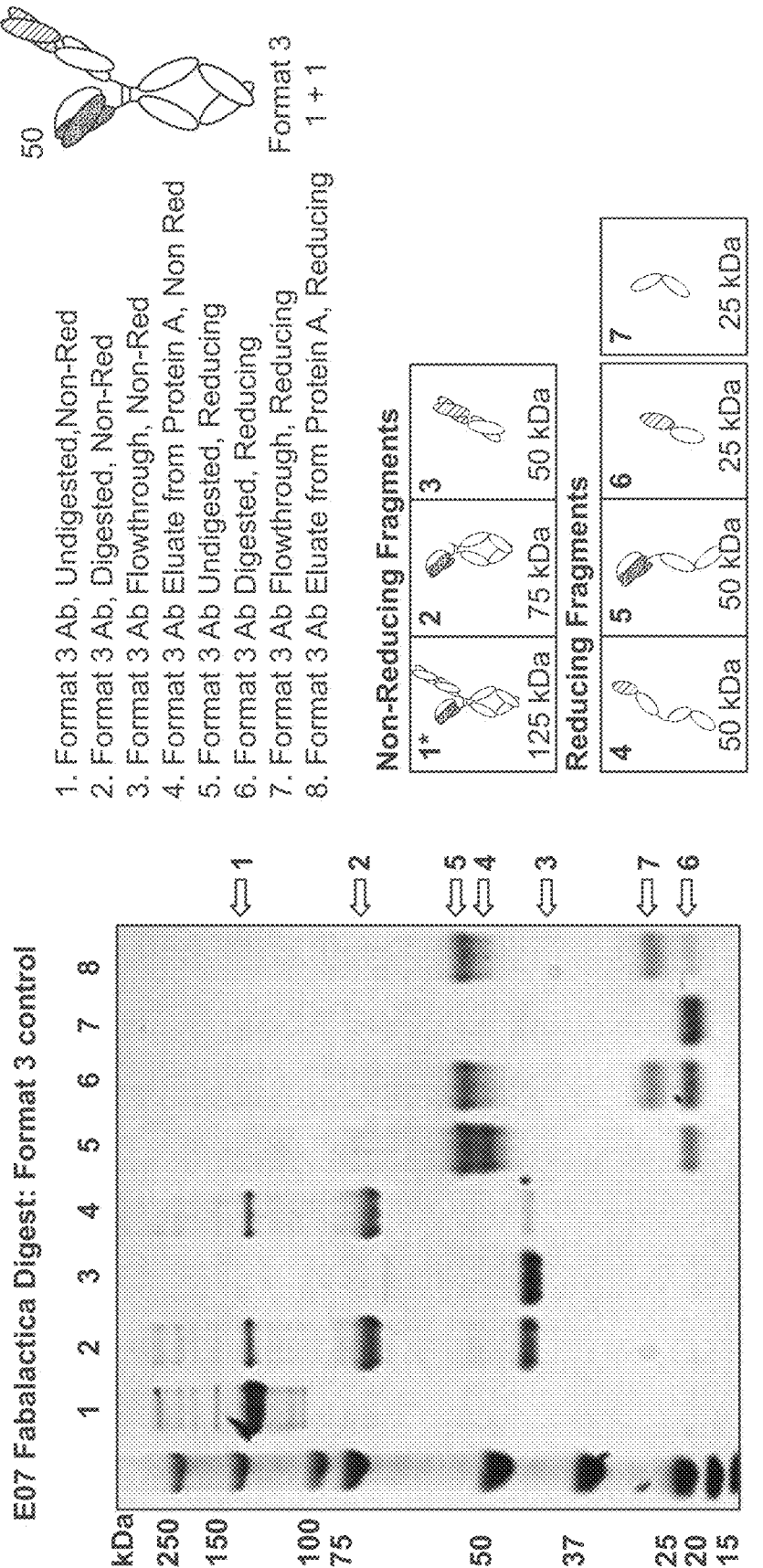

As shown in FIGS. 43A and 43B, the Format 41 antibody formed a diabody. After fabalactica digestion of format 41, whole content was passed through protein A column. The diabody formed by non-covalent interactions between VH (knob)-VL (hole) and VH (hole)-VL (Knob) resulted in retaining of digested fragments in the protein A column. A Format 3 antibody was used as a control. In case of the Format 3 antibody, after FabALACTICA digestion, the Fab portion of the molecule flows through protein A column showing the corresponding band in the SDS-PAGE gel. This can be seen by comparing lanes 3 and 7 of the FIG. 43A (Format 41) and FIG. 43B (Format 3).

Example 5: Cytotoxicity Screening in Format 41

Following the affinity maturation and screening to the select clones from D5 and C11, selected clones were incorporated into Format 41 and tested. E07 (which had been affinity matured from D5) was identified as a preferred clone.

Cytotoxicity Assay

Target and control cells were plated at 50,000 cells per well of 96 well plate. The target density was confirmed via mass spectrometry. These lines were transduced with luciferase. The target cell line were A375 melanoma cell lines (ATCC) transduced with CT83 and luciferase: while the A375 transduced with luciferase alone serves as the negative control. After allowing the cells to adhere for 3 hours, human T cells (All Cells) were added at a ratio of 5:1 effector to target (5:1 E:T) cells. Bispecific antibody (E07-CD3 diabody or D05 incorporate into Format 41 anti-CD3 antibody) was added to the well at indicated final concentration. Cultures were incubated for three days. Luciferase signal was assessed using Promega's Bio-Glo assay system (Cat. #G7941) according to manufacturer's instructions and read on the SpectraMax M5. Signal was normalized to control wells to determine the percent of cytotoxicity. Loss of luciferase signal is interpreted as loss of cell viability.

Figures 8B, 9:
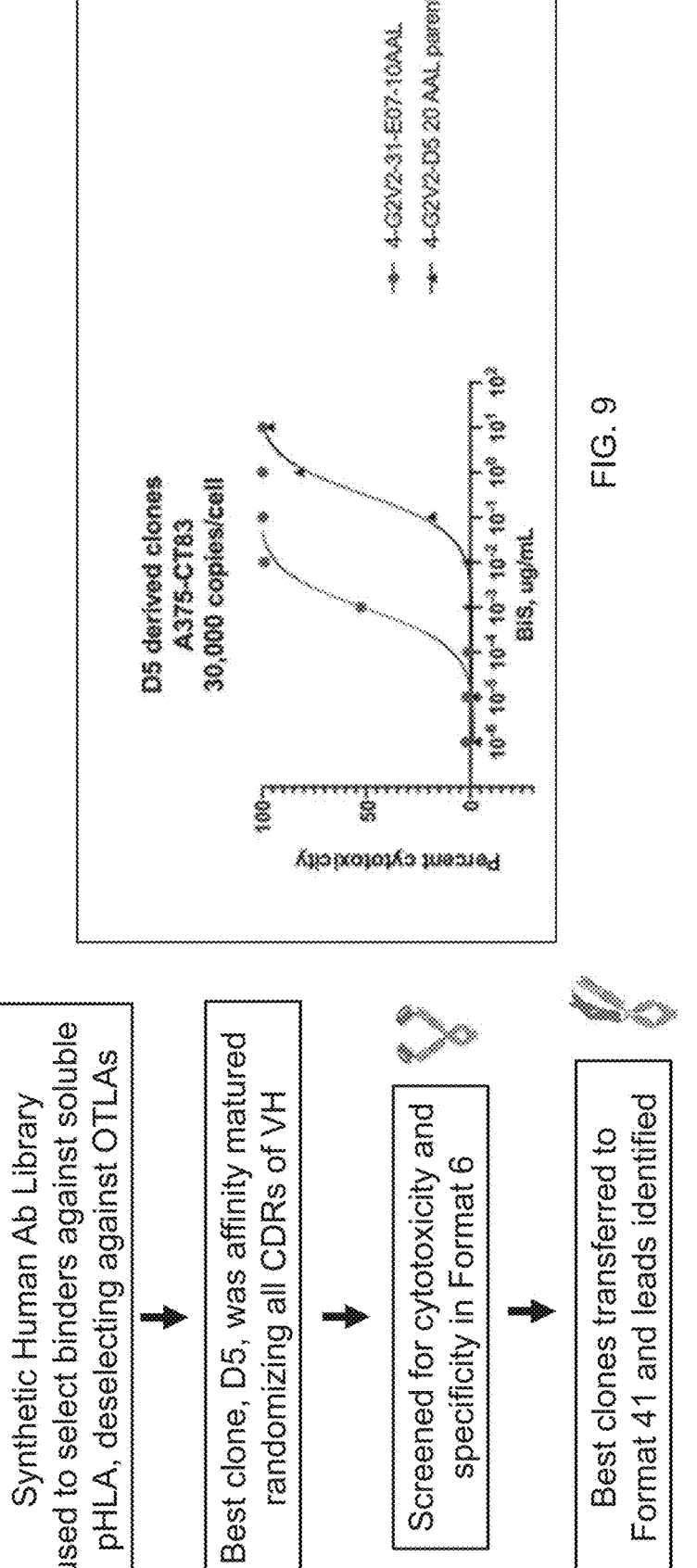
FIG. 8B includes a flow chart showing the screening process to identify preferred clones that were incorporated into Format 41 antibodies for further experimentation.
FIG. 9 depicts greater cytotoxicity resulting from the E07-CD3 diabody compared to a Format 41 antibody that incorporated the VH and VL sequences from D5 clone.

The results, as shown in FIG. 9, revealed significantly higher levels of cytotoxicity of the target cells (having a high copy number, e.g., 30,000 copies/cell) when using the affinity matured E07 lead compared to D05. Cytotoxicity screening revealed the E07 lead clone increased EC50 by approximately 350-fold.

Additional target cells lines were used in cytotoxicity assays. For example, the NCI-H1703 and NCI-H820, which were obtained from ATCC, were tested. The target density was confirmed via mass spectrometry.

The results, as shown in FIGS. 10A-10D, revealed high potency of the 41-E07 hOKT3a antibodies even when used on cells with low copy number (e.g., NCI-H820 cells with an A*01:01_NTDNNLAVY (SEQ ID NO: 214) copy number of 500 copies/cell). Potency was demonstrated across a broad copy number range and relevant target density cell lines. See Table 6 and FIGS. 10A-10D.

TABLE 6

| Luciferase-cytotoxicity assays with 41-E07 hOKT3a antibodies | |
|---|---|
| Cell line | EC50 (ug/ml) |
| A375-CT83 | 0.00017 |
| NCI-H1703 | 0.0025 |
| NCI-H820 | 0.077 |

Example 6: Examination and Optimization for Liabilities

The 41-E07 hOKT3a diabody was evaluated to determine potential off-target liabilities. These potential off target liabilities are peptide sequences predicted by EDGE and presented by the A01:01 HLA and have sequence similarity to the G2 target peptide.

Off-Target Liability Assessment (OTLA)

Figure 13:
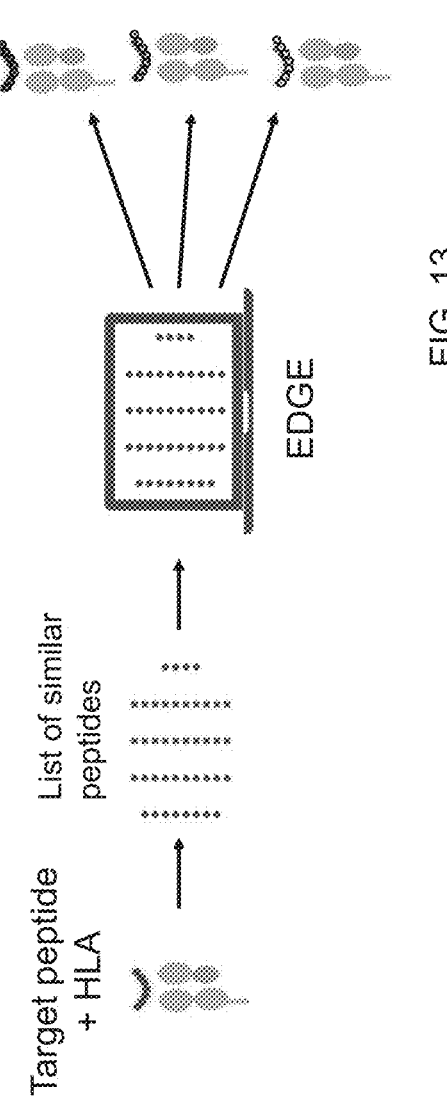
FIG. 13 depicts the procedures for conducting the off-target liability assessment (OTLA) with EDGE™ to identify OTLA sequences.

Peptides were prioritized for deselection and screening in the discovery campaign through our off-target liability analysis (OTLA) process. Briefly, EDGE™ (the proprietary presentation prediction algorithm EDGE, as described in Bulik-Sullivan, et al. *Nat Biotechnol.* 2018 Dec. 17. doi: 10.1038/nbt.4313, which is hereby incorporated by reference in its entirety) generated a large list of off-target liabilities for CT83 target sequence. This list was further prioritized based on their EDGE score (likelihood of being presented) and the number of mismatched amino acids (<4 mismatches) from the target sequence. The reduced sequence list was then validated by mass spectrometry on relevant tumor cells yielding 3 OTLAs. See FIG. 13.

Cell-Based Off-Target Liability Assessment

To evaluate specificity for target vs. off-target validated OTLAs, pulsed K562-HLA cells were treated with the bispecifics (41-E07 hOKT3a diabody)

K562 Cell Line Generation:

The Phoenix-AMPHO cells (ATCC®, CRL-3213™) were cultured in DMEM (Corning™, 17-205-CV) supplemented with 10% FBS (Seradigm, 97068-091) and Gluta-max (Gibco™, 35050079). K-562 cells (ATCC®, CRL-243™) were cultured in IMDM (Gibco™, 31980097) supplemented with 10% FBS. Lipofectamine LTX PLUS (Fisher Scientific, 15338100) contains a Lipofectamine reagent and a PLUS reagent. Opti-MEM (Gibco™ 31985062) was purchased from Fisher Scientific.

Phoenix cells were plated at 5×10e5 cells/well in a 6 well plate and incubated overnight at 37° C. For the transfection, 10 μg plasmid, 10 μL Plus reagent and 100 μL Opti-MEM were incubated at room temperature for 15 minutes. Simultaneously, 8 μL Lipofectamine was incubated with 92 μL Opti-MEM at room temperature for 15 minutes. These two reactions were combined and incubated again for 15 minutes at room temperature after which 800 μL Opti-MEM was added. The culture media was aspirated from the Phoenix cells and they were washed with 5 mL pre-warmed Opti-MEM. The Opti-MEM was aspirated from the cells and the lipofectamine mixture was added. The cells were incubated for 3 hours at 37° C. and 3 mL complete culture medium was added. The plate was then incubated overnight at 37° C. The media was replaced with Phoenix culture medium and the plate incubated an additional 2 days at 37° C.

The media was collected and filtered through a 45 μm filter into a clean 6 well dish. 20 μL Plus reagent was added to each virus suspension and incubated at room temperature for 15 minutes followed by the addition of 8 μL/well of Lipofectamine and another 15 min room temperature incubation. K562 cells were counted and resuspended to $5 \times 10^6$ cells/mL and 100 μL added to each virus suspension. The 6 well plate was centrifuged at 700 g for 30 minutes and then incubated at 37° C. for 5-6 hours. The cells and virus suspension were then transferred to a T25 flask and 7 mL K562 culture medium was added. The cells were then incubated for three days. The transduced K562 cells were then cultured in medium supplemented with 0.6 μg/mL Puromycin (Invivogen, ant-pr-1) and selection monitored by flow cytometry.

Flow Cytometry Methods:

HLA-transduced K562 cells were pulsed the night before with 50 μM of peptide (Genscript) in IDMEM containing 1% FBS in 6 well plates and incubated under standard tissue culture conditions. Cells were harvested, washed in PBS, and stained with eBioscience Fixable Viability Dye eFluor 450 for 15 minutes at room temperature. Following another wash in PBS+2% FBS, cells were resuspended with 41-E07 hOKT3a diabody at varying concentrations. Cells were incubated with bispecifics (41-E07 hOKT3a diabody) for 1 hour at 4° C. After another wash, PE-conjugated goat anti-human IgG secondary antibody (Jackson ImmunoResearch) was added at 1:100. After incubating at 4° C. for 45 minutes and washing in PBS+2% FBS, cells were resuspended in PBS+2% FBS and analyzed by flow cytometry. Flow cytometric analysis was performed on the Attune NxT Flow Cytometer (ThermoFisher) using the Attune NxT Software. Data was analyzed using FlowJo.

Results

Figure 14:
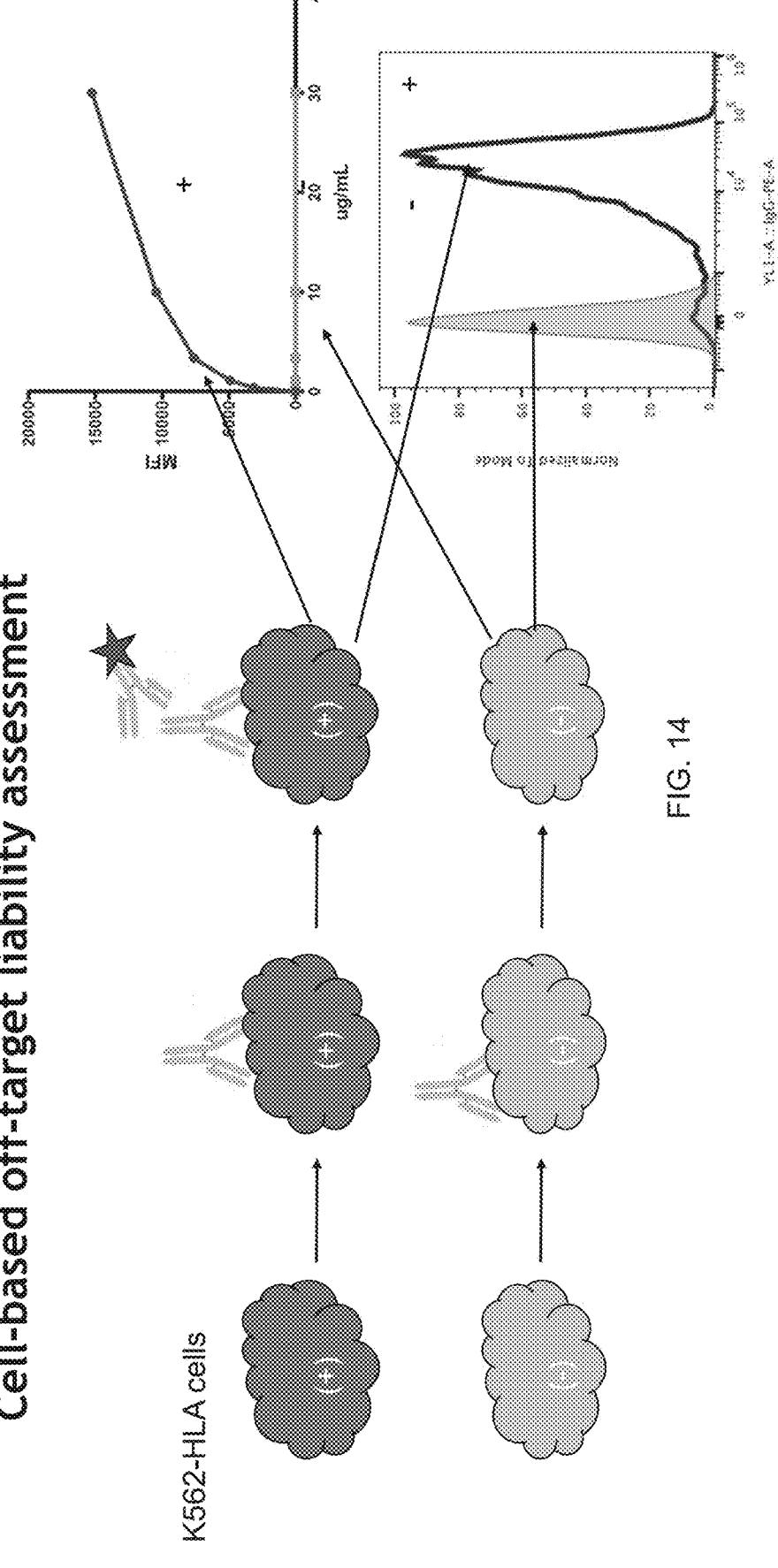
FIG. 14 includes a schematic showing the evaluation of K562 cells pulsed with the target antigen or off-target OTLAs and evaluated by flow cytometry.
Figure 15:
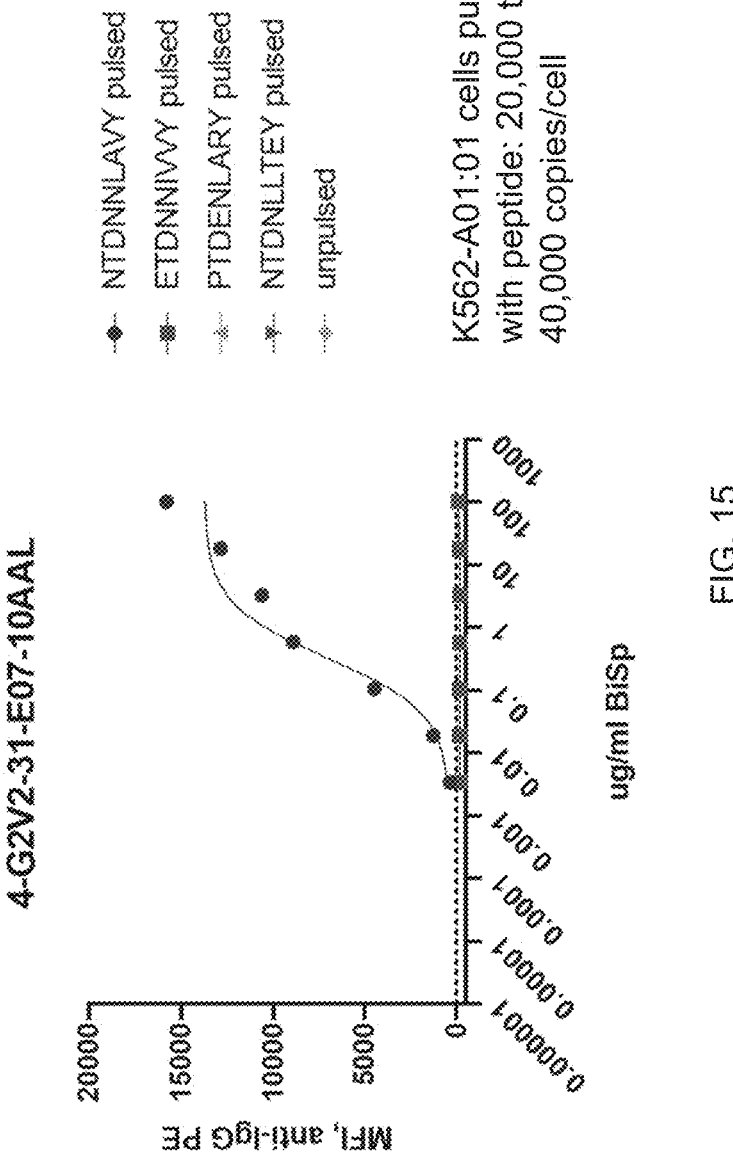
FIG. 15 depicts the flow cytometry results from the cell-based off-target liability assessment using K562-pulsed cells.

FIG. 14 is a schematic showing the binding of HLA-transduced K562 cells and expected exemplary MFI signals where there is binding specificity for the pulsed target (+) and there is no (or negligible) binding affinity to the pulsed OTLAs or unpulsed cells (−). As shown in FIG. 15, the flow cytometry results revealed 41-E07 hOKT3a diabody binds to its specific G2 target (NTDNNLAVY (SEQ ID NO: 214)) but not to the validated OTLAs.

Example 7: Additional Molecular Assessments for Drug-Ability

The 41-E07 hOKT3a diabody was evaluated to determine potential protein liabilities using Geneious Biologics software. See FIGS. 11 and 12.

Additional testing is conducted on the 41-E07 hOKT3a diabody to demonstrate its drug-ability and manufacturing. For example, the following assays are conducted on the 41-E07 hOKT3a diabody:

Polyreactivity assays to assess specificity

Figure 16A:
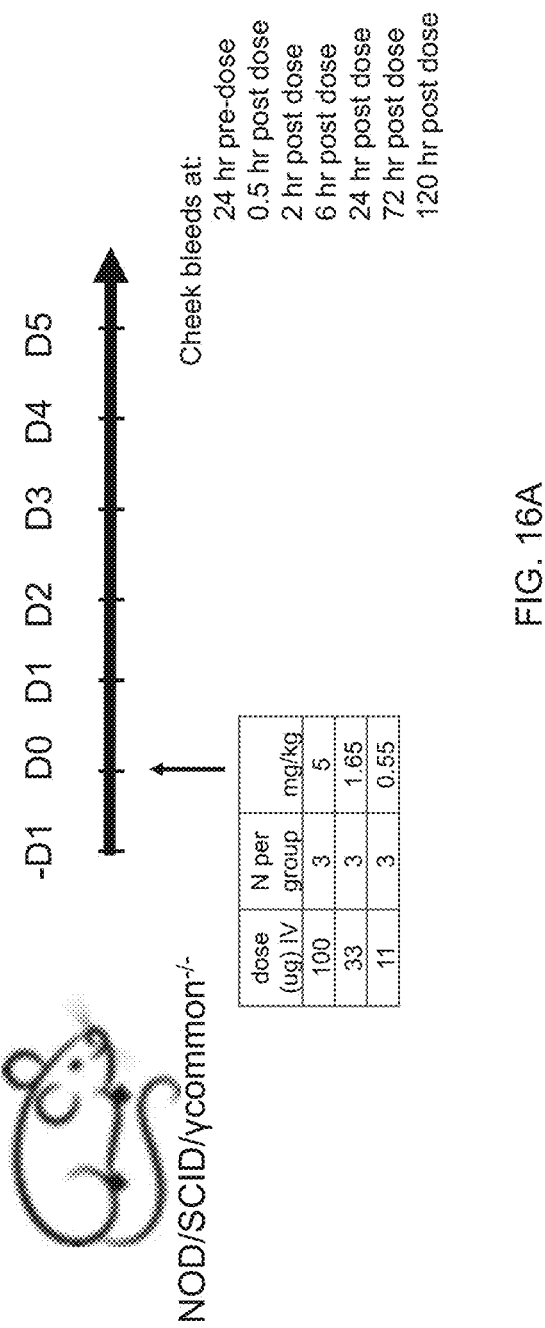
FIG. 16A depicts the study design for NOD/SCID/γcommon$^{-/-}$ mice treated with the indicated doses of E07-CD3 diabody for a pharmacokinetic assessment.

AC-SINS (affinity-capture self-interaction nanoparticle spectroscopy) to assess self-interaction DSF (Temperature stability measurements) to determine the melting temperature Analytical SEC to determine purity pH Hold Assay to determine stability of the molecule at low pH High concentration buffer screen over time (0, 1, 3, and 6 weeks) and at various temperatures (4° C., 37° C., and 40° C.) to determine best buffer to formulate and its stability Viscosity measurements to determine at what concentrations the material stays in solution Expression in Expi-CHO Titer and QC (quality control) to determine the level of expression and quality of material generated by CHO cells Example 8: In Vivo Pharmacokinetic (PK) Profiling PK in NSG Mice The 41-E07 hOKT3a diabody was administered to mice to examine the pharmacokinetic profile of the antibody. Briefly, eight to ten week old female NOD.Ch-Prkd$^{cscid}$Il2rg$^{tm1Wj1}$/SzJ (JAX) mice were used to assess PK in vivo. Blood was collected pre-dose from the submandibular vein. Mice were then dosed IV (intravitreally) with drug at varying concentrations as listed in FIG. 16A. Blood was collected from the submandibular vein at timepoints indicated. Blood samples were spun down in the presence of EDTA to collect plasma. Concentration of drug in the plasma was determined by Meso Scale Discovery (MSD). Briefly, an MSD GOLD Streptavidin plate (MSD) was coated with 1 ug/ml biotinylated pHLA antigen overnight. The plasma samples were diluted in PBS+10% FBS and mixed 1:1 with 1 ug/ml SulfoTag labeled anti-Fc antibody (Jackson ImmunoResearch) and incubated for 2 hours at room temperature. The pHLA coated plate was washed in PBS+0.1% Tween and plasma/antibody mixture was transferred to the plate and incubated for an additional 2 hours. The plate was then washed again and 2× read buffer was added before reading on MSD Qplex. Plasma concentration was determined by comparing to standard curve with purified drug on the same plate. Calculated concentrations were analyzed by two phase decay on GraphPad Prism V8.4.2 to determine half-life.

Figure 16B:
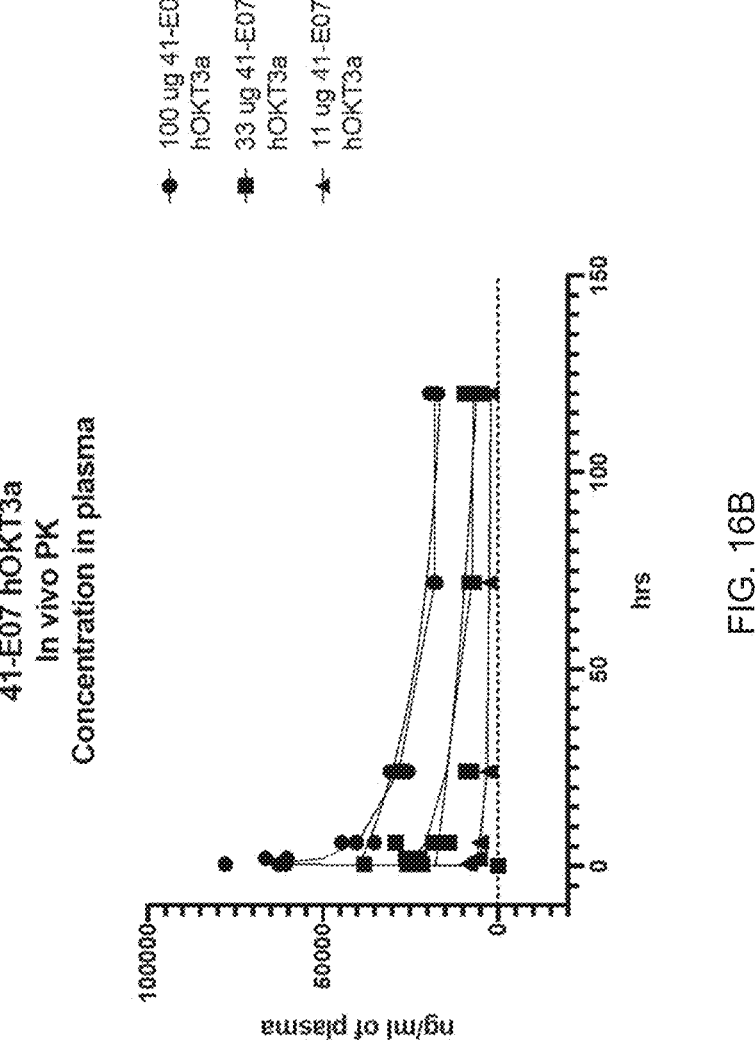
FIG. 16B shows the plasma levels of the different doses of E07-CD3 diabody in the mice.

The half-life for the 41-E07 hOKT3a diabody in mice was approximately 5 days. See Table 7 and FIGS. 16A-16B.

TABLE 7

| Dose | Apparent $t_{1/2}$ (hr) |
|---|---|
| 100 ug | 140 |
| 33 ug | 113 |
| 11 ug | LoD |

PK in Tg32 Mice

Figure 17:
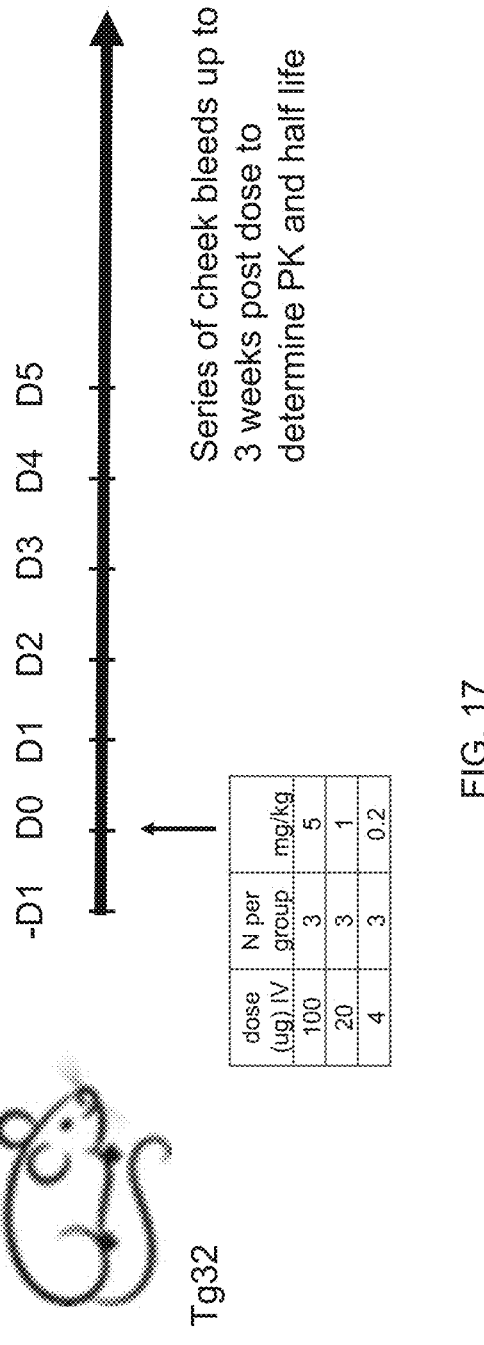
FIG. 17 depicts the study design for Tg32 mice treated with the indicated doses of E07-CD3 diabody for a pharmacokinetic assessment.

The pharmacokinetic profile for 41-E07 hOKT3a diabody is evaluated in Tg32 mice. These mice are knock-out KO for mouse FcRn receptor with knock-in of human FcRn receptor. It is a better predictor of the PK in humans. The dosing and overall procedure is illustrated in FIG. 17. Drug concentration in the plasma is determined by MSD using methods described supra.

Example 9: In Vivo Efficacy Tests

Figure 18:
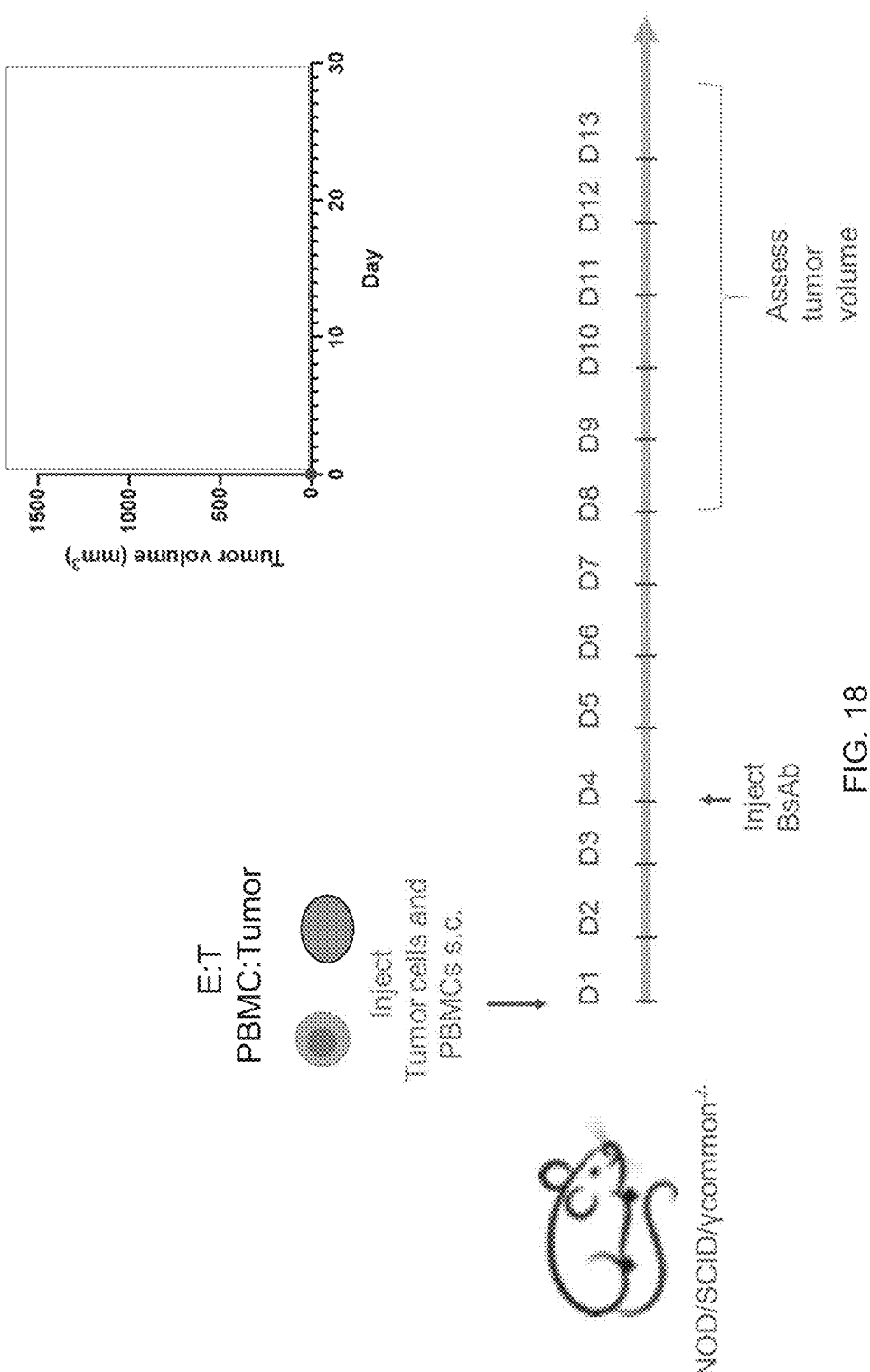
FIG. 18 depicts the study design for an in vivo efficacy assessment using NOD/SCID/γcommon$^{-/-}$ mice injected with tumor cells and PBMCs at Day 1 followed by E07-CD3 diabody at Day 4.
Figure 20:
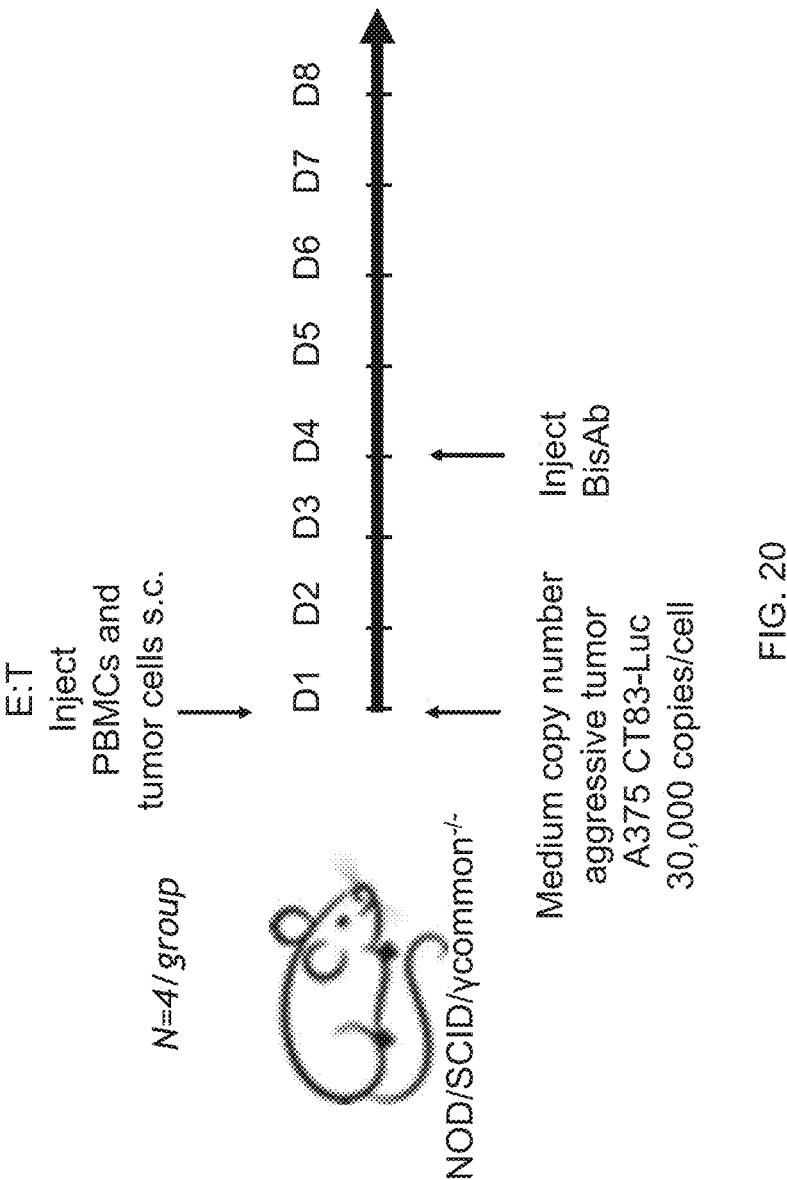
FIG. 20 depicts the study design for an in vivo efficacy assessment using NOD/SCID/γcommon$^{-/-}$ mice injected with tumor cells and PBMCs at Day 1 followed by E07-CD3 diabody at Day 4

Eight to ten week old female NOD.Ch-Prkd$^{cscid}$Il2rg$^{tm1Wj1}$/SzJ (JAX) mice were used to assess in vivo efficacy. FIG. 18 illustrates the general study design. Modeling data from Applied Biomath analysis shows a bell-shaped curve in the relationship between drug concentration and trimer formation (see FIG. 19).

Briefly, the A375 tumor cell line (ATCC) transduced to overexpress the CT83 gene and luciferase was used. This target cell was mixed with human PBMCs (All Cells) at 1:10 or 1:5 effector to target ratio (E:T). Namely, $1 \times 10^6$ tumor cells and $1 \times 10^5$ PBMCs per mouse for 1:10 E:T and $1 \times 10^6$ tumor cells and $5 \times 10^5$ PBMCs for 1:5 E:T. The mix of tumor and effector cells were injected s.c. (subcutaneously) in the flank of mouse. Tumors were allowed to form for three days. Tumors were measured by caliper and mice were randomized into groups based on tumor volumes. Then 41-E07 hOKT3a diabody diluted in PBS was dosed IV at the concentration indicated. Mice were monitored by caliper measurements of tumors as well as body weight. Mice were sacrificed at humane endpoints. Tumor volume data measurements were analyzed by 2-way ANOVA in GraphPad Prism V8.4.2 to determine significance.

Effect of E:T Ratios with Titration Curve of E07-CD3 Diabody with High Copy Number Tumors The 41-E07 hOKT3a diabody was dosed at day 4 and the E:T ratio was varied with titration curve of 41-E07 hOKT3a diabody to determine the correct values for each. Table 8 shows the groups and respective doses tested. This experiment was conducted with mice administered with medium copy number aggressive tumors (A375 CT83-Luc: 30,000 copies/cell).

TABLE 8

| Group | E:T (PBMCs:A375-CT83-Luc)* | Drug dose (ug/mouse) |
|---|---|---|
| 1 | 1 to 2 | 4 |
| 2 | | 0.8 |
| 3 | | 0.16 |
| 4 | | 0.032 |
| 5 | | 0 |
| 6 | 1 to 5 | 4 |
| 7 | | 0.8 |
| 8 | | 0.16 |
| 9 | | 0.032 |
| 10 | | 0 |
| 11 | 1 to 10 | 4 |
| 12 | | 0.8 |
| 13 | | 0.16 |
| 14 | | 0.032 |
| 15 | | 0 |
| 16 | 1 to 25 | 4 |
| 17 | | 0.8 |
| 18 | | 0.16 |
| 19 | | 0.032 |
| 20 | | 0 |
| 21 | 1 to 50 | 4 |
| 22 | | 0.8 |
| 23 | | 0.16 |

81

TABLE 8-continued

| Group | E:T (PBMCs:A375-CT83-Luc)* | Drug dose (ug/mouse) |
|---|---|---|
| 24 | | 0.032 |
| 25 | | 0 |
| 26 | 1 to 100 | 4 |
| 27 | | 0.8 |
| 28 | | 0.16 |
| 29 | | 0.032 |
| 30 | | 0 |

Tumor regression without the drug was observed in the 1:2 E:T ratio group. As shown in FIGS. 21A-21F, when the E07-CD3 diabody was dosed at day 4, tumor inhibition was observed at 1:10 E:T and 0.8 ug/mouse dose. There was some growth suppression observed at the 1:5 E:T with 0.16 and 0.8 ug/mouse doses. See FIGS. 21A-22B.

Alternative Models to Test Dosing Timing and Efficacy

Figure 23:
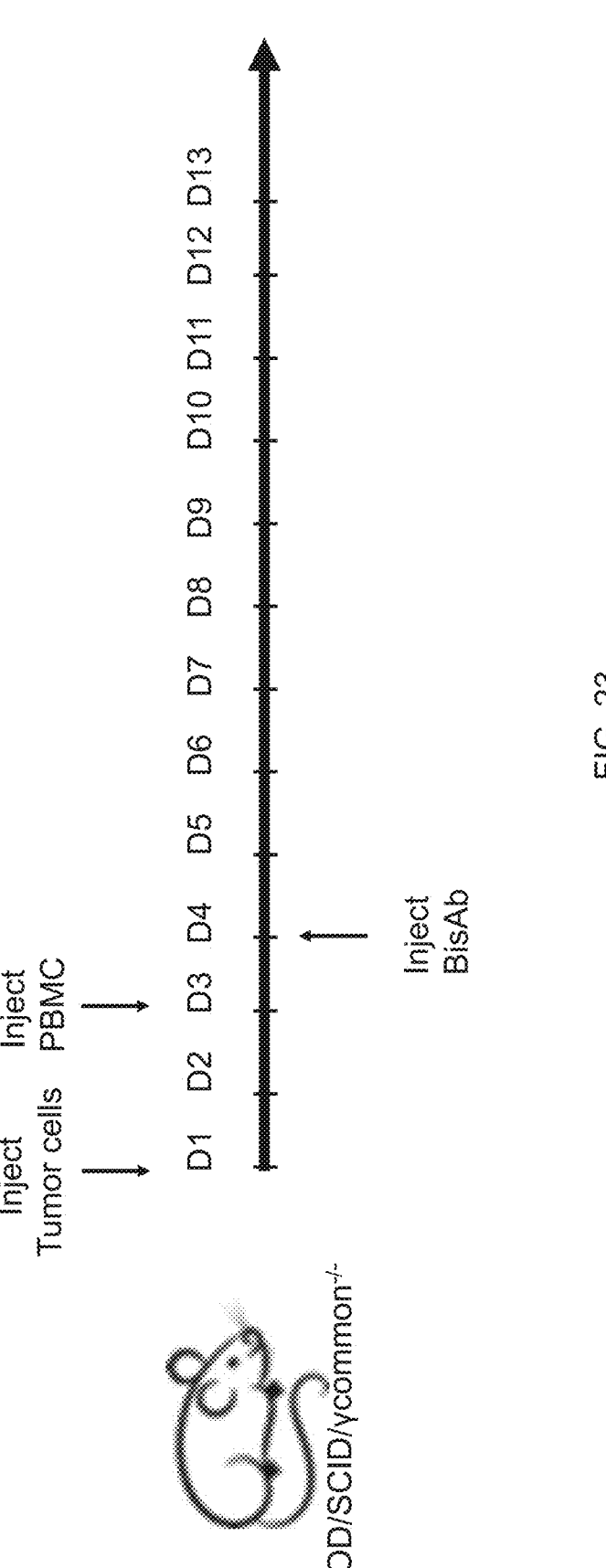
FIG. 23 depicts the study design for an in vivo efficacy assessment using NOD/SCID/γcommon$^{-/-}$ mice injected with tumor cells at Day 1, PBMCs at Day 3 followed by E07-CD3 diabody at Day 4.

To evaluate the effect of alternative dosing strategies, the tumor cells are injected in the mice at Day 1, the PBMC injected at Day 3, and the 41-E07 hOKT3a diabody dosed (by injection) at Day 4. The E:T ratio is varied with titration curve of 41-E07 hOKT3a diabody to determine the correct values for each. Tumor volume measurements will be taken throughout the study to evaluate efficacy of treatment. See FIG. 23 for general experimental design.

Example 10: Optimizing CD3 Antigen Binding Fragment

Figure 24:
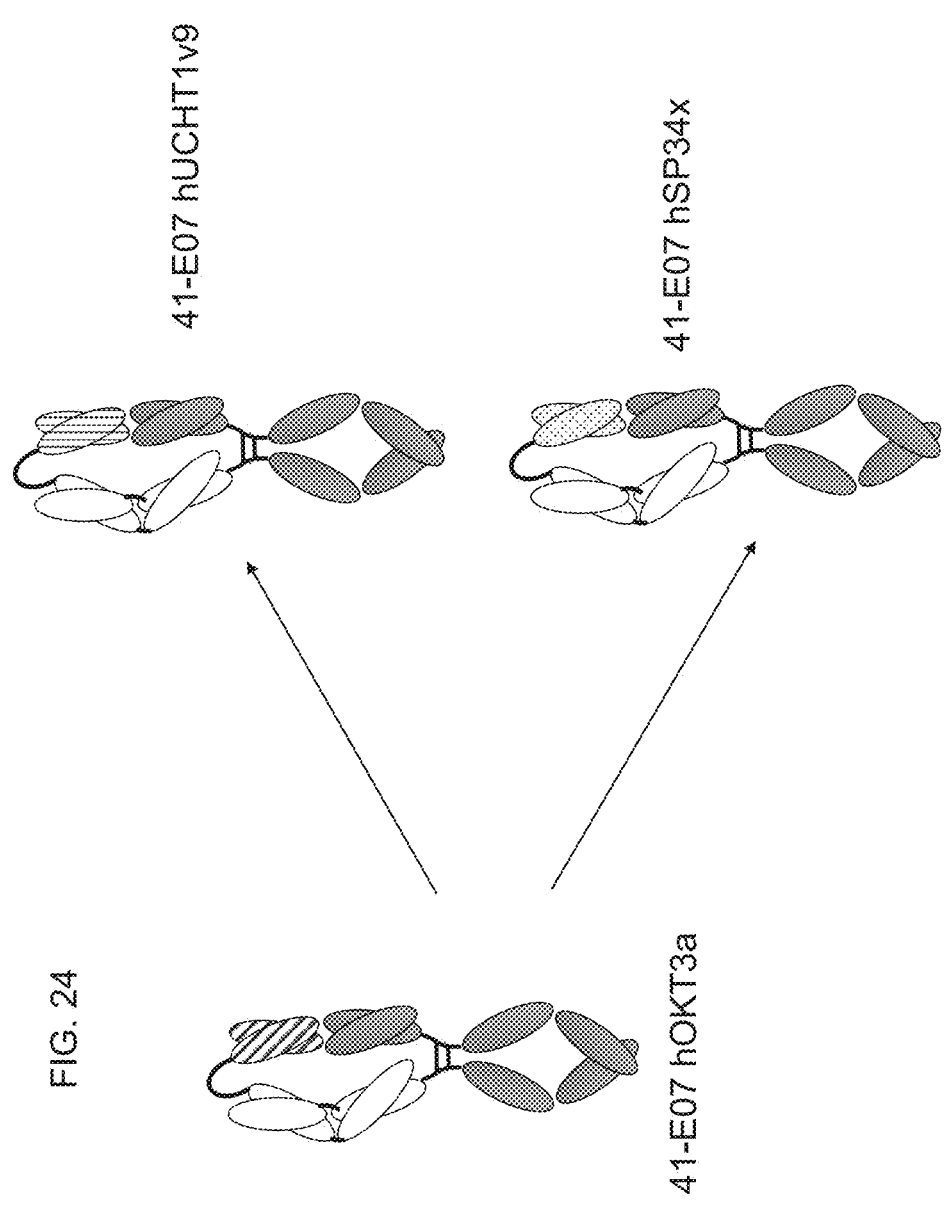
FIG. 24 shows schematics of the 41-E07-hOKT3a, 41-E07-hUCHT1v9, and 41-E07-hSP34x bispecific antibodies.

The CD3 binder was optimized in combination with the G2(31E07) antibody and the G5(1C12) antibody in the Format 41 orientation. The hOKT3a CD3 binder (Kd=2 μM) in the Format 41 diabody was replaced with UCHT1v9 (Kd=2 nM) or hSP34x (Kd=8 nM). Diagrams of the new 41-E07 binder formats are provided in FIG. 24.

Binding of each of the three 41-E07 CD3 binders (hOKT3, UCHT1 v9, and hSP34x) to G2 pHLA was assessed in a A375 cell line expressing $1\times10^6$ copies of the CT83 pHLA 9-mer. A375 transduced with luciferase alone served as the negative control. Cells were incubated with increasing concentrations of the different 41-E07 CD3 antibodies. Binding was determined by flow cytometery using an anti IgG-PE antibody for detection.

Figure 25:
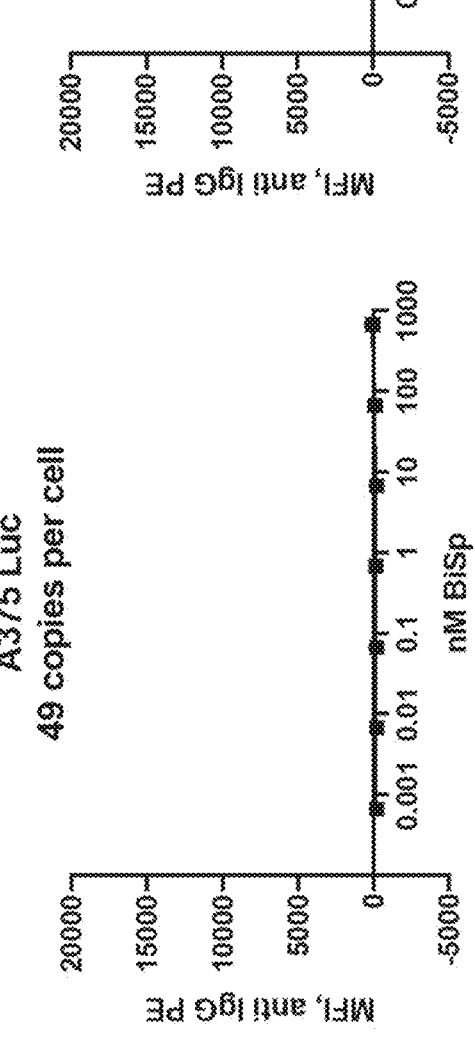
FIG. 25 shows binding of the 41-E07 hOKT3, 41-E07 hUCHT1v9, or 41-E07 hSP34x antibodies to the cells expressing 1×10$^6$ copies of the pHLA 9mer or control cells (A375 Luc).

As shown in FIG. 25, there was no difference in binding of the 41-E07 hOKT3, 41-E07 UCHT1v9, or 41-E07 hSP34x antibodies to the cells expressing $1\times10^6$ copies of the pHLA 9-mer.

Next, binding of the three 41-E07 CD3 binders (hOKT3, UCHTIv9, and hSP34x) to CD3 was assessed in Jurkat cells. Increasing concentrations of the antibodies were incubated with CD3(+) and CD9(−) Jurkat cells. Binding was determined by flow cytometery using an anti IgG-PE antibody for detection.

Figure 26:
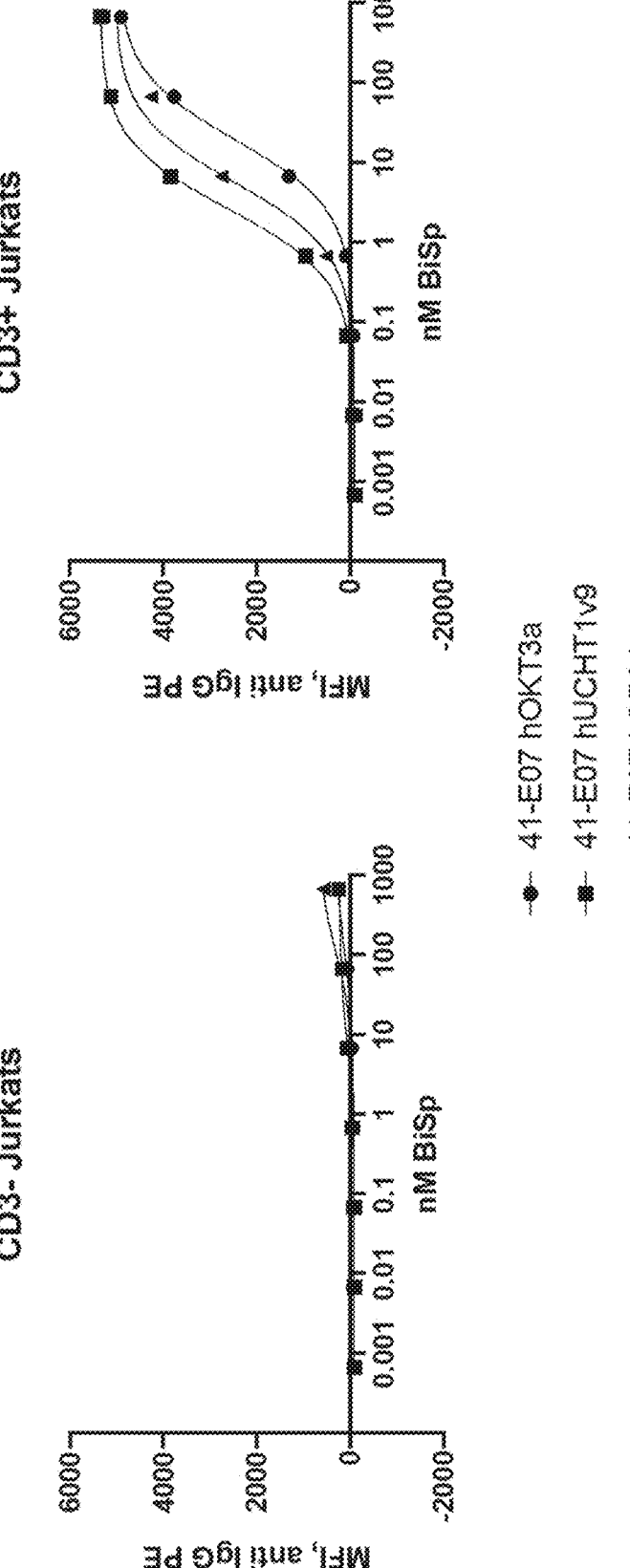
FIG. 26 shows binding of the 41-E07 hOKT3, 41-E07 hUCHT1v9, or 41-E07 hSP34x antibodies to CD3– and CD3+ Jurkat cells.

As shown in FIG. 26, 41-E07 UCHT1 v9 showed the highest binding to CD3 in the CD3+ Jurkat cells. Little to no binding was observed by all antibodies in the control CD3 (−) Jurkat cells.

Next, cytotoxicity of the three 41-E07 CD3 antibodies was assessed as described in Example 5. Increasing concentrations of the three antibodies were incubated with the A375 luciferase control cell line, the A375 CT83 cell line expressing 30,000 copies of the pHLA, the NCI H1703 cell line expressing 4,500 copies of the pHLA, and the NCI H820 cell line expressing 500 copies of the pHLA. Luciferase activity was assessed after incubation with the indicated antibody, and loss of luciferase signal indicated cell death, as described in Example 5.

Figure 27:
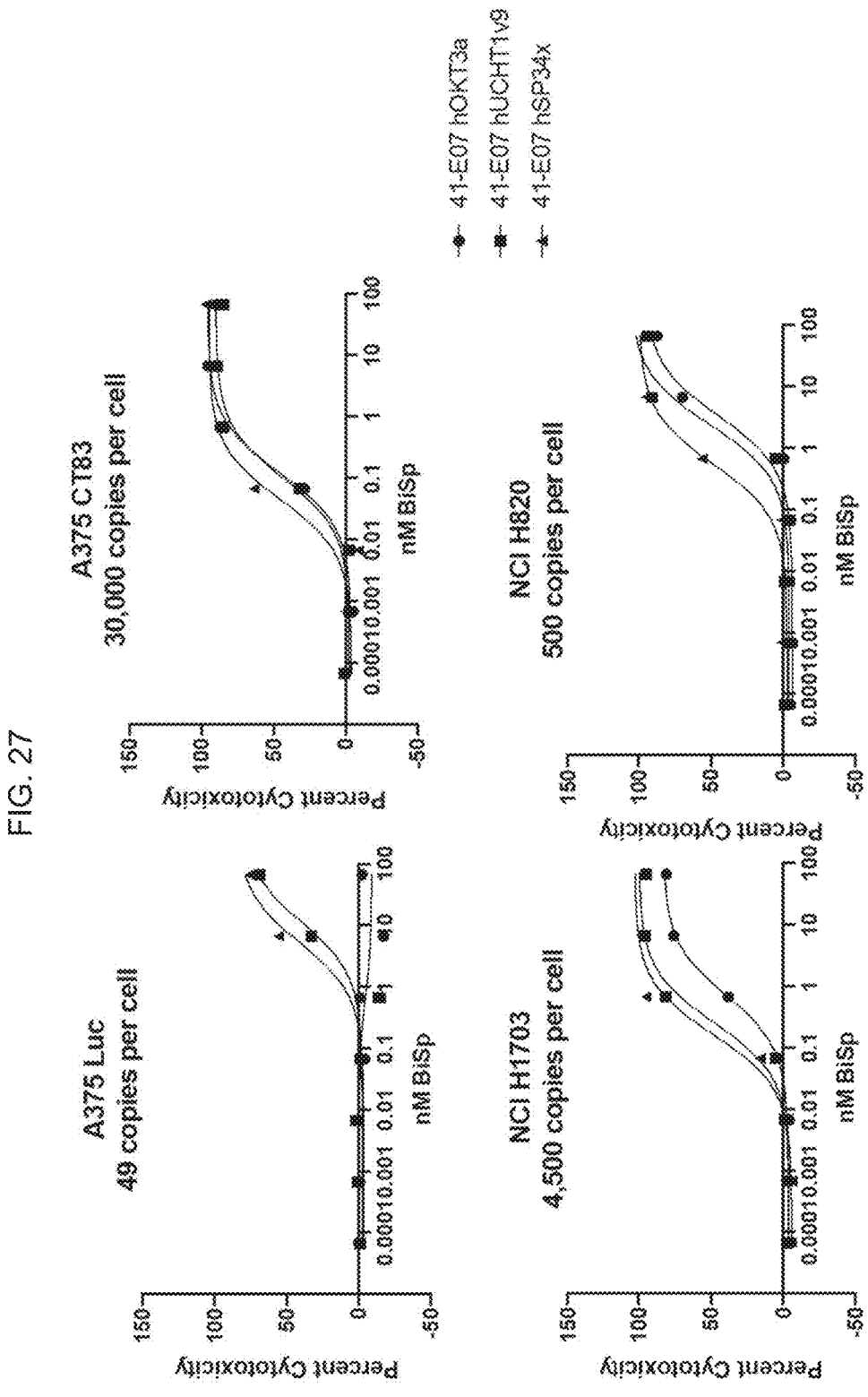
FIG. 27 shows binding of the 41-E07 hOKT3, 41-E07 hUCHT1v9, or 41-E07 hSP34x antibodies to the indicated cell lines.

As shown in FIG. 27, 41-E07-hSP34x was more cytotoxic against tumor cells with low density pHLA expression than 41-E07 UCHT1v9 and 41-E07 hOKT3a antibodies.

In sum, similar binding of 41-E07 bispecific antibody with different CD3 antibody binding fragments to G2 pHLA was observed. The 41-E07-UCHT1v9 bispecific antibody exhibited improved binding to CD3 as compared to the 41-E07 OKT3 bispecific antibody. The 41-E07-hSP34x bispecific antibody was more potent at killing tumor cells with pHLA ranging from 500-30,000 copies per cell.

Figure 32:
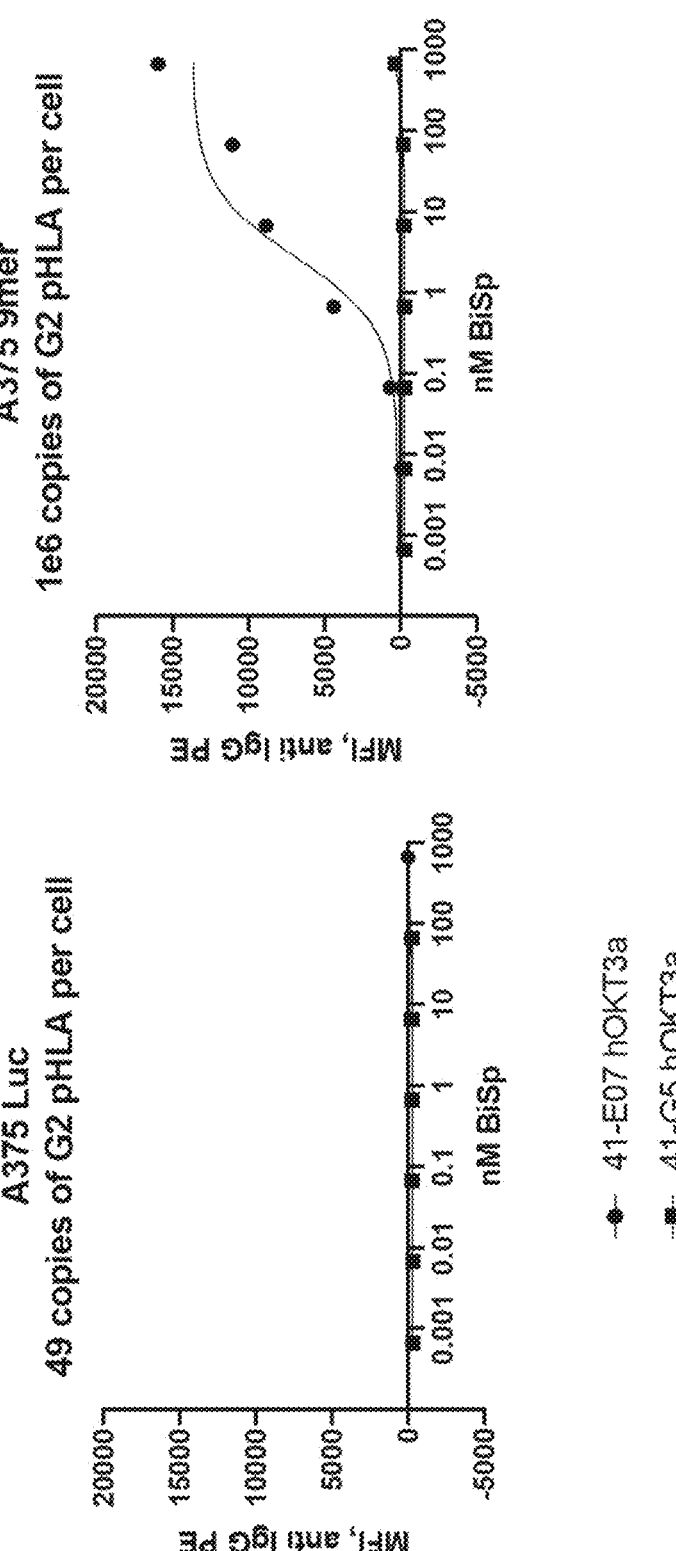
FIG. 32 shows binding of the 41-E07 hOKT3a or 41-G5 (1C12) hOKT3a to the cells expressing 1×10$^6$ copies of the G2 pHLA or control cells (A375 Luc).
Figure 33:
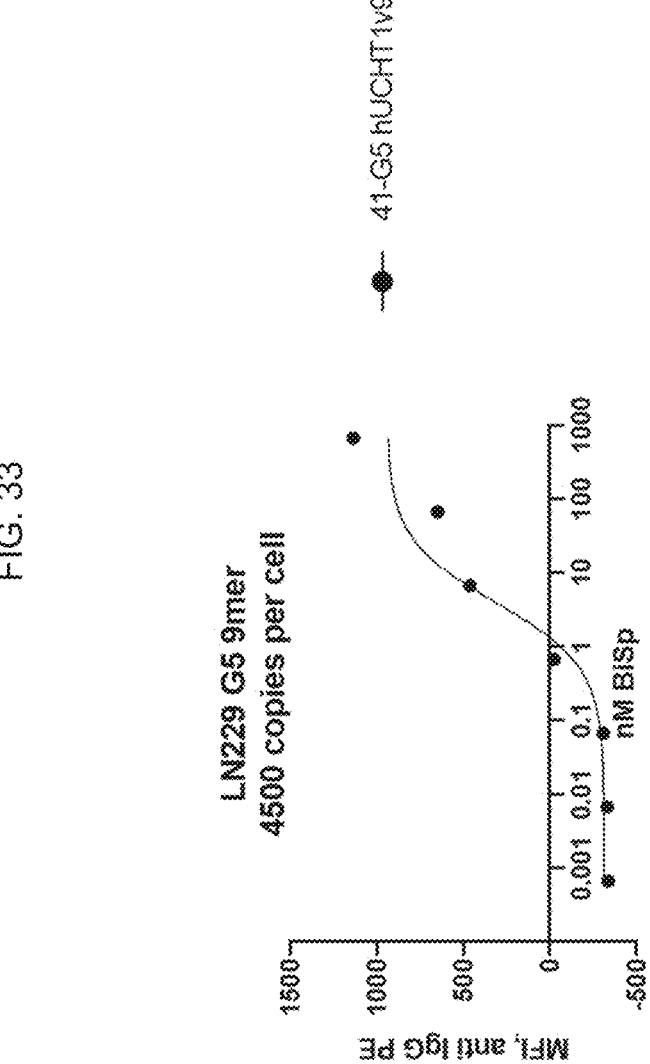
FIG. 33 shows binding of the 41-G5(1C12) hUCHT1v9 to the cells expressing 4500 copies of the G5 pHLA.
Figure 34:
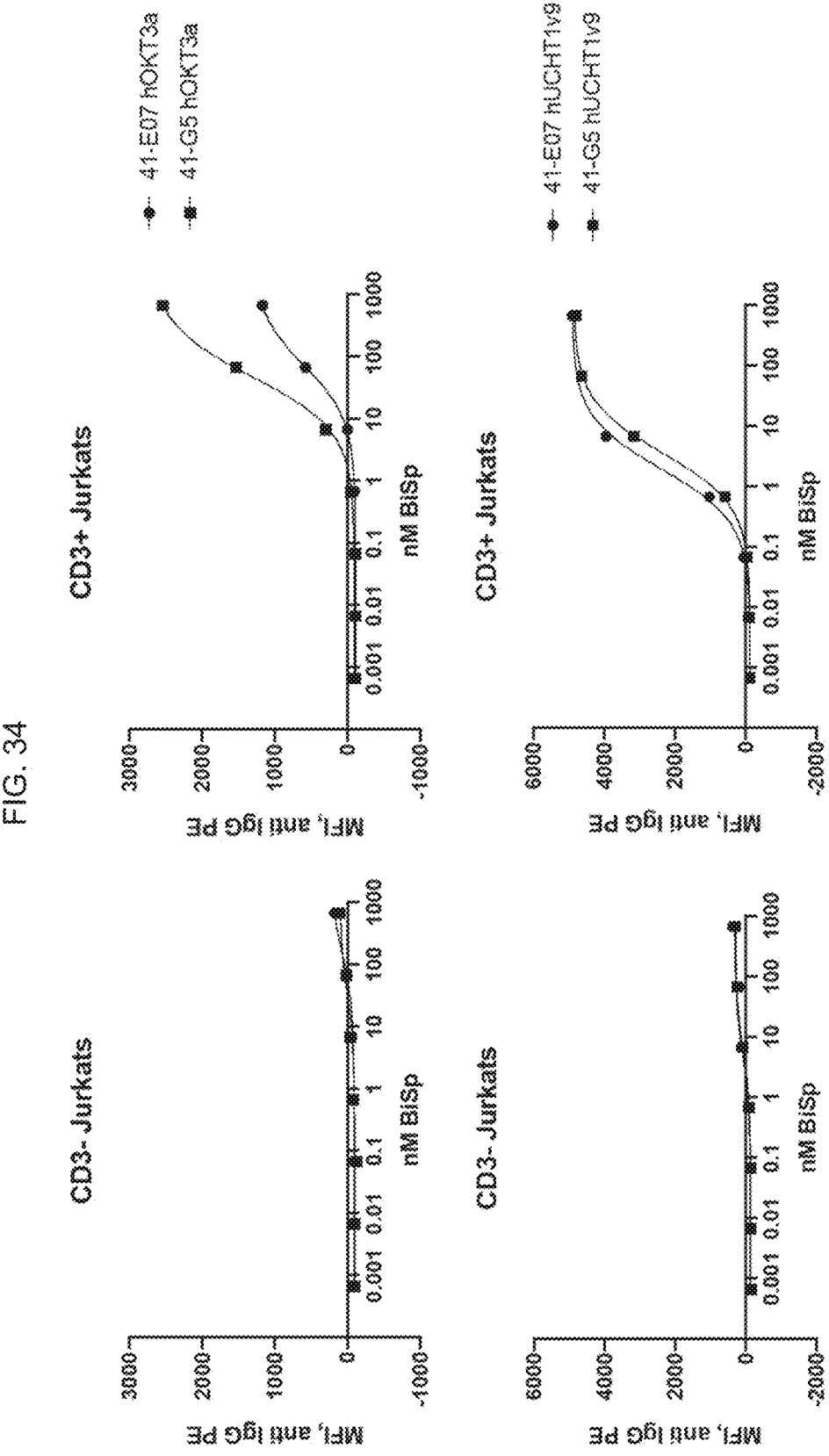
FIG. 34 shows binding of the 41-E07 hOKT3a or 41-G5 (1C12) hOKT3a antibodies to CD3– and CD3+ Jurkat cells.
Figure 35:
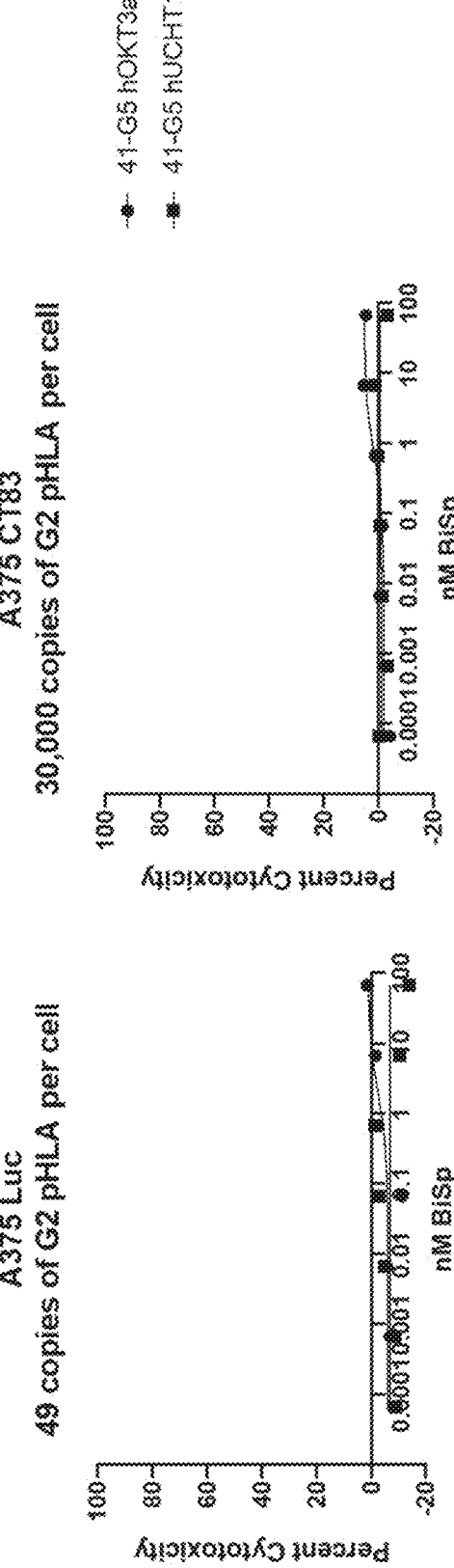
FIG. 35 shows binding of the 41-G5(1C12) hOKT3a or 41-G5(1C12) UCHT1v9 antibodies to the cells expressing 30,000 copies of the G2 pHLA or control cells (A375 Luc).

Next, the binding and cytotoxicity of the 41-G5(1C12) UCHTIv9 diabody was assessed in the A375-G2 expressing cell line. 41-G5(1C12) UCHT1v9 did not bind to cells expressing G2 pHLA (FIG. 32) but did bind to cells expressing G5 pHLA (FIG. 33). 41-G5(1C12) UCHT1v9 bound similarly to Jurkat CD3+ cells as compared to 41-E07 UCHT1v9 (FIG. 34). 41-G5(1C12) hOKT3a and 41-G5 (1C12) UCHT1v9 did not induce killing of G2 pHLA positive cell lines (FIG. 35). In sum, 41-G5(1C12) UCHT1v9 exhibited G5 specific binding, did not bind to the off target G2 antigen, and did not induce off target cytotoxicity. In addition, altering the CD3 binder from OKT3 to UCHT1v9 did not adversely affect CD3 binding.

Example 11: Alternative Antibody Formats

A new bispecific antibody format, 43, was constructed with the anti-CD3 and anti-pHLA binders. The format is shown in FIG. 28. In this new format, the two ABRs on the second arm (non-Fab arm) are encoded partially on the first polypeptide chain and partially on the second polypeptide chain (e.g., one VH domain and one VL domain from each ABR is encoded on each of polypeptide chain one and two). For example, a VH domain that binds target 1 can be linked to the VL domain that binds target 2 and encoded on polypeptide one while polypeptide two encodes a VL domain that binds target 1 linked to the VH domain that binds target 2. The respective paired VH and VL domains on polypeptide one and polypeptide two can interact with each other and thus form two complete ABRs to each respective target (target 1 and target 2). The Format 43 also places a Fab fragment against target 1 (e.g., an anti-pHLA Fab) on one arm. One variable region of the target 1 binder (e.g., a pHLA binder) is linked to the CH2 and CH3 regions of the Fc region on polypeptide chain one, while one variable region of the target 2 binder (e.g., a CD3 binder) is linked to the Fab heavy chain on polypeptide chain two such that the target 2 binder is sandwiched between two target 1 binders in the circularized antibody (see FIG. 28).

Binding of the 41-E07 UCHTIv9 and 43-E07 UCHT1v9 to the G2 pHLA was assessed in a A375 cell line expressing $1\times10^6$ copies of the CT83 pHLA 9-mer. A375 transduced with luciferase alone served as the negative control. Cells were incubated with increasing concentrations of the 41-E07 UCHT1v9 and 43-E07 UCHT1v9 antibodies. Binding was determined by flow cytometery using an anti IgG-PE antibody for detection.

Figure 29:
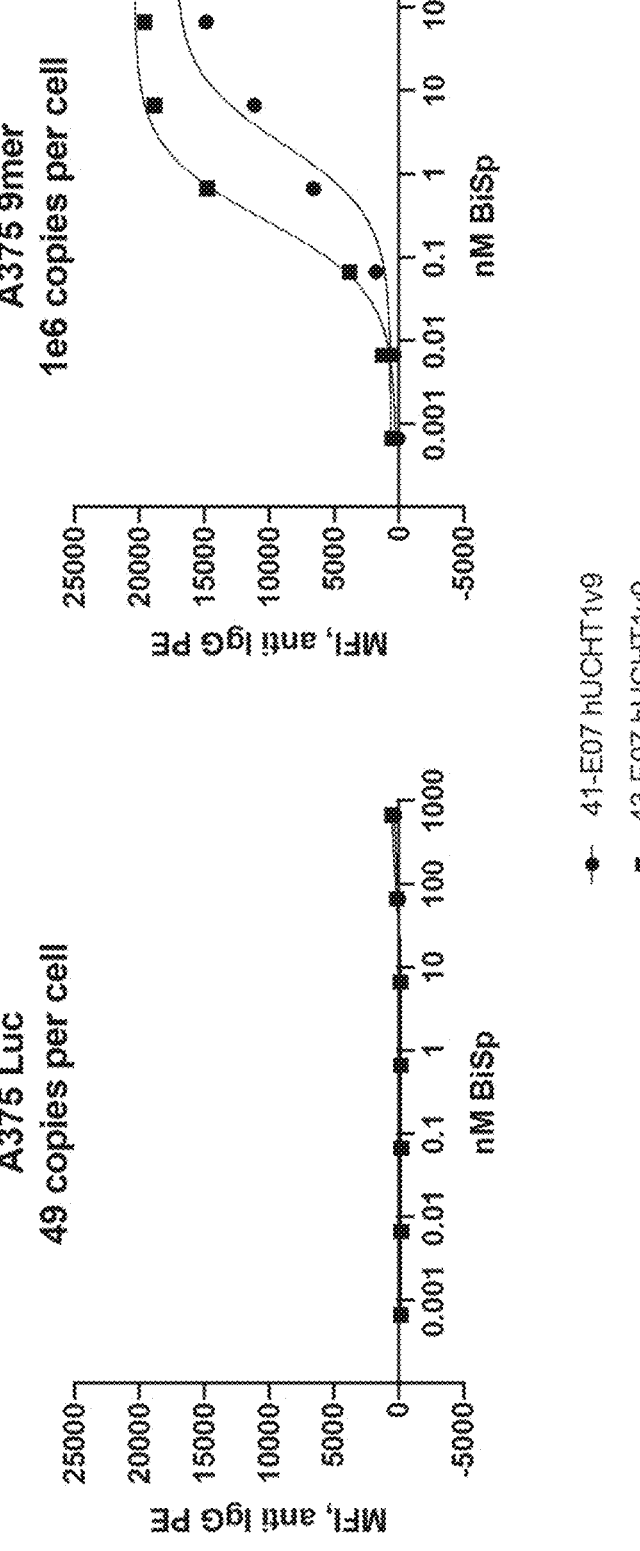
FIG. 29 shows binding of the 41-E07 hUCHT1v9 or 43-E07 hUCHT1v9 antibodies to the cells expressing 1×10$^6$ copies of the pHLA 9mer or control cells (A375 Luc).

As shown in FIG. 29, 43-E07 UCHT1v9 showed improved binding (approximately 10 fold increase) to the cells expressing $1\times10^6$ copies of the pHLA 9-mer as compared to 41-E07 UCHT1v9. Thus, the change in the format from Format 41 to Format 43 improved the binding ability of the bispecific antibody to the pHLA target.

Next, binding of the 41-E07 UCHT1v9 and 43-E07 UCHT1v9 to CD3 was assessed in Jurkat cells. Increasing concentrations of the antibodies were incubated with CD3 (+) and CD9(–) Jurkat cells. Binding was determined by flow cytometery using an anti IgG-PE antibody for detection.

As shown in FIG. 30, 43-E07 UCHTIv9 has similar binding to CD3 as 41-E07 UCHT1v9 in the CD3+ Jurkat cells. Little to no binding was observed by both antibodies in the CD3-Jurkat cells.

Next, cytotoxicity of the 41-E07 UCHTIv9 and 43-E07 UCHTIv9 antibodies was assessed as described in Example to antibody dosing. Tumors were measured by caliper and mice were randomized into groups based on tumor volumes. Mice were bled on day 7 prior to antibody dosing and PBMC engraftment was monitored via flow cytometry. Mice were bled on day 14 and day 21 post PBMC injection to also assess PBMC engraftment and expansion. 41-E07 hOKT3a, 43-E07 UCHT1v9 or 41-E07 hSP34x were diluted in PBS and administered intravenously at the indicated concentration on day 7 (Table 9). 41-G5(1C12) hOKT3a, which binds to a different pHLA target, was used as a control. Mice were monitored by caliper measurements of tumors as well as body weight twice a week. Mice were sacrificed at humane endpoints or by day 40.

TABLE 9

| Group | Tumor cells s.c. | PBMC IV | Dugs IV (mg/kg) | Antibody |
|---|---|---|---|---|
| 1 | $1 \times 10^6$ A375 CT83-Luc | 0 PBMC | 0 | |
| 2 | 0 | $1 \times 10^7$ | 0 | |
| 3 | $1 \times 10^6$ A375 CT83-Luc | $1 \times 10^7$ | 0 | PBS |
| 4 | $1 \times 10^6$ A375 CT83-Luc | $1 \times 10^7$ | 1 | 41-E07-hOKT3a |
| 5 | $1 \times 10^6$ A375 CT83-Luc | $1 \times 10^7$ | 0.1 | 41-E07-hOKT3a |
| 6 | $1 \times 10^6$ A375 CT83-Luc | $1 \times 10^7$ | 0.01 | 41-E07-hOKT3a |
| 7 | $1 \times 10^6$ A375 CT83-Luc | $1 \times 10^7$ | 1 | 43-E07-UCHT1v9 |
| 8 | $1 \times 10^6$ A375 CT83-Luc | $1 \times 10^7$ | 0.1 | 43-E07-UCHT1v9 |
| 9 | $1 \times 10^6$ A375 CT83-Luc | $1 \times 10^7$ | 0.01 | 43-E07-UCHT1v9 |
| 10 | $1 \times 10^6$ A375 CT83-Luc | $1 \times 10^7$ | 1 | 41-G5(1C12)-hOKT3a |
| 11 | $1 \times 10^6$ A375 CT83-Luc | $1 \times 10^7$ | 0.1 | 41-G5(1C12)--hOKT3a |
| 12 | $1 \times 10^6$ A375 CT83-Luc | $1 \times 10^7$ | 0.01 | 41-G5(1C12)--hOKT3a |
| 13 | $1 \times 10^6$ A375 CT83-Luc | $1 \times 10^7$ | 1 | 41-31E07-hSP34x |
| 14 | $1 \times 10^6$ A375 CT83-Luc | $1 \times 10^7$ | 0.1 | 41-31E07-hSP34x |
| 15 | $1 \times 10^6$ A375 CT83-Luc | $1 \times 10^7$ | 0.01 | 41-31E07-hSP34x |

5. Increasing concentrations of the two antibodies were incubated with the A375 luciferase control cell line, the A375 CT83 cell line expressing 30,000 copies of the pHLA, and the NCI H820 cell line expressing 500 copies of the pHLA. Luciferase activity was assessed after incubation with the indicated antibody, and loss of luciferase signal indicated cell death, as described in Example 5.

Figure 31:
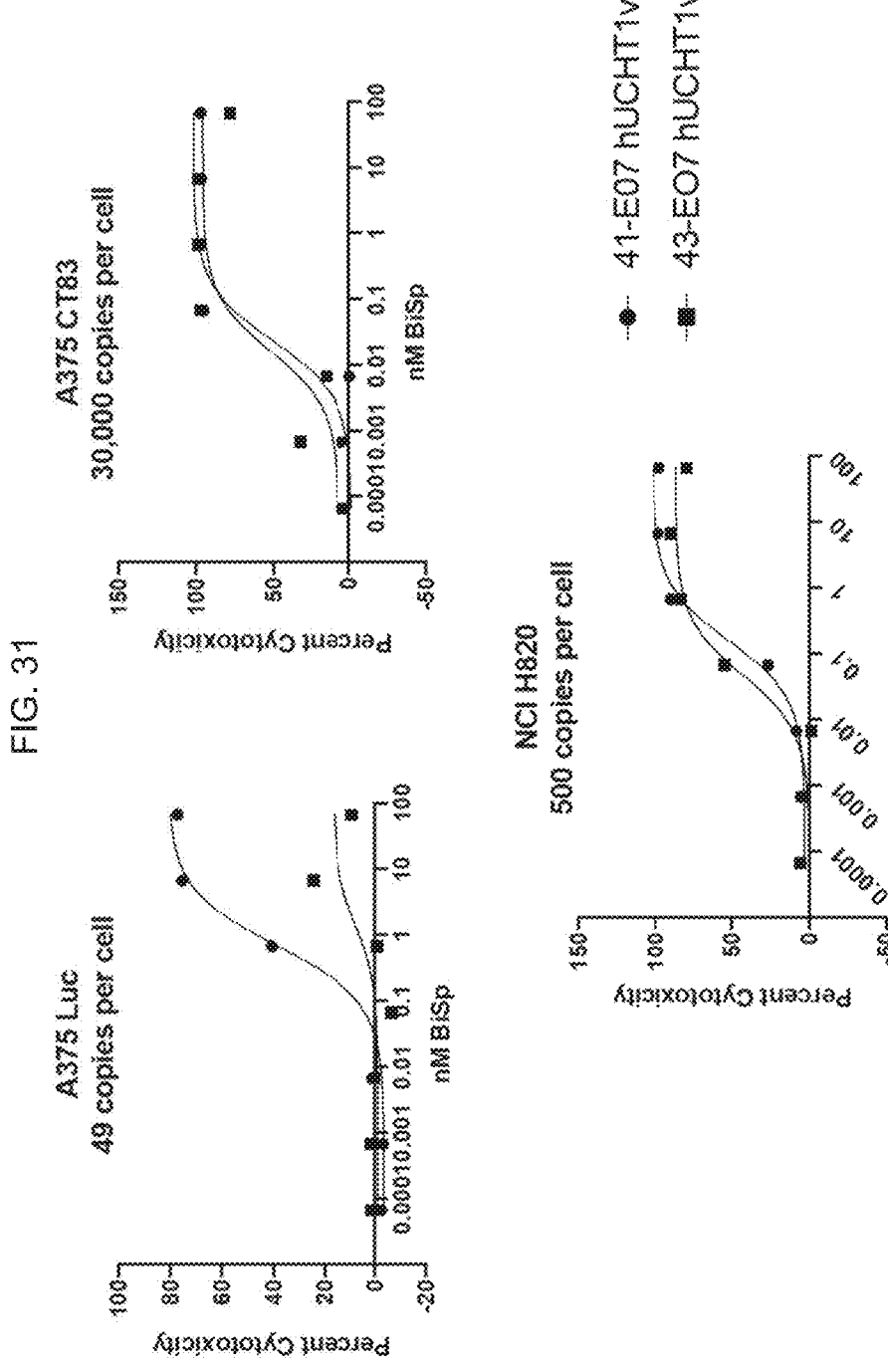
FIG. 31 shows binding of the 41-E07 UCHT1v9 or 43-E07 UCHT1v9 antibodies to the indicated cell lines.

As shown in FIG. 31, 41-E07 UCHT1v9 and 43-E07 UCHT1 v9 has similar cytotoxicity potency on tumor cells expressing 500-30,000 copies of pHLA.

In sum, 43-E07 UCHT1v9 showed an approximately 10-fold increase in binding to pHLA relative to 41-E07 UCHT1v9. In addition, altering the position of CD3 and E07 in the bispecific antibody did not affect CD3 binding, as the format 43-E07 UCHTIv9 showed the same level of CD3 binding as the format 41-E07 UCHT1v9. Furthermore, 41-E07 UCHT1v9 and 43-E07 UCHT1v9 had similar cytotoxicity potency on tumor cells with pHLA ranging from 500-30,000 copies per cell

Figures 36A, 36B, 36C, 36D:
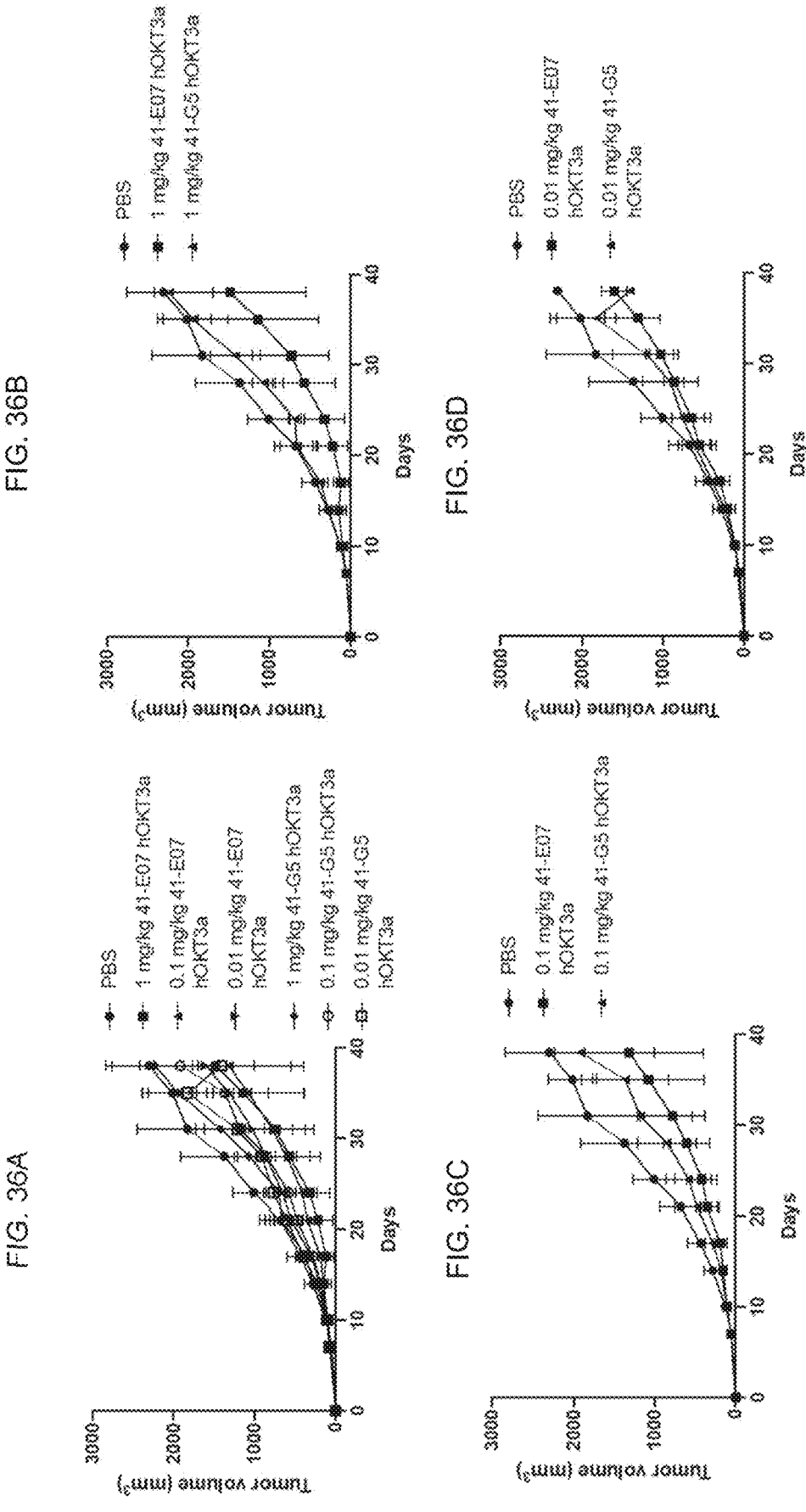
FIG. 36A shows tumor volume in mice treated with 0.01 mg/kg, 0.1 mg/kg, or 1 mg/kg of the indicated antibody.
FIG. 36B shows tumor volume in mice treated with 1 mg/kg of the indicated antibody.
FIG. 36C shows tumor volume in mice treated with 0.1 mg/kg of the indicated antibody.
FIG. 36D shows tumor volume in mice treated with 0.01 mg/kg of the indicated antibody.

Example 12: In Vivo Efficacy of 41-E07 hOKT3a, 43-E07 hUCHT1v9 and 41-E07 hSP3 Bispecific Antibodies Methods Eight-week-old female NOD.Cg-Prkdc$^{scid}$ H2-K1$^{tm1Bpe}$ H2-Ab1$^{em1Mvw}$ H2 D1$^{tm1Bpe}$ Il2rg$^{tm1Wjl}$/SzJ (JAX) mice were used to assess in vivo efficacy of the bispecific antibodies with different CD3 binders. The A375 tumor cell line (ATCC) transduced to overexpress the CT83 gene and luciferase. $1 \times 10^6$ A375-CT83-Luc (A375 CT83) cells were injected subcutaneously in the flank of each mouse on day 0. $1 \times 10^7$ human PBMCs were injected intravenously (i.v.) on either day 0 (groups 2-6 and $10^{-12}$) or day 1 (groups 7-9 and 13-15). Tumors were allowed to grow to 50-100 mm³ prior Results Mice treated with 1 mg/kg 41-E07 hOKT3a showed a reduction in A375-CT83 tumor growth when compared to mice treated with the control antibody, 1 mg/kg 41-G5 (1C12) hOKT3a (FIGS. 36A and B). Mice treated with 0.1 mg/kg E07 hOKT3a demonstrated a decreasing trend in tumor growth compared 0.1 mg/kg 41-G5(1C12) hOKT3a but was not significantly different (FIG. 36C). Additionally, there was no significant difference in tumor growth between mice treated with 0.01 mg/kg 41-E07 hOKT3a when compared to mice treated with 0.01 mg/kg 41-G5(1C12) hOKT3a (FIG. 36D). Mice treated with 1 mg/kg and 0.1 mg/kg 41-E07 hOKT3a showed a decreased in A375-CT83 tumor growth compared to PBS control group (FIG. 36A).

Mice treated with 1 and 0.1 mg/kg 43-E07 UCHT1v9 demonstrated a significant reduction in tumor growth compared to mice treated with PBS (FIGS. 37A, B, and C). However, mice treated with 0.01 mg/kg 43-E07 UCHT1v9 did not show a significant difference in tumor growth compared to PBS group (FIG. 37D).

Figures 38A, 38B, 38C, 38D:
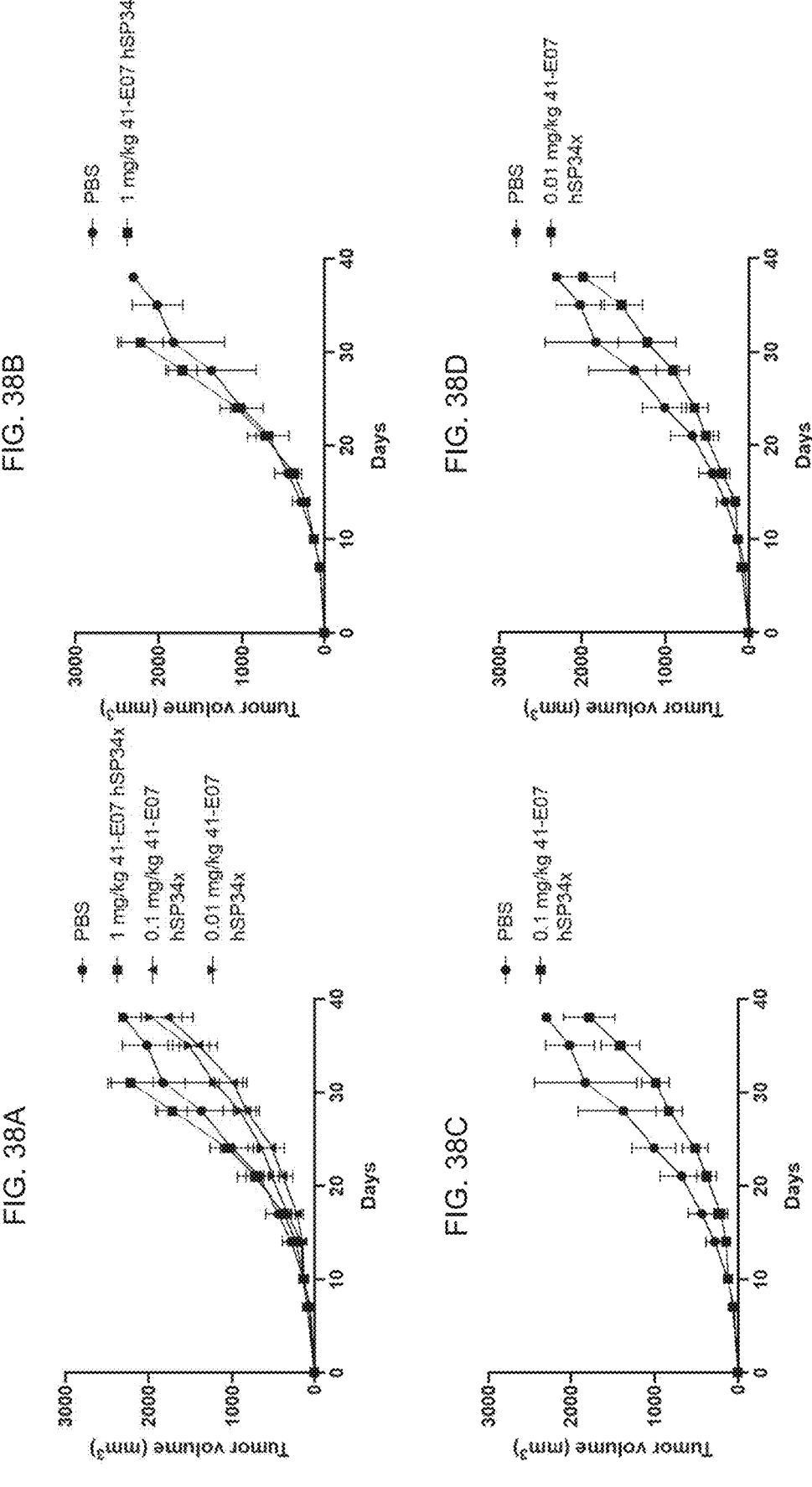
FIG. 38A shows tumor volume in mice treated with 0.01 mg/kg, 0.1 mg/kg, or 1 mg/kg of the indicated antibody.
FIG. 38B shows tumor volume in mice treated with 1 mg/kg of the indicated antibody.
FIG. 38C shows tumor volume in mice treated with 0.1 mg/kg of the indicated antibody.
FIG. 38D shows tumor volume in mice treated with 0.01 mg/kg of the indicated antibody.

Mice treated with 1 and 0.01 mg/kg 41-E07 hSP34x did not have a significant reduction in tumor growth when compared to PBS control group (FIGS. 38A, B, and D). In contrast, mice treated with 0.1 mg/kg 41-E07 hSP34x demonstrated a slight reduction in tumor growth compared to mice treated with PBS (FIGS. 38A and C).

In sum, mice treated with 1 mg/kg 41-E07 hOKT3a had reduced tumor growth compared to mice treated with 1 mg/kg 41-G5(1C12) hOKT3a. Mice treated with 1 and 0.1 mg/kg 43-E07 UCHT1v9 demonstrated a reduction in tumor growth compared to mice treated with PBS. Similarly, mice treated with 0.1 mg/kg 41-E07 hSP34x demonstrated a reduction in tumor growth compared to mice treated with PBS. Mice treated with all concentrations of 41-G5(1C12) hOKT3a did not have a significant impact on tumor growth when compared to PBS control group.

Example 13: In Vivo Efficacy of 41-E07 UCHT1v9 Bispecific Antibody

Methods

Eight-week-old female NOD.Cg-Prkdc$^{scid}$Il2rg$^{tm1Wjl}$/SzJ (JAX) mice were used to assess in vivo efficacy of the Format 41 and 43 antibodies. The A375 tumor cell line (ATCC) transduced to overexpress the CT83 gene and luciferase. $1\times10^6$ A375-CT83-Luc (A375 CT83) cells were injected subcutaneously in the flank of each mouse on day 0. $0.1\times10^7$ human PBMCs were injected intravenously (i.v.) on day 0. Tumors were allowed to grow to 50-100 mm$^3$ prior to antibody dosing. Tumors were measured by caliper and mice were randomized into groups based on tumor volumes. Mice were bled on day 7 prior to antibody dosing and PBMC engraftment was monitored via flow cytometry. Mice were bled on day 14 and day 21 post PBMC injection to assess PBMC engraftment and expansion. 41-E07 UCHT1v9 or 41-G5(1C12) UCHT1v9 antibody was diluted in PBS and administered via intravenous (i.v.) route at the indicated concentration on day 7 (Table 10). Mice were monitored by caliper measurements of tumors as well as body weight twice a week. Mice were sacrificed at humane endpoints or by day 40.

TABLE 10

| Group | Tumor cells s.c. | PBMC IV | Dugs IV (mg/kg) | Antibody |
|---|---|---|---|---|
| 1 | $1 \times 10^6$ A375 CT83-Luc | 0 PBMC | 0 | |
| 2 | 0 | $1 \times 10^7$ | 0 | |
| 3 | $1 \times 10^6$ A375 CT83-Luc | $1 \times 10^7$ | 0 | PBS |
| 4 | $1 \times 10^6$ A375 CT83-Luc | $1 \times 10^7$ | 2 | 41-E07-UCHT1v9 |
| 5 | $1 \times 10^6$ A375 CT83-Luc | $1 \times 10^7$ | 1 | 41-E07-UCHT1v9 |
| 6 | $1 \times 10^6$ A375 CT83-Luc | $1 \times 10^7$ | 0.1 | 41-E07-UCHT1v9 |
| 7 | $1 \times 10^6$ A375 CT83-Luc | $1 \times 10^7$ | 0.01 | 41-E07-UCHT1v9 |
| 8 | $1 \times 10^6$ A375 CT83-Luc | $1 \times 10^7$ | 2 | 41-G5(1C12)-UCHT1v9 |
| 9 | $1 \times 10^6$ A375 CT83-Luc | $1 \times 10^7$ | 1 | 41-G5(1C12)-UCHT1v9 |
| 10 | $1 \times 10^6$ A375 CT83-Luc | $1 \times 10^7$ | 0.1 | 41-G5(1C12)-UCHT1v9 |
| 11 | $1 \times 10^6$ A375 CT83-Luc | $1 \times 10^7$ | 0.01 | 41-G5(1C12)-UCHT1v9 |

Results

Mice treated with 1 and 0.01 mg/kg 41-E07 UCHT1v9 did not have a significant reduction in tumor growth compared to mice treated with 41-G5 UCHT1v9 (FIGS. 39A, B, and D). However, mice treated with 0.1 mg/kg 41-E07 UCHT1v9 demonstrated a significant reduction in tumor growth compared to mice treated with 0.1 mg/kg 41-G5 (1C12) UCHT1v9 (FIG. 39C). However, mice treated with 1 and 0.01 mg/kg 41-E07 UCHT1v9 had very little to no PBMC engraftment while the mice treated with 0.1 mg/kg 41-E07 UCHT1v9 did have PBMC engraftment.

In sum, mice treated with 0.1 mg/kg 41-E07 UCHT1v9 demonstrated an 80-100% tumor inhibition as compared to mice treated with 41-G5(1C12) UCHT1v9 or PBS (FIG. 39C). Three of the six mice had complete tumor regression while two of the six mice had 80-90% tumor inhibition. However, the mice dosed with 2 mg/kg and 1 mg/kg 41-E07-v9 had no PBMC engraftment. In addition, no signs of GvHD was observed in the mice treated with 41-E07-UCHT1v9 and 41-G5-UCHT1v9.

86

Example 14: Off-Target Liabilities Assessment (OTLA) of E07-hOKT3a

Materials

HLA Refolding

HLA A*01:01 binding peptides of interest for the OTLA positional scanning were synthesized with a purity of >95% (Genscript Inc). The alpha chain of HLA-A*01:01 and beta chain β2-microglobulin, separately expressed in E. coli as inclusion bodies, were purified and then solubilized in 8 M Urea containing 10 mM DTT. Peptides resuspended in DMSO at 10 mg/ml were used in the refolding process. Refolding of the pHLA complex was initiated by rapid dilution of 20 mg B 2-microglobulin, 10 mg peptide of interest and 20 mg HLA-A*01:01 alpha chain in 1 L of 100 mM Tris-HCl pH 8.0 buffer containing 400 mM L-arginine, 2 mM EDTA, 1.5 mM L-glutathione reduced and 0.5 mM of L-glutathione oxidized. The 1L refolding reaction was concentrated using tangential flow filtration process (Sarotorius Corporation) and purified by size exclusion method. Fractions containing the correctly folded pHLA complex were collected and biotinylated (Avidity). Quality of the pHLA complexes were analyzed by analytical HPLC-SEC (Agilent), SDS-PAGE under denaturing conditions, and ELISA using the W6/32 antibody (BioLegend).

Off-Target Liabilities Assessment in Alanine Scan

The Off-Target Liabilities Assessment (OTLA) of E07-hOKT3a was evaluated substituting each amino acid position in the G2 peptide, NTDNNLAVY (SEQ ID NO: 214), with alanine or a conserved or a divergent single amino acid substitution (valine or glutamic acid). The resulting peptides were pulsed on K562-HLA cells to evaluate the binding property of the 41-E07-hOKT3a antibody. The alanine and valine or glutamic acid substituted peptide sequences are provided in Table 11.

TABLE 11

| SEQ ID NO | Name | Peptide |
|---|---|---|
| 120 | ALA 1 | ATDNNLAVY |
| 121 | ALA 2 | NADNNLAVY |
| 122 | ALA 3 | NTANNLAVY |
| 123 | ALA 4 | NTDANLAVY |
| 124 | ALA 5 | NTDNALAVY |
| 125 | ALA 6 | NTDNNAAVY |

TABLE 11-continued

| SEQ ID NO | Name | Peptide |
|---|---|---|
| 126 | ALA 7 | NTDNNLAAY |
| 127 | ALA 8 | NTDNNLAVA |
| 128 | Vor E 1 | NTENNLAVY |
| 129 | Vor E 2 | NTDENLAVY |
| 130 | Vor E 3 | NTDNVLAVY |
| 131 | Vor E 4 | NTDNNVAVY |
| 132 | Vor E 5 | NTDNNLVVY |
| 133 | Vor E 6 | NTDNNLVEY |

EDGE Prediction

EDGE prediction was done as described in Example 6.

Pulsing Method

Cells were pulsed with the resulting peptides as described in Examples 2 and 6 to evaluate the binding property of the 41-E07-hOKT3a antibody.

IP-MS Immunoprecipitation of HLA/Peptide Complexes from Cell Lysates $2 \times 10^8$ cells expressing A*01:01/CT83 (NCI-H1703, A375+CT83) were re-suspended in 5 ml lysis buffer (1% CHAPS, 150 mM sodium chloride, 20 mM Tris pH 8) in the presence of phosphatase, and protease inhibitors. The cells were homogenized by sonication, rotated at 4° C. for 1 hr, and spun at 21,000×g for 30 min. to pellet cell debris. To the cleared lysates, 3 mg of ProteinA-conjugated 41-E07 hOKT3a, W6/32, or control IgG antibodies, were added, and the lysate-antibody mixture was rotated at 4° C. overnight.

After immunoprecipitation, the IP beads were isolated using filter plates, then washed to remove non-specific binding using Tris pH 8 buffers with increasing levels of NaCl. The HLA/peptide complex was eluted from the beads using 2N acetic acid. The protein components were removed from the peptides using C18 fractionation. The resultant peptides were taken to dryness by SpeedVac evaporation and stored at −20° C. prior to MS analysis.

Dried peptides were reconstituted along with the relevant stable isotopically labeled peptides in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 lower resolution scans collected in the ion trap detector after HCD fragmentation of the selected ion. MS2 spectra were measured with high resolution mass accuracy in the Orbitrap detector with targeted method known as parallel reaction monitoring. In targeted PRM, specific peptide precursor ions are isolated in the Orbitrap detector and all resulting HCD fragmentation ions are scanned across the elution of the peptide peak. This enables both peptide identification and quantitation of endogenous peptide in the presence of a co-injected stable isotopically labeled peptide standard. Targeted MS1 and MS2 spectra obtained from the endogenous and synthetic standard peptides were processed through Skyline software (University of Washington).

Affinity Measurements

The affinities of the monovalent Format 3-E07-hOKT3a antibody with HLA complexes refolded with different peptides of interest was measured using Octet HTX (ForteBio) in 96-channel mode with biolayer interferometry (BLI) detection. The binding constants (KD) of the interactions were measured using the buffer A (0.02% Tween-20 and 0.1% BSA in PBS). All the assay conditions were prepared in a volume of 200 μL. The pHLA complex biotinylated at the C-terminal AviTag was used to ensure uniform directionality of the protein. Biotinylated-pHLA was diluted into assay buffer at 0.6 μg/mL and immobilized onto High Precision Streptavidin SAX biosensors (P/N 18-5117 to a minimum response value of 1 nm on the Octet System (ForteBio). A baseline response was established in assay buffer (120 s) prior to each association. The purified monovalent Format 3-E07 hOKT3a antibody was diluted in the assay buffer at the specified concentrations (typically 500-0 nM, diluted 2-fold). The monovalent Format 3-E07 hOKT3a antibody was allowed to associate for 120 s followed by dissociation for 120 s in the same baseline wells. The assay included one Referencing biosensor with no immobilized ligand dipped into analytes. Using the ForteBio Data Analysis suite, the data was normalized to the association curves followed by background normalization. Curve fitting using global fitting of the sensor data with the Octet™ software using 1:1 kinetic model with errors within 10%, X2below 3, and R2above 0.9 to determine the association and dissociation constants.

Results

In the valine and glutamic acid replacement assay using 41-E07-hOKT3a, the flow cytometry binding results indicate that replacement of residues 3, 6, 7, and 9 with valine or glutamic acid resulted in a significant reduction in binding of 41-E07-hOKT3a (FIG. 40A). Substitution of residues 2, 4, 5, and 8 with valine or glutamic acid showed minimal impact on binding (FIG. 40A). Results are also shown in Table 12.

TABLE 12

| Position | Max Binding | Fold change in max binding | EC50 | Fold change in EC50 |
|---|---|---|---|---|
| WT | 5563 | | 0.9353 | |
| V or E 1 | 1885 | 0.3388 | 1.128 | 1.206 |
| V or E 2 | 4683 | 0.8418 | 1.14 | 1.218 |
| V or E 3 | 5685 | 1.0219 | 1.788 | 1.911 |
| V or E 4 | 1558 | 0.2800 | 20.24 | 21.640 |
| V or E 5 | 2634 | 0.4734 | 5.435 | 5.810 |
| V or E 6 | 1401 | 0.2518 | 91.7 | 98.043 |

In the alanine scan assay using 41-E07-hOKT3a, the flow cytometry binding results indicate that replacement of residues 3, 6, and 9 with alanine resulted in a significant reduction in binding, while substitution of 5th residue with alanine increased the EC50 by approximately 4-fold (FIG. 40B). Substitution of residues 1, 2, 4, and 8 with alanine showed minimal impact on binding (FIG. 40B).

The alanine scan results were substantiated with affinity measurement of peptide-HLA complex with the monovalent Format 3 E07-hOKT3a antibody using Bio-layer interferometry affinity measurement methods (Table 13).

TABLE 13

| Position | Max Response (nm) | KD (nM) | Fold change in Response | Fold change in affinity | Fold change in max binding | EC50 | Fold change in EC50 |
|---|---|---|---|---|---|---|---|
| WT | 0.24 | 1.2 | — | — | — | 0.5536 | |
| Ala 1 | 0.26 | 3 | — | 2.5 decrease | 0.90 | 0.7489 | 1.35 |
| Ala 2 | 0.24 | 1.5 | — | — | 0.88 | 0.6301 | 1.14 |
| Ala 3 | 0.15 | 17 | 1.6 decrease | 14.2 decrease | 0.19 | 7.355 | 13.29 |
| Ala 4 | 0.24 | 8.7 | — | 7.3 decrease | 0.86 | 0.9113 | 1.65 |
| Ala 5 | 0.21 | 16 | — | 13.3 decrease | 0.64 | 2.062 | 3.72 |
| Ala 6 | 0.09 | 16 | 2.7 decrease | 13.3 decrease | 0.28 | 9.866 | 17.86 |
| Ala 8 | 0.24 | 8 | — | 6.7 decrease | 0.71 | 0.8319 | 1.50 |
| Ala 9 | 0 | n/a | Complete loss | n/a | 0.15 | 7.648 | 13.82 |

Based on highest response (nm) on the Octet, Positions 3, 6, and 9, showed the least response to non-binding of the peptide complex to the peptide. Substitution at position 9 resulted in complete loss of binding and therefore is a critical residue for binding.

Based on the cytometry and affinity measurements, close analogues of G2 peptide (up to five mismatches in the human genome, 800 peptides) were chosen to evaluate the cross reactivity of the 41-E07-hOKT3a antibody. Using the EDGE prediction, 66 peptides with highest predicted binding to A*01:01 allele were identified (Table 14).

TABLE 14

| Gene | Peptides with positional change | SEQ ID NO |
|---|---|---|
| AAMP | YLDGTLAIY | 134 |
| ABCB4 | FSDKELAAY | 135 |
| ALDH5A1 | AADVGLAGY | 136 |
| AP4S1 | DTENEMAIY | 137 |
| ARRDC4 | RVDYSLAVY | 138 |
| ATP8B1 | YADGKLAFY | 140 |
| BCOR | GADPTLATY | 141 |
| CC2D2B (C10orf131) | QTEFALAVY | 142 |
| CCND2 | ATDFKFAMY | 143 |
| CCND3 | ATDYTFAMY | 144 |
| CD2 | GTDPELNLY | 145 |
| CFAP47 (CXorf22) | WTDVFLQIY | 146 |
| CNP | RLDEDLAAY | 147 |
| CYP2J2 | TVDTTLAGY | 148 |
| DMD | FIDKQLAAY | 149 |
| DNAH1 | QTDFPLQAY | 150 |
| DNAH7 | YIDIFLNVY | 151 |
| DSG3 | YTDNWLAVY | 152 |
| DYRK1A | AMDVNLTVY | 153 |
| E2F2 | RTEDNLQIY | 154 |

TABLE 14-continued

| Gene | Peptides with positional change | SEQ ID NO |
|---|---|---|
| ERICH3 (C1orf173) | LMDKHLAGY | 155 |
| F13B | VADGILASY | 156 |
| FBXO21 | SLDLYLAMY | 157 |
| GABRB3 | NMDYTLTMY | 158 |
| GABRD | NLDGLIAGY | 159 |
| GFAP | EAENNLAAY | 160 |
| HYDIN | VTDFKFALY | 161 |
| JAK2 | QIDPVLQVY | 162 |
| LEP | KMDQTLAVY | 163 |
| LMLN | NMDRPIAGY | 164 |
| LRPPRC | NLDFVLSFY | 165 |
| MCM3 | ETEYGLSVY | 166 |
| MKKS | CTETHLAAY | 167 |
| MMP8 | EADINIAFY | 168 |
| NAV2 | MTDGGLGLY | 169 |
| NAV3 | MTDGGLNLY | 170 |
| NHLRC2 | NTEEPISVY | 171 |
| NID2 | NVDRVFALY | 172 |
| NT5C2 | DMDYTLAVY | 173 |
| OARD1 (C6orf130) | ATDIKITVY | 174 |
| OTULIN (FAM105B) | NTEEFITVY | 175 |
| PASK | RLDEPLASY | 176 |
| PPAN-P2RY11 | TADHGLAAY | 177 |
| PSME1 | KTENLLGSY | 178 |
| PTPRO | WTDYLLAFY | 179 |
| RNF212B (C14orf164) | QTDLLIAFY | 180 |

TABLE 14-continued

| Gene | Peptides with positional change | SEQ ID NO |
|------|------|------|
| ROBO1 | NSDSNLTTY | 190 |
| SH2B3 | KTDHFLSCY | 191 |
| SLC16A8 | CTDRAFAVY | 192 |
| SLC25A10 | RTDGILALY | 193 |
| SND1 | CVDWSIAVY | 194 |
| STIP1 | NIDDALQCY | 195 |
| SYN3 | FSELNLAAY | 196 |
| TLE6 | GMDDFLGVY | 197 |
| TMEM232 | NTDSDMGGY | 198 |
| TRIM47 | YADRALAFY | 199 |
| ZNF503 | GTDKLLSGY | 200 |
| ZNF507 | QVDSTLAAY | 201 |
| ZNF653 | WSDAKLAAY | 202 |
| DSG4 | GTDNWLAQY | 203 |
| PTS | ETDNNIVVY | 204 |

TABLE 14-continued

| Gene | Peptides with positional change | SEQ ID NO |
|------|------|------|
| KDM7A (JHDM1D) | PTDENLARY | 205 |
| ICE1 (KIAA0947) | NTDNLLTEY | 206 |
| RBM4 | LTEQYNEQY | 207 |
| ERGIC3 | TTEVHPELY | 208 |
| UBR2 | ATDLTREVY | 209 |

Immunoprecipitation combined with targeted mass spectrometry (IPMS) method was used to assess the presentation of these 66 peptides by the HLA (allele A*01:01) that could be recognized by the 41-E07-hOKT3a antibody. The 41-E07-hOKT3a antibody as well as pan HLA1 (b2m specific) antibody was used to assess two cancer cell lines, K562-A*01:01 (engineered to express HLA A*01:01) and NCI-H1703 (naturally harbor HLA A*01:01). These two cell lines express the majority of these OTLA genes (expression >1 TPM per CCLE, Cancer Cell Line Encyclopedia). Six of those peptides presented by HLA, were identified by the IPMS experiment as possible off target interactions (Table 15). Where targets of the OTLA peptides were detected, target densities as given by copies per cell are shown.

TABLE 15

Target densities of G2, OTLA peptides in A*01:01-expressing cell lines

| Peptide (Gene) | NCI-H1703 | | | K562-A*01:01 | | | Potential OTLA |
|------|------|------|------|------|------|------|------|
| | 41E07 Rep1:Rep2 | IgG Rep1:Rep2 | W6/32 Rep1:Rep2 | 41E07 | IgG | W6/32 | |
| NTDNNLAVY (SEQ ID NO: 214) (CT83) | 2958; 2959 | ND; ND | 3789; 4040 | ND | ND | ND | |
| ATDLTREVY (SEQ ID NO: 209) (UBR2) | 146; 147 | 6; 4 | 891; 876 | 6 | ND | 6 | Yes |
| LTEQYNEQY (SEQ ID NO: 207) (RBM4) | 1146; 1127 | 113; 79 | 16727; 16746 | 60 | ND | 1004 | Yes |
| TTEVHPELY (SEQ ID NO: 208) (ERGIC3) | 34; 37 | 25; 15 | 3358; 3352 | ND | ND | 96 | Yes |
| ETDNNIVVY (SEQ ID NO: 204) (PTS) | 40; 42 | 32; 25 | 2927; 2980 | 12 | ND | 91 | Yes |
| PTDENLARY (SEQ ID NO: 205) (KDM7A) | 0; 0 | 0; 0 | 2; 2 | ND | ND | ND | No |
| NTDNLLTEY (SEQ ID NO: 206) (IC1) | 33; 32 | 35; 21 | 2661; 2745 | ND | ND | ND | Yes |
| GTDNWLAQY (SEQ ID NO: 203) (DGS4) | 0; 0 | 0; 0 | 0; 0 | ND | ND | ND | No |

TABLE 15-continued

| Target densities of G2, OTLA peptides in A*01:01-expressing cell lines | | | | | | | |
|---|---|---|---|---|---|---|---|
| | NCI-H1703 | | | K562-A*01:01 | | | |
| Peptide (Gene) | 41E07 Rep1:Rep2 | IgG Rep1:Rep2 | W6/32 Rep1:Rep2 | 41E07 | IgG | W6/32 | Potential OTLA |
| NSDSNLTTY (SEQ ID NO: 190) (ROBO1) | 85; 79 | 0; 0 | 554; 517 | ND | ND | ND | Yes |
| YTDNWLAVY (SEQ ID NO: 152) (DSG3) | 0; 0 | 0; 0 | 0; 0 | ND | ND | ND | Yes |

ND: Not detected

Figure 41:
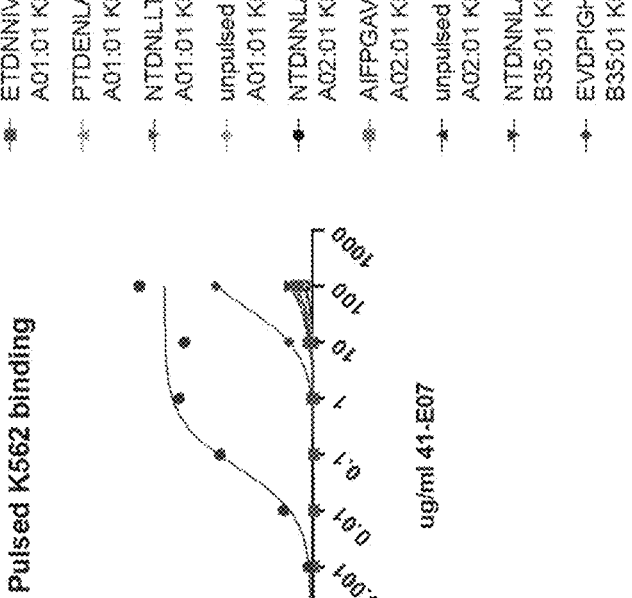
FIG. 41 shows binding of the 41-E07 hOKT3a antibody to cells pulsed with the indicated peptide complex.

Peptides identified by IPMS experiment were de-risked by in vitro assays. The A01:01 HLA presenting cells pulsed with the OTLA peptides of interest show no or minimal interactions (FIG. 41). Some binding to EVDPIGHVY (SEQ ID NO: 233) pulsed B35:01 cells was observed, but there was a more than 3 log difference in EC50 as compared to the G2 peptide NTDNNLAVY (SEQ ID NO: 214).

Of these OTLA peptides, only the peptide from ROBO1 gene, when presented on HLA showed a prominent interaction with 41-E07-UCHT1v9 (FIG. 42A). The EC50 for 41-E07-UCHT1v9 to the G2 target peptide was 0.1461, while the EC50 for 41-E07-UCHT1v9 to the ROBO1 target was 7.331. However, when this peptide was refolded into A*01:01/b2m complex, it showed 5000 times less binding affinity to 41-E07-UCHT1v9, as compared to the G2-peptide A*01:01/b2m complex, as measured by octet experiment (FIG. 42B).

Example 15: SEC-HPLC Analysis of Format 4 Bispecific Antibodies Reveal Presence of an Alternative Isomer Methods Analytical SEC-HPLC was performed on an Agilent 1200 series HPLC system equipped with a degasser (G1379B), binary pump (G1312B), high performance autosampler (G1367D), and wide range diode array detector (DAD, G7115A). Approximately 50-100 ug of Format 4 G5(1C12) proteinA eluate, neutralized to pH 7 using 1M Tris buffer pH 7.5, was loaded onto a TSKgel SuperSW mAb HTP column (4.6 mm ID×15 cm) with the TSKgel Guardcolumn SuperSW mAb guard column in line, or TSKgel G3000 SWx1 column (7.8 mm ID×30 cm) with the TSKgel G2000SWx1-G4000SWx1 Guard Column in line from Tosoh Bioscience. The TSKgel SuperSW mAb HTP column was operated at 0.35 ml/min for 7 min in PBS pH 7.4. The TSKgel G3000 SWx1 column was operated at 0.5 ml/min for 35 min in PBS, pH 7.4. The DAD was set to collect absorbance at 280 nm for both methods.

Results:

Analysis of Format 4-G5(1C12) hOKT3a proteinA eluate using the TSKgel SuperSW mAb HTP column (FIG. 44A, top), used for quick product quality screening of antibodies, revealed the presence of aggregates between 3-4 min, a main peak, and an unexpected significant tailing between 4.5-5.5 minutes. The observed tailing suggested the presence of an additional antibody moiety that either interacts more with the SEC column, or is more compacted and thus migrates slower than the main antibody conformation. Analyzing the same proteinA eluate using the TSKgel G3000SWx1 column, which has greater resolving power than the shorter TSKgel SuperSW mAb HTP column, shows that the tailing initially observed resolves into a "split peak" (FIG. 44A, bottom). Mass spectrometry analysis of the Format 4-G5 (1C12) hOKT3a antibody suggested no fragmentation (data not shown). Accordingly, the "split peak" was hypothesized to be a diabody isoform of the Format 4 antibody, where the VH of one of the scFvs interacts with the VL of the other scFv and vice versa. (FIG. 44B, bottom panel, bispecific diagram on the right).

These results indicated that the antibodies can exist in two conformations. They further indicated that in solution, the antibody will be in equilibrium between (1) a dual scFv conformation and (2) a diabody conformation (see FIG. 5).

Example 16: Determination of Alternate Diabody Isoform

Materials and Methods

Antibody Digestion Experiment 0.4 mg each of purified G5(1C12) hOKT3a format 3, 4 and 5 bispecific antibodies were buffer exchanged from PBS pH 7.4 into 150 mM sodium phosphate buffer at pH 7.0. The samples were then concentrated to a volume of approximately 100 µL, with corresponding concentrations ranging from 3-4 mg/mL, loaded onto FabALACTICA microspin columns (Genovis), and incubated for 16 hr with end-over-end mixing. FabALACTICA antibody digestion involves a cysteine protease that digests human IgG1 at one specific site above the hinge (KSCDKT/HTCPPC (SEQ ID NO: 211)), generating intact Fab and Fc fragments. The name of the enzyme is derived from the pathogen *Streptococcus agalactiae*, where it was first discovered. Spoerry, Christian & Hessle, Pontus & Lewis, Melanie & Paton, Lois & Woof, Jenny & Pawel-Rammingen, Ulrich. (2016). Novel IgG-Degrading Enzymes of the IgdE Protease Family Link Substrate Specificity to Host Tropism of *Streptococcus* Species. PLOS ONE. 11. e0164809. 10.1371/journal-.pone.0164809), which is hereby incorporated by reference in its entirety. To collect the digested products, the columns were centrifuged at 1000×g for 1 min, followed by two additional rounds of elution using 100 µL PBS pH 7.4. The elution fractions were pooled and subsequently loaded onto a CaptureSelect (Genovis) column, and incubated for 30 min with end-over-end mixing. The flowthrough was collected by centrifugation at 200×g for 1 min, followed by two wash steps with 100 µL PBS (200×g for 1 min, and 100×g for 1 min, respectively). The flowthrough and wash fractions were pooled, and are henceforth referred to as "ProteinA Flowthrough". The ProteinA bound fragments were eluted using 100 μL of 0.1M Glycine, pH 3 by centrifugation at 200×g for 1 min, and immediately neutralized with 50 L 1M tris pH 7.5. A second elution step was performed by centrifugation at 1000×g for 1 min, and neutralized immediately as described. The elution fractions were pooled and are henceforth referred to as "ProteinA bound/Eluted"

SEC-HPLC Analysis

Analytical SEC-HPLC was performed on an Agilent 1200 series HPLC system equipped with a degasser (G1379B), binary pump (G1312B), high performance autosampler (G1367D), and wide range diode array detector (DAD, G7115A. Approximately 40 μL of each of untreated antibody, digested proteinA flowthrough, and digested ProteinA bound/eluted was loaded onto a TSKgel G3000 SWx1 column (7.8 mm ID×30 cm) with the TSKgel G2000SWx1-G4000SWx1 Guard Column in line from Tosoh Bioscience. The column was operated at 0.5 ml/min for 60 min in PBS, pH 7.4. The DAD was set to collect absorbance at 280 nm.

Results

FIG. 45A depicts expected protein digestion fragments of "standard" Format 4 antibodies and a "diabody" isomer of Format 4. FabALACTICA digestion of "standard" Format 4 conformation (scFv/scFv-Fab) antibodies with two separate scFvs, without presence of any alternative "diabody" isoforms, would be expected to yield two peaks: one corresponding to the scFv-Fc fragment and one corresponding to the scFv-Fab fragment. Presence of a Format 4 "alternative diabody" conformation would be expected to reveal presence of a third peak that aligns with the undigested Format 4 main peak.

SEC-HPLC results are depicted in FIG. 45B. Digested format 5 ProteinA flowthrough is used as the scFv Fab standard, and digested format 3 Protein A bound/Eluted is used as the ScFv-Fc standard. The undigested Format 4 SEC-HPLC profile shows the previously described split peak. Digested Format 4 ProteinA flowthrough showed a peak with a retention time that aligned with the scFv-Fab standard. Digested Format 4 ProteinA bound/Eluted SEC-HPLC profile showed a peak that aligned with the scFv-Fc standard expected to be seen for the "standard" Format 4, as well as a peak that aligned with the undigested format 4. The presence of the latter peak indicated the presence of the alternate diabody conformation.

FIG. 46 depicts a diagram representation of the undigested Format 4 "separate scFv" conformation (left), the alternate diabody conformation without digestion (middle), and the alternate diabody conformation with digestion (right).

Example 17: Negative Stain Electron Microscopy and 2D Class Averaging

Materials and Methods

Grid Preparation

A sample of Format 4-G5(1C12) hOKT3 bispecific antibody was diluted to 18 μg/mL using PBS prior to imaging. The sample was imaged over a layer of continuous carbon supported by nitro-cellulose on a 400-mesh copper grid. The grids were prepared by applying 3 μl of sample suspension to a cleaned grid, blotting away with filter paper, and immediately staining with uranyl formate.

EM Imaging

Electron microscopy was performed using an FEI Tecnai T12 electron microscope (serial number D1100), operating at 120 keV equipped with an FEI Eagle 4 k×4 k CCD camera. Negative stain grids were transferred into the electron microscope using a room temperature stage.

Images of each grid were acquired at multiple scales to assess the overall distribution of the specimen. After identifying potentially suitable target areas for imaging at lower magnifications, high magnification images were acquired at nominal magnifications of 110,000× (0.10 nm/pixel) and 67,000× (0.16 nm/pixel). The images were acquired at a nominal underfocus of −1.6 μm to −0.8 μm and electron doses of ~25 e/Å.

2D Averaging Analysis

Particles were identified in the high magnification images prior to alignment and classification. The individual particles were then selected, boxed out, and individual sub-images are combined into a stack to be processed using reference-free classification.

Particle Selection: Individual particles in the 67,000× high magnification images were selected using automated picking protocols described in Lander, G. C., S. M. Stagg, et al. (2009). "Appion: an integrated, database-driven pipeline to facilitate EM image processing." J Struct Biol 166(1): 95-102, which is hereby incorporated by reference in its entirety, and manual picking. An initial round of alignments was done on each sample and from that alignment class averages that appeared to contain recognizable particles were selected for additional rounds of alignment.

Particle Alignment and Classification: A reference-free alignment strategy based on the XMIPP (Sorzano, Marabini et al. 2004) processing package, described in Sorzano, C., R. Marabini, et al. (2004). XMIPP: a new generation of an open-source image-processing package for electron microscopy. J Struct Biol. 148: 194-204, which is hereby incorporated by reference in its entirety, was used. Algorithms in this package align the selected particles and sort them into self-similar groups of classes.

Results

FIG. 47 depicts electron microscopy results. Visible in the sample were particles that displayed different sizes and morphologies. Particles ranged from ~16-22 nm in their longest dimension and had a wide range of conformations; some particles had a branched appearance and others were irregular in shape. Class averages showed particles that ranged from ~5 to 10 nm in width and ~16 to 18 nm in length (see FIG. 47). The majority of the class averages contained features that resembled those seen for IgG molecules: a single Fc domain and two antibody arms. However, there were aspects that distinguished these particles from a typical antibody sample: 1. One of the antibody arms contained a peanut-shaped moiety closely resembling a typical Fab (FIG. 47, panel A, black arrow). The other arm appeared to contain two spherical domains, but at a greater distance from each other when compared to that seen in a standard Fab arm (FIG. 47, panel A, light gray arrow). Based on the model of this bispecific antibody, it is likely that only one of these two spherical domains was connected to the Fc region, whereas the other was in fact connected to the end of the neighboring arm. It seems to be flexibly linked, as it can bend down and interact with the tip of the neighboring Fab arm. These interacting spherical domains are mostly likely the two scFv domains of the Format 4 antibody. Thus the EM revealed visual evidence of the alternative diabody isomer.

It should be noted that in a few class averages, the Fc and Fab domains were stacked in a straight line making it impossible to distinguish between them (FIG. 47, panels E and F). These are likely side views of the particle described above.

Averages were generally well-defined, with some portions of the Fc domain not as clearly resolved as others.

Example 18: Introduction of DSB44/100 Removes Putative Diabody Peak

Materials and Methods

DSB Engineering

Position 44 of the VH (Kabat) is often in close proximity to position 100 of VL (Kabat). By introducing Cys residues at both of these positions, a disulfide bond (DSB) can be formed that stabilizes the VH/VL interactions within each scFv, prior to assembly of the bispecific antibody chains. Such a stabilizing DSB would be expected to reduce the probability that the two scFvs of the Format 4 antibodies interact to form the alternative diabody isomer.

Gene fragments incorporating the H44-L100 DSB mutations (Kabat numbering) were ordered through Genewiz, incorporating 18-base pair overlaps with digested vector. Fragments were cloned using In-Fusion homologous recombination (Takara) according to manufacturer's instructions. Clones were confirmed to be correct by sequencing (Elim Biopharmaceuticals). Molecules were generated by transfection of Expi293F cells according to manufacturer's recommended protocols (Life Technologies). Molecules were purified on Akta AVANT using protein A and Kappa Select Light columns (GE Healthcare) and polished using CHT (Bio-Rad) for aggregate removal.

SEC-HPLC

Analytical SEC-HPLC was performed on an Agilent 1200 series HPLC system equipped with a degasser (G1379B), binary pump (G1312B), high performance autosampler (G1367D), and wide range diode array detector (DAD, G7115A). Purified Format 4 G5(1C12) and G2(1H11) antibodies, with and without the DSB were loaded onto a TSKgel G3000 SWx1 column (7.8 mm IDx30 cm) with the TSKgel G2000SWx1-G4000SWx1 Guard Column in line from Tosoh Bioscience. The column was operated at 0.5 ml/min for 30 min in PBS, pH 7.4. The DAD was set to collect absorbance at 280 nm.

Results

Bottom panels of FIG. 48 and FIG. 49 show the previously observed split peak for both Format 4-G5 and G2 molecules, indicating the presence of both "standard" (with two separate scFvs) and alternate diabody conformation across all Format 4 molecules. Introduction of a stabilizing disulfide bond within the scFv regions of both molecules is shown to remove the split peak (top panels of FIG. 48 and FIG. 49). A retention time that aligns with that of the Format 4 "standard" conformation suggests that the introduction of a disulfide bond stabilizes the standard conformation with two separate scFvs for both G5 and G2 molecules and reduces their isomerization into the alternative diabody format.

Example 19: Digestion of Format 4 Antibody with DSB44/100

Materials and Methods

Proteolysis by FabALACTICA:

0.3-0.5 mg of Format 4 G5(1C12)-hOKT3_DSBH44/L100 and Format 4 G2(1H11)-hOKT3_DSBH44/L100 antibodies (both having non-shortened linkers: L1=L2=(G4S)×4 (SEQ ID NO: 228); L3=L4=(G4S)×2 (SEQ ID NO: 111)) were buffer exchanged from PBS pH 7.4 into 150 mM sodium phosphate buffer at pH 7.0. The samples were then concentrated to a volume of approximately 100 μL, with corresponding concentrations ranging from 3-5 mg/mL, loaded onto FabALACTICA microspin columns (Genovis), and incubated for 18 hr with end-over-end mixing. To collect the digested products, the columns were centrifuged at 1000×g for 1 min, followed by three additional rounds of elution using 100 μL PBS pH 7.4. The elution fractions were pooled (referred to as "digested pool"), and subsequently loaded onto a CaptureSelect ProteinA (Genovis) column, and incubated for a minimum of 30 min with end-over-end mixing. The flowthrough was collected by centrifugation at 200×g for 1 min, followed by three wash steps with 100 μL PBS pH 7.4. The flowthrough and wash fractions were pooled, and are henceforth referred to as "'Fab' Fraction". The Protein A bound fragments were eluted using 100 μL of 0.1 M Glycine, pH 3, by centrifugation at 200×g for 1 min, and immediately neutralized with 10 μL 1M Tris pH 8. Four additional elution steps were performed by centrifugation at 1000×g for 1 min, and neutralized immediately as described. The elution fractions are henceforth referred to as "'Fc' fraction".

SEC-HPLC

Analytical SEC-HPLC was performed on an Agilent 1260 series HPLC system equipped with a degasser (G4225A), binary pump (G1312B), autosampler (G1329B), and diode array detector (DAD, G4212B). Approximately 60 to 100 μg of each untreated antibody, and 100 μL of the "Fab" fraction, and "Fc" fraction were loaded onto a TSKgel G3000 SWx1 column (7.8 mm IDx30 cm) with the TSKgel G2000SWx1-G4000SWx1 Guard Column in line from Tosoh Bioscience. The column was operated at 0.5 mL/min for 30 min in PBS, pH 7.4. The DAD was set to collect absorbance at 280 nm.

CE-SDS

Capillary gel electrophoresis was performed using the LabChip GXII Touch HT system (PerkinElmer), and samples were analyzed using the ProteinExpress 200 High Sensitivity assay (PerkinElmer, #CLS960008) under reducing and non-reducing conditions. 2 μg of each untreated antibody, and 5 μL of each of the digested pool, "Fab" fraction, and "Fc" fraction were mixed with 7 μL of reducing or non-reducing denaturing solution, and incubated at 70° C. for $10^{-12}$ min. The reducing denaturing solution was prepared by adding 24.5 μL of 1 M DTT to 700 μL of non-reducing denaturing solution provided in the kit. Denatured samples were diluted with 32 μL of MilliQ water, mixed well, and spun down prior to analysis. The Protein Express LabChip (PerkinElmer, #760499), and ladder were prepared according to manufacturer instructions.

Results

Format 4 molecules stabilized in the 2×ScFv conformation were expected to exhibit a single peak when analyzed by SEC-HPLC. Both undigested G2 and G5 molecules containing the DSB H44/L100 mutation were observed to migrate as single peaks, with a retention time of approximately 17.3 minutes (FIG. 50A and FIG. 51A), suggesting that the putative diabody formation had been eliminated via disulfide bond stabilization. Further, proteolysis of these Format 4 molecules resulted in two fragments, namely the scFv-Fc fragment (#2 in FIG. 50A and FIG. 51A), and the scFv-Fab fragment (#3 in FIG. 50B and FIG. 51B), as observed in the non-reducing gel. Complete separation of these fragments is observed upon purification of the digested pool by protein A when analyzed by both, CE-SDS and SEC-HPLC. The absence of residual scFv-Fab related bands in the "Fc" fraction lanes under both reducing and non-reducing conditions indicated stabilization of the 2×scFv conformation for both the G2 and G5 antibodies. Additionally, the absence of a significant peak that aligns with the undigested samples in the Fc-fraction when analyzed by SEC-HPLC also indicated that the 2×scFv conformation has been successfully stabilized in both G2 (FIG. 51A) and G5 (FIG. 50A) molecules.

Example 20: Effect of Engineered DSB on Apparent Affinity as Measured by BLI

Format 4 bispecific antibodies with or without DSB mutations as described in Example 18 were generated. The affinity of wildtype and DSB mutants were analyzed on the ForteBio Octet HTX in 96-channel mode with biolayer interferometry (BLI) detection. High Precision Streptavidin SAX biosensors (P/N 18-5117) were loaded into the instrument. Biotinylated G2-pHLA or G5-pHLA was captured on the SAX biosensor at 2 μg/mL and ran for 120 s in the assay buffer composed of 0.02% Tween-20 and 0.1% BSA. The biosensors were then dipped in assay buffer for a baseline. Subsequently, the biosensors were dipped into wells containing varying concentrations of the bispecific antibody samples (3.125, 6.25, 12.5, 25, 50, 100 and 200 nM) to measure the association rate for 50 seconds. The biosensors were finally dipped into wells containing assay buffer to measure the dissociation rate for another 50 seconds. Referencing was completed by having a biosensor with no immobilized ligand dipped into analyte. Kinetic data was processed with Octet™ software using a 1:1 kinetic model with errors within 10%, $X^2$ below 3, and $R^2$ above 0.9.

Results are depicted in FIG. 52. Introduction of the DSB mutation increased the Kp of the G2 Format 4 bispecific from 18 nM to 35.1 nM. Introduction of the DSB mutation increased the Kp of the G5 Format 4 bispecific from 1.09 nM to 1.35 nM.

Example 21: Effect of DSB on Apparent Affinity as Measured by MSD

The effect of the stabilizing DSB on cell binding of Format 4 G2 and G5 antibodies was assessed using the Meso Scale Discovery (MSD) U-PLEX Development Pack, 9-assay (cat. No. K15234N). Biotinylated pHLA and biotinylated Protein A were each diluted to 33 nM using PBS+0.5% BSA. For each plate, 200 μL of the diluted pHLA or protein A was mixed with 300 μL Linker and incubated at room temperature for 30 minutes.

Following the 30 minute incubation, 200 μL Stop solution was added to each linker-pHLA solution. They were again incubated for 30 minutes at room temperature. These volumes were scaled based on the number of plates. At this point, the linker-pHLA solutions were a 10× solution. They were then pooled together and further diluted with stop solution to the final 1× concentration. All volumes were scaled for additional plates. The pooled linker-pHLA solutions were then coated onto the 10-spot plate as 50 μL/well, the plate sealed and stored at 4° C. overnight.

Format 4-G2(1H11) hOKT3a and Format 4-G5(1C12) hOKT3a antibodies, with or without the DSB described in Example 18, were serially diluted 3-fold with PBS+1% BSA. The plate was washed 3 times with PBS+0.05% Tween and samples added as 50 μL/well. Plates were incubated at room temperature shaking for 2 hours. The plates were washed as before and 50 μL of 1 μg/mL SulfoTag donkey anti-human Fc, (Jackson ImmunoResearch 709-005-098) was added to each well. The anti-human Fc antibody was sulfo-tag labeled using the MSD Gold Sulfo-tag NHS- Ester Conjugation kit (Meso Scale Discovery, R31AA-2) at a challenge ratio of 10. The plates were incubated for 1 hour shaking at room temperature. The plate wash was repeated and 150 μL 2× Read Buffer T (Meso Scale Discovery, R92TC-2) was added to all wells and the plate read immediately on the Quickplex SQ 120.

Results

Results are depicted in FIG. 53. G2 Format 4 binding as measured by MSD was 0.546 nM without the DSB and 46.42 nM with the DSB. The G5 data did not fit a curve. However, the G5 dose-response curve without the DSB was leftward shifted as compared to the G5 dose-response curve with the DSB.

Example 22: Effect of Engineered DSB on Cell Binding

Format 4 bispecific antibodies with and without the stabilizing DSB as described in Example 18 were tested for their ability to specifically bind to the HLA-PEPTIDE targets on the surface of antigen presenting cells.

The cell lines used to express the desired HLA-PEPTIDE targets were as follows: A375 cells (which express HLA subtype*01:01) engineered to express the G2 restricted peptide NTDNNLAVY (SEQ ID NO: 214), LN229 (which express HLA subtype B*35:01) engineered to express the G5 restricted peptide EVDPIGHVY (SEQ ID NO: 233). All cell lines were also engineered to express luciferase.

Tumor cells engineered to express target peptide were harvested, washed in PBS, and stained with eBioscience Fixable Viability Dye eFluor 450 for 15 minutes at room temperature. Following another wash in PBS+1-2% FBS, cells were resuspended with the indicated molecules at varying concentrations and incubated for 1 hour at 4° C. After another wash, PE-conjugated goat anti-human IgG secondary antibody (Jackson ImmunoResearch) was added at 1:100 to 1:200 for 30 minutes at 4° C. After washing in PBS+1-2% FBS, cells were resuspended in PBS+1-2% FBS and analyzed by flow cytometry. Flow cytometric analysis was performed on the Attune N×T Flow Cytometer (ThermoFisher) using the Attune N×T Software. Data was analyzed using FlowJo.

Results

Results are depicted in FIG. 54. Introduction of the stabilizing H44/L100 DSB reduces cell binding for 4-G2 (1H11) hOKT3a as measured by an EC50 shift from 9.8 nM without the DSB to 1.75 M with the DSB. For 4-G5(1C12) hOKT3a, addition of the DSB shifted the EC50 from 14.3 nM to 43.2 nM.

Example 23: In Vitro Cytotoxicity for G2 Format 4+/−DSB

Materials and Methods

Spheroid Toxicity

The cell lines used to express the desired HLA-PEPTIDE targets were as follows: A375 cells (which express HLA subtype*01:01) engineered to express the G2 restricted peptide NTDNNLAVY (SEQ ID NO: 214). The cell line was also engineered to express luciferase.

Luciferase expressing cells were plated in 100 μL at 10,000-15,000 cells/well in Corning ultra-low attachment plates (Corning #4515) in corresponding culture medium without selection. Plates were incubated for two days at 37° C. and 5% CO2 to allow spheroid formation. Antibody (Format 4-G2(1H11) hOKT3a), plus or minus the stabilizing disulfide bond described in Example 12), was titrated at and added as 10 μL/well. Normal human PBMCs were thawed and rested for 4-6 hours at 37° C. and added as 100,000 cells/well in 50 μL giving an Effector:Target ratio of 10:1. Plates were then incubated for 4 days at 37° C. and 5% CO2. At the end of the incubation period 100 μL Luciferin (Pierce #88292) at 300 μg/mL was added to the plate. Luciferase was read on the SpectraMax iE3. Percent cytotoxicity was calculated as (Media control-sample signal)/(Media control-maximum lysis)*100.

2D Cytotoxicity

Target and control cells were plated at 40,000 cells per well of 96 well plate. For the G2 molecules the target cell line with A375 transduced with a 10×9mer cassette expressing the target peptide and luciferase. A375s transduced with luciferase alone serve as a negative control. After allowing the cells to adhere for 30 minutes, human PBMCs (Stem Cell Technologies) were added at a ratio of 5:1 effector to target cells. Bispecific antibody was added to the well at indicated final concentration. Each concentration was performed in duplicate. Cultures were incubated for three days. Luciferase signal was assessed using Promega's Bio-Glo assay system (Cat. #G7941) according to manufacturer's instructions and read on the SpectraMax M5. Signal was normalized to control wells to determine the percent of cytotoxicity. Loss of luciferase signal is interpreted as loss of cell viability.

Results

Results for G2 are depicted in FIG. 55. G2 Format 4 antibodies with the stabilizing disulfide bond resulted in lower cytotoxicity, as indicated by the rightward shift in the dose-response curve.

Example 24: Preparation of Samples for Diabody Experiments

Samples/molecules used in Examples 24-29 and corresponding linker lengths are provided in Table 16 below.

Example 25: Effect of Shortened Linker on Diabody Formation

Materials and Methods

Proteolysis by FabALACTICA 0.3-0.5 mg of G5(1C12)-hOKT3a and G2(1H11)-hOKT3a Format 4 antibodies with and without shortened linkers in L1 and L2 were buffer exchanged from PBS pH 7.4 into 150 mM sodium phosphate buffer at pH 7.0. Format 4 antibodies with shortened L1 and L2 linkers had 10 amino acid residues at each of the L1 and L2 linkers, specifically (GGGGS)$_2$ (SEQ ID NO: 111), The samples were then concentrated to a volume of approximately 100 μL, with corresponding concentrations ranging from 35 mg/mL, loaded onto FabALACTICA microspin columns (Genovis), and incubated for 16 hr with end-over-end mixing. To collect the digested products, the columns were centrifuged at 1000×g for 1 min, followed by two additional rounds of elution using 100 μL PBS pH 7.4. The elution fractions were pooled (referred to as "digested pool"), and subsequently loaded onto a CaptureSelect ProteinA (Genovis) column, and incubated for a minimum of 30 min with end-over-end mixing. The flowthrough was collected by centrifugation at 200×g for 1 min, followed by two wash steps with 100 μL PBS pH 7.4. The flowthrough and wash fractions were pooled, and are henceforth referred to as "'Fab' fraction". The ProteinA bound fragments were eluted using 100 μL of 0.1 M Glycine, pH 3 by centrifugation at 200×g for 1 min, and immediately neutralized with 10 μL 1M tris pH 8. A second elution step was performed by centrifugation at 1000×g for 1 min, and neutralized immediately as described. The elution fractions are henceforth referred to as "'Fc' Fraction"

SEC-HPLC

For the Format 4-G5(1C12) hOKT3a molecule with L1=L2=(G4S)×4 (SEQ ID NO: 228), analytical SEC-HPLC was performed on an Agilent 1200 series HPLC system equipped with a degasser (G1379B), binary pump (G1312B), high performance autosampler (G1367D), and wide range diode array detector (DAD, G7115A). Approximately 40 μL of each of the untreated antibody, "Fab" Fraction, and "Fc" fraction was loaded onto a TSKgel

TABLE 16

| Target | Sample # | Format | Molecule ID | L1 = L2 (Linker Length) | L3 = L4 (Linker Length) |
|---|---|---|---|---|---|
| G5 | 1 | 3 | 3-G5(1C12)-hOKT3a_N97G | | |
| | 2 | 5 | 5-G5(1C12)-hOKT3A DSB H44/L100 | | |
| | 3 | 4 | 4-G5(1C12)-hOKT3a | (G4S) × 4 (SEQ ID NO: 228) | (G4S) × 2 (SEQ ID NO: 111) |
| | 4 | 4_DSB | 4-G5(1C12) hOKT3a_DSB H44/L100 TM(+)cys; N97G; 153R; Y100dV | (G4S) × 4 (SEQ ID NO: 228) | (G4S) × 2 (SEQ ID NO: 111) |
| | 5 | 41(Diabody) | 4-G5(1C12)_10AAL hOKT3a | (G4S) × 4 (SEQ ID NO: 228) | (G4S) × 2 (SEQ ID NO: 111) |
| G2 | 6 | 4 | 4-G2(1H11)-hOKT3a | (G4S) × 4 (SEQ ID NO: 228) | (G4S) × 2 (SEQ ID NO: 111) |
| | 7 | 4-DSB | 4-G2(1H11)-H44/L100 hOKT3a-TM | (G4S) × 4 (SEQ ID NO: 228) | (G4S) × 2 (SEQ ID NO: 111) |
| | 8 | 41(Diabody) | 4-G2(1H11)-10AAL hOKT3a | (G4S) × 2 (SEQ ID NO: 111) | (G4S) × 2 (SEQ ID NO: 111) |
| | 9 | 41(Diabody) X DSB | 4-G2(1H11)-10AAL -DSB H44/L100 hOKT3a-TM | (G4S) × 2 (SEQ ID NO: 111) | (G4S) × 2 (SEQ ID NO: 111) |

\* TM denotes the TM mutations (L234F/L235E/P331S) in the variant CH2-CH3 domains (both arms of the antibody).

G3000 SWx1 column (7.8 mm ID×30 cm) with the TSKgel G2000SWx1-G4000SWx1 Guard Column in line from Tosoh Bioscience. The column was operated at 0.5 mL/min for 60 min in PBS, pH 7.4. The DAD was set to collect absorbance at 280 nm.

For all other molecules, analytical SEC-HPLC was performed on an Agilent 1260 series HPLC system equipped with a degasser (G4225A), binary pump (G1312B), autosampler (G1329B), and diode array detector (DAD, G4212B). Approximately 60 to 100 μg of each untreated antibody, and 100 μL of the "Fab" fraction, and "Fc" fraction were loaded onto a TSKgel G3000 SWx1 column (7.8 mm ID×30 cm) with the TSKgel G2000SWx1-G4000SWx1 Guard Column in line from Tosoh Bioscience. The column was operated at 0.5 mL/min for 30 min in PBS, pH 7.4. The DAD was set to collect absorbance at 280 nm.

SDS-PAGE

For all molecules tested, 2 μg of undigested antibody, and 5-10 μL of digested pool, "Fab" fraction, and "Fc" fraction were denatured under non-reducing and reducing conditions using NuPage 4×LDS sample buffer (Invitrogen). Samples analyzed under non-reducing conditions were left at ambient temperature. Samples analyzed under reducing conditions, using 2 μL of 1M DTT, were incubated at 70° C. for 5-10 minutes. All samples were analyzed using NuPage 4-12% Bis-Tris gradient gels (Invitrogen) against Precision Plus Protein™ Dual Color Standards (Bio-Rad), with NuPage MOPS SDS running buffer (Invitrogen). Gels were visualized after staining with InstantBlue stain (Expedeon).

Results

SEC-HPLC analysis of undigested Format 4-G2(1H11) hOKT3a and G5(1C12) hOKT3a molecules with L1=L2= (G4S)×4 (SEQ ID NO: 228) showed the characteristic "split-peak" profile described previously (FIG. 56 and FIG. 57), where the peak with retention time around 17.3 minutes corresponds to the 2×scFv conformation, and the peak with retention time around 17.7 minutes corresponds to the putative diabody conformation. This "split-peak" was more pronounced for the G2(1H11) hOKT3a molecule, indicating that the scFv of this molecule undergoes more "breathing", resulting in more frequent shuffling between the two conformations.

SEC-HPLC analysis of the "Fab" fraction for both molecules revealed a single peak that aligns with the retention time of scFv-Fab marker. The "Fc" fractions had a peak with retention time that aligned with the scFv-Fc marker, as well as a second peak with retention time that aligned with the undigested antibody. The absence of an intense band migrating around 150 kDa under non-reducing conditions, and around 75 kDa under reducing conditions in the "Fc" fraction lane for the G5 molecule indicated that the digestion was near complete. Yet, the second peak on the SEC-HPLC chromatogram that aligned with the retention time of the undigested antibody appeared in roughly equal proportion to the ScFv-Fc peak. The presence of this second peak, which likely corresponds to a clipped diabody, further indicated that the Format 4-G5(1C12) hOKT3a molecule with a 20 amino acid-long linker at locations L1 and L2 exists as a mixture of the 2×ScFv and diabody conformations. The observation that the second peak for the G2(1H11) hOKT3a molecule in the "Fc" fraction was not as significant as was observed for G5(1C12) hOKT3a is likely explained by more frequent shuffling between the diabody and 2×scFv conformations mentioned supra. During the 16 hr digestion period, the clipped diabody form can more readily dissociate into the scFv-Fc and scFv-Fab fragments, contributing to the results obtained for this molecule (FIG. 56 and FIG. 57).

On the other hand, SEC-HPLC analysis of undigested format 4 G2(1H11) hOKT3a and G5(1C12) hOKT3a molecules with shortened L1 and L2 linkers (L1=L2=(G4S)×2 (SEQ ID NO: 111)) showed a single peak with retention time around 17.7-18 minutes (FIG. 58 and FIG. 59). This retention time aligns with what we hypothesized to be the peak corresponding to the diabody conformation in the split-peak profile observed prior to shortening the linker. Therefore, this indicated that shortening the linker from 20 amino acids to 10 amino acids forced both Format 4 molecules into the diabody conformation.

To further support this, no protein was recovered in the G5(1C12) hOKT3a "Fab" fraction, as shown in the SEC-HPLC chromatogram, and reducing and non-reducing gels. Additionally, the "Fc" fraction that resulted from digestion of this molecule resulted in a single peak on the SEC-HPLC chromatogram which aligned with the retention time of the undigested molecule, corresponding to a clipped diabody. The newly formed "split peak" in the Fc-fraction is likely due to the clipped diabody existing in compact and extended conformations. Furthermore, the reducing and non-reducing gels showed that any bands corresponding the scFv-Fab fragment, which would be expected to be present in the "Fab" fraction lane in the absence of diabody, were present in the scFv-Fc fraction instead (FIG. 58).

Similar analysis of the "Fc" fraction for the G2(1H11) hOKT3a molecule supported diabody formation, where the SEC-HPLC chromatogram showed a "split peak" corresponding to the clipped diabody conformation, and bands corresponding to scFc-Fab fragment present in the "Fc" lane of the reducing and non-reducing gel. The "Fab" fraction of the G2(1H11) hOKT3a molecule, however did contain some residual scFv-Fab, which likely dimerized into a diabody, as the SEC-HPLC trace for this fraction had an earlier retention time than would be expected for the scFv-Fab fragment (FIG. 59). This is likely a result of the G2(1H11) hOKT3a scFv being more prone to "breathing", as mentioned above, where the clipped diabody can readily fall apart into the scFv-Fc and scFv-Fab fractions. The increased "breathing" observed for the G2(1H11) hOKT3a molecule indicated that the G2(1H11) hOKT3a molecule with shortened linker might not form the diabody conformation as stably as the G5(1C12) hOKT3a molecule.

Example 26: Effect of Combining DSB with Shortened Linker

Materials and Methods

Proteolysis by FabALACTICA:

0.3-0.5 mg of G2(1H11)-hOKT3a Format 4 with L1=L2= (G4S)×2 (SEQ ID NO: 111) and DSB H44/L100 mutation, was buffer exchanged from PBS pH 7.4 into 150 mM sodium phosphate buffer at pH 7.0. The samples were then concentrated to a volume of approximately 100 μL, with corresponding concentrations ranging from 35 mg/mL, loaded onto FabALACTICA microspin columns (Genovis), and incubated for 18 hr with end-over-end mixing. To collect the digested products, the columns were centrifuged at 1000×g for 1 min, followed by three additional rounds of elution using 100 μL PBS pH 7.4. The elution fractions were pooled (referred to as "digested pool"), and subsequently loaded onto a CaptureSelect ProteinA (Genovis) column, and incubated for a minimum of 30 min with end-over-end mixing. The flowthrough was collected by centrifugation at 200×g for 1 min, followed by three wash steps with 100 μL PBS pH 7.4. The flowthrough and wash fractions were pooled, and are henceforth referred to as "'Fab' fraction". The ProteinA bound fragments were eluted using 10 μL of 0.1 M Glycine, pH 3 by centrifugation at 200×g for 1 min, and immediately neutralized with 10 μL 1 M Tris pH 8. Four additional elution steps were performed by centrifugation at 1000×g for 1 min, and neutralized immediately as described. The elution fractions are henceforth referred to as "'Fc' Fraction"

SEC-HPLC

Analytical SEC-HPLC was performed on an Agilent 1260 series HPLC system equipped with a degasser (G4225A), binary pump (G1312B), autosampler (G1329B), and diode array detector (DAD, G4212B). Approximately 60 μg to 100 μg of each untreated antibody, and 100 μL of the "Fab" fraction, and "Fc" fraction were loaded onto a TSKgel G3000 SWx1 column (7.8 mm ID×30 cm) with the TSKgel G2000SWx1-G4000SWx1 Guard Column in line from Tosoh Bioscience. The column was operated at 0.5 mL/min for 30 min in PBS, pH 7.4. The DAD was set to collect absorbance at 280 nm.

CE-SDS

Capillary gel electrophoresis was performed using the LabChip GXII Touch HT system (PerkinElmer), and samples were analyzed using the ProteinExpress 200 High Sensitivity assay (PerkinElmer, #CLS960008) under reducing and non-reducing conditions. 2 μg of each untreated antibody, and 5 μL of each of digested pool, digested "Fab" fraction, and digested "Fc" fraction were mixed with 7 μL of reducing or non-reducing denaturing solution, and incubated at 70° C. for $10^{-12}$ min. The reducing denaturing solution was prepared by adding 24.5 μL of 1M DTT to 700 μL of non-reducing denaturing solution provided in the kit. Denatured samples were diluted with 32 μL of MilliQ water, mixed well, and spun down prior to analysis. The Protein Express LabChip (PerkinElmer, #760499), and ladder were prepared according to manufacturer instructions.

Results

SEC-HPLC analysis of undigested Format 4 G2(1H11) hOKT3a with shortened L1 and L2 linkers (L1=L2= (G4S)×2 (SEQ ID NO: 111)), along with the incorporation of the DSB H44/L100 mutation showed a single peak with retention time around 17.7-18 minutes (FIG. 60). This retention time aligned with what was hypothesized to be the peak corresponding to the diabody conformation in the split-peak profile observed prior to shortening the linker. Contrary to what was seen in the absence of the DSB H44/L100 stabilizing mutation (Example 25), no protein was recovered in the "Fab" fraction, as was observed in the SEC-HPLC chromatogram, and reducing and non-reducing gels. Absence of bands corresponding to scFv-Fc and scFv-Fab fragments following digestion under non-reducing conditions indicated that the disulfide bond formation was complete, and was effective at stabilizing the diabody conformation and preventing "breathing" (FIG. 60).

Additionally, the "Fc" fraction that resulted from digestion of this molecule resulted in a single peak on the SEC-HPLC chromatogram which aligned with the retention time of the undigested molecule, corresponding to a clipped diabody. The newly formed "split peak" in this "Fc" fraction was likely due to the clipped diabody existing in compact and extended conformations. Furthermore, the reducing gel showed that any bands corresponding to the scFv-Fab fragment, which would be expected in the "Fab" fraction lane in the absence of diabody, was instead present only in the scFv-Fc fraction (FIG. 60). These results indicate that shortening the linker and introduction of a disulfide bond together force and stabilize diabody conformation for the Format 4-G2(1H11) hOKT3a molecule.

Example 27: Effect of Diabody on Affinity as Measured by BLI

Materials and Methods

The affinity of 2×scFv-conformed ABPs and diabody-conformed ABPs (i.e. G5(1C12) hOKT3a and G2(1H11) hOKT3a Format 4 antibodies with and without shortened linkers L1 and L2) was evaluated using the ForteBio Octet HTX in 96-channel mode with biolayer interferometry (BLI) detection. The experiment utilized G2(1H11)-hOKT3a and G5(1C12)-hOKT3a Format 4 antibodies with shortened linkers (L1=L2-(GGGGS)₂ (SEQ ID NO: 111), "DAB") and with non-shortened linkers (L1=L2=(GGGGS)₄ (SEQ ID NO: 228), "2×scFv"). High Precision Streptavidin SAX biosensors (P/N 18-5117) were loaded into the instrument. Biotinylated G2-pHLA or G5-pHLA was captured on the SAX biosensor at 2 μg/mL and ran for 120 s in the assay buffer composed of 0.02% Tween-20 and 0.1% BSA. The biosensors were then dipped in assay buffer for a baseline. Subsequently, the biosensors were dipped into wells containing varying concentrations of the bispecific antibody samples (3.125, 6.25, 12.5, 25, 50, 100 and 200 nM) to measure the association rate for 50 seconds. The biosensors were finally dipped into wells containing assay buffer to measure the dissociation rate for another 50 seconds. Referencing was completed by having a biosensor with no immobilized ligand dipped into analyte. Kinetic data was processed with Octet™ software using a 1:1 kinetic model with errors within 10%, X² below 3, and R² above 0.9.

Results

Results are shown in FIG. 61. The results revealed a significantly lower K_D value for the Format 4-G2(1H11) hOKT3a antibody with shortened linker than with the non-shortened linker.

Example 28: Effect of Diabody Formation on Cell Binding

For G2 cell binding, the experiment utilized Format 4-G2(1H11) hOKT3a antibody having L1=L2=(GGGGS)₄ (SEQ ID NO: 228) with/or without the DSB44/100. It also utilized a Format 4-G2(1H11) hOKT3a antibody with the shortened linker (10AAL=L1=L2=(GGGGS)₂ (SEQ ID NO: 111)). For the G5 cell binding, the experiment utilized Format 4-G5(1C12) hOKT3a antibody having L1=L2= (GGGGS)₄ (SEQ ID NO: 228) with/or without the DSB44/100. It also utilized a Format 4-G5(1C12) hOKT3a antibody with the shortened linker (10AAL=L1=L2=(GGGGS)₂ (SEQ ID NO: 111)). The cell lines used to express the desired HLA-PEPTIDE targets were as follows: A375 cells (which express HLA subtype*01:01) engineered to express the G2 restricted peptide NTDNNLAVY (SEQ ID NO: 214), LN229 (which express HLA subtype B*35:01) engineered to express the G5 restricted peptide EVDPIGHVY (SEQ ID NO: 233). All cell lines were also engineered to express luciferase, using a lentivirus transduction of a cassette containing a 10× repeat of the peptide, Luciferase, and puromycin-resistance. Cassette-expressing cells were selected using 0.5 μg/mL of puromycin. Jurkat E6-1 (ATCC TIB-152) and Jurkat T3.5 (ATCC TIB-153) cells were grown under standard tissue culture conditions. Cells were harvested, washed in PBS, and stained with eBioscience Fixable Viability Dye eFluor 450 for 15 minutes at room temperature. Following another wash in PBS+2% FBS, cells were resuspended with bispecifics at varying concentrations. Cells were incubated with bispecifics for 1 hour at 4° C. After another wash, PE-conjugated goat anti-human IgG secondary antibody (Jackson ImmunoResearch) was added at 1:100. After incubating at 4° C. for 45 minutes and washing in PBS+2% FBS, cells were resuspended in PBS+ 2% FBS and analyzed by flow cytometry. Flow cytometric analysis was performed on the Attune NxT Flow Cytometer (ThermoFisher) using the Attune NxT Software. Data was analyzed using FlowJo.

Results

Results are shown in FIG. 62. All the G2 and G5 molecule bound their pHLA targets. For both G2 and G5 groups, the cell binding to molecule with the shortened linker (diabody conformed) exhibited higher levels of cell binding than the non-shortened linker+DSB44/100 groups (FIG. 62).

Example 29: Effect of Diabody Formation on Cytotoxicity

For G2 cell binding, the experiment utilized Format 4-G2(1H11) hOKT3a antibody having L1=L2=(GGGGS)$_4$ (SEQ ID NO: 228) with/or without the DSB44/100. It also utilized a Format 4-G2(1H11) hOKT3a antibody with the shortened linker (10AAL=L1=L2=(GGGGS)$_2$ (SEQ ID NO: 111)). For the G5 cell binding, the experiment utilized Format 4-G5(1C12) hOKT3a antibody having L1=L2= (GGGGS)$_4$ (SEQ ID NO: 228) with/or without the DSB44/ 100. It also utilized a Format 4-G5(1C12) hOKT3a antibody with the shortened linker (10AAL=L1=L2=(GGGGS)$_2$ (SEQ ID NO: 111)). The cell lines used to express the desired HLA-PEPTIDE targets were as follows: A375 cells (which express HLA subtype*01:01) engineered to express the G2 restricted peptide NTDNNLAVY (SEQ ID NO: 214), LN229 (which express HLA subtype B*35:01) engineered to express the G5 restricted peptide EVDPIGHVY (SEQ ID NO: 233). All cell lines were also engineered to express luciferase, using a lentivirus transduction of a cassette containing a 10× repeat of the peptide, Luciferase, and puromycin-resistance. Cassette-expressing cells were selected using 0.5 μg/mL of puromycin. For the assay, cells were pelleted, washed in PBS, and re-suspended at 2E6/mL in RPMI with 10% FBS. 25 μL of target cells were plated in opaque white 96-well plates. Serial dilutions of the bispecific molecules were added as described above. T cells were added to the plates to give a 10:1 T cell:target ratio as described above. Following 24-hour incubation, Bio-Glo luciferase substrate (Promega cat #G7941) was added and plate incubated and read according to manufacturer's instructions. To calculate % killing, RPMI background RLU was first subtracted from all values. % killing was determined as % cytotoxicity w/Ab-% cytotoxicity w/o Ab, where % cytotoxicity was calculated as 100%-% viability. % viability was calculated as % of RLU in experimental wells normalized against target cells alone.

Results

The results are shown in FIG. 63. All the G2 and G5 molecule exhibited varying degrees of cytotoxic potency. In the case of the G2 molecules, the G2(1H11)hOKT3a (non-shortened linkers; 2×scFv) and the G2(1H11)_10 AAL (shortened linkers; diabody) groups showed significantly more cytotoxic potential than the DSB group. In the case of the G5 molecules, the cytotoxic potential of the G5(1C12) hOKT3a (non-shortened linkers; 2×scFv) and the G5(1C12) _10 AAL (shortened linkers; diabody) groups showed significantly higher cytotoxic potential.

Example 30: Digestion of Format 4 Antibodies with Engineered External DSBs

In order to stabilize molecules in the diabody format, without Fv modification, linkers were engineered that contain Cys residues to introduce disulfide bonds (DSBs) downstream of the diabody domains. First, the diabody conformation of the molecule was forced by shortening the VH-VL linker of the Fv on both chains to 10 amino acids (10AAL). It is known in the art that the C termini of the two chains that dimerize to form a diabody can exist in close or distal conformations relative to each other. See Olafsen, Tove, et al. *Protein Engineering Design and Selection* 17.1 (2004): 21-27, which is incorporated by reference in its entirety. By introducing a DSB immediately downstream of the second domain of each half-diabody construct, the proximal conformation is forced, and the overall assembly is stabilized. Constructs were generated that introduced Cys residues 3 amino acids (GGC) or 4 amino acids (GGGC (SEQ ID NO: 210)) downstream of the end of the diabody sequences. In the case of format 4-like molecules, after forming a DSB, the linkers both continue, either in the knob-Fc chain, or into hole-Fab-Fc chain as depicted in FIG. 64 (top right). Additionally, we designed constructs that disconnect one of the ABRs from the hole-Fab-Fc side and provide it as a separate chain in trans (FIG. 64; bottom). Similarly, we introduced Cys residues 3 amino acids (GGC) or 4 amino acids (GGGC (SEQ ID NO: 210)) downstream of the end of the diabody sequences, but in this case, the new 4th chain terminated after the Cys rather than continuing into the hole-Fab-Fc. Schematic diagrams of the assembled constructs are presented in FIG. 64, linkers are presented in Tables 17 and 18. In order to demonstrate that these sequences form diabody, they are subjected to FabALACTICA digestion and analyzed by SEC-HPLC and CE-SDS.

TABLE 17

Cysteine mutations in the linkers of ABP
constructs that result in external DSBs.
Cysteines that form the DSBs are underlined.

| Construct | L1 & L2 | L3 | L4 |
|---|---|---|---|
| D-1H11xhOKT3 | GGGGSGGGGS (SEQ ID NO: 111) | GGGGSEPKSSDKTHT (SEQ ID NO: 112) | GGGGSGGGGS (SEQ ID NO: 111) |
| D-1H11-LL-GGCxhOKT3 | GGGGSGGGGS (SEQ ID NO: 111) | GGCGGGGSGSEPKSSDKTHT (SEQ ID NO: 113) | GGCGGGGSGSGGGGS (SEQ ID NO: 114) |

TABLE 17-continued

Cysteine mutations in the linkers of ABP
constructs that result in external DSBs.
Cysteines that form the DSBs are underlined.

| Construct | L1 & L2 | L3 | L4 |
|---|---|---|---|
| D-1H11-LS-GGCxhOKT3 | GGGGSGGGGS (SEQ ID NO: 111) | GGCGSEPKSSDKTHT (SEQ ID NO: 115) | GGCGGGGSGSGGGGS (SEQ ID NO: 114) |
| D-1H11-SL-GGCxhOKT3 | GGGGSGGGGS (SEQ ID NO: 111) | GGCGGGGSGSEPKSSDKTHT (SEQ ID NO: 113) | GGCGS (SEQ ID NO: 116) |
| D-1H11-LL-GGGCxhOKT3 | GGGGSGGGGS (SEQ ID NO: 111) | GGGCGGGGSGSEPKSSDKTHT (SEQ ID NO: 117) | GGGCGGGGSGSGGGGS (SEQ ID NO: 118) |
| D-1H11-LS-GGGCxhOKT3 | GGGGSGGGGS (SEQ ID NO: 111) | GGGCGSEPKSSDKTHT (SEQ ID NO: 234) | GGGCGGGGSGSGGGGS (SEQ ID NO: 118) |
| D-1H11-SL-GGGCxhOKT3 | GGGGSGGGGS (SEQ ID NO: 111) | GGGCGGGGSGSEPKSSDKTHT (SEQ ID NO: 117) | GGGCGS (SEQ ID NO: 119) |

TABLE 18

Cysteine mutations in the linkers of ABP
constructs that result in external DSBs.
Cysteines that form the DSBs are underlined.

| Construct | L1 & L2 | L3 | L4 |
|---|---|---|---|
| D-1H11xhOKT3 | GGGGSGGGGS (SEQ ID NO: 111) | GGGGSEPKSSDKTHT (SEQ ID NO: 112) | GGGGSGGGGS (SEQ ID NO: 111) |
| D-1H11-LL-GGCxhOKT3 | GGGGSGGGGS (SEQ ID NO: 111) | GGCGGGGSGSEPKSSDKTHT (SEQ ID NO: 113) | GGCGGGGSGSGGGGS (SEQ ID NO: 114) |
| D-1H11-LS-GGCxhOKT3 | GGGGSGGGGS (SEQ ID NO: 111) | GGCGSEPKSSDKTHT (SEQ ID NO: 115) | GGCGGGGSGSGGGGS (SEQ ID NO: 114) |
| D-1H11-SL-GGCxhOKT3 | GGGGSGGGGS (SEQ ID NO: 111) | GGCGGGGSGSEPKSSDKTHT (SEQ ID NO: 113) | GGCGS (SEQ ID NO: 116) |
| D-1H11-LL-GGGCxhOKT3 | GGGGSGGGGS (SEQ ID NO: 111) | GGGCGGGGSGSEPKSSDKTHT (SEQ ID NO: 117) | GGGCGGGGSGSGGGGS (SEQ ID NO: 118) |
| D-1H11-LS-GGGCxhOKT3 | GGGGSGGGGS (SEQ ID NO: 111) | GGGCGSEPKSSDKTHT (SEQ ID NO: 234) | GGGCGGGGSGSGGGGS (SEQ ID NO: 118) |
| D-1H11-SL-GGGCxhOKT3 | GGGGSGGGGS (SEQ ID NO: 111) | GGGCGGGGSGSEPKSSDKTHT (SEQ ID NO: 117) | GGGCGS (SEQ ID NO: 119) |

Materials and Methods

Proteolysis by FabALACTICA:

0.3-0.5 mg of Format 4-G2(1H11) hOKT3a with L1=L2=(G4S)×2 (SEQ ID NO: 111) and DSB introduced into linker regions as described above, is buffer exchanged from PBS pH 7.4 into 150 mM sodium phosphate buffer at pH 7.0. The samples are then concentrated to a volume of approximately 100 μL, with corresponding concentrations ranging from 35 mg/mL, loaded onto FabALACTICA microspin columns (Genovis), and incubated for 18 hr with end-over-end mixing. To collect the digested products, the columns are centrifuged at 1000×g for 1 min, followed by three additional rounds of elution using 100 μL PBS pH 7.4. The elution fractions are pooled (referred to as "digested pool"), and subsequently loaded onto a CaptureSelect ProteinA (Genovis) column and incubated for a minimum of 30 min with end-over-end mixing. The flowthrough is collected by centrifugation at 200×g for 1 min, followed by three wash steps with 100 μL PBS pH 7.4. The flowthrough and wash fractions are pooled, and are henceforth referred to as "'Fab' fraction". The ProteinA bound fragments are eluted using 100 μL of 0.1M Glycine, pH 3 by centrifugation at 200×g for 1 min, and immediately neutralized with 10 μL 1M tris pH 8. Four additional elution steps are performed by centrifugation at 1000×g for 1 min, and neutralized immediately as described. The elution fractions are henceforth referred to as "'FC' Fraction"

SEC-HPLC

Analytical SEC-HPLC are performed on an Agilent 1260 series HPLC system equipped with a degasser (G4225A), binary pump (G1312B), autosampler (G1329B), and diode array detector (DAD, G4212B). Approximately 60 to 100 μg of each untreated antibody, and 100 μL of the "Fab" fraction, and "Fc" fraction are loaded onto a TSKgel G3000 SWx1 column (7.8 mm ID×30 cm) with the TSKgel G2000SWx1-G4000SWx1 Guard Column in line from Tosoh Bioscience. The column is operated at 0.5 ml/min for 30 min in PBS, pH 7.4. The DAD is set to collect absorbance at 280 nm.

CE-SDS

Capillary gel electrophoresis is performed using the LabChip GXII Touch HT system (PerkinElmer), and samples are analyzed using the ProteinExpress 200 High Sensitivity assay (PerkinElmer, #CLS960008) under reducing and non-reducing conditions. 2 μg of each untreated antibody, and 5 μL of each of digested pool, digested "Fab" fraction, and digested "Fc" fraction are mixed with 7 μL of reducing or non-reducing denaturing solution, and incubated at 70° C. for $10^{-12}$ min. The reducing denaturing solution is prepared by adding 24.5 μL of 1M DTT to 700 μL of non-reducing denaturing solution provided in the kit. Denatured samples are diluted with 32 μL of MilliQ water, mixed well, and spun down prior to analysis. The Protein Express LabChip (PerkinElmer, #760499), and ladder were prepared according to manufacturer instructions.

Results

SEC-HPLC analysis of undigested Format 4-G2(1H11) hOKT3a with shortened L1 and L2 linkers (L1=L2= (G4S)×2 (SEQ ID NO: 111)), along with the incorporation of the DSB introduced into the linkers downstream of the diabody sequences are expected to show a single peak with retention time around 17.7-18 minutes. This retention time aligns with what is hypothesized to be the peak corresponding to the diabody conformation in the split-peak profile observed prior to shortening the linker. Due to stabilization, no protein will be recovered in the "Fab" fraction for the Format 4-like constructs, as shown in SEC-HPLC chromatograms, and reducing and non-reducing gels. By contrast, in the 4 chain constructs, the Fab will be liberated by digestion and the diabody will remain with the proteinA bindable fraction. Absence of bands corresponding to subassemblies or partially digested products following digestion under non-reducing conditions (other than free Fab in the case of the 4-chain constructs) will indicate that the disulfide bond formation was complete, and is effective at stabilizing the diabody conformation and preventing breathing. Additionally, the "Fc" fraction that results from digestion of this molecule will result in a single peak on the SEC-HPLC chromatogram which aligns with the retention time of the undigested molecule, corresponding to a clipped diabody for the format 4-like molecules and will be slightly right-shifted for the 4-chain constructs, due to removal of the Fab domain.

Example 31: Effect of Engineered External DSBs on the Activity of Format 4 Antibodies The ABPs described in Example 30 are further analyzed to determine functional activity.

First, their affinity to G2 pHLA is measured using a ForteBio Octet HTX in 96-channel mode with biolayer interferometry (BLI) detection. High Precision Streptavidin SAX biosensors (P/N 18-5117) are loaded into the instrument. Biotinylated G2-pHLA is captured on the SAX biosensor at 2 μg/mL and ran for 120 s in the assay buffer composed of 0.02% Tween-20 and 0.1% BSA. The biosensors are then dipped in assay buffer for a baseline. Subsequently, the biosensors are dipped into wells containing varying concentrations of the bispecific antibody samples (3.125, 6.25, 12.5, 25, 50, 100 and 200 nM) to measure the association rate for 50 seconds. The biosensors are finally dipped into wells containing assay buffer to measure the dissociation rate for another 50 seconds. Referencing is completed by having a biosensor with no immobilized ligand dipped into analyte. Kinetic data is processed with Octet™ software using a 1:1 kinetic model with errors within 10%, X2 below 3, and R2 above 0.9.

Second, their binding to cells expressing the G2 pHLA target or the CD3 target is measured by flow cytometry. A375 cells, which express HLA-A*01:01, are engineered to express the restricted peptide NTDNNLAVY (SEQ ID NO: 214) using a lentivirus transduction of a cassette containing a 10× repeat of the peptide, Luciferase, and puromycin-resistance. Cassette-expressing cells are selected using 0.5 μg/mL of puromycin. Jurkat E6-1 (ATCC TIB-152) and Jurkat T3.5 (ATCC TIB-153) cells are grown under standard tissue culture conditions. Cells are harvested, washed in PBS, and stained with eBioscience Fixable Viability Dye eFluor 450 for 15 minutes at room temperature. Following another wash in PBS+2% FBS, cells are resuspended with bispecifics at varying concentrations. Cells are incubated with bispecifics for 1 hour at 4° C. After another wash, PE-conjugated goat anti-human IgG secondary antibody (Jackson ImmunoResearch) is added at 1:100. After incubating at 4° C. for 45 minutes and washing in PBS+2% FBS, cells are resuspended in PBS+2% FBS and analyzed by flow cytometry. Flow cytometric analysis is performed on the Attune NxT Flow Cytometer (ThermoFisher) using the Attune NxT Software. Data is analyzed using FlowJo.

Finally, cytotoxicity is measured. The cell lines used to express the desired HLA-PEPTIDE targets are as follows: A375 cells (which express HLA subtype A*01:01) engineered to express the G2 restricted peptide NTDNNLAVY (SEQ ID NO: 214), LN229 (which express HLA subtype B*35:01) engineered to express the G5 restricted peptide EVDPIGHVY (SEQ ID NO: 233). All cell lines are also engineered to express luciferase, using a lentivirus transduction of a cassette containing a 10× repeat of the peptide, Luciferase, and puromycin-resistance. Cassette-expressing cells are selected using 0.5 μg/mL of puromycin. For the assay, cells are pelleted, washed in PBS, and re-suspended at $2×10^6$ cells/mL in RPMI with 10% FBS. 25 μL of target cells are plated in opaque white 96-well plates. Serial dilutions of the bispecific molecules are added as described above. T cells are added to the plates to give a 10:1 T cell:target ratio as described above. Following 24-hour incubation, Bio-Glo luciferase substrate (Promega cat #G7941) is added and plate incubated and read according to manufacturer's instructions. To calculate % killing, RPMI background RLU is first subtracted from all values. % killing is determined as % cytotoxicity w/Ab-% cytotoxicity w/o Ab, where % cytotoxicity is calculated as 100%-% viability. % viability is calculated as % of RLU in experimental wells normalized against target cells alone.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes. Sequences

TABLE 19

VH and VL sequences for G2 scFv Selective Binders, selective for HLA-PEPTIDE Target HLA-A*01:01 NTDNNLAVY (SEQ ID NO: 214)

| Target group | Clone name | VH | VL |
|---|---|---|---|
| G2 | C11 (2F10) | QVQLVQSGAEVKKPGASVKVSCK ASGYTFTTYNIHWVRQAPGQGLE WMGWINPNSGGTNYAQKFQGRVT MTRDTSTSTVYMELSSLRSEDTA VYYCARANWLDYWGQGTLVTVS S (SEQ ID NO: 1) | DIQMTQSPSSLSASVGDRVTITCRAS QEIRRWLAWYQQKPGKAPKLLIYAA SNLETGVPSRFSGSGSGTDFTLTIS SLQPEDFATYYCQQSYSIPYTFGQG TKLEIK (SEQ ID NO: 2) |
| G2 | D5 (2H03) | QVQLVQSGAEVKKPGASVKVSCK ASGYTFTNYPIHWVRQAPGQGLE WMGWINPNSGGTNYAQKLQGRVT MTRDTSTSTVYMELSSLRSEDTA VYYCARDQGAGWDYWGQGTLVT VSS (SEQ ID NO: 3) | DIQMTQSPSSLSASVGDRVTITCRAS QEIRRWLAWYQQKPGKAPKLLIYAA SNLQSGVPSRFSGSGSGTDFTLTIS SLQPEDFATYYCQQSYSTPYTFGQG TKLEIK (SEQ ID NO: 4) |
| G2 | 52C11 | QVQLVQSGAEVKKPGASVKVSCK ASGATFTGYTIHWVRQAPGQGLE WMGWINPNSGGTNYAQSFQGRVT MTRDTSTSTVYMELSSLRSEDTA VYYCARAEWLDKWGQGTLVTVSS (SEQ ID NO: 5) | DIQMTQSPSSLSASVGDRVTITCRAS QEIRRWLAWYQQKPGKAPKLLIYAA SNLETGVPSRFSGSGSGTDFTLTIS SLQPEDFATYYCQQSYSIPYTFGQG TKLEIK (SEQ ID NO: 2) |
| G2 | E07 (31E07) | QVQLVQSGAEVKKPGASVKVSCK ASGFTFTNYLIHWVRQAPGQGLE WMGWINPNSGGTNYAQRLQGRVT MTRDTSTSTVYMELSSLRSEDTA VYYCARDYGAGNDYWGQGTLVT VSS (SEQ ID NO: 6) | DIQMTQSPSSLSASVGDRVTITCRAS QEIRRWLAWYQQKPGKAPKLLIYAA SNLQSGVPSRFSGSGSGTDFTLTIS SLQPEDFATYYCQQSYSTPYTFGQG TKLEIK (SEQ ID NO: 4) |
| G2 | G2(1H11) | QVQLVQSGAEVKKPGASVKVSCK ASGYTFTNYYMHWVRQAPGQGLE WMGMINPSGGGTSYAQKFQGRVT MTRDTSTSTVYMELSSLRSEDTA VYYCARGNPWELRLDYWGQGTLV TVSS (SEQ ID NO: 60) | DIQMTQSPSSLSASVGDRVTITCQAS QDISNYLNWYQQKPGKAPKLLIYAA SSLQSGVPSRFSGSGSGTDFTLTIS SLQPEDFATYYCQQYYSYPFTFGPG TKVDIK (SEQ ID NO: 61) |

TABLE 20

CDR sequences for G2 scFv Selective Binders, selective for HLA-PEPTIDE Target HLA-A*01:01_NTDNNLAVY (SEQ ID NO: 214) (according to Kabat numbering scheme)

| Clone name | HCDR1 | HCDR2 | HCDR3 | LCDR1 | LCDR2 | LCDR3 |
|---|---|---|---|---|---|---|
| C11 (2F10) | TYNIH (SEQ ID NO: 7) | WINPNSGG TNYAQKF QG (SEQ ID NO: 8) | ANWLDY (SEQ ID NO: 9) | RASQEIRR WLA (SEQ ID NO: 21) | AASNLET (SEQ ID NO: 10) | QQSYSIPY T (SEQ ID NO: 11) |
| D5 (2H03) | NYPIH (SEQ ID NO: 12) | WINPNSGG TNYAQKL QG (SEQ ID NO: 13) | DQGAGWD Y (SEQ ID NO: 14) | RASQEIRR WLA (SEQ ID NO: 21) | AASNLQS (SEQ ID NO: 22) | QQSYSTPY T (SEQ ID NO: 23) |
| 52C11 | GYTIH (SEQ ID NO: 15) | WINPNSGG TNYAQSFQ G (SEQ ID NO: 16) | AEWLDK (SEQ ID NO: 17) | RASQEIRR WLA (SEQ ID NO: 21) | AASNLET (SEQ ID NO: 10) | QQSYSIPY T (SEQ ID NO: 11) |
| E07 (31E07) | NYLIH (SEQ ID NO: 18) | WINPNSGG TNYAQRL QG (SEQ ID NO: 19) | DYGAGND Y (SEQ ID NO: 20) | RASQEIRR WLA (SEQ ID NO: 21) | AASNLQS (SEQ ID NO: 22) | QQSYSTPY T (SEQ ID NO: 23) |

TABLE 20-continued

| CDR sequences for G2 scFv Selective Binders, selective for HLA-PEPTIDE Target HLA-A*01:01_NTDNNLAVY (SEQ ID NO: 214) (according to Kabat numbering scheme) | | | | | | |
|---|---|---|---|---|---|
| Clone name | HCDR1 | HCDR2 | HCDR3 | LCDR1 | LCDR2 | LCDR3 |
| G2(1H11) | YTFTNYY MH (SEQ ID NO: 67) | GMINPSGG GTSYA (SEQ ID NO: 68) | CARGNPW ELRLDYW (SEQ ID NO: 69) | QASQDISN YLN (SEQ ID NO: 70) | AASSLQS (SEQ ID NO: 71) | CQQYYSY PPTF (SEQ ID NO: 72) |

TABLE 21

| VH and VL sequences for Anti-CD3 Binder | | |
|---|---|---|
| Clone name | VH | VL |
| Anti-CD3 (hOKT3a) | QVQLVQSGAEVKKPGASVKVSCKASG YTFTRYTMHWVRQAPGQGLEWMGYIN PSRGYTNYNQKFKDRVTLTTDKSSST AYMELSSLRSEDTAVYYCARYYDDHY SLDYWGQGTLVTVSS (SEQ ID NO: 24) | DIQMTQSPSSLSASVGDRVTITCSASSS VSYMNWYQQKPGKAPKRLIYDTSKLASG VPSRFSGSGSGTDFTLTISSLQPEDFAT YYCQQWSSNPFTFGQGTKLEIK (SEQ ID NO: 25) |
| Anti-CD3 (UCHT1v9) | EVQLVESGGGLVQPGGSLRLSCAASG YSFTGYTMNWVRQAPGKGLEWVALIN PYKGVSTYNQKFKDRFTISVDKSKNT AYLQMNSLRAEDTAVYYCARSGYYGD SDWYFDVWGQGTLVTVSS (SEQ ID NO: 32) | DIQMTQSPSSLSASVGDRVTITCRASQD IRNYLNWYQQKPGKAPKLLIYYTSRLES GVPSRFSGSGSGTDYTLTISSLQPEDFA TTYCQQGNTLPWTFGQGTKVEIK (SEQ ID NO: 33) |
| Anti-CD3 (hSP34) | EVQLVESGGGLVQPGGSLRLSCAASGF TFSTYAMNWVRQAPGKGLEWVGRIRSK YNNYATYYADSVKGRFTISRDDSKNTL YLQMNSLRAEDTAVYYCVRHGNFGDSY VSWFAYWGQGTLVTVSS (SEQ ID NO: 34) | QAVVTQEPSLTVSPGGTVTLTCGSSTGA VTTSNYANWVQQKPGKSPRGLIGGTNKR APGVPARFSGSLLGGKAALTISGAQPED EADYYCALWYSNHWVFGGGTKLTVL (SEQ ID NO: 35) |

TABLE 22

| CDR sequences for Anti-CD3 Binder (according to Kabat numbering scheme) | | | | | | |
|---|---|---|---|---|---|---|
| Clone name | HCDR1 | HCDR2 | HCDR3 | LCDR1 | LCDR2 | LCDR3 |
| Anti-CD3 (hOKT3a) | RYTMH (SEQ ID NO: 26) | YINPSRGYTN YNQKFKD (SEQ ID NO: 27) | YYDDHYS LDY (SEQ ID NO: 28) | SASSSVSY MN (SEQ ID NO: 29) | DTSKLAS (SEQ ID NO: 30) | QQWSSNPF T (SEQ ID NO: 31) |
| Anti-CD3 (UCHT1v9) | GYTMN (SEQ ID NO: 36) | LINPYKGVSTY NQKFKD (SEQ ID NO: 37) | SGYYGDS DWYFDV (SEQ ID NO: 38) | RASQDIRN YLN (SEQ ID NO: 39) | YTSRLES (SEQ ID NO: 40) | QQGNTLP WT (SEQ ID NO: 41) |
| Anti-CD3 (hSP34x) | TYAMN (SEQ ID NO: 42) | RIRSKYNNYA TYYADSVKG (SEQ ID NO: 43) | GSSTGAVT TSNYAN (SEQ ID NO: 44) | GSSTGAVT TSNYAN (SEQ ID NO: 45) | GTNKRAP (SEQ ID NO: 46) | ALWYSNH WV (SEQ ID NO: 47) |

TABLE 23

| Sequence of Format 41 31E07-CD3 bispecific antibodies | | | | |
|---|---|---|---|---|
| Name | L3 Linker-Fc (Chain1) | L4 Linker-VH-CH1-hinge-CH2-CH3 (Chain2) | LC (Chain 3) | ABR (Chain 4; VH-Linker-VL) |
| 41-31E0-hOKT3a | GGGGSEPKSSD KTHTCPPCPAP EFEGGPSVFLFP PKPKDTLMISR | GGGGSGGGGSQVQLVQSG AEVKKPGASVKVSCKASG YTFTRYTMHWVRQAPGQ GLEWMGYINPSRGYTNYN | DIQMTQSPSSLS ASVGDRVTITC SASSSVSYMN WYQQKPGKAP | QVQLVQSGAEV KKPGASVKVSC KASGFTFTNYLI HWVRQAPGQG |

TABLE 23-continued

Sequence of Format 41 31E07-CD3 bispecific antibodies

| Name | L3 Linker-Fc (Chain1) | L4 Linker-VH-CH1-hinge-CH2-CH3 (Chain2) | LC (Chain 3) | ABR (Chain 4; VH-Linker-VL) |
|---|---|---|---|---|
| | TPEVTCVVVDV SHEDPEVKFNW YVDGVEVHNA KTKPREEQYNS TYRVVSVLTVL HQDWLNGKEY KCKVSNKALPA SIEKTISKAKGQ PREPQVYTLPP CREEMTKNQV SLWCLVKGFYP SDIAVEWESNG QPENNYKTTPP VLDSDGSFFLY SKLTVDKSRW QQGNVFSCSV MHEALHNHYT QKSLSLSPGK (SEQ ID NO: 48) | QKFKDRVTLTTDKSSSTAY MELSSLRSEDTAVYYCARY YDDHYSLDYWGQGTLVTV SSASTKGPSVFPLAPSSKSTSG GTAALGCLVKDYFPEPVTVSW NSGALTSGVHTFPAVLQSSGLY SLSSVVTVPSSSLGTQTYICNVN HKPSNTKVDKRVepkscdktht cpPCPAPEFEGGPSVFLFPPKP KDTLMISRTPEVTCVVVDVS HEDPEVKFNWYVDGVEVHN AKTKPREEQYNSTYRVVSVL TVLHQDWLNGKEYKCKVSN KALPASIEKTISKAKGQPREP QVCTLPPSREEMTKNQVSLSC AVKGFYPSDIAVEWESNGQPE NNYKTTPPVLDSDGSFFLVSK LTVDKSRWQQGNVFSCSVMH EALHNRFTQKSLSLSPGK (SEQ ID NO: 49) | KRLIYDTSKLA SGVPSRFSGSGS GTDFTLTISSLQ PEDFATYYCQQ WSSNPFTFGQG TKLEIKRTVAA PSVFIFPPSDEQ LKSGTASVVCL LNNFYPREAKV QWKVDNALQS GNSQESVTEQD SKDSTYSLSSTL TLSKADYEKHK VYACEVTHQG LSSPVTKSFNR GEC (SEQ ID NO: 50) | LEWMGWINPN SGGTNYAQRLQ GRVTMTRDTST STVYMELSSLR SEDTAVYYCAR DYGAGNDYWG QGTLVTVSSGG GGSGGGGSDIQ MTQSPSSLSAS VGDRVTITCRA SQEIRRWLAW YQQKPGKAPK LLIYAASNLQS GVPSRFSGSGS GTDFTLTISSL QPEDFATYYC QQSYSTPYTFG QGTKLEIK (SEQ ID NO: 55) |
| 41-31E07-UCHT1v9 | GGGGSEPKSSD KTHTCPPCPAP EFEGGPSVFLFP PKPKDTLMISR TPEVTCVVVDV SHEDPEVKFNW YVDGVEVHNA KTKPREEQYNS TYRVVSVLTVL HQDWLNGKEY KCKVSNKALPA SIEKTISKAKGQ PREPQVYTLPP CREEMTKNQV SLWCLVKGFYP SDIAVEWESNG QPENNYKTTPP VLDSDGSFFLY SKLTVDKSRW QQGNVFSCSV MHEALHNHYT QKSLSLSPGK (SEQ ID NO: 48) | GGGGSGGGGSEVQLVESGG GLVQPGGSLRLSCAASGYS FTGYTMNWVRQAPGKGL EWVALINPYKGVSTYNQK FKDRFTISVDKSKNTAYLQ MNSLRAEDTAVYYCARSG YYGDSDWYFDVWGQGTL VTVSSASTKGPSVFPLAPSSKS TSGGTAALGCLVKDYFPEPVT VSWNSGALTSGVHTFPAVLQSS GLYSLSSVVTVPSSSLGTQTYI CNVNHKPSNTKVDKRVepkscd kthtcpPCPAPEFEGGPSVFLF PPPKPKDTLMISRTPEVTCVV VDVSHEDPEVKFNWYVDGV EVHNAKTKPREEQYNSTYRV VSVLTVLHQDWLNGKEYKC KVSNKALPASIEKTISKAKGQ PREPQVCTLPPSREEMTKNQV SLSCAVKGFYPSDIAVEWESN GQPENNYKTTPPVLDSDGSFF LVSKLTVDKSRWQQGNVFSCS VMHEALHNRFTQKSLSLSPGK (SEQ ID NO: 51) | DIQMTQSPSSLS ASVGDRVTITC RASQDIRNYLN WYQQKPGKAP KLLIYYTSRLES GVPSRFSGSGS GTDYTLTISSLQ PEDFATYYCQQ GNTLPWTFGQ GTKVEIKRTVA APSVFIFPPSDE QLKSGTASVVC LLNNFYPREAK VQWKVDNALQ SGNSQESVTEQ DSKDSTYSLSS TLTLSKADYEK HKVYACEVTH QGLSSPVTKSE NRGEC (SEQ ID NO: 52) | QVQLVQSGAEV KKPGASVKVSC KASGFTFTNYLI HWVRQAPGQG LEWMGWINPN SGGTNYAQRLQ GRVTMTRDTST STVYMELSSLR SEDTAVYYCAR DYGAGNDYWG QGTLVTVSSGG GGSGGGGSDIQ MTQSPSSLSAS VGDRVTITCRA SQEIRRWLAW YQQKPGKAPK LLIYAASNLQS GVPSRFSGSGS GTDFTLTISSL QPEDFATYYC QQSYSTPYTFG QGTKLEIK (SEQ ID NO: 55) |
| 41-31E07-hSP34x | GGGGSEPKSSD KTHTCPPCPAP EFEGGPSVFLFP PKPKDTLMISR TPEVTCVVVDV SHEDPEVKFNW YVDGVEVHNA KTKPREEQYNS TYRVVSVLTVL HQDWLNGKEY KCKVSNKALPA SIEKTISKAKGQ PREPQVYTLPP CREEMTKNQV SLWCLVKGFYP SDIAVEWESNG QPENNYKTTPP VLDSDGSFFLY SKLTVDKSRW QQGNVFSCSV MHEALHNHYT QKSLSLSPGK (SEQ ID NO: 48) | GGGGSGGGGS EVQLVESGGGLVQPGGSL RLSCAASGFTFSTYAMNW VRQAPGKGLEWVGRIRSK YNNYATYYADSVKGRFTIS RDDSKNTLYLQMNSLRAE DTAVYYCVRHGNFGDSYV SWFAYWGQGTLVTVSSAS TKGPSVFPLAPSSKSTSG GTAALGCLVKDYFPEPVT VSWNSGALTSGVHTFPAV LQSSGLYSLSSVVTVPSS SLGTQTYICNVNHKPSNT KVDKRVEPKSCDKTHTCP PCPAPEFEGGPSVFLFPPKP KDTLMISRTPEVTCVVVDVS HEDPEVKFNWYVDGVEVHN AKTKPREEQYNSTYRVVSVL TVLHQDWLNGKEYKCKVSN KALPASIEKTISKAKGQPREP QVCTLPPSREEMTKNQVSLSC AVKGFYPSDIAVEWESNGQPE NNYKTTPPVLDSDGSFFLVSK LTVDKSRWQQGNVFSCSVMH EALHNRFTQKSLSLSPGK (SEQ ID NO: 53) | QAVVTQEPSLT VSPGGTVTLTC GSSTGAVTTSN YANWVQQKPG KSPRGLIGGTN KRAPGVPARFS GSLLGGKAALT ISGAQPEDEAD YYCALWYSNH WVFGGGTKLT VL RTVAAPSVFIFP PSDEQLKSGTA SVVCLLNNFYP REAKVQWKVD NALQSGNSQES VTEQDSKDSTY SLSSTLTLSKAD YEKHKVYACE VTHQGLSSPVT KSFNRGEC (SEQ ID NO: 54) | QVQLVQSGAEV KKPGASVKVSC KASGFTFTNYLI HWVRQAPGQG LEWMGWINPN SGGTNYAQRLQ GRVTMTRDTST STVYMELSSLR SEDTAVYYCAR DYGAGNDYWG QGTLVTVSSGG GGSGGGGSDIQ MTQSPSSLSAS VGDRVTITCRA SQEIRRWLAW YQQKPGKAPK LLIYAASNLQS GVPSRFSGSGS GTDFTLTISSL QPEDFATYYC QQSYSTPYTFG QGTKLEIK (SEQ ID NO: 55) |

Fragments of the Formats 41, 42, and 43 antibody herein have text formatted differently. In Chain 1, the L3 linker is non-bold and underlined, the Fc is non-bold. In Chain 2, the LA linker is non-bold and underlined, the VH is bold, the CH1 is non-bold, italics and underlined, the hinge is lower case, CH2 is bold and italics, CH3 is non-bold and italics. In Chain 3, the CL is underlined. In the ABR (Chain 4), the VH is non-bold and italics, the linker (L1 or L2) is non-bold and underlined, and the VL is bold.

TABLE 24

| | | Linker-VH- | | Mixed ABR | Mixed ABR |
|---|---|---|---|---|---|
| | Linker-Fc | CH1-hinge- | LC | (chain 4) | (chain 4) |
| Name | (Chain1) | CH2-CH3 (Chain2) | (Chain 3) | VH-VL | VH-VL |

Sequences of Format 42 31E07-CD3 bispecific antibodies

| | | | | | |
|---|---|---|---|---|---|
| 42-31E07 | GGGGSEPKS | GGGGSGGGGS*QVQLV* | DIQMTQSP | QVQLVQSGA | EVQLVESGGGL |
| UCHT1v9 | SDKTHTCPP | QSGAEVKKPGASVK | SSLSASVG | EVKKPGASV | VQPGGSLRLSC |
| | CPAPEFEGG | *VSCKASGFTFTNYLI* | DRVTITCR | KVSCKASGFT | AASGYSFTGYT |
| | PSVFLFPPKP | HWVRQAPGQGLEW | ASQEIRRW | FTNYLIHWV | MNWVRQAPGK |
| | KDTLMISRT | MGWINPNSGGTNYA | LAWYQQK | RQAPGQGLE | GLEWVALINPY |
| | PEVTCVVVD | QRLQGRVTMTRDTS | PGKAPKLLI | WMGWINPNS | KGVSTYNQKFK |
| | VSHEDPEVK | TSTVYMELSSLRSED | YAASNLQS | GGTNYAQRL | DRFTISVDKSKN |
| | FNWYVDGV | TAVYYCARDYGAGN | GVPSRFSGS | QGRVTMTRD | TAYLQMNSLRA |
| | EVHNAKTKP | DYWGQGTLVTVSS*AST* | GSGTDFTL | TSTSTVYMEL | EDTAVYYCARS |
| | REEQYNSTY | *KGPSVFPLAPSSKSTSG* | TISSLQPED | SSLRSEDTAV | GYYGDSDWYF |
| | RVVSVLTVL | *GTAALGCLVKDYFPEPV* | FATYYCQQ | YYCARDYGA | DVWGQGTLVT |
| | HQDWLNGK | *TVSWNSGALTSGVHTFP* | SYSTPYTFG | GNDYWGQG | VSSGGGGSGGG |
| | EYKCKVSN | *AVLQSSGLYSLSSVVTVP* | QGTKLEIK | TLVTVSSGGG | GSDIQMTQSPS |
| | KALPASIEK | *SSSLGTQTYICNVNHKPS* | RTVAAPSV | GSGGGGSDI | SLSASVGDRVT |
| | TISKAKGQP | *NTKVDKRV*epkscdktht | QMTQSPSSL | QMTQSPSSL | ITCRASQEIRR |
| | REPQVYTLP | cp*PCPAPEFEGGPSVFLF* | SASVGDRVTI | SASVGDRVTI | WLAWYQQKP |
| | PCREEMTKN | *PPKPKDTLMISRTPEV* | VCLLNNFY | TCRASQDIR | GKAPKLLIYAA |
| | QVSLWCLV | *TCVVVDVSHEDPEVK* | PREAKVQ | NYLNWYQQ | SNLQSGVPSRF |
| | KGFYPSDIA | *FNWYVDGVEVHNAKT* | WKVDNAL | KPGKAPKLL | SGSGSGTDFTL |
| | VEWESNGQ | *KPREEQYNSTYRVVSV* | QSGNSQES | IYYTSRLESG | TISSLQPEDFAT |
| | PENNYKTTP | *LTVLHQDWLNGKEYK* | VTEQDSKD | VPSRFSGSGS | YYCQQSYSTPY |
| | PVLDSDGSF | *CKVSNKALPASIEKTIS* | STYSLSSTL | GTDYTLTISS | TFGQGTKLEIK |
| | FLYSKLTVD | *KAKGQPREPQVCTLPP* | TLSKADYE | LQPEDFATY | (SEQ ID NO: 58) |
| | KSRWQQGN | *SREEMTKNQVSLSCAVK* | KHKVYACE | YCQQGNTLP | |
| | VFSCSVMHE | *GFYPSDIAVEWESNGQP* | VTHQGLSS | WTFGQGTK | |
| | ALHNHYTQ | *ENNYKTTPPVLDSDGSF* | PVTKSFNR | VEIK | |
| | KSLSLSPGK | *FLVSKLTVDKSRWQQG* | GEC | (SEQ ID | |
| | (SEQ ID | *NVFSCSVMHEALHNRF* | (SEQ ID | NO: 59) | |
| | NO: 48) | *TQKSLSLSPGK* | NO: 57) | | |
| | | (SEQ ID NO: 56) | | | |

TABLE 25

| | | Linker-VH- | | Mixed ABR | Mixed ABR |
|---|---|---|---|---|---|
| | Linker-Fc | CH1-hinge- | LC | (chain 4) | (chain 4) |
| Name | (Chain1) | CH2-CH3 (Chain2) | (Chain 3) | VH-VL | VH-VL |

Sequences of Format 43 31E07-CD3 bispecific antibodies

| | | | | | |
|---|---|---|---|---|---|
| 43-31E07- | GGGGSEPKS | GGGGSGGGGS*QVQL* | DIQMTQSPS | EVQLVESGGG | QVQLVQSGAE |
| GGGGS- | SDKTHTCPP | VQSGAEVKKPGASV | SLSASVGDR | LVQPGGSLRL | VKKPGASVKV |
| UCHT1v9 | CPAPEFEGG | KVSCKASGFTFTNY | VTITCRASQ | SCAASGYSFT | SCKASGFTFTN |
| | PSVFLFPPKP | LIHWVRQAPGQGLE | EIRRWLAW | GYTMNWVRQ | YLIHWVRQAP |
| | KDTLMISRT | WMGWINPNSGGTN | YQQKPGKA | APGKGLEWVA | GQGLEWMGWI |
| | PEVTCVVVD | YAQRLQGRVTMTR | PKLLIYAAS | LINPYKGVST | NPNSGGTNYA |
| | VSHEDPEVK | DTSTSTVYMELSSLR | NLQSGVPSR | YNQKFKDRPT | QRLQGRVTMT |
| | FNWYVDGV | SEDTAVYYCARDYG | FSGSGSGTD | ISVDKSKNTA | RDTSTSTVYM |
| | EVHNAKTKP | AGNDYWGQGTLVT | FTLTISSLQP | YLQMNSLRAE | ELSSLRSEDTA |
| | REEQYNSTY | VSS*ASTKGPSVFPLAPS* | EDFATYYCQ | DTAVYYCARS | VYYCARDYGA |
| | RVVSVLTVL | *SKSTSGGTAALGCLVK* | QSYSTPYTF | GYYGDSDWY | GNDYWGQGTL |
| | HQDWLNGK | *DYFPEPVTVSWNSGAL* | GQGTKLEIK | FDVWGQGTL | VTVSSGGGGS |
| | EYKCKVSN | *TSGVHTFPAVLQSSGL* | RTVAAPSVE | VTVSSGGGGS | GGGGSDIQMT |
| | KALPASIEK | *YSLSSVVTVPSSSLGTQ* | IFPPSDEQLK | GGGGSDIQMT | QSPSSLSASVG |
| | TISKAKGQP | *TYICNVNHKPSNTKVD* | SGTASVVCL | QSPSSLSASV | DRVTITCRAS |
| | REPQVYTLP | *KRV*epkscdkthtcp | LNNFYPREA | GDRVTITCRA | QDIRNYLNWY |
| | PCREEMTKN | *PCPAPEFEGGPSVFLF* | KVQWKVDN | SQEIRRWLA | QQKPGKAPK |
| | QVSLWCLV | *PPKPKDTLMISRTPE* | ALQSGNSQE | WYQQKPGKA | LLIYYTSRLES |
| | KGFYPSDIA | *VTCVVVDVSHEDPEV* | SVTEQDSKD | PKLLIYAASN | GVPSRFSGSGS |
| | VEWESNGQ | *KFNWYVDGVEVHNAK* | STYSLSSTLT | LQSGVPSRFS | GTDYTLTISSL |
| | PENNYKTTP | *TKPREEQYNSTYRVV* | LSKADYEKH | GSGSGTDFTL | QPEDFATYYC |
| | PVLDSDGSF | *SVLTVLHQDWLNGKEY* | KVYACEVT | TISSLQPEDFA | QQGNTLPWT |
| | FLYSKLTVD | *KCKVSNKALPASIEKT* | HQGLSSPVT | TYYCQQSYST | FGQGTKVEIK |
| | KSRWQQGN | *ISKAKGQPREPQVCTL* | KSFNRGEC | PYTFGQGTK | (SEQ ID |

TABLE 25-continued

Sequences of Format 43 31E07-CD3 bispecific antibodies

| Name | Linker-Fc (Chain1) | Linker-VH-CH1-hinge-CH2-CH3 (Chain2) | LC (Chain 3) | Mixed ABR (chain 4) VH-VL | Mixed ABR (chain 4) VH-VL |
|---|---|---|---|---|---|
| | VFSCSVMHE ALHNHYTQ KSLSLSPGK (SEQ ID NO: 48) | *PPSREEMTKNQVSLSC AVKGFYPSDIAVEWES NGQPENNYKTTPPVLD SDGSFFLVSKLTVDKS RWQQGNVFSCSVMHE ALHNRFTQKSLSLSPG K* (SEQ ID NO: 56) | (SEQ ID NO: 57) | LEIK (SEQ ID NO: 58) | NO: 59) |

TABLE 26

CDR sequences of identified scFvs to G5-pHLA, numbered according to the Kabat numbering scheme
CDR sequences of identified scFvs to G5, numbered according to the Kabat numbering scheme

| Target group | Clone name | HCDR1 | HCDR2 | HCDR3 | LCDR1 | LCDR2 | LCDR3 |
|---|---|---|---|---|---|---|---|
| G5 | G5 (1C12) | GTFSNF GVS (SEQ ID NO: 73) | GGIIPILGT ANYA (SEQ ID NO: 74) | CATPTNSG YYGPYYYY GMDVW (SEQ ID NO: 75) | RASQSISSW LA (SEQ ID NO: 76) | AASTLQ S (SEQ ID NO: 77) | CQQSYSIP LTF (SEQ ID NO: 78) |

TABLE 27

VH and VL sequences of scFv hits that bind target G5-pHLA
VH and VL sequences of scFv hits that bind target G5

| Target group | Clone name | V$_H$ | V$_L$ |
|---|---|---|---|
| G5 | G5(1C12) | QVQLVQSGAEVKK PGSSVKVSCKASG GTFSNFGVSWLRQ APGQGLEWMGGII PILGTANYAQKFQ GRVTITADESTST AYMELSSLRSEDT | DIQMTQSPSSLSA SVGDRVTITCRAS QSISSWLAWYQQK PGKAPKLLIYAAS TLQSGVPSRFSGS GSGTDFTLTISSL QPEDFATYYCQQS |

35

TABLE 27-continued

VH and VL sequences of scFv hits that bind target G5-pHLA
VH and VL sequences of scFv hits that bind target G5

| Target group | Clone name | V$_H$ | V$_L$ |
|---|---|---|---|
| | | AVYYCATPTNSGY YGPYYYYGMDVWG QGTTVTVSS (SEQ ID NO: 79) | YSIPLTFGGGTKV EIK (SEQ ID NO: 80) |

40

45

TABLE 28

Exemplary Bispecific Format 4 Constructs

| Name | Linker-Fc (Chain1) | scFv (Chains 1 and 2) | Linker (Chain2) | VH (Chain 2) | CH1-CH2-CH3 (Chain2) | LC (Chain 3) |
|---|---|---|---|---|---|---|
| 4-G2(1H11)-hOKT3 | GGGGSEPK SSDKTHTC PPCPAPELL GGPSVFLF PPKPKDTL MISRTPEV TCVVVDVS HEDPEVKF NWYVDGV EVHNAKT KPREEQYQ STYRVVSV LTVLHQD | QVQLVQSG AEVKKPGAS VKVSCKASG YTFTNYYM HWVRQAPG QGLEWMGM INPSGGGTS YAQKFQGR VTMTRDTST STVYMELSS LRSEDTAVY YCARGNPW ELRLDYWG | GGGGSG GGGS (SEQ ID NO: 111) | QVQL VQSG AEVK KPGAS VKVS CKAS GYTFT RYTM HWVR QAPG QGLE WMGY INPSR | ASTKGPSVFPL APSSKSTSGGT AALGCLVKDY FPEPVTVSWNS GALTSGVHTFP AVLQSSGLYSL SSVVTVPSSSL GTQTYICNVNH KPSNTKVDKR VEPKSCDKTHT CPPCPAPELLG GPSVFLFPPKPK DTLMISRTPEV | DIQMTQSP SSLSASVG DRVTITCS ASSSVSYM NWYQQKP GKAPKRLI YDTSKLAS GVPSRFSG SGSGTDFT LTISSLQPE DFATYYC QQWSSNPF TFGQGTKL |

TABLE 28-continued

Exemplary Bispecific Format 4 Constructs

| Name | Linker-Fc (Chain1) | scFv (Chains 1 and 2) | Linker (Chain2) | VH (Chain 2) | CH1-CH2-CH3 (Chain2) | LC (Chain 3) |
|---|---|---|---|---|---|---|
| | WLNGKEY | QGTLVTVSS | | GYTN | TCVVVDVSHE | EIKRTVAA |
| | KCKVSNK | GGGGSGGG | | YNQK | DPEVKFNWYV | PSVFIFPPS |
| | ALPAPIEKT | GSGGGGSG | | FKDR | DGVEVHNAKT | DEQLKSGT |
| | ISKAKGQP | GGGSDIQMT | | VTLTT | KPREEQYQSTY | ASVVCLLN |
| | REPQVYTL | QSPSSLSASV | | DKSSS | RVVSVLTVLHQ | NFYPREAK |
| | PPCREEMT | GDRVTITCQ | | TAYM | DWLNGKEYKC | VQWKVDN |
| | KNQVSLW | ASQDISNYL | | ELSSL | KVSNKALPAPI | ALQSGNSQ |
| | CLVKGFYP | NWYQQKPG | | RSEDT | EKTISKAKGQP | ESVTEQDS |
| | SDIAVEWE | KAPKLLIYA | | AVYY | REPQVCTLPPS | KDSTYSLS |
| | SNGQPENN | ASSLQSGVP | | CARY | REEMTKNQVS | STLTLSKA |
| | YKTTPPVL | SRFSGSGSG | | YDDH | LSCAVKGFYPS | DYEKHKV |
| | DSDGSFFL | TDFTLTISSL | | YSLD | DIAVEWESNGQ | YACEVTH |
| | YSKLTVDK | QPEDFATYY | | YWGQ | PENNYKTTPPV | QGLSSPVT |
| | SRWQQGN | CQQYYSYPF | | GTLVT | LDSDGSFFLVS | KSFNRGEC |
| | VFSCSVMH | TFGPGTKVD | | VSS | KLTVDKSRWQ | (SEQ ID NO: 85) |
| | EALHNHYT | IK (SEQ ID NO: 82) | | (SEQ ID NO: 83) | QGNVFSCSVM | |
| | QKSLSLSP | | | | HEALHNRFTQK | |
| | GK (SEQ ID NO: 81) | | | | SLSLSPGK (SEQ ID NO: 84) | |
| 4-G2 (1H11) hSP34x | GGGGSEPK | QVQLVQSG | GGGGSG | EVQL | ASTKGPSVFPL | QAVVTQE |
| | SSDKTHTC | AEVKKPGAS | GGGS | VESG | APSSKSTSGGT | PSLTVSPG |
| | PPCPAPELL | VKVSCKASG | (SEQ ID NO: 111) | GGLV | AALGCLVKDY | GTVTLTCG |
| | GGPSVFLF | YTFTNYYM | | QPGGS | FPEPVTVSWNS | SSTGAVTT |
| | PPKPKDTL | HWVRQAPG | | LRLSC | GALTSGVHTFP | SNYANWV |
| | MISRTPEV | QGLEWMGM | | AASGF | AVLQSSGLYSL | QQKPGKSP |
| | TCVVVDVS | INPSGGGTS | | TFSTY | SSVVTVPSSSL | RGLIGGTN |
| | HEDPEVKF | YAQKFQGR | | AMNW | GTQTYICNVNH | KRAPGVP |
| | NWYVDGV | VTMTRDTST | | VRQA | KPSNTKVDKR | ARFSGSLL |
| | EVHNAKT | STVYMELSS | | PGKG | VEPKSCDKTHT | GGKAALTI |
| | KPREEQYQ | LRSEDTAVY | | LEWV | CPPCPAPELLG | SGAQPEDE |
| | STYRVVSV | YCARGNPW | | GRIRS | GPSVFLFPPKPK | ADYYCAL |
| | LTVLHQD | ELRLDYWG | | KYNN | DTLMISRTPEV | WYSNHWV |
| | WLNGKEY | QGTLVTVSS | | YATY | TCVVVDVSHE | FGGGTKLT |
| | KCKVSNK | GGGGSGGG | | YADS | DPEVKFNWYV | VLRTVAAP |
| | ALPAPIEKT | GSGGGGSG | | VKGR | DGVEVHNAKT | SVFIFPPSD |
| | ISKAKGQP | GGGSDIQMT | | FTISR | KPREEQYQSTY | EQLKSGTA |
| | REPQVYTL | QSPSSLSASV | | DDSK | RVVSVLTVLHQ | SVVCLLNN |
| | PPCREEMT | GDRVTITCQ | | NTLYL | DWLNGKEYKC | FYPREAKV |
| | KNQVSLW | ASQDISNYL | | QMNS | KVSNKALPAPI | QWKVDNA |
| | CLVKGFYP | NWYQQKPG | | LRAE | EKTISKAKGQP | LQSGNSQE |
| | SDIAVEWE | KAPKLLIYA | | DTAV | REPQVCTLPPS | SVTEQDSK |
| | SNGQPENN | ASSLQSGVP | | YYCV | REEMTKNQVS | DSTYSLSS |
| | YKTTPPVL | SRFSGSGSG | | RHGN | LSCAVKGFYPS | TLTLSKAD |
| | DSDGSFFL | TDFTLTISSL | | FGDSY | DIAVEWESNGQ | YEKHKVY |
| | YSKLTVDK | QPEDFATYY | | VSWF | PENNYKTTPPV | ACEVTHQ |
| | SRWQQGN | CQQYYSYPF | | AYWG | LDSDGSFFLVS | GLSSPVTK |
| | VFSCSVMH | TFGPGTKVD | | QGTL | KLTVDKSRWQ | SFNRGEC |
| | EALHNHYT | IK (SEQ ID NO: 87) | | VTVSS | QGNVFSCSVM | (SEQ ID NO: 90) |
| | QKSLSLSP | | | (SEQ ID NO: 88) | HEALHNRFTQK | |
| | GK (SEQ ID NO: 86) | | | | SLSLSPGK (SEQ ID NO: 89) | |
| 4-G5 (1C12) hOKT3a | GGGGSEPK | QVQLVQSG | GGGGSG | QVQL | ASTKGPSVFPL | DIQMTQSP |
| | SSDKTHTC | AEVKKPGSS | GGGS | VQSG | APSSKSTSGGT | SSLSASVG |
| | PPCPAPELL | VKVSCKASG | (SEQ ID NO: 111) | AEVK | AALGCLVKDY | DRVTITCS |
| | GGPSVFLF | GTFSNFGVS | | KPGAS | FPEPVTVSWNS | ASSSVSYM |
| | PPKPKDTL | WLRQAPGQ | | VKVS | GALTSGVHTFP | NWYQQKP |
| | MISRTPEV | GLEWMGGII | | CKAS | AVLQSSGLYSL | GKAPKRLI |
| | TCVVVDVS | PILGTANYA | | GYTFT | SSVVTVPSSSL | YDTSKLAS |
| | HEDPEVKF | QKFQGRVTI | | RYTM | GTQTYICNVNH | GVPSRFSG |
| | NWYVDGV | TADESTSTA | | HWVR | KPSNTKVDKR | SGSGTDFT |
| | EVHNAKT | YMELSSLRS | | QAPG | VEPKSCDKTHT | LTISSLQPE |
| | KPREEQYQ | EDTAVYYC | | QGLE | CPPCPAPELLG | DFATYYC |
| | STYRVVSV | ATPTNSGYY | | WMGY | GPSVFLFPPKPK | QQWSSNPF |
| | LTVLHQD | GPYYYGM | | INPSR | DTLMISRTPEV | TFGQGTKL |
| | WLNGKEY | DVWGQGTT | | GYTN | TCVVVDVSHE | EIKRTVAA |
| | KCKVSNK | VTVSSGGGG | | YNQK | DPEVKFNWYV | PSVFIFPPS |
| | ALPAPIEKT | SGGGGSGG | | FKDR | DGVEVHNAKT | DEQLKSGT |
| | ISKAKGQP | GGSGGGGS | | VTLTT | KPREEQYQSTY | ASVVCLLN |
| | REPQVYTL | DIQMTQSPS | | DKSSS | RVVSVLTVLHQ | NFYPREAK |
| | PPCREEMT | SLSASVGDR | | TAYM | DWLNGKEYKC | VQWKVDN |
| | KNQVSLW | VTITCRASQ | | ELSSL | KVSNKALPAPI | ALQSGNSQ |
| | CLVKGFYP | SISSWLAWY | | RSEDT | EKTISKAKGQP | ESVTEQDS |

TABLE 28-continued

Exemplary Bispecific Format 4 Constructs

| Name | Linker-Fc (Chain1) | scFv (Chains 1 and 2) | Linker (Chain2) | VH (Chain 2) | CH1-CH2-CH3 (Chain2) | LC (Chain 3) |
|---|---|---|---|---|---|---|
| | SDIAVEWE SNGQPENN YKTTPPVL DSDGSFFL YSKLTVDK SRWQQGN VFSCSVMH EALHNHYT QKSLSLSP GK (SEQ ID NO: 91) | QQKPGKAP KLLIYAAST LQSGVPSRF SGSGSGTDF TLTISSLQPE DFATYYCQ QSYSIPLTFG GGTKVEIK (SEQ ID NO: 92) | | AVYY CARY YDDH YSLD YWGQ GTLVT VSS (SEQ ID NO: 93) | REPQVCTLPPS REEMTKNQVS LSCAVKGFYPS DIAVEWESNGQ PENNYKTTPPV LDSDGSFFLVS KLTVDKSRWQ QGNVFSCSVM HEALHNRFTQK SLSLSPGK (SEQ ID NO: 94) | KDSTYSLS STLTLSKA DYEKHKV YACEVTH QGLSSPVT KSFNRGEC (SEQ ID NO: 95) |
| 4-G5 (1C12) hSP34x | GGGGSEPK SSDKTHTC PPCPAPELL GGPSVFLF PPKPKDTL MISRTPEV TCVVVDVS HEDPEVKF NWYVDGV EVHNAKT KPREEQYQ STYRVVSV LTVLHQD WLNGKEY KCKVSNK ALPAPIEKT ISKAKGQP REPQVYTL PPCREEMT KNQVSLW CLVKGFYP SDIAVEWE SNGQPENN YKTTPPVL DSDGSFFL YSKLTVDK SRWQQGN VFSCSVMH EALHNHYT QKSLSLSP GK (SEQ ID NO: 96) | QVQLVQSG AEVKKPGSS VKVSCKASG GTFSNFGVS WLRQAPGQ GLEWMGGII PILGTANYA QKFQGRVTI TADESTSTA YMELSSLRS EDTAVYYC ATPTNSGYY GPYYYGM DVWGQGTT VTVSSGGGG GGSGGGGS DIQMTQSPS SLSASVGDR VTITCRASQ SISSWLAWY QQKPGKAP KLLIYAAST LQSGVPSRF SGSGSGTDF TLTISSLQPE DFATYYCQ QSYSIPLTFG GGTKVEIK (SEQ ID NO: 97) | GGGGSG GGGS (SEQ ID NO: 111) | EVQL VESG GGLV QPGGS LRLSC AASGF TFSTY AMNW VRQA PGKG LEWV GRIRS KYNN YATY YADS VKGR FTISR DDSK NTLYL QMNS LRAE DTAV YYCV RHGN FGDSY VSWF AYWG QGTL VTVSS (SEQ ID NO: 98) | ASTKGPSVFPL APSSKSTSGGT AALGCLVKDY FPEPVTVSWNS GALTSGVHTFP AVLQSSGLYSL SSVVTVPSSSL GTQTYICNVNH KPSNTKVDKR VEPKSCDKTHT CPPCPAPELLG GPSVFLFPPKP KDTLMISRTPEV TCVVVDVSHE DPEVKFNWYV DGVEVHNAKT KPREEQYQSTY RVVSVLTVLHQ DWLNGKEYKC KVSNKALPAPI EKTISKAKGQP REPQVCTLPPS REEMTKNQVS LSCAVKGFYPS DIAVEWESNGQ PENNYKTTPPV LDSDGSFFLVS KLTVDKSRWQ QGNVFSCSVM HEALHNRFTQK SLSLSPGK (SEQ ID NO: 99) | QAVVTQE PSLTVSPG GTVTLTCG SSTGAVTT SNYANWV QQKPGKSP RGLIGGTN KRAPGVP ARFSGSLL GGKAALTI SGAQPEDE ADYYCAL WYSNHWV FGGGTKLT VLRTVAAP SVFIFPPSD EQLKSGTA SVVCLLNN FYPREAKV QWKVDNA LQSGNSQE SVTEQDSK DSTYSLSS TLTLSKAD YEKHKVY ACEVTHQ GLSSPVTK SFNRGEC (SEQ ID NO: 100) |

TABLE 29

Exemplary sequences of Format 4 bispecific antibodies with
engineered disulfide bond (DSB)
bold text indicates the engineered cysteine residue

| Name | Linker-Fc (Chain1) | scFv (Chains 1 and 2) | Linker (Chain2) | VH (Chain2) | CH1-CH2-CH3 (Chain2) | LC (Chain 3) |
|---|---|---|---|---|---|---|
| 4-G2 (1H11) hOKT3 | GGGGSEPKSS DKTHTCPPCP APELLGGPSV FLFPPKPKDT LMISRTPEVT CVVVDVSHE DPEVKFNWY VDGVEVHNA KTKPREEQYQ STYRVVSVLT VLHQDWLNG KEYKCKVSN KALPAPIEKTI SKAKGQPREP QVYTLPPCRE EMTKNQVSL | QVQLVQSG AEVKKPGAS VKVSCKASG YTFTNYYM HWVRQAPG QCLEWMGM INPSGGGTS YAQKFQGR VTMTRDTST STVYMELSS LRSEDTAVY YCARGNPW QGTLVTVSS GGGGSGGG GSGGGGSG | GGGGS GGGGS (SEQ ID NO: 111) | QVQLVQ SGAEVK KPGASVK VSCKASG YTFTRYT MHWVRQ APGQGLE WMGYIN PSRGYTN YNQKFK DRVTLTT DKSSSTA YMELSSL RSEDTAV YYCARY YDDHYS | ASTKGPSVFPLA PSSKSTSGGTAA LGCLVKDYFPEP VTVSWNSGALT SGVHTFPAVLQS SGLYSLSSVVTV NVNHKPSNTKV DKRVEPKSCDK THTCPPCPAPEL LGGPSVFLFPPK PKDTLMISRTPE VTCVVVDVSHE DPEVKFNWYVD GVEVHNAKTKP REEQYQSTYRV | DIQMTQSP SSLSASVG DRVTITCS ASSSVSYM NWYQQKP GKAPKRLI YDTSKLAS GVPSRFSG SGSGTDFT LTISSLQPE DFATYYC QQWSSNP FTFGQGTK LEIKRTVA APSVFIFPP SDEQLKSG |

TABLE 29-continued

Exemplary sequences of Format 4 bispecific antibodies with
engineered disulfide bond (DSB)
bold text indicates the engineered cysteine residue

| Name | Linker-Fc (Chain1) | scFv (Chains 1 and 2) | Linker (Chain2) | VH (Chain2) | CH1-CH2-CH3 (Chain2) | LC (Chain 3) |
|---|---|---|---|---|---|---|
| | WCLVKGFYP SDIAVEWESN GQPENNYKTT PPVLDSDGSF FLYSKLTVDK SRWQQGNVF SCSVMHEAL HNHYTQKSLS LSPGK (SEQ ID NO: 101) | GGGSDIQMT QSPSSLSASV GDRVTITCQ ASQDISNYL NWYQQKPG KAPKLLIYA ASSLQSGVP SRFSGSGSG TDFTLTISSL QPEDFATYY CQQYYSYPF TFGCGTKVD IK (SEQ ID NO: 102) | | LDYWGQ GTLVTVS S (SEQ ID NO: 103) | VSVLTVLHQDW LNGKEYKCKVS NKALPAPIEKTIS KAKGQPREPQV CTLPPSREEMTK NQVSLSCAVKG FYPSDIAVEWES NGQPENNYKTT PPVLDSDGSFFL VSKLTVDKSRW QQGNVFSCSVM HEALHNRFTQK SLSLSPGK (SEQ ID NO: 104) | TASVVCLL NNFYPREA KVQWKVD NALQSGN SQESVTEQ DSKDSTYS LSSTLTLS KADYEKH KVYACEV THQGLSSP VTKSFNRG EC (SEQ ID NO: 105) |
| 4- G5 (1C12) hOKT3 | GGGGSEPKSS DKTHTCPPCP APELLGGPSV FLFPPKPKDT LMISRTPEVT CVVVDVSHE DPEVKFNWY VDGVEVHNA KTKPREEQYQ STYRVVSVLT VLHQDWLNG KEYKCKVSN KALPAPIEKTI SKAKGQPREP QVYTLPPCRE EMTKNQVSL WCLVKGFYP SDIAVEWESN GQPENNYKTT PPVLDSDGSF FLYSKLTVDK SRWQQGNVF SCSVMHEAL HNHYTQKSLS LSPGK (SEQ ID NO: 106) | QVQLVQSG AEVKKPGSS VKVSCKASG GTFSNFGVS WLRQAPGQ CLEWMGGII PILGTANYA QKFQGRVTI TADESTSTA YMELSSLRS EDTAVYYC ATPTNSGYY GPYYYYGM DVWGQGTT VTVSSGGGG SGGGGSGG GGSGGGGS DIQMTQSPS SLSASVGDR VTITCRASQ SISSWLAWY QQKPGKAP KLLIYAAST LQSGVPSRF SGSGSGTDF TLTISSLQPE DFATYYCQ QSYSIPLTFG GGTKVEIK (SEQ ID NO: 107) | GGGGS GGGGS (SEQ ID NO: 111) | QVQLVQ SGAEVK KPGASVK VSCKASG YTFTRYT MHWVRQ APGQGLE WMGYIN PSRGYTN YNQKFK DRVTLTT DKSSSTA YMELSSL RSEDTAV YYCARY YDDHYS LDYWGQ GTLVTVS S (SEQ ID NO: 108) | ASTKGPSVFPLA PSSKSTSGGTAA LGCLVKDYFPEP VTVSWNSGALT SGVHTFPAVLQS SGLYSLSSVVTV PSSSLGTQTYIC NVNHKPSNTKV DKRVEPKSCDK THTCPPCPAPEL LGGPSVFLFPPK PKDTLMISRTPE VTCVVVDVSHE DPEVKFNWYVD GVEVHNAKTKP REEQYQSTYRV VSVLTVLHQDW LNGKEYKCKVS NKALPAPIEKTI SKAKGQPREPQV CTLPPSREEMTK NQVSLSCAVKG FYPSDIAVEWES NGQPENNYKTT PPVLDSDGSFFL VSKLTVDKSRW QQGNVFSCSVM HEALHNRFTQK SLSLSPGK (SEQ ID NO: 109) | DIQMTQSP SSLSASVG DRVTITCS ASSVSYM NWYQQKP GKAPKRLI YDTSKLAS GVPSRFSG SGSGTDFT LTISSLQPE DFATYYC QQWSSNP FTFGQGTK LEIKRTVA APSVFIFPP SDEQLKSG TASVVCLL NNFYPREA KVQWKVD NALQSGN SQESVTEQ DSKDSTYS LSSTLTLS KADYEKH KVYACEV THQGLSSP VTKSFNRG EC (SEQ ID NO: 110) |

SEQUENCE LISTING

Sequence total quantity: 237
SEQ ID NO: 1               moltype = AA   length = 115
FEATURE                    Location/Qualifiers
source                     1..115
                           mol_type = protein
                           organism = synthetic construct
SEQUENCE: 1
QVQLVQSGAE VKKPGASVKV SCKASGYTFT TYNIHWVRQA PGQGLEWMGW INPNSGGTNY    60
AQKFQGRVTM TRDTSTSTVY MELSSLRSED TAVYYCARAN WLDYWGQGTL VTVSS          115

SEQ ID NO: 2               moltype = AA   length = 107
FEATURE                    Location/Qualifiers
source                     1..107
                           mol_type = protein
                           organism = synthetic construct
SEQUENCE: 2
DIQMTQSPSS LSASVGDRVT ITCRASQEIR RWLAWYQQKP GKAPKLLIYA ASNLETGVPS    60
RFSGSGSGTD FTLTISSLQP EDFATYYCQQ SYSIPYTFGQ GTKLEIK                    107

```
SEQ ID NO: 3               moltype = AA  length = 117
FEATURE                    Location/Qualifiers
source                     1..117
                           mol_type = protein
                           organism = synthetic construct
SEQUENCE: 3
QVQLVQSGAE VKKPGASVKV SCKASGYTFT NYPIHWVRQA PGQGLEWMGW INPNSGGTNY  60
AQKLQGRVTM TRDTSTSTVY MELSSLRSED TAVYYCARDQ GAGWDYWGQG TLVTVSS     117

SEQ ID NO: 4               moltype = AA  length = 107
FEATURE                    Location/Qualifiers
source                     1..107
                           mol_type = protein
                           organism = synthetic construct
SEQUENCE: 4
DIQMTQSPSS LSASVGDRVT ITCRASQEIR RWLAWYQQKP GKAPKLLIYA ASNLQSGVPS  60
RFSGSGSGTD FTLTISSLQP EDFATYYCQQ SYSTPYTFGQ GTKLEIK             107

SEQ ID NO: 5               moltype = AA  length = 115
FEATURE                    Location/Qualifiers
source                     1..115
                           mol_type = protein
                           organism = synthetic construct
SEQUENCE: 5
QVQLVQSGAE VKKPGASVKV SCKASGATFT GYTIHWVRQA PGQGLEWMGW INPNSGGTNY  60
AQSFQGRVTM TRDTSTSTVY MELSSLRSED TAVYYCARAE WLDKWGQGTL VTVSS      115

SEQ ID NO: 6               moltype = AA  length = 117
FEATURE                    Location/Qualifiers
source                     1..117
                           mol_type = protein
                           organism = synthetic construct
SEQUENCE: 6
QVQLVQSGAE VKKPGASVKV SCKASGFTFT NYLIHWVRQA PGQGLEWMGW INPNSGGTNY  60
AQRLQGRVTM TRDTSTSTVY MELSSLRSED TAVYYCARDY GAGNDYWGQG TLVTVSS     117

SEQ ID NO: 7               moltype = AA  length = 5
FEATURE                    Location/Qualifiers
source                     1..5
                           mol_type = protein
                           organism = synthetic construct
SEQUENCE: 7
TYNIH                                                               5

SEQ ID NO: 8               moltype = AA  length = 17
FEATURE                    Location/Qualifiers
source                     1..17
                           mol_type = protein
                           organism = synthetic construct
SEQUENCE: 8
WINPNSGGTN YAQKFQG                                                 17

SEQ ID NO: 9               moltype = AA  length = 6
FEATURE                    Location/Qualifiers
source                     1..6
                           mol_type = protein
                           organism = synthetic construct
SEQUENCE: 9
ANWLDY                                                             6

SEQ ID NO: 10              moltype = AA  length = 7
FEATURE                    Location/Qualifiers
source                     1..7
                           mol_type = protein
                           organism = synthetic construct
SEQUENCE: 10
AASNLET                                                            7

SEQ ID NO: 11              moltype = AA  length = 9
FEATURE                    Location/Qualifiers
source                     1..9
                           mol_type = protein
                           organism = synthetic construct
SEQUENCE: 11
QQSYSIPYT                                                          9

SEQ ID NO: 12              moltype = AA  length = 5
FEATURE                    Location/Qualifiers
source                     1..5
```

-continued

```
                         mol_type = protein
                         organism = synthetic construct
SEQUENCE: 12
NYPIH                                                             5

SEQ ID NO: 13          moltype = AA   length = 17
FEATURE                Location/Qualifiers
source                 1..17
                       mol_type = protein
                       organism = synthetic construct
SEQUENCE: 13
WINPNSGGTN YAQKLQG                                                17

SEQ ID NO: 14          moltype = AA   length = 8
FEATURE                Location/Qualifiers
source                 1..8
                       mol_type = protein
                       organism = synthetic construct
SEQUENCE: 14
DQGAGWDY                                                          8

SEQ ID NO: 15          moltype = AA   length = 5
FEATURE                Location/Qualifiers
source                 1..5
                       mol_type = protein
                       organism = synthetic construct
SEQUENCE: 15
GYTIH                                                             5

SEQ ID NO: 16          moltype = AA   length = 17
FEATURE                Location/Qualifiers
source                 1..17
                       mol_type = protein
                       organism = synthetic construct
SEQUENCE: 16
WINPNSGGTN YAQSFQG                                                17

SEQ ID NO: 17          moltype = AA   length = 6
FEATURE                Location/Qualifiers
source                 1..6
                       mol_type = protein
                       organism = synthetic construct
SEQUENCE: 17
AEWLDK                                                            6

SEQ ID NO: 18          moltype = AA   length = 5
FEATURE                Location/Qualifiers
source                 1..5
                       mol_type = protein
                       organism = synthetic construct
SEQUENCE: 18
NYLIH                                                             5

SEQ ID NO: 19          moltype = AA   length = 17
FEATURE                Location/Qualifiers
source                 1..17
                       mol_type = protein
                       organism = synthetic construct
SEQUENCE: 19
WINPNSGGTN YAQRLQG                                                17

SEQ ID NO: 20          moltype = AA   length = 8
FEATURE                Location/Qualifiers
source                 1..8
                       mol_type = protein
                       organism = synthetic construct
SEQUENCE: 20
DYGAGNDY                                                          8

SEQ ID NO: 21          moltype = AA   length = 11
FEATURE                Location/Qualifiers
source                 1..11
                       mol_type = protein
                       organism = synthetic construct
SEQUENCE: 21
RASQEIRRWL A                                                      11

SEQ ID NO: 22          moltype = AA   length = 7
FEATURE                Location/Qualifiers
```

-continued

```
source                  1..7
                        mol_type = protein
                        organism = synthetic construct
SEQUENCE: 22
AASNLQS                                                         7

SEQ ID NO: 23           moltype = AA   length = 9
FEATURE                 Location/Qualifiers
source                  1..9
                        mol_type = protein
                        organism = synthetic construct
SEQUENCE: 23
QQSYSTPYT                                                       9

SEQ ID NO: 24           moltype = AA   length = 119
FEATURE                 Location/Qualifiers
source                  1..119
                        mol_type = protein
                        organism = synthetic construct
SEQUENCE: 24
QVQLVQSGAE VKKPGASVKV SCKASGYTFT RYTMHWVRQA PGQGLEWMGY INPSRGYTNY  60
NQKFKDRVTL TTDKSSSTAY MELSSLRSED TAVYYCARYY DDHYSLDYWG QGTLVTVSS  119

SEQ ID NO: 25           moltype = AA   length = 106
FEATURE                 Location/Qualifiers
source                  1..106
                        mol_type = protein
                        organism = synthetic construct
SEQUENCE: 25
DIQMTQSPSS LSASVGDRVT ITCSASSSVS YMNWYQQKPG KAPKRLIYDT SKLASGVPSR  60
FSGSGSGTDF TLTISSLQPE DFATYYCQQW SSNPFTFGQG TKLEIK             106

SEQ ID NO: 26           moltype = AA   length = 5
FEATURE                 Location/Qualifiers
source                  1..5
                        mol_type = protein
                        organism = synthetic construct
SEQUENCE: 26
RYTMH                                                           5

SEQ ID NO: 27           moltype = AA   length = 17
FEATURE                 Location/Qualifiers
source                  1..17
                        mol_type = protein
                        organism = synthetic construct
SEQUENCE: 27
YINPSRGYTN YNQKFKD                                             17

SEQ ID NO: 28           moltype = AA   length = 10
FEATURE                 Location/Qualifiers
source                  1..10
                        mol_type = protein
                        organism = synthetic construct
SEQUENCE: 28
YYDDHYSLDY                                                     10

SEQ ID NO: 29           moltype = AA   length = 10
FEATURE                 Location/Qualifiers
source                  1..10
                        mol_type = protein
                        organism = synthetic construct
SEQUENCE: 29
SASSSVSYMN                                                     10

SEQ ID NO: 30           moltype = AA   length = 7
FEATURE                 Location/Qualifiers
source                  1..7
                        mol_type = protein
                        organism = synthetic construct
SEQUENCE: 30
DTSKLAS                                                         7

SEQ ID NO: 31           moltype = AA   length = 9
FEATURE                 Location/Qualifiers
source                  1..9
                        mol_type = protein
                        organism = synthetic construct
SEQUENCE: 31
QQWSSNPFT                                                       9
```

-continued

```
SEQ ID NO: 32            moltype = AA  length = 122
FEATURE                  Location/Qualifiers
source                   1..122
                         mol_type = protein
                         organism = synthetic construct
SEQUENCE: 32
EVQLVESGGG LVQPGGSLRL SCAASGYSFT GYTMNWVRQA PGKGLEWVAL INPYKGVSTY  60
NQKFKDRFTI SVDKSKNTAY LQMNSLRAED TAVYYCARSG YYGDSDWYFD VWGQGTLVTV  120
SS                                                                 122

SEQ ID NO: 33            moltype = AA  length = 107
FEATURE                  Location/Qualifiers
source                   1..107
                         mol_type = protein
                         organism = synthetic construct
SEQUENCE: 33
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIK               107

SEQ ID NO: 34            moltype = AA  length = 125
FEATURE                  Location/Qualifiers
source                   1..125
                         mol_type = protein
                         organism = synthetic construct
SEQUENCE: 34
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 35            moltype = AA  length = 109
FEATURE                  Location/Qualifiers
source                   1..109
                         mol_type = protein
                         organism = synthetic construct
SEQUENCE: 35
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL             109

SEQ ID NO: 36            moltype = AA  length = 5
FEATURE                  Location/Qualifiers
source                   1..5
                         mol_type = protein
                         organism = synthetic construct
SEQUENCE: 36
GYTMN                                                              5

SEQ ID NO: 37            moltype = AA  length = 17
FEATURE                  Location/Qualifiers
source                   1..17
                         mol_type = protein
                         organism = synthetic construct
SEQUENCE: 37
LINPYKGVST YNQKFKD                                                 17

SEQ ID NO: 38            moltype = AA  length = 13
FEATURE                  Location/Qualifiers
source                   1..13
                         mol_type = protein
                         organism = synthetic construct
SEQUENCE: 38
SGYYGDSDWY FDV                                                     13

SEQ ID NO: 39            moltype = AA  length = 11
FEATURE                  Location/Qualifiers
source                   1..11
                         mol_type = protein
                         organism = synthetic construct
SEQUENCE: 39
RASQDIRNYL N                                                       11

SEQ ID NO: 40            moltype = AA  length = 7
FEATURE                  Location/Qualifiers
source                   1..7
                         mol_type = protein
                         organism = synthetic construct
SEQUENCE: 40
YTSRLES                                                            7
```

-continued

```
SEQ ID NO: 41            moltype = AA   length = 9
FEATURE                  Location/Qualifiers
source                   1..9
                         mol_type = protein
                         organism = synthetic construct
SEQUENCE: 41
QQGNTLPWT                                                         9

SEQ ID NO: 42            moltype = AA   length = 5
FEATURE                  Location/Qualifiers
source                   1..5
                         mol_type = protein
                         organism = synthetic construct
SEQUENCE: 42
TYAMN                                                             5

SEQ ID NO: 43            moltype = AA   length = 19
FEATURE                  Location/Qualifiers
source                   1..19
                         mol_type = protein
                         organism = synthetic construct
SEQUENCE: 43
RIRSKYNNYA TYYADSVKG                                              19

SEQ ID NO: 44            moltype = AA   length = 14
FEATURE                  Location/Qualifiers
source                   1..14
                         mol_type = protein
                         organism = synthetic construct
SEQUENCE: 44
GSSTGAVTTS NYAN                                                   14

SEQ ID NO: 45            moltype = AA   length = 14
FEATURE                  Location/Qualifiers
source                   1..14
                         mol_type = protein
                         organism = synthetic construct
SEQUENCE: 45
GSSTGAVTTS NYAN                                                   14

SEQ ID NO: 46            moltype = AA   length = 7
FEATURE                  Location/Qualifiers
source                   1..7
                         mol_type = protein
                         organism = synthetic construct
SEQUENCE: 46
GTNKRAP                                                           7

SEQ ID NO: 47            moltype = AA   length = 9
FEATURE                  Location/Qualifiers
source                   1..9
                         mol_type = protein
                         organism = synthetic construct
SEQUENCE: 47
ALWYSNHWV                                                         9

SEQ ID NO: 48            moltype = AA   length = 237
FEATURE                  Location/Qualifiers
source                   1..237
                         mol_type = protein
                         organism = synthetic construct
SEQUENCE: 48
GGGGSEPKSS DKTHTCPPCP APEFEGGPSV FLFPPKPKDT LMISRTPEVT CVVVDVSHED  60
PEVKFNWYVD GVEVHNAKTK PREEQYNSTY RVVSVLTVLH QDWLNGKEYK CKVSNKALPA  120
SIEKTISKAK GQPREPQVYT LPPCREEMTK NQVSLWCLVK GFYPSDIAVE WESNGQPENN  180
YKTTPPVLDS DGSFFLYSKL TVDKSRWQQG NVFSCSVMHE ALHNHYTQKS LSLSPGK     237

SEQ ID NO: 49            moltype = AA   length = 459
FEATURE                  Location/Qualifiers
source                   1..459
                         mol_type = protein
                         organism = synthetic construct
SEQUENCE: 49
GGGGSGGGGS QVQLVQSGAE VKKPGASVKV SCKASGYTFT RYTMHWVRQA PGQGLEWMGY  60
INPSRGYTNY NQKFKDRVTL TTDKSSSTAY MELSSLRSED TAVYYCARYY DDHYSLDYWG  120
QGTLVTVSSA STKGPSVFPL APSSKSTSGG TAALGCLVKD YFPEPVTVSW NSGALTSGVH  180
TFPAVLQSSG LYSLSSVVTV PSSSLGTQTY ICNVNHKPSN TKVDKRVEPK SCDKTHTCPP  240
CPAPEFEGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PASIEKTISK AKGQPREPQV  360
```

```
CTLPPSREEM TKNQVSLSCA VKGFYPSDIA VEWESNGQPE NNYKTTPPVL DSDGSFFLVS  420
KLTVDKSRWQ QGNVFSCSVM HEALHNRFTQ KSLSLSPGK                         459

SEQ ID NO: 50             moltype = AA  length = 213
FEATURE                   Location/Qualifiers
source                    1..213
                          mol_type = protein
                          organism = synthetic construct
SEQUENCE: 50
DIQMTQSPSS LSASVGDRVT ITCSASSSVS YMNWYQQKPG KAPKRLIYDT SKLASGVPSR   60
FSGSGSGTDF TLTISSLQPE DFATYYCQQW SSNPFTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 51             moltype = AA  length = 462
FEATURE                   Location/Qualifiers
source                    1..462
                          mol_type = protein
                          organism = synthetic construct
SEQUENCE: 51
GGGGSGGGGS EVQLVESGGG LVQPGGSLRL SCAASGYSFT GYTMNWVRQA PGKGLEWVAL   60
INPYKGVSTY NQKFKDRFTI SVDKSKNTAY LQMNSLRAED TAVYYCARSG YYGDSDWYFD  120
VWGQGTLVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKRV EPKSCDKTHT  240
CPPCPAPEFE GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPASIEKT ISKAKGQPRE  360
PQVCTLPPSR EEMTKNQVSL SCAVKGFYPS DIAVEWESNG QPENNYKTTP PVLDSDGSFF  420
LVSKLTVDKS RWQQGNVFSC SVMHEALHNR FTQKSLSLSP GK                     462

SEQ ID NO: 52             moltype = AA  length = 214
FEATURE                   Location/Qualifiers
source                    1..214
                          mol_type = protein
                          organism = synthetic construct
SEQUENCE: 52
DIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 53             moltype = AA  length = 465
FEATURE                   Location/Qualifiers
source                    1..465
                          mol_type = protein
                          organism = synthetic construct
SEQUENCE: 53
GGGGSGGGGS EVQLVESGGG LVQPGGSLRL SCAASGFTFS TYAMNWVRQA PGKGLEWVGR   60
IRSKYNNYAT YYADSVKGRF TISRDDSKNT LYLQMNSLRA EDTAVYYCVR HGNFGDSYVS  120
WFAYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KRVEPKSCDK  240
THTCPPCPAP EFEGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPASI EKTISKAKGQ  360
PREPQVCTLP PSREEMTKNQ VSLSCAVKGF YPSDIAVEWE SNGQPENNYK TTPPVLDSDG  420
SFFLVSKLTV DKSRWQQGNV FSCSVMHEAL HNRFTQKSLS LSPGK                  465

SEQ ID NO: 54             moltype = AA  length = 216
FEATURE                   Location/Qualifiers
source                    1..216
                          mol_type = protein
                          organism = synthetic construct
SEQUENCE: 54
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 55             moltype = AA  length = 234
FEATURE                   Location/Qualifiers
source                    1..234
                          mol_type = protein
                          organism = synthetic construct
SEQUENCE: 55
QVQLVQSGAE VKKPGASVKV SCKASGFTFT NYLIHWVRQA PGQGLEWMGW INPNSGGTNY   60
AQRLQGRVTM TRDTSTSTVY MELSSLRSED TAVYYCARDY GAGNDYWGQG TLVTVSSGGG  120
GSGGGGSDIQ MTQSPSSLSA SVGDRVTITC RASQEIRRWL AWYQQKPGKA PKLLIYAASN  180
LQSGVPSRFS GSGSGTDFTL TISSLQPEDF ATYYCQQSYS TPYTFGQGTK LEIK        234

SEQ ID NO: 56             moltype = AA  length = 457
FEATURE                   Location/Qualifiers
```

-continued

```
source                   1..457
                         mol_type = protein
                         organism = synthetic construct
SEQUENCE: 56
GGGGSGGGGS QVQLVQSGAE VKKPGASVKV SCKASGFTFT NYLIHWVRQA PGQGLEWMGW    60
INPNSGGTNY AQRLQGRVTM TRDTSTSTVY MELSSLRSED TAVYYCARDY GAGNDYWGQG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APEFEGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA SIEKTISKAK GQPREPQVCT   360
LPPSREEMTK NQVSLSCAVK GFYPSDIAVE WESNGQPENN YKTTPPVLDS DGSFFLVSKL   420
TVDKSRWQQG NVFSCSVMHE ALHNRFTQKS LSLSPGK                            457

SEQ ID NO: 57          moltype = AA  length = 214
FEATURE                Location/Qualifiers
source                 1..214
                       mol_type = protein
                       organism = synthetic construct
SEQUENCE: 57
DIQMTQSPSS LSASVGDRVT ITCRASQEIR RWLAWYQQKP GKAPKLLIYA ASNLQSGVPS    60
RFSGSGSGTD FTLTISSLQP EDFATYYCQQ SYSTPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 58          moltype = AA  length = 239
FEATURE                Location/Qualifiers
source                 1..239
                       mol_type = protein
                       organism = synthetic construct
SEQUENCE: 58
EVQLVESGGG LVQPGGSLRL SCAASGYSFT GYTMNWVRQA PGKGLEWVAL INPYKGVSTY    60
NQKFKDRFTI SVDKSKNTAY LQMNSLRAED TAVYYCARSG YYGDSDWYFD VWGQGTLVTV   120
SSGGGGSGGG GSDIQMTQSP SSLSASVGDR VTITCRASQE IRRWLAWYQQ KPGKAPKLLI   180
YAASNLQSGV PSRFSGSGSG TDFTLTISSL QPEDFATYYC QQSYSTPYTF GQGTKLEIK    239

SEQ ID NO: 59          moltype = AA  length = 234
FEATURE                Location/Qualifiers
source                 1..234
                       mol_type = protein
                       organism = synthetic construct
SEQUENCE: 59
QVQLVQSGAE VKKPGASVKV SCKASGFTFT NYLIHWVRQA PGQGLEWMGW INPNSGGTNY    60
AQRLQGRVTM TRDTSTSTVY MELSSLRSED TAVYYCARDY GAGNDYWGQG TLVTVSSGGG   120
GSGGGGSDIQ MTQSPSSLSA SVGDRVTITC RASQDIRNYL NWYQQKPGKA PKLLIYYTSR   180
LESGVPSRFS GSGSGTDYTL TISSLQPEDF ATYYCQQGNT LPWTFGQGTK VEIK         234

SEQ ID NO: 60          moltype = AA  length = 119
FEATURE                Location/Qualifiers
source                 1..119
                       mol_type = protein
                       organism = synthetic construct
SEQUENCE: 60
QVQLVQSGAE VKKPGASVKV SCKASGYTFT NYYMHWVRQA PGQGLEWMGM INPSGGGTSY    60
AQKFQGRVTM TRDTSTSTVY MELSSLRSED TAVYYCARGN PWELRLDYWG QGTLVTVSS    119

SEQ ID NO: 61          moltype = AA  length = 107
FEATURE                Location/Qualifiers
source                 1..107
                       mol_type = protein
                       organism = synthetic construct
SEQUENCE: 61
DIQMTQSPSS LSASVGDRVT ITCQASQDIS NYLNWYQQKP GKAPKLLIYA ASSLQSGVPS    60
RFSGSGSGTD FTLTISSLQP EDFATYYCQQ YYSYPFTFGP GTKVDIK                 107

SEQ ID NO: 62          moltype =    length =
SEQUENCE: 62
000

SEQ ID NO: 63          moltype =    length =
SEQUENCE: 63
000

SEQ ID NO: 64          moltype =    length =
SEQUENCE: 64
000

SEQ ID NO: 65          moltype =    length =
SEQUENCE: 65
000
```

-continued

```
SEQ ID NO: 66            moltype =   length =
SEQUENCE: 66
000

SEQ ID NO: 67            moltype = AA   length = 9
FEATURE                  Location/Qualifiers
source                   1..9
                         mol_type = protein
                         organism = synthetic construct
SEQUENCE: 67
YTFTNYYMH                                                            9

SEQ ID NO: 68            moltype = AA   length = 13
FEATURE                  Location/Qualifiers
source                   1..13
                         mol_type = protein
                         organism = synthetic construct
SEQUENCE: 68
GMINPSGGGT SYA                                                       13

SEQ ID NO: 69            moltype = AA   length = 14
FEATURE                  Location/Qualifiers
source                   1..14
                         mol_type = protein
                         organism = synthetic construct
SEQUENCE: 69
CARGNPWELR LDYW                                                      14

SEQ ID NO: 70            moltype = AA   length = 11
FEATURE                  Location/Qualifiers
source                   1..11
                         mol_type = protein
                         organism = synthetic construct
SEQUENCE: 70
QASQDISNYL N                                                         11

SEQ ID NO: 71            moltype = AA   length = 7
FEATURE                  Location/Qualifiers
source                   1..7
                         mol_type = protein
                         organism = synthetic construct
SEQUENCE: 71
AASSLQS                                                              7

SEQ ID NO: 72            moltype = AA   length = 11
FEATURE                  Location/Qualifiers
source                   1..11
                         mol_type = protein
                         organism = synthetic construct
SEQUENCE: 72
CQQYYSYPFT F                                                         11

SEQ ID NO: 73            moltype = AA   length = 9
FEATURE                  Location/Qualifiers
source                   1..9
                         mol_type = protein
                         organism = synthetic construct
SEQUENCE: 73
GTFSNFGVS                                                            9

SEQ ID NO: 74            moltype = AA   length = 13
FEATURE                  Location/Qualifiers
source                   1..13
                         mol_type = protein
                         organism = synthetic construct
SEQUENCE: 74
GGIIPILGTA NYA                                                       13

SEQ ID NO: 75            moltype = AA   length = 21
FEATURE                  Location/Qualifiers
source                   1..21
                         mol_type = protein
                         organism = synthetic construct
SEQUENCE: 75
CATPTNSGYY GPYYYYGMDV W                                              21

SEQ ID NO: 76            moltype = AA   length = 11
FEATURE                  Location/Qualifiers
```

```
source                  1..11
                        mol_type = protein
                        organism = synthetic construct
SEQUENCE: 76
RASQSISSWL A                                                            11

SEQ ID NO: 77           moltype = AA   length = 7
FEATURE                 Location/Qualifiers
source                  1..7
                        mol_type = protein
                        organism = synthetic construct
SEQUENCE: 77
AASTLQS                                                                 7

SEQ ID NO: 78           moltype = AA   length = 11
FEATURE                 Location/Qualifiers
source                  1..11
                        mol_type = protein
                        organism = synthetic construct
SEQUENCE: 78
CQQSYSIPLT F                                                            11

SEQ ID NO: 79           moltype = AA   length = 126
FEATURE                 Location/Qualifiers
source                  1..126
                        mol_type = protein
                        organism = synthetic construct
SEQUENCE: 79
QVQLVQSGAE VKKPGSSVKV SCKASGGTFS NFGVSWLRQA PGQGLEWMGG IIPILGTANY       60
AQKFQGRVTI TADESTSTAY MELSSLRSED TAVYYCATPT NSGYYGPYYY YGMDVWGQGT      120
TVTVSS                                                                 126

SEQ ID NO: 80           moltype = AA   length = 107
FEATURE                 Location/Qualifiers
source                  1..107
                        mol_type = protein
                        organism = synthetic construct
SEQUENCE: 80
DIQMTQSPSS LSASVGDRVT ITCRASQSIS SWLAWYQQKP GKAPKLLIYA ASTLQSGVPS       60
RFSGSGSGTD FTLTISSLQP EDFATYYCQQ SYSIPLTFGG GTKVEIK                    107

SEQ ID NO: 81           moltype = AA   length = 237
FEATURE                 Location/Qualifiers
source                  1..237
                        mol_type = protein
                        organism = synthetic construct
SEQUENCE: 81
GGGGSEPKSS DKTHTCPPCP APELLGGPSV FLFPPKPKDT LMISRTPEVT CVVVDVSHED       60
PEVKFNWYVD GVEVHNAKTK PREEQYQSTY RVVSVLTVLH QDWLNGKEYK CKVSNKALPA      120
PIEKTISKAK GQPREPQVYT LPPCREEMTK NQVSLWCLVK GFYPSDIAVE WESNGQPENN      180
YKTTPPVLDS DGSFFLYSKL TVDKSRWQQG NVFSCSVMHE ALHNHYTQKS LSLSPGK        237

SEQ ID NO: 82           moltype = AA   length = 246
FEATURE                 Location/Qualifiers
source                  1..246
                        mol_type = protein
                        organism = synthetic construct
SEQUENCE: 82
QVQLVQSGAE VKKPGASVKV SCKASGYTFT NYYMHWVRQA PGQGLEWMGM INPSGGGTSY       60
AQKFQGRVTM TRDTSTSTVY MELSSLRSED TAVYYCARGN PWELRLDYWG QGTLVTVSSG      120
GGGSGGGGSG GGGSGGGGSD IQMTQSPSSL SASVGDRVTI TCQASQDISN YLNWYQQKPG      180
KAPKLLIYAA SSLQSGVPSR FSGSGSGTDF TLTISSLQPE DFATYYCQQY YSYPFTFGPG      240
TKVDIK                                                                 246

SEQ ID NO: 83           moltype = AA   length = 119
FEATURE                 Location/Qualifiers
source                  1..119
                        mol_type = protein
                        organism = synthetic construct
SEQUENCE: 83
QVQLVQSGAE VKKPGASVKV SCKASGYTFT RYTMHWVRQA PGQGLEWMGY INPSRGYTNY       60
NQKFKDRVTL TTDKSSSTAY MELSSLRSED TAVYYCARYY DDHYSLDYWG QGTLVTVSS       119

SEQ ID NO: 84           moltype = AA   length = 330
FEATURE                 Location/Qualifiers
source                  1..330
                        mol_type = protein
                        organism = synthetic construct
SEQUENCE: 84
```

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEYQ    180
STYRVVSVLT VLHQDWLNGK EYKCKVSNKA LPAPIEKTIS KAKGQPREPQ VCTLPPSREE   240
MTKNQVSLSC AVKGFYPSDI AVEWESNGQP ENNYKTTPPV LDSDGSFFLV SKLTVDKSRW   300
QQGNVFSCSV MHEALHNRFT QKSLSLSPGK                                    330
```

```
SEQ ID NO: 85              moltype = AA  length = 213
FEATURE                    Location/Qualifiers
source                     1..213
                           mol_type = protein
                           organism = synthetic construct
SEQUENCE: 85
DIQMTQSPSS LSASVGDRVT ITCSASSSVS YMNWYQQKPG KAPKRLIYDT SKLASGVPSR    60
FSGSGSGTDF TLTISSLQPE DFATYYCQQW SSNPFTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213
```

```
SEQ ID NO: 86              moltype = AA  length = 237
FEATURE                    Location/Qualifiers
source                     1..237
                           mol_type = protein
                           organism = synthetic construct
SEQUENCE: 86
GGGGSEPKSS DKTHTCPPCP APELLGGPSV FLFPPKPKDT LMISRTPEVT CVVVDVSHED    60
PEVKFNWYVD GVEVHNAKTK PREEYQSTY RVVSVLTVLH QDWLNGKEYK CKVSNKALPA    120
PIEKTISKAK GQPREPQVYT LPPCREEMTK NQVSLWCLVK GFYPSDIAVE WESNGQPENN   180
YKTTPPVLDS DGSFFLYSKL TVDKSRWQQG NVFSCSVMHE ALHNHYTQKS LSLSPGK      237
```

```
SEQ ID NO: 87              moltype = AA  length = 246
FEATURE                    Location/Qualifiers
source                     1..246
                           mol_type = protein
                           organism = synthetic construct
SEQUENCE: 87
QVQLVQSGAE VKKPGASVKV SCKASGYTFT NYYMHWVRQA PGQGLEWMGM INPSGGGTSY    60
AQKFQGRVTM TRDTSTSTVY MELSSLRSED TAVYYCARGN PWELRLDYWG QGTLVTVSSG   120
GGGSGGGGSG GGGSGGGGSD IQMTQSPSSL SASVGDRVTI TCQASQDISN YLNWYQQKPG   180
KAPKLLIYAA SSLQSGVPSR FSGSGSGTDF TLTISSLQPE DFATYYCQQY YSYPFTFGPG   240
TKVDIK                                                             246
```

```
SEQ ID NO: 88              moltype = AA  length = 125
FEATURE                    Location/Qualifiers
source                     1..125
                           mol_type = protein
                           organism = synthetic construct
SEQUENCE: 88
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSS                                                              125
```

```
SEQ ID NO: 89              moltype = AA  length = 330
FEATURE                    Location/Qualifiers
source                     1..330
                           mol_type = protein
                           organism = synthetic construct
SEQUENCE: 89
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEYQ    180
STYRVVSVLT VLHQDWLNGK EYKCKVSNKA LPAPIEKTIS KAKGQPREPQ VCTLPPSREE   240
MTKNQVSLSC AVKGFYPSDI AVEWESNGQP ENNYKTTPPV LDSDGSFFLV SKLTVDKSRW   300
QQGNVFSCSV MHEALHNRFT QKSLSLSPGK                                    330
```

```
SEQ ID NO: 90              moltype = AA  length = 216
FEATURE                    Location/Qualifiers
source                     1..216
                           mol_type = protein
                           organism = synthetic construct
SEQUENCE: 90
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVLR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216
```

```
SEQ ID NO: 91              moltype = AA  length = 237
FEATURE                    Location/Qualifiers
source                     1..237
                           mol_type = protein
```

```
                                organism = synthetic construct
SEQUENCE: 91
GGGGSEPKSS DKTHTCPPCP APELLGGPSV FLFPPKPKDT LMISRTPEVT CVVVDVSHED    60
PEVKFNWYVD GVEVHNAKTK PREEQYQSTY RVVSVLTVLH QDWLNGKEYK CKVSNKALPA   120
PIEKTISKAK GQPREPQVYT LPPCREEMTK NQVSLWCLVK GFYPSDIAVE WESNGQPENN   180
YKTTPPVLDS DGSFFLYSKL TVDKSRWQQG NVFSCSVMHE ALHNHYTQKS LSLSPGK      237

SEQ ID NO: 92               moltype = AA  length = 253
FEATURE                     Location/Qualifiers
source                      1..253
                            mol_type = protein
                            organism = synthetic construct
SEQUENCE: 92
QVQLVQSGAE VKKPGSSVKV SCKASGGTFS NFGVSWLRQA PGQGLEWMGG IIPILGTANY    60
AQKFQGRVTI TADESTSTAY MELSSLRSED TAVYYCATPT NSGYYGPYYY YGMDVWGQGT   120
TVTVSSGGGG SGGGGSGGGG SGGGGSDIQM TQSPSSLSAS VGDRVTITCR ASQSISSWLA   180
WYQQKPGKAP KLLIYAASTL QSGVPSRFSG SGSGTDFTLT ISSLQPEDFA TYYCQQSYSI   240
PLTFGGGTKV EIK                                                      253

SEQ ID NO: 93               moltype = AA  length = 119
FEATURE                     Location/Qualifiers
source                      1..119
                            mol_type = protein
                            organism = synthetic construct
SEQUENCE: 93
QVQLVQSGAE VKKPGASVKV SCKASGYTFT RYTMHWVRQA PGQGLEWMGY INPSRGYTNY    60
NQKFKDRVTL TTDKSSSTAY MELSSLRSED TAVYYCARYY DDHYSLDYWG QGTLVTVSS    119

SEQ ID NO: 94               moltype = AA  length = 330
FEATURE                     Location/Qualifiers
source                      1..330
                            mol_type = protein
                            organism = synthetic construct
SEQUENCE: 94
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEYQ    180
STYRVVSVLT VLHQDWLNGK EYKCKVSNKA LPAPIEKTIS KAKGQPREPQ VCTLPPSREE   240
MTKNQVSLSC AVKGFYPSDI AVEWESNGQP ENNYKTTPPV LDSDGSFFLV SKLTVDKSRW   300
QQGNVFSCSV MHEALHNRFT QKSLSLSPGK                                    330

SEQ ID NO: 95               moltype = AA  length = 213
FEATURE                     Location/Qualifiers
source                      1..213
                            mol_type = protein
                            organism = synthetic construct
SEQUENCE: 95
DIQMTQSPSS LSASVGDRVT ITCSASSSVS YMNWYQQKPG KAPKRLIYDT SKLASGVPSR    60
FSGSGSGTDF TLTISSLQPE DFATYYCQQW SSNPFTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 96               moltype = AA  length = 237
FEATURE                     Location/Qualifiers
source                      1..237
                            mol_type = protein
                            organism = synthetic construct
SEQUENCE: 96
GGGGSEPKSS DKTHTCPPCP APELLGGPSV FLFPPKPKDT LMISRTPEVT CVVVDVSHED    60
PEVKFNWYVD GVEVHNAKTK PREEQYQSTY RVVSVLTVLH QDWLNGKEYK CKVSNKALPA   120
PIEKTISKAK GQPREPQVYT LPPCREEMTK NQVSLWCLVK GFYPSDIAVE WESNGQPENN   180
YKTTPPVLDS DGSFFLYSKL TVDKSRWQQG NVFSCSVMHE ALHNHYTQKS LSLSPGK      237

SEQ ID NO: 97               moltype = AA  length = 253
FEATURE                     Location/Qualifiers
source                      1..253
                            mol_type = protein
                            organism = synthetic construct
SEQUENCE: 97
QVQLVQSGAE VKKPGSSVKV SCKASGGTFS NFGVSWLRQA PGQGLEWMGG IIPILGTANY    60
AQKFQGRVTI TADESTSTAY MELSSLRSED TAVYYCATPT NSGYYGPYYY YGMDVWGQGT   120
TVTVSSGGGG SGGGGSGGGG SGGGGSDIQM TQSPSSLSAS VGDRVTITCR ASQSISSWLA   180
WYQQKPGKAP KLLIYAASTL QSGVPSRFSG SGSGTDFTLT ISSLQPEDFA TYYCQQSYSI   240
PLTFGGGTKV EIK                                                      253

SEQ ID NO: 98               moltype = AA  length = 125
FEATURE                     Location/Qualifiers
source                      1..125
                            mol_type = protein
```

-continued

```
                         organism = synthetic construct
SEQUENCE: 98
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 99           moltype = AA  length = 330
FEATURE                 Location/Qualifiers
source                  1..330
                        mol_type = protein
                        organism = synthetic construct
SEQUENCE: 99
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYQ  180
STYRVVSVLT VLHQDWLNGK EYKCKVSNKA LPAPIEKTIS KAKGQPREPQ VCTLPPSREE  240
MTKNQVSLSC AVKGFYPSDI AVEWESNGQP ENNYKTTPPV LDSDGSFFLV SKLTVDKSRW  300
QQGNVFSCSV MHEALHNRFT QKSLSLSPGK                                    330

SEQ ID NO: 100          moltype = AA  length = 216
FEATURE                 Location/Qualifiers
source                  1..216
                        mol_type = protein
                        organism = synthetic construct
SEQUENCE: 100
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 101          moltype = AA  length = 237
FEATURE                 Location/Qualifiers
source                  1..237
                        mol_type = protein
                        organism = synthetic construct
SEQUENCE: 101
GGGGSEPKSS DKTHTCPPCP APELLGGPSV FLFPPKPKDT LMISRTPEVT CVVVDVSHED  60
PEVKFNWYVD GVEVHNAKTK PREEQYQSTY RVVSVLTVLH QDWLNGKEYK CKVSNKALPA  120
PIEKTISKAK GQPREPQVYT LPPCREEMTK NQVSLWCLVK GFYPSDIAVE WESNGQPENN  180
YKTTPPVLDS DGSFFLYSKL TVDKSRWQQG NVFSCSVMHE ALHNHYTQKS LSLSPGK     237

SEQ ID NO: 102          moltype = AA  length = 246
FEATURE                 Location/Qualifiers
source                  1..246
                        mol_type = protein
                        organism = synthetic construct
SEQUENCE: 102
QVQLVQSGAE VKKPGASVKV SCKASGYTFT NYYMHWVRQA PGQCLEWMGM INPSGGGTSY  60
AQKFQGRVTM TRDTSTSTVY MELSSLRSED TAVYYCARGN PWELRLDYWG QGTLVTVSSG  120
GGGSGGGGSG GGGSGGGGSD IQMTQSPSSL SASVGDRVTI TCQASQDISN YLNWYQQKPG  180
KAPKLLIYAA SSLQSGVPSR FSGSGSGTDF TLTISSLQPE DFATYYCQQY YSYPFTFGCG  240
TKVDIK                                                             246

SEQ ID NO: 103          moltype = AA  length = 119
FEATURE                 Location/Qualifiers
source                  1..119
                        mol_type = protein
                        organism = synthetic construct
SEQUENCE: 103
QVQLVQSGAE VKKPGASVKV SCKASGYTFT RYTMHWVRQA PGQGLEWMGY INPSRGYTNY  60
NQKFKDRVTL TTDKSSSTAY MELSSLRSED TAVYYCARYY DDHYSLDYWG QGTLVTVSS   119

SEQ ID NO: 104          moltype = AA  length = 330
FEATURE                 Location/Qualifiers
source                  1..330
                        mol_type = protein
                        organism = synthetic construct
SEQUENCE: 104
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYQ  180
STYRVVSVLT VLHQDWLNGK EYKCKVSNKA LPAPIEKTIS KAKGQPREPQ VCTLPPSREE  240
MTKNQVSLSC AVKGFYPSDI AVEWESNGQP ENNYKTTPPV LDSDGSFFLV SKLTVDKSRW  300
QQGNVFSCSV MHEALHNRFT QKSLSLSPGK                                    330

SEQ ID NO: 105          moltype = AA  length = 213
FEATURE                 Location/Qualifiers
source                  1..213
                        mol_type = protein
```

-continued

```
                              organism = synthetic construct
SEQUENCE: 105
DIQMTQSPSS LSASVGDRVT ITCSASSSVS YMNWYQQKPG KAPKRLIYDT SKLASGVPSR    60
FSGSGSGTDF TLTISSLQPE DFATYYCQQW SSNPFTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 106          moltype = AA  length = 237
FEATURE                 Location/Qualifiers
source                  1..237
                        mol_type = protein
                        organism = synthetic construct
SEQUENCE: 106
GGGGSEPKSS DKTHTCPPCP APELLGGPSV FLFPPKPKDT LMISRTPEVT CVVVDVSHED    60
PEVKFNWYVD GVEVHNAKTK PREEQYQSTY RVVSVLTVLH QDWLNGKEYK CKVSNKALPA   120
PIEKTISKAK GQPREPQVYT LPPCREEMTK NQVSLWCLVK GFYPSDIAVE WESNGQPENN   180
YKTTPPVLDS DGSFFLYSKL TVDKSRWQQG NVFSCSVMHE ALHNHYTQKS LSLSPGK      237

SEQ ID NO: 107          moltype = AA  length = 253
FEATURE                 Location/Qualifiers
source                  1..253
                        mol_type = protein
                        organism = synthetic construct
SEQUENCE: 107
QVQLVQSGAE VKKPGSSVKV SCKASGGTFS NFGVSWLRQA PGQCLEWMGG IIPILGTANY    60
AQKFQGRVTI TADESTSTAY MELSSLRSED TAVYYCATPT NSGYYGPYYY YGMDVWGQGT   120
TVTVSSGGGG SGGGGSGGGG SGGGGSDIQM TQSPSSLSAS VGDRVTITCR ASQSISSWLA   180
WYQQKPGKAP KLLIYAASTL QSGVPSRFSG SGSGTDFTLT ISSLQPEDFA TYYCQQSYSI   240
PLTFGGGTKV EIK                                                     253

SEQ ID NO: 108          moltype = AA  length = 119
FEATURE                 Location/Qualifiers
source                  1..119
                        mol_type = protein
                        organism = synthetic construct
SEQUENCE: 108
QVQLVQSGAE VKKPGASVKV SCKASGYTFT RYTMHWVRQA PGQGLEWMGY INPSRGYTNY    60
NQKFKDRVTL TTDKSSSTAY MELSSLRSED TAVYYCARYY DDHYSLDYWG QGTLVTVSS    119

SEQ ID NO: 109          moltype = AA  length = 330
FEATURE                 Location/Qualifiers
source                  1..330
                        mol_type = protein
                        organism = synthetic construct
SEQUENCE: 109
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYQ   180
STYRVVSVLT VLHQDWLNGK EYKCKVSNKA LPAPIEKTIS KAKGQPREPQ VCTLPPSREE   240
MTKNQVSLSC AVKGFYPSDI AVEWESNGQP ENNYKTTPPV LDSDGSFFLV SKLTVDKSRW   300
QQGNVFSCSV MHEALHNRFT QKSLSLSPGK                                   330

SEQ ID NO: 110          moltype = AA  length = 213
FEATURE                 Location/Qualifiers
source                  1..213
                        mol_type = protein
                        organism = synthetic construct
SEQUENCE: 110
DIQMTQSPSS LSASVGDRVT ITCSASSSVS YMNWYQQKPG KAPKRLIYDT SKLASGVPSR    60
FSGSGSGTDF TLTISSLQPE DFATYYCQQW SSNPFTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 111          moltype = AA  length = 10
FEATURE                 Location/Qualifiers
source                  1..10
                        mol_type = protein
                        organism = synthetic construct
SEQUENCE: 111
GGGGSGGGGS                                                          10

SEQ ID NO: 112          moltype = AA  length = 15
FEATURE                 Location/Qualifiers
source                  1..15
                        mol_type = protein
                        organism = synthetic construct
SEQUENCE: 112
GGGGSEPKSS DKTHT                                                    15
```

-continued

```
SEQ ID NO: 113            moltype = AA   length = 20
FEATURE                   Location/Qualifiers
source                    1..20
                          mol_type = protein
                          organism = synthetic construct
SEQUENCE: 113
GGCGGGGSGS EPKSSDKTHT                                           20

SEQ ID NO: 114            moltype = AA   length = 15
FEATURE                   Location/Qualifiers
source                    1..15
                          mol_type = protein
                          organism = synthetic construct
SEQUENCE: 114
GGCGGGGSGS GGGGS                                                15

SEQ ID NO: 115            moltype = AA   length = 15
FEATURE                   Location/Qualifiers
source                    1..15
                          mol_type = protein
                          organism = synthetic construct
SEQUENCE: 115
GGCGSEPKSS DKTHT                                                15

SEQ ID NO: 116            moltype = AA   length = 5
FEATURE                   Location/Qualifiers
source                    1..5
                          mol_type = protein
                          organism = synthetic construct
SEQUENCE: 116
GGCGS                                                            5

SEQ ID NO: 117            moltype = AA   length = 21
FEATURE                   Location/Qualifiers
source                    1..21
                          mol_type = protein
                          organism = synthetic construct
SEQUENCE: 117
GGGCGGGGSG SEPKSSDKTH T                                         21

SEQ ID NO: 118            moltype = AA   length = 16
FEATURE                   Location/Qualifiers
source                    1..16
                          mol_type = protein
                          organism = synthetic construct
SEQUENCE: 118
GGGCGGGGSG SGGGGS                                               16

SEQ ID NO: 119            moltype = AA   length = 6
FEATURE                   Location/Qualifiers
source                    1..6
                          mol_type = protein
                          organism = synthetic construct
SEQUENCE: 119
GGGCGS                                                           6

SEQ ID NO: 120            moltype = AA   length = 9
FEATURE                   Location/Qualifiers
source                    1..9
                          mol_type = protein
                          organism = synthetic construct
SEQUENCE: 120
ATDNNLAVY                                                        9

SEQ ID NO: 121            moltype = AA   length = 9
FEATURE                   Location/Qualifiers
source                    1..9
                          mol_type = protein
                          organism = synthetic construct
SEQUENCE: 121
NADNNLAVY                                                        9

SEQ ID NO: 122            moltype = AA   length = 9
FEATURE                   Location/Qualifiers
source                    1..9
                          mol_type = protein
                          organism = synthetic construct
SEQUENCE: 122
NTANNLAVY                                                        9
```

-continued

```
SEQ ID NO: 123           moltype = AA  length = 9
FEATURE                  Location/Qualifiers
source                   1..9
                         mol_type = protein
                         organism = synthetic construct
SEQUENCE: 123
NTDANLAVY                                                            9

SEQ ID NO: 124           moltype = AA  length = 9
FEATURE                  Location/Qualifiers
source                   1..9
                         mol_type = protein
                         organism = synthetic construct
SEQUENCE: 124
NTDNALAVY                                                            9

SEQ ID NO: 125           moltype = AA  length = 9
FEATURE                  Location/Qualifiers
source                   1..9
                         mol_type = protein
                         organism = synthetic construct
SEQUENCE: 125
NTDNNAAVY                                                            9

SEQ ID NO: 126           moltype = AA  length = 9
FEATURE                  Location/Qualifiers
source                   1..9
                         mol_type = protein
                         organism = synthetic construct
SEQUENCE: 126
NTDNNLAAY                                                            9

SEQ ID NO: 127           moltype = AA  length = 9
FEATURE                  Location/Qualifiers
source                   1..9
                         mol_type = protein
                         organism = synthetic construct
SEQUENCE: 127
NTDNNLAVA                                                            9

SEQ ID NO: 128           moltype = AA  length = 9
FEATURE                  Location/Qualifiers
source                   1..9
                         mol_type = protein
                         organism = synthetic construct
SEQUENCE: 128
NTENNLAVY                                                            9

SEQ ID NO: 129           moltype = AA  length = 9
FEATURE                  Location/Qualifiers
source                   1..9
                         mol_type = protein
                         organism = synthetic construct
SEQUENCE: 129
NTDENLAVY                                                            9

SEQ ID NO: 130           moltype = AA  length = 9
FEATURE                  Location/Qualifiers
source                   1..9
                         mol_type = protein
                         organism = synthetic construct
SEQUENCE: 130
NTDNVLAVY                                                            9

SEQ ID NO: 131           moltype = AA  length = 9
FEATURE                  Location/Qualifiers
source                   1..9
                         mol_type = protein
                         organism = synthetic construct
SEQUENCE: 131
NTDNNVAVY                                                            9

SEQ ID NO: 132           moltype = AA  length = 9
FEATURE                  Location/Qualifiers
source                   1..9
                         mol_type = protein
                         organism = synthetic construct
SEQUENCE: 132
```

-continued

```
NTDNNLVVY                                                         9

SEQ ID NO: 133          moltype = AA  length = 9
FEATURE                 Location/Qualifiers
source                  1..9
                        mol_type = protein
                        organism = synthetic construct
SEQUENCE: 133
NTDNNLVEY                                                         9

SEQ ID NO: 134          moltype = AA  length = 9
FEATURE                 Location/Qualifiers
source                  1..9
                        mol_type = protein
                        organism = Homo sapiens
SEQUENCE: 134
YLDGTLAIY                                                         9

SEQ ID NO: 135          moltype = AA  length = 9
FEATURE                 Location/Qualifiers
source                  1..9
                        mol_type = protein
                        organism = Homo sapiens
SEQUENCE: 135
FSDKELAAY                                                         9

SEQ ID NO: 136          moltype = AA  length = 9
FEATURE                 Location/Qualifiers
source                  1..9
                        mol_type = protein
                        organism = Homo sapiens
SEQUENCE: 136
AADVGLAGY                                                         9

SEQ ID NO: 137          moltype = AA  length = 9
FEATURE                 Location/Qualifiers
source                  1..9
                        mol_type = protein
                        organism = Homo sapiens
SEQUENCE: 137
DTENEMAIY                                                         9

SEQ ID NO: 138          moltype = AA  length = 9
FEATURE                 Location/Qualifiers
source                  1..9
                        mol_type = protein
                        organism = Homo sapiens
SEQUENCE: 138
RVDYSLAVY                                                         9

SEQ ID NO: 139          moltype =    length =
SEQUENCE: 139
000

SEQ ID NO: 140          moltype = AA  length = 9
FEATURE                 Location/Qualifiers
source                  1..9
                        mol_type = protein
                        organism = Homo sapiens
SEQUENCE: 140
YADGKLAFY                                                         9

SEQ ID NO: 141          moltype = AA  length = 9
FEATURE                 Location/Qualifiers
source                  1..9
                        mol_type = protein
                        organism = Homo sapiens
SEQUENCE: 141
GADPTLATY                                                         9

SEQ ID NO: 142          moltype = AA  length = 9
FEATURE                 Location/Qualifiers
source                  1..9
                        mol_type = protein
                        organism = Homo sapiens
SEQUENCE: 142
QTEFALAVY                                                         9

SEQ ID NO: 143          moltype = AA  length = 9
```

-continued

```
FEATURE           Location/Qualifiers
source            1..9
                  mol_type = protein
                  organism = Homo sapiens
SEQUENCE: 143
ATDFKFAMY                                                                            9

SEQ ID NO: 144    moltype = AA  length = 9
FEATURE           Location/Qualifiers
source            1..9
                  mol_type = protein
                  organism = Homo sapiens
SEQUENCE: 144
ATDYTFAMY                                                                            9

SEQ ID NO: 145    moltype = AA  length = 9
FEATURE           Location/Qualifiers
source            1..9
                  mol_type = protein
                  organism = Homo sapiens
SEQUENCE: 145
GTDPELNLY                                                                            9

SEQ ID NO: 146    moltype = AA  length = 9
FEATURE           Location/Qualifiers
source            1..9
                  mol_type = protein
                  organism = Homo sapiens
SEQUENCE: 146
WTDVFLQIY                                                                            9

SEQ ID NO: 147    moltype = AA  length = 9
FEATURE           Location/Qualifiers
source            1..9
                  mol_type = protein
                  organism = Homo sapiens
SEQUENCE: 147
RLDEDLAAY                                                                            9

SEQ ID NO: 148    moltype = AA  length = 9
FEATURE           Location/Qualifiers
source            1..9
                  mol_type = protein
                  organism = Homo sapiens
SEQUENCE: 148
TVDTTLAGY                                                                            9

SEQ ID NO: 149    moltype = AA  length = 9
FEATURE           Location/Qualifiers
source            1..9
                  mol_type = protein
                  organism = Homo sapiens
SEQUENCE: 149
FIDKQLAAY                                                                            9

SEQ ID NO: 150    moltype = AA  length = 9
FEATURE           Location/Qualifiers
source            1..9
                  mol_type = protein
                  organism = Homo sapiens
SEQUENCE: 150
QTDFPLQAY                                                                            9

SEQ ID NO: 151    moltype = AA  length = 9
FEATURE           Location/Qualifiers
source            1..9
                  mol_type = protein
                  organism = Homo sapiens
SEQUENCE: 151
YIDIFLNVY                                                                            9

SEQ ID NO: 152    moltype = AA  length = 9
FEATURE           Location/Qualifiers
source            1..9
                  mol_type = protein
                  organism = Homo sapiens
SEQUENCE: 152
YTDNWLAVY                                                                            9
```

-continued

```
SEQ ID NO: 153          moltype = AA  length = 9
FEATURE                 Location/Qualifiers
source                  1..9
                        mol_type = protein
                        organism = Homo sapiens
SEQUENCE: 153
AMDVNLTVY                                                                 9

SEQ ID NO: 154          moltype = AA  length = 9
FEATURE                 Location/Qualifiers
source                  1..9
                        mol_type = protein
                        organism = Homo sapiens
SEQUENCE: 154
RTEDNLQIY                                                                 9

SEQ ID NO: 155          moltype = AA  length = 9
FEATURE                 Location/Qualifiers
source                  1..9
                        mol_type = protein
                        organism = Homo sapiens
SEQUENCE: 155
LMDKHLAGY                                                                 9

SEQ ID NO: 156          moltype = AA  length = 9
FEATURE                 Location/Qualifiers
source                  1..9
                        mol_type = protein
                        organism = Homo sapiens
SEQUENCE: 156
VADGILASY                                                                 9

SEQ ID NO: 157          moltype = AA  length = 9
FEATURE                 Location/Qualifiers
source                  1..9
                        mol_type = protein
                        organism = Homo sapiens
SEQUENCE: 157
SLDLYLAMY                                                                 9

SEQ ID NO: 158          moltype = AA  length = 9
FEATURE                 Location/Qualifiers
source                  1..9
                        mol_type = protein
                        organism = Homo sapiens
SEQUENCE: 158
NMDYTLTMY                                                                 9

SEQ ID NO: 159          moltype = AA  length = 9
FEATURE                 Location/Qualifiers
source                  1..9
                        mol_type = protein
                        organism = Homo sapiens
SEQUENCE: 159
NLDGLIAGY                                                                 9

SEQ ID NO: 160          moltype = AA  length = 9
FEATURE                 Location/Qualifiers
source                  1..9
                        mol_type = protein
                        organism = Homo sapiens
SEQUENCE: 160
EAENNLAAY                                                                 9

SEQ ID NO: 161          moltype = AA  length = 9
FEATURE                 Location/Qualifiers
source                  1..9
                        mol_type = protein
                        organism = Homo sapiens
SEQUENCE: 161
VTDFKFALY                                                                 9

SEQ ID NO: 162          moltype = AA  length = 9
FEATURE                 Location/Qualifiers
source                  1..9
                        mol_type = protein
                        organism = Homo sapiens
SEQUENCE: 162
QIDPVLQVY                                                                 9
```

```
SEQ ID NO: 163            moltype = AA  length = 9
FEATURE                   Location/Qualifiers
source                    1..9
                          mol_type = protein
                          organism = Homo sapiens
SEQUENCE: 163
KMDQTLAVY                                                            9

SEQ ID NO: 164            moltype = AA  length = 9
FEATURE                   Location/Qualifiers
source                    1..9
                          mol_type = protein
                          organism = Homo sapiens
SEQUENCE: 164
NMDRPIAGY                                                            9

SEQ ID NO: 165            moltype = AA  length = 9
FEATURE                   Location/Qualifiers
source                    1..9
                          mol_type = protein
                          organism = Homo sapiens
SEQUENCE: 165
NLDFVLSFY                                                            9

SEQ ID NO: 166            moltype = AA  length = 9
FEATURE                   Location/Qualifiers
source                    1..9
                          mol_type = protein
                          organism = Homo sapiens
SEQUENCE: 166
ETEYGLSVY                                                            9

SEQ ID NO: 167            moltype = AA  length = 9
FEATURE                   Location/Qualifiers
source                    1..9
                          mol_type = protein
                          organism = Homo sapiens
SEQUENCE: 167
CTETHLAAY                                                            9

SEQ ID NO: 168            moltype = AA  length = 9
FEATURE                   Location/Qualifiers
source                    1..9
                          mol_type = protein
                          organism = Homo sapiens
SEQUENCE: 168
EADINIAFY                                                            9

SEQ ID NO: 169            moltype = AA  length = 9
FEATURE                   Location/Qualifiers
source                    1..9
                          mol_type = protein
                          organism = Homo sapiens
SEQUENCE: 169
MTDGGLGLY                                                            9

SEQ ID NO: 170            moltype = AA  length = 9
FEATURE                   Location/Qualifiers
source                    1..9
                          mol_type = protein
                          organism = Homo sapiens
SEQUENCE: 170
MTDGGLNLY                                                            9

SEQ ID NO: 171            moltype = AA  length = 9
FEATURE                   Location/Qualifiers
source                    1..9
                          mol_type = protein
                          organism = Homo sapiens
SEQUENCE: 171
NTEEPISVY                                                            9

SEQ ID NO: 172            moltype = AA  length = 9
FEATURE                   Location/Qualifiers
source                    1..9
                          mol_type = protein
                          organism = Homo sapiens
SEQUENCE: 172
```

-continued

```
NVDRVFALY                                                                 9

SEQ ID NO: 173            moltype = AA  length = 9
FEATURE                   Location/Qualifiers
source                    1..9
                          mol_type = protein
                          organism = Homo sapiens
SEQUENCE: 173
DMDYTLAVY                                                                  9

SEQ ID NO: 174            moltype = AA  length = 9
FEATURE                   Location/Qualifiers
source                    1..9
                          mol_type = protein
                          organism = Homo sapiens
SEQUENCE: 174
ATDIKITVY                                                                  9

SEQ ID NO: 175            moltype = AA  length = 9
FEATURE                   Location/Qualifiers
source                    1..9
                          mol_type = protein
                          organism = Homo sapiens
SEQUENCE: 175
NTEEFITVY                                                                  9

SEQ ID NO: 176            moltype = AA  length = 9
FEATURE                   Location/Qualifiers
source                    1..9
                          mol_type = protein
                          organism = Homo sapiens
SEQUENCE: 176
RLDEPLASY                                                                  9

SEQ ID NO: 177            moltype = AA  length = 9
FEATURE                   Location/Qualifiers
source                    1..9
                          mol_type = protein
                          organism = Homo sapiens
SEQUENCE: 177
TADHGLAAY                                                                  9

SEQ ID NO: 178            moltype = AA  length = 9
FEATURE                   Location/Qualifiers
source                    1..9
                          mol_type = protein
                          organism = Homo sapiens
SEQUENCE: 178
KTENLLGSY                                                                  9

SEQ ID NO: 179            moltype = AA  length = 9
FEATURE                   Location/Qualifiers
source                    1..9
                          mol_type = protein
                          organism = Homo sapiens
SEQUENCE: 179
WTDYLLAFY                                                                  9

SEQ ID NO: 180            moltype = AA  length = 9
FEATURE                   Location/Qualifiers
source                    1..9
                          mol_type = protein
                          organism = Homo sapiens
SEQUENCE: 180
QTDLLIAFY                                                                  9

SEQ ID NO: 181            moltype =    length =
SEQUENCE: 181
000

SEQ ID NO: 182            moltype =    length =
SEQUENCE: 182
000

SEQ ID NO: 183            moltype =    length =
SEQUENCE: 183
000

SEQ ID NO: 184            moltype =    length =
```

```
SEQUENCE: 184
000

SEQ ID NO: 185          moltype =   length =
SEQUENCE: 185
000

SEQ ID NO: 186          moltype =   length =
SEQUENCE: 186
000

SEQ ID NO: 187          moltype =   length =
SEQUENCE: 187
000

SEQ ID NO: 188          moltype =   length =
SEQUENCE: 188
000

SEQ ID NO: 189          moltype =   length =
SEQUENCE: 189
000

SEQ ID NO: 190          moltype = AA  length = 9
FEATURE                 Location/Qualifiers
source                  1..9
                        mol_type = protein
                        organism = Homo sapiens
SEQUENCE: 190
NSDSNLTTY                                                                9

SEQ ID NO: 191          moltype = AA  length = 9
FEATURE                 Location/Qualifiers
source                  1..9
                        mol_type = protein
                        organism = Homo sapiens
SEQUENCE: 191
KTDHFLSCY                                                                9

SEQ ID NO: 192          moltype = AA  length = 9
FEATURE                 Location/Qualifiers
source                  1..9
                        mol_type = protein
                        organism = Homo sapiens
SEQUENCE: 192
CTDRAFAVY                                                                9

SEQ ID NO: 193          moltype = AA  length = 9
FEATURE                 Location/Qualifiers
source                  1..9
                        mol_type = protein
                        organism = Homo sapiens
SEQUENCE: 193
RTDGILALY                                                                9

SEQ ID NO: 194          moltype = AA  length = 9
FEATURE                 Location/Qualifiers
source                  1..9
                        mol_type = protein
                        organism = Homo sapiens
SEQUENCE: 194
CVDWSIAVY                                                                9

SEQ ID NO: 195          moltype = AA  length = 9
FEATURE                 Location/Qualifiers
source                  1..9
                        mol_type = protein
                        organism = Homo sapiens
SEQUENCE: 195
NIDDALQCY                                                                9

SEQ ID NO: 196          moltype = AA  length = 9
FEATURE                 Location/Qualifiers
source                  1..9
                        mol_type = protein
                        organism = Homo sapiens
SEQUENCE: 196
FSELNLAAY                                                                9
```

-continued

```
SEQ ID NO: 197        moltype = AA  length = 9
FEATURE               Location/Qualifiers
source                1..9
                      mol_type = protein
                      organism = Homo sapiens
SEQUENCE: 197
GMDDFLGVY                                                              9

SEQ ID NO: 198        moltype = AA  length = 9
FEATURE               Location/Qualifiers
source                1..9
                      mol_type = protein
                      organism = Homo sapiens
SEQUENCE: 198
NTDSDMGGY                                                              9

SEQ ID NO: 199        moltype = AA  length = 9
FEATURE               Location/Qualifiers
source                1..9
                      mol_type = protein
                      organism = Homo sapiens
SEQUENCE: 199
YADRALAFY                                                              9

SEQ ID NO: 200        moltype = AA  length = 9
FEATURE               Location/Qualifiers
source                1..9
                      mol_type = protein
                      organism = Homo sapiens
SEQUENCE: 200
GTDKLLSGY                                                              9

SEQ ID NO: 201        moltype = AA  length = 9
FEATURE               Location/Qualifiers
source                1..9
                      mol_type = protein
                      organism = Homo sapiens
SEQUENCE: 201
QVDSTLAAY                                                              9

SEQ ID NO: 202        moltype = AA  length = 9
FEATURE               Location/Qualifiers
source                1..9
                      mol_type = protein
                      organism = Homo sapiens
SEQUENCE: 202
WSDAKLAAY                                                              9

SEQ ID NO: 203        moltype = AA  length = 9
FEATURE               Location/Qualifiers
source                1..9
                      mol_type = protein
                      organism = Homo sapiens
SEQUENCE: 203
GTDNWLAQY                                                              9

SEQ ID NO: 204        moltype = AA  length = 9
FEATURE               Location/Qualifiers
source                1..9
                      mol_type = protein
                      organism = Homo sapiens
SEQUENCE: 204
ETDNNIVVY                                                              9

SEQ ID NO: 205        moltype = AA  length = 9
FEATURE               Location/Qualifiers
source                1..9
                      mol_type = protein
                      organism = Homo sapiens
SEQUENCE: 205
PTDENLARY                                                              9

SEQ ID NO: 206        moltype = AA  length = 9
FEATURE               Location/Qualifiers
source                1..9
                      mol_type = protein
                      organism = Homo sapiens
SEQUENCE: 206
NTDNLLTEY                                                              9
```

-continued

```
SEQ ID NO: 207          moltype = AA   length = 9
FEATURE                 Location/Qualifiers
source                  1..9
                        mol_type = protein
                        organism = Homo sapiens SEQUENCE: 207
LTEQYNEQY                                                           9

SEQ ID NO: 208          moltype = AA   length = 9
FEATURE                 Location/Qualifiers
source                  1..9
                        mol_type = protein
                        organism = Homo sapiens SEQUENCE: 208
TTEVHPELY                                                           9

SEQ ID NO: 209          moltype = AA   length = 9
FEATURE                 Location/Qualifiers
source                  1..9
                        mol_type = protein
                        organism = Homo sapiens SEQUENCE: 209
ATDLTREVY                                                           9

SEQ ID NO: 210          moltype = AA   length = 4
FEATURE                 Location/Qualifiers
source                  1..4
                        mol_type = protein
                        organism = synthetic construct SEQUENCE: 210
GGGC                                                                4

SEQ ID NO: 211          moltype = AA   length = 12
FEATURE                 Location/Qualifiers
source                  1..12
                        mol_type = protein
                        organism = Homo sapiens SEQUENCE: 211
KSCDKTHTCP PC                                                       12

SEQ ID NO: 212          moltype = AA   length = 4
FEATURE                 Location/Qualifiers
source                  1..4
                        mol_type = protein
                        organism = Homo sapiens SEQUENCE: 212
ELLG                                                                4

SEQ ID NO: 213          moltype = AA   length = 4
FEATURE                 Location/Qualifiers
source                  1..4
                        mol_type = protein
                        organism = Homo sapiens SEQUENCE: 213
EFLG                                                                4

SEQ ID NO: 214          moltype = AA   length = 9
FEATURE                 Location/Qualifiers
source                  1..9
                        mol_type = protein
                        organism = Homo sapiens SEQUENCE: 214
NTDNNLAVY                                                           9

SEQ ID NO: 215          moltype = AA   length = 15
FEATURE                 Location/Qualifiers
VARIANT                 6..15
                        note = GGGGS repeats may be deleted
source                  1..15
                        mol_type = protein
                        organism = synthetic construct SEQUENCE: 215
GGGGSGGGGS GGGGS                                                    15

SEQ ID NO: 216          moltype = AA   length = 10
FEATURE                 Location/Qualifiers
source                  1..10
                        mol_type = protein
```

-continued

```
                           organism = synthetic construct
SEQUENCE: 216
GSGGGGSGGG                                                        10

SEQ ID NO: 217         moltype = AA  length = 5
FEATURE                Location/Qualifiers
source                 1..5
                       mol_type = protein
                       organism = synthetic construct
SEQUENCE: 217
GGGGS                                                             5

SEQ ID NO: 218         moltype = AA  length = 40
FEATURE                Location/Qualifiers
VARIANT                3..40
                       note = GS repeats may be deleted
source                 1..40
                       mol_type = protein
                       organism = synthetic construct
SEQUENCE: 218
GSGSGSGSGS GSGSGSGSGS GSGSGSGSGS GSGSGSGSGS                       40

SEQ ID NO: 219         moltype = AA  length = 60
FEATURE                Location/Qualifiers
VARIANT                4..60
                       note = GGS repeats may be deleted
source                 1..60
                       mol_type = protein
                       organism = synthetic construct
SEQUENCE: 219
GGSGGSGGSG GSGGSGGSGG SGGSGGSGGS GGSGGSGGSG GSGGSGGSGG SGGSGGSGGS  60

SEQ ID NO: 220         moltype = AA  length = 80
FEATURE                Location/Qualifiers
VARIANT                5..80
                       note = GGGS repeats may be deleted
source                 1..80
                       mol_type = protein
                       organism = synthetic construct
SEQUENCE: 220
GGGSGGGSGG GSGGGSGGGS GGGSGGGSGG GSGGGSGGGS GGGSGGGSGG GSGGGSGGGS  60
GGGSGGGSGG GSGGGSGGGS                                             80

SEQ ID NO: 221         moltype = AA  length = 80
FEATURE                Location/Qualifiers
VARIANT                5..80
                       note = GGSG repeats may be deleted
source                 1..80
                       mol_type = protein
                       organism = synthetic construct
SEQUENCE: 221
GGSGGGGSGGG SGGGSGGGSG GGSGGGSGGG SGGGSGGGSG GGSGGGSGGG SGGGSGGGSG  60
GGSGGGSGGG SGGGSGGGSG                                             80

SEQ ID NO: 222         moltype = AA  length = 100
FEATURE                Location/Qualifiers
VARIANT                6..100
                       note = GGSGG repeats may be deleted
source                 1..100
                       mol_type = protein
                       organism = synthetic construct
SEQUENCE: 222
GGSGGGGSGG GGSGGGGSGG GGSGGGGSGG GGSGGGGSGG GGSGGGGSGG GGSGGGGSGG  60
GGSGGGGSGG GGSGGGGSGG GGSGGGGSGG GGSGGGGSGG                       100

SEQ ID NO: 223         moltype = AA  length = 100
FEATURE                Location/Qualifiers
VARIANT                6..100
                       note = GGGGS repeats may be deleted
source                 1..100
                       mol_type = protein
                       organism = synthetic construct
SEQUENCE: 223
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS                       100

SEQ ID NO: 224         moltype = AA  length = 100
FEATURE                Location/Qualifiers
VARIANT                6..100
```

-continued

```
                               note = GSGGG repeats may be deleted
source                         1..100
                               mol_type = protein
                               organism = synthetic construct
SEQUENCE: 224
GSGGGGSGGG GSGGGGSGGG GSGGGGSGGG GSGGGGSGGG GSGGGGSGGG GSGGGGSGGG   60
GSGGGGSGGG GSGGGGSGGG GSGGGGSGGG GSGGGGSGGG                        100

SEQ ID NO: 225                 moltype = AA  length = 100
FEATURE                        Location/Qualifiers
VARIANT                        6..100
                               note = GGGSG repeats may be deleted
source                         1..100
                               mol_type = protein
                               organism = synthetic construct
SEQUENCE: 225
GGGSGGGGSG GGGSGGGGSG GGGSGGGGSG GGGSGGGGSG GGGSGGGGSG GGGSGGGGSG   60
GGGSGGGGSG GGGSGGGGSG GGGSGGGGSG GGGSGGGGSG                        100

SEQ ID NO: 226                 moltype = AA  length = 100
FEATURE                        Location/Qualifiers
VARIANT                        6..100
                               note = GGGGG repeats may be deleted
source                         1..100
                               mol_type = protein
                               organism = synthetic construct
SEQUENCE: 226
GGGGGGGGGG GGGGGGGGGG GGGGGGGGGG GGGGGGGGGG GGGGGGGGGG GGGGGGGGGG   60
GGGGGGGGGG GGGGGGGGGG GGGGGGGGGG GGGGGGGGGG                        100

SEQ ID NO: 227                 moltype = AA  length = 50
FEATURE                        Location/Qualifiers
VARIANT                        16..50
                               note = GGGGS repeats may be deleted
source                         1..50
                               mol_type = protein
                               organism = synthetic construct
SEQUENCE: 227
GGGGSGGGGS GGGGSGGGGS GGGGSGGGGS GGGGSGGGGS GGGGSGGGGS               50

SEQ ID NO: 228                 moltype = AA  length = 20
FEATURE                        Location/Qualifiers
source                         1..20
                               mol_type = protein
                               organism = synthetic construct
SEQUENCE: 228
GGGGSGGGGS GGGGSGGGGS                                                20

SEQ ID NO: 229                 moltype = DNA  length = 22
FEATURE                        Location/Qualifiers
source                         1..22
                               mol_type = other DNA
                               organism = synthetic construct
                               note = primer
SEQUENCE: 229
ctcgcggccc agccggccat gg                                            22

SEQ ID NO: 230                 moltype = DNA  length = 31
FEATURE                        Location/Qualifiers
source                         1..31
                               mol_type = other DNA
                               organism = synthetic construct
                               note = primer
SEQUENCE: 230
gttggcctcc cgggccacta gttttgatct c                                  31

SEQ ID NO: 231                 moltype = AA  length = 6
FEATURE                        Location/Qualifiers
source                         1..6
                               mol_type = protein
                               organism = synthetic construct
SEQUENCE: 231
GSGGGG                                                               6

SEQ ID NO: 232                 moltype = AA  length = 17
FEATURE                        Location/Qualifiers
source                         1..17
                               mol_type = protein
                               organism = synthetic construct
```

-continued

```
SEQUENCE: 232
GGGGSEPKSS DKTHTCP                                                        17

SEQ ID NO: 233         moltype = AA  length = 9
FEATURE                Location/Qualifiers
source                 1..9
                       mol_type = protein
                       organism = Homo sapiens
SEQUENCE: 233
EVDPIGHVY                                                                 9

SEQ ID NO: 234         moltype = AA  length = 16
FEATURE                Location/Qualifiers
source                 1..16
                       mol_type = protein
                       organism = synthetic construct
SEQUENCE: 234
GGGCGSEPKS SDKTHT                                                         16

SEQ ID NO: 235         moltype = AA  length = 117
FEATURE                Location/Qualifiers
source                 1..117
                       mol_type = protein
                       organism = synthetic construct
SEQUENCE: 235
QVQLVQSGAE VKKPGASVKV SCKASGFTFT NYLIHWVRQA PGQGLEWMGW INPNSGGTNY         60
AQRLQGRVTM TRDTSTSTVY MELSSLRSED TACYYCARDY GAGNDYWGQG TLVTVSS            117

SEQ ID NO: 236         moltype = AA  length = 10
FEATURE                Location/Qualifiers
source                 1..10
                       mol_type = protein
                       organism = Homo sapiens
SEQUENCE: 236
AIFPGAVPAA                                                                10

SEQ ID NO: 237         moltype = AA  length = 8
FEATURE                Location/Qualifiers
source                 1..8
                       mol_type = protein
                       organism = synthetic construct
SEQUENCE: 237
GSGGGGCP                                                                  8
```

The invention claimed is:

1. An isolated antigen binding protein (ABP) that comprises:

a first antigen binding region (ABR) and a second ABR that each specifically bind a first target antigen, a Fab that specifically binds a second target antigen CD3, and an Fc domain, wherein the ABP comprises a first polypeptide, a second polypeptide, and a third polypeptide; wherein the first polypeptide comprises, in an N→C direction, the first ABR-a first hinge-CH2-CH3; wherein the second polypeptide comprises, in an N→C direction, the second ABR-a variable heavy chain (VH) domain of the Fab-a CH1 domain of the Fab-a second hinge-CH2-CH3; wherein the third polypeptide comprises, in an N→C direction, a variable light chain (VL) domain of the Fab-a CL domain of the Fab;

wherein the first ABR and second ABR each comprise, in an N→C direction: (i) a VH domain-a VL domain or (ii) a VL domain-VH domain;

wherein the VH domain of the first ABR is attached to the VL domain of the first ABR via a first linker;

wherein the VH domain of the second ABR is attached to the VL domain of the second ABR via a second linker;

wherein the first linker and second linker are each about 5-15 amino acids in length; and wherein the first target antigen is an HLA-PEPTIDE target comprising an HLA-restricted peptide complexed with an HLA Class I molecule, wherein the HLA Class I molecule is HLA subtype HLA-A*01:01 and the HLA-restricted peptide comprises the sequence NTDNNLAVY (SEQ ID NO: 214); and wherein the VH domains of the first and second ABRs each comprise complementarity-determining regions (CDR)-H1, CDR-H2, and CDR-H3 comprising the sequences set forth in SEQ ID NOS: 18, 19, and 20, respectively and wherein the VL comprises CDR-L1, CDR-L2, and CDR-L3 comprising the sequences set forth in SEQ ID NOS: 21, 22, and 23, respectively.

2. The isolated ABP of claim 1, wherein the first linker and second linker are each individually 5-15, 5-14, 5-13, 5-12, 5-11, 5-10, 5-9, 5-8, 5-7, 5-6, 6-15, 6-14, 6-13, 6-12, 6-11, 6-10, 6-9, 6-8, 6-7, 7-15, 7-14, 7-13, 7-12, 7-11, 7-10, 7-9, 7-8, 8-15, 8-14, 8-13, 8-12, 8-11, 8-10, 8-9, 9-15, 9-14, 9-13, 9-12, 9-11 or 9-10 amino acids in length.

3. The isolated ABP of claim 1, wherein the VH and VL domains of the Fab comprise CDR-H1, CDR-H2, CDR-H3, CDR-L1, CDR-L2, and CDR-L3 comprising the sequences set forth in SEQ ID NOS: 36, 37, 38, 39, 40, and 41; 26, 27, 28, 29, 30, and 31; or 42, 43, 44, 45, 46, and 47 respectively.

4. The isolated ABP of claim 1, wherein the VH of the first and second ABRs comprises the sequence set forth in SEQ ID NO: 6 and wherein the VL of the first and second ABR comprises the sequence set forth in SEQ ID NO: 4.

5. The isolated ABP of claim 1, wherein the VH and VL of the Fab comprises the sequence set forth in SEQ ID NOS: 32 and 33; 24 and 25; or 34 and 35, respectively.

6. The isolated ABP of claim 1, wherein the first polypeptide comprises the sequence set forth in SEQ ID NO: 55 or the sequences set forth in SEQ ID NO: 55 and 48.

7. The isolated ABP of claim 1, wherein the second polypeptide comprises the sequence set forth in SEQ ID NOs: 55 or the sequences set forth in SEQ ID NOs: 55 and 51, 49, or 53.

8. The isolated ABP of claim 1, wherein the third polypeptide comprises the sequence set forth in SEQ ID NOs: 52, 50, or 54.

9. The isolated ABP of claim 1, wherein the first polypeptide comprises the sequence set forth in SEQ ID NO: 55 and 48, the second polypeptide comprises the sequence set forth in SEQ ID NO: 55 and 51, and the third polypeptide comprises the sequence set forth in SEQ ID NOs: 52.

10. The isolated ABP of claim 1, wherein the VL domain of the first ABR interacts with the VH domain of the second ABR and wherein the VH domain of the first ABR interacts with the VL domain of the second ABR.

11. The isolated ABP of claim 1, wherein the antigen binding protein is linked to a scaffold, optionally wherein the scaffold comprises serum albumin or Fc, optionally wherein Fc is human Fc and is an IgG (IgG1, IgG2, IgG3, IgG4), an IgA (IgAQ1, IgA2), an IgD, an IgE, or an IgM.

12. The isolated ABP of claim 1, comprising a variant CH2-CH3 domain, wherein the variant CH2-CH3 domain of the first or second polypeptide comprises a knob-in-hole modification.

13. An isolated polynucleotide or set of polynucleotides encoding the antigen binding protein of claim 1 or an antigen-binding portion thereof.

14. A vector or set of vectors comprising the polynucleotide or set of polynucleotides of claim 13.

15. A host cell comprising the polynucleotide or set of polynucleotides of claim 13, optionally wherein the host cell is CHO or HEK293, or optionally wherein the host cell is a T cell.

16. A method of producing an antigen binding protein comprising expressing the antigen binding protein with the host cell of claim 15 and isolating the expressed antigen binding protein.

17. A pharmaceutical composition comprising the antigen binding protein of claim 1 and a pharmaceutically acceptable excipient.

18. A method of increasing an immune response in a subject, comprising administering to the subject the ABP of claim 1, optionally wherein the subject has cancer.

\* \* \* \* \*